(12) United States Patent
Nussenzweig et al.

(10) Patent No.: US 8,673,307 B1
(45) Date of Patent: Mar. 18, 2014

(54) HIV-1 ANTI-CORE NEUTRALIZING ANTIBODIES THAT TARGET A CONFORMATIONAL EPITOPE WITHIN THE ALPHA5-HELIX OF GP120

(75) Inventors: Michel C. Nussenzweig, New York, NY (US); Johannes Scheid, New York, NY (US); John Pietzsch, New York, NY (US)

(73) Assignee: The Rockefeller University, New York, NY (US)

( * ) Notice: Subject to any disclaimer, the term of this patent is extended or adjusted under 35 U.S.C. 154(b) by 586 days.

(21) Appl. No.: 12/719,356

(22) Filed: Mar. 8, 2010

Related U.S. Application Data

(60) Provisional application No. 61/158,465, filed on Mar. 9, 2009.

(51) Int. Cl.
*A61K 39/42* (2006.01)
*C07K 16/00* (2006.01)

(52) U.S. Cl.
USPC ................. 424/148.1; 424/160.1; 530/388.35

(58) Field of Classification Search
None
See application file for complete search history.

(56) References Cited

PUBLICATIONS

Brown, M., et al., 1996, Tolerance to single, but not multiple, amino acid replacements in antibody VH CDR2, J. Immunol. 156:3285-3291.*
Chen, C., et al., Sep. 1992, Generation and analysis of random point mutations in an antibody CDR2 sequence: many mutated antibodies lose their ability to bind antigen, J. Exp. Med. 176:855-866.*
Gallo, R. C., Nov. 2005, The end or the beginning of the drive to an HIV-preventive vaccine: a view from over 20 years, The Lancet, 366:1894-1898.*
Walker, B. D., and D. R. Burton, May 2008, Toward an AIDS vaccine, Science 320:760-764.*
Thomas, C., Aug. 2009, Roadblocks in HIV research: five questions, Nat. Med. 15(8):855-859.*
Bansal, G. P., 2007, A summary of the workshop on passive immunization using monoclonal antibodies for HIV/AIDS, held at the National Institute of Allergy and Infectious Diseases, Bethesda, Mar. 10, 2006, Biologicals 35:367-371.*
Zwick, M. B., et al., May 2003, Molecular features of the broadly neutralizing immunoglobulin G1 b12 required for recognition of human immunodeficiency virus type 1 gp120, J. Virol. 77(10):5863-5876.*
Korber, B. T., et al., Dec. 1998, Numbering positions in HIV relative to HXB2CG, in Human Retroviruses and AIDS 1998: A compilation and analysis of nucleic acid and amino acid sequences, Korber, B. T., et al., eds., Theoretical Biology and Biophysics Group, Los Alamos National Laboratory, Los Alamos, NM, III-102-III-111.*
Pietzsch, J., et al., Aug. 2010, Human and anti-HIV-neutralizing antibodies frequently target a conserved epitope essential for viral fitness, J. Exp. Med. 207(9):1995-2010.*

* cited by examiner

*Primary Examiner* — Jeffrey S. Parkin
(74) *Attorney, Agent, or Firm* — Fox Rothschild LLP; Gerard P. Norton; Adam Forman

(57) ABSTRACT

Broad neutralizing antibodies directed to epitopes of Human Immunodeficiency Virus, or HIV, especially the preparation and use of highly neutralizing antibodies directed to HIV gp120 envelope protein, in the vaccination and treatment of HIV-infected patients.

4 Claims, 52 Drawing Sheets

Neutralizing activity of patient serum in TZM-bl assays.

Clonal Relationships between gp140 binding antibodies

Serum absorption by YU2-gp140 trimer and binding to control antibodies

Clinical information of patients and healthy controls

| | gender | date of birth | diagnosis | cd4+ Tcells/μl | virus copies/ml | clinical status |
|---|---|---|---|---|---|---|
| pt1 | male | 17-Jul-1948 | 1985 | 448 | 3610 | non progressor |
| pt2 | male | 01-Aug-1956 | 10-Jul-2003 | 1070 | 49 | elite controller |
| pt3 | male | 04-Jan-1965 | 24-Jun-2002 | 565 | 399 | elite controller |
| pt4 | male | 1966 | 2005 | 569 | 4828 | / |
| pt5 | male | 01-Feb-1966 | 01-Jan-1991 | 447 | 66 | elite controller |
| pt6 | male | 1950 | 1997 | 647 | 12709 | slow progressor |
| HC1 | male | 1977 | / | ND | / | HIV neg |
| HC2 | male | 1983 | / | ND | / | HIV neg |

Figure 14

Repertoire and reactivity of gp140 binding antibodies, patient 1

| Ab name | VH | D | JH | (-) | CDR3 (aa) | Length | κ/λ | Vκ/λ | Jκ/λ | (-) | CDR3 (aa) | (+) | Length | Binding | Peptide Library | NEUT | # of relatives |
|---|---|---|---|---|---|---|---|---|---|---|---|---|---|---|---|---|---|
| 1-64 | 4-59 | 5-5/5-18 | 6 | 2 | HEAPRYSYAFRRYYHYGLDV (SEQ ID NO.: 1) | 20 | λ | 1-44 | 3 | 2 | ASWDDSLSGWV (SEQ ID NO.: 40) | 0 | 11 | CD4bs | NEG | + | 1 |
| 1-676 | 4-59 | 5-5/5-18 | 6 | 2 | HEAPRYSYAFRNYYHYGLDV (SEQ ID NO.: 2) | 20 | λ | 1-44 | 3 | 2 | AAWDDSLNGWV (SEQ ID NO.: 41) | 0 | 11 | CD4bs | NEG | + | 1 |
| 1-154 | 3-74 | 3-3/3-9 | 6 | 3 | DRRRFLEWSLYGMDV (SEQ ID NO.: 3) | 15 | κ | 3-20 | 2 | 1 | QQYGSSPEYT (SEQ ID NO.: 42) | 0 | 10 | CD4bs | NEG | + | 1 |
| 1-695 | 4-59 | 3-3/3-9 | 3 | 2 | AGLDYNFWNGKGRKGAFDV (SEQ ID NO.: 4) | 19 | κ | 1-5 | 1 | 1 | QQYDS (SEQ ID NO.: 43) | 0 | 5 | CD4bs | NEG | + | 2 |
| 1-577 | 3-48 | 3-10/3-16 | 6 | 2 | GTLWFGESGLRLDH (SEQ ID NO.: 5) | 14 | κ | 1-16 | 2 | 0 | QQYNSFPPT (SEQ ID NO.: 44) | 0 | 9 | CD4bs | NEG | ND | 3 |
| 1-711 | 3-48 | 3-10/3-16 | 1/4 | 2 | GSLWFGESGLRLDH (SEQ ID NO.: 6) | 14 | κ | 1-16 | 2 | 0 | QQYNSFPPT (SEQ ID NO.: 45) | 0 | 9 | CD4bs | NEG | + | 2 |
| 1-732 | 3-72/3-73 | 3-22/3-10 | 6 | 2 | NRRVAM/PEAMILSFYMDV (SEQ ID NO.: 7) | 18 | κ | 3-20/3D-20 | 3 | 0 | QQYGRSP (SEQ ID NO.: 46) | 1 | 7 | CD4bs | NEG | + | 1 |
| 1-863 | 3-30 | 3-3/3-9 | 4 | 6 | GIQEDYDFWREYRELDY (SEQ ID NO.: 8) | 17 | κ | 2-30/2-24 | 1 | 0 | MQGTHWPRT (SEQ ID NO.: 47) | 2 | 9 | CD4bs | NEG | + | 1 |
| 1-74 | 4-34 | 3-3/3-9 | 4 | 1 | VVPMFSIFGVVKANYFDY (SEQ ID NO.: 9) | 18 | λ | 1-51 | 3 | 1 | GTWDSSLSAVL (SEQ ID NO.: 48) | 0 | 11 | Core | NEG | + | 1 |
| 1-621 | 20179 | 3-3/3-9 | 6 | 1 | VISGRITIFYNYIDV (SEQ ID NO.: 10) | 16 | λ | 15706 | 3 | 1 | ASWDNSLSGPV (SEQ ID NO.: 49) | 0 | 11 | Core | NEG | + | 2 |
| 1-756 | 20179 | 3-3/3-9 | 6 | 1 | VLSGRITIFYYYMDV (SEQ ID NO.: 11) | 16 | λ | 15706 | 3 | 1 | ASWDNSLSGPV (SEQ ID NO.: 50) | 0 | 11 | Core | NEG | ND | 1 |
| 1-479 | 1-69 | 3-22/1-26/2-8 | 4 | 1 | GFRGSPFSSGSLYFDS (SEQ ID NO.: 12) | 16 | κ | 3-20 | 1 | 0 | HQYAYSPRT (SEQ ID NO.: 51) | 2 | 9 | Core | NEG | + | 9 |
| 1-705 | 1-69 | 2-8/2-15/7-27 | 4 | 1 | GFRGSPFSSGSLYFDS (SEQ ID NO.: 13) | 16 | κ | 3-20 | 1/2 | 0 | HQYASSPRT (SEQ ID NO.: 52) | 2 | 9 | Core | NEG | + | 2 |
| 1-795 | 1-69 | 6-19/3-22/2-2 | 4 | 1 | GFRGNVFSTGWFYLDF (SEQ ID NO.: 14) | 16 | κ | 3-20 | 1/2 | 0 | QQYSSPRT (SEQ ID NO.: 53) | 1 | 9 | Core | NEG | + | 3 |
| 1-809 | 1-69 | 6-19/3-22/2-2 | 4 | 1 | GFRGSPLSSGSLYFDS (SEQ ID NO.: 15) | 16 | κ | 3-20 | 1/2 | 0 | HQYASSPRT (SEQ ID NO.: 54) | 2 | 9 | Core | NEG | + | 1 |
| 1-608 | 1-69 | 6-19/7-27 | 4 | 1 | GFRGSPFSSGSMYFDS (SEQ ID NO.: 16) | 16 | κ | 3-20 | 1 | 0 | HQYASSPRT (SEQ ID NO.: 55) | 2 | 9 | Core | NEG | + | 1 |
| 1-664 | 1-69 | 3-3/3-9 | 6 | 3 | DFPRFHRLVGNYDFWRGTLDR FSYMDL (SEQ ID NO.: 17) | 27 | κ | 2D-29/2-29 | 4 | 0 | MQSIQ (SEQ ID NO.: 56) | 0 | 5 | Core | NEG | ND | 1 |
| 1-687 | 3-53/3-66 | 3-16/2-21 | 6 | 1 | STPLVWPPANGLDV (SEQ ID NO.: 18) | 14 | κ | 3-20/3D-20 | 2 | 1 | QEYGRSPPFP (SEQ ID NO.: 57) | 1 | 10 | Core | NEG | - | 1 |
| 1-752 | 1-69 | 6-19/6-13/5-12 | 5 | 2 | DNRDQWLVLRSWFDP (SEQ ID NO.: 19) | 15 | κ | 1D-39/1-39 | 1/4 | 0 | QQSYTTPVT (SEQ ID NO.: 58) | 0 | 9 | Core | NEG | + | 1 |

Figure 15

| | | | | | | | | | | | |
|---|---|---|---|---|---|---|---|---|---|---|---|
| 1-68 | 1-26/4-17/3-22 | 6 | 5 | SVITDLHTFDYESGDPSYYMDV (SEQ ID NO.: 20) | 1 | 24 | κ | 1-5 | 1/4 | 0 | QQYNSYSGT (SEQ ID NO.: 59) | 0 | 9 | CD4i | NEG | ND | 4 |
| 1-692 | 1-69 | 6 | 5 | AVITDLHTFADYELGDPSYFYMDV (SEQ ID NO.: 21) | 1 | 24 | κ | 1-5 | 1/4 | 0 | QQYKSYSGT (SEQ ID NO.: 60) | 1 | 9 | CD4i | NEG | ND | 1 |
| 1-182 | 1-69 | 6 | 6 | AVITDLHTFGDYELEDPSYYMDV (SEQ ID NO.: 22) | 1 | 24 | κ | 1-5 | 1 | 0 | QQYKSYSGT (SEQ ID NO.: 61) | 1 | 9 | CD4i | NEG | + | 1 |
| 1-319 | 3-23 | 4 | 1 | RGRROIGDY (SEQ ID NO.: 23) | 3 | 9 | κ | 1D-39 | 2 | 0 | QQSFGIPPWT (SEQ ID NO.: 62) | 0 | 10 | CD4i | NEG | ND | 1 |
| 1-693 | 3-23 | 4 | 1 | RGRROIGDY (SEQ ID NO.: 24) | 3 | 9 | κ | 1D-39 | 2 | 0 | QHSFGSPPWT (SEQ ID NO.: 63) | 1 | 10 | CD4i | NEG | - | 1 |
| 1-79 | 3-9/3-3 | 3 | 4 | SYYDFSIGDGNDAFDV (SEQ ID NO.: 25) | 0 | 16 | λ | 1-47 | 1 | 3 | AAWDDSFDYV (SEQ ID NO.: 64) | 0 | 10 | V3 | + | 1 |
| 1-509 | 3-3/3-9 | 3 | 4 | SYYDFQTDSGNDAFDV (SEQ ID NO.: 26) | 0 | 16 | λ | 1-47 | 1/6 | 3 | AAWDDSLDYV (SEQ ID NO.: 65) | 0 | 10 | V3 | + | 2 |
| 1-542 | 3-3/3-9 | 3 | 4 | SYYDFRSDSGNDAFDI (SEQ ID NO.: 27) | 1 | 16 | λ | 1-47 | 1/6 | 3 | AAWDDSLDYV (SEQ ID NO.: 66) | 0 | 10 | V3 | + | 9 |
| 1-11 | 2-15 | 6 | 1 | GGGYPRGNMDV (SEQ ID NO.: 28) | 1 | 11 | κ | 1-5 | 1 | 0 | QQYTNYPWT (SEQ ID NO.: 67) | 0 | 9 | gp41 | NEG | - | 1 |
| 1-27 | 3-3/5-5 | 5 | 2 | DTTTFTFGGGPNMGGFDP (SEQ ID NO.: 29) | 0 | 19 | κ | 1-9 | 1 | 0 | QQLRT (SEQ ID NO.: 68) | 1 | 5 | gp41 | NEG | - | 5 |
| 1-193 | 3-3/3-5 | 5 | 2 | DTTTFSSFGSPPHMGGLDP (SEQ ID NO.: 30) | 1 | 19 | κ | 1-9 | 1 | 0 | QQLRT (SEQ ID NO.: 69) | 1 | 5 | gp41 | NEG | ND | 1 |
| 1-523 | 3-3/3-16 | 5 | 2 | DTTTFSFGSPPRMGGLDP (SEQ ID NO.: 31) | 1 | 19 | κ | 1-9 | 1 | 0 | QQLRT (SEQ ID NO.: 70) | 1 | 5 | gp41 | NEG | ND | 1 |
| 1-641 | 3-3/3-16 | 5 | 2 | DTTTFGAFGGGANMGGLDP (SEQ ID NO.: 32) | 0 | 19 | κ | 1-9 | 1 | 0 | QQLRT (SEQ ID NO.: 71) | 1 | 5 | gp41 | NEG | ND | 1 |
| 1-723 | 3-3/2-2 | 5 | 2 | DTTTFSSFGSPPNMGGLDP (SEQ ID NO.: 33) | 0 | 19 | κ | 1-9 | 1 | 0 | QQLRT (SEQ ID NO.: 72) | 1 | 5 | gp41 | NEG | ND | 1 |
| 1-751 | 3-3/3-16 | 5 | 2 | DTTTFGAFGGSPNMGGLDP (SEQ ID NO.: 34) | 0 | 19 | λ | 2-23 | 2/3 | 0 | QQLRT (SEQ ID NO.: 73) | 1 | 5 | gp41 | NEG | - | 1 |
| 1-96 | 5-12 | 4 | 1 | PYVQTVATTFDF (SEQ ID NO.: 35) | 0 | 13 | κ | 3-20 | 2 | 0 | CSYAGGRTVV (SEQ ID NO.: 74) | 1 | 10 | gp41 | NEG | - | 1 |
| 1-167 | 5-12 | 4 | 1 | PVVNTILPYCDV (SEQ ID NO.: 36) | 0 | 12 | κ | 3-20 | 2 | 0 | QQYGRSPYT (SEQ ID NO.: 75) | 1 | 9 | gp41 | NEG | - | 1 |
| 1-491 | 5-5/5-18/5-12 | 4 | 1 | RGHSFTSPFDS (SEQ ID NO.: 37) | 2 | 11 | κ | 1-5 | 5 | 1 | QQYGSSLR (SEQ ID NO.: 76) | 1 | 8 | gp41 | NEG | - | 1 |
| 1-696 | 3-3/3-16 | 5/4 | 2 | EFQTSGVVREG (SEQ ID NO.: 38) | 1 | 11 | κ | 1-5 | 3 | 0 | QQYSDSIT (SEQ ID NO.: 77) | 0 | 9 | gp41 | IMMUNODOM | - | 1 |
| 1-763 | 4-39 | 4 | 1 | RRRSAWSPFDS (SEQ ID NO.: 39) | 3 | 11 | κ | 1-9/1-13 | 3 | 0 | QLLQSN (SEQ ID NO.: 78) | 0 | 6 | gp41 | NEG | - | 1 |

Figure 15 (continued)

Supplementary Table 2b. Repertoire and reactivity of gp140 binding antibodies, patient 2

| Ab name | VH | D | JH | (±) | CDR3 (aa) | (±) | Length | κ/λ | Vκ/λ | Jκ/λ | CDR3 (aa) | (±) | Length | Binding | Peptide | NEUT | # of |
|---|---|---|---|---|---|---|---|---|---|---|---|---|---|---|---|---|---|
| 2-470 | 3-11 | 6-13 | 4/5 | 2 | DRMFWQQLAKYDS (SEQ ID NO.: 79) | 2 | 13 | κ | 1-6 | 1 | LQTHSYPRT (SEQ ID NO.: 133) | 2 | 9 | CD4bs | NEG | + | 1 |
| 2-1113 | 3-11 | 6-13 | 4/5 | 2 | DRMFWQQLAKYDS (SEQ ID NO.: 80) | 2 | 13 | κ | 1-6 | 1 | LQNHNYPRT (SEQ ID NO.: 134) | 2 | 9 | CD4bs | NEG | ND | 1 |
| 2-1262 | 3-74 | 3-3/3-16 | 6 | 2 | GPLGDYDF (SEQ ID NO.: 81) | 0 | 8 | κ | 1-5 | 1 | QQYTAYPWT (SEQ ID NO.: 135) | 0 | 9 | CD4bs | NEG | + | 4 |
| 2-1207 | 4-61/4-4/4-59 | 3-3/3-9 | 4 | 2 | GRDYNFWSGGGRYFDF (SEQ ID NO.: 82) | 1 | 17 | λ | 1-40 | 3 | QSYDSSLSGSWV (SEQ ID NO.: 136) | 0 | 12 | CD4bs | NEG | + | 1 |
| 2-588 | 4-61/4-4/4-59 | 3-3/3-10 | 4/5 | 1 | GRDYNFWGGGKINFP (SEQ ID NO.: 83) | 2 | 17 | λ | 1-40 | 3 | QSYDSSLSGSWV (SEQ ID NO.: 137) | 1 | 12 | CD4bs | NEG | ND | 1 |
| 2-491 | 4-61 | 3-3/3-9 | 4 | 3 | SRGDYNFWSGYPEYHFDR (SEQ ID NO.: 84) | 3 | 18 | κ | 2-28 | 2 | MQPLQTPYT (SEQ ID NO.: 138) | 0 | 9 | Core | NEG | + | 3 |
| 2-1176 | 3-21 | 7-27/3-9/3-16 | 4/5 | 4 | EYRFDDWGPLDH (SEQ ID NO.: 85) | 2 | 12 | κ | 2-28 | 1 | MKSQHSPRT (SEQ ID NO.: 139) | 3 | 9 | Core | NEG | - | 1 |
| 2-73 | 1-24 | 3-10/3-16 | 6 | 3 | LDWVRGVMNLVENHYAMDV (SEQ ID NO.: 86) | 2 | 19 | κ | 3-20 | 3 | QQSGTSLLT (SEQ ID NO.: 140) | 0 | 9 | CD4i | NEG | + | 4 |
| 2-301 | 1-69 | 6-13/6-19/6-25 | 6 | 5 | GDLLGYTDSWYEFDYYYMDV (SEQ ID NO.: 87) | 0 | 20 | κ | 3-20 | 1 | QQYAGSLT (SEQ ID NO.: 141) | 0 | 8 | CD4i | NEG | + | 6 |
| 2-52 | 1-8 | 6-19 | 5 | 1 | GRLFVQWPPGGGFDT (SEQ ID NO.: 88) | 1 | 15 | κ | 3-20 | 2 | QEYGRAPPYP (SEQ ID NO.: 142) | 1 | 10 | VL | NEG | - | 14 |
| 2-189 | 1-8 | 6-19 | 5 | 1 | GRLFMQWPPQGGFDP (SEQ ID NO.: 89) | 1 | 15 | κ | 3-20 | 2 | QEYGRSPPYP (SEQ ID NO.: 143) | 1 | 10 | VL | NEG | ND | 10 |
| 2-192 | 1-8 | 6-19 | 5 | 1 | GRLFVQWPPQGGFDT (SEQ ID NO.: 90) | 1 | 15 | κ | 3-20 | 2 | QEYGRAPPYP (SEQ ID NO.: 144) | 1 | 10 | VL | NEG | ND | 1 |
| 2-408 | 1-8 | 6-19 | 5 | 1 | GRLFVQWPPQGGFDT (SEQ ID NO.: 91) | 1 | 15 | κ | 3-20 | 2 | QEYGRAPPYP (SEQ ID NO.: 145) | 1 | 10 | VL | NEG | ND | 2 |
| 2-1076 | 1-8 | 6-19 | 5 | 1 | GRLFVQWPPQGGFDT (SEQ ID NO.: 92) | 1 | 15 | κ | 3-20 | 2 | QEYGRAPPYP (SEQ ID NO.: 146) | 1 | 10 | VL | NEG | ND | 1 |
| 2-445 | 1-8 | 6-19 | 5 | 1 | GRLFVQWPPQGGFDT (SEQ ID NO.: 93) | 1 | 15 | κ | 3-20 | 2 | QEFGRAPPYP (SEQ ID NO.: 147) | 1 | 10 | VL | NEG | ND | 1 |
| 2-1030 | 1-8 | 6-19 | 5 | 1 | GRLFVQWPPQGGFDP (SEQ ID NO.: 94) | 1 | 15 | κ | 3-20 | 2 | QEYGRAPPYP (SEQ ID NO.: 148) | 1 | 10 | VL | NEG | ND | 1 |
| 2-558 | 1-8 | 6-19 | 5 | 1 | GRLFMQWPPRGGFDP (SEQ ID NO.: 95) | 1 | 15 | κ | 3-20 | 2 | QEYGRAPPYP (SEQ ID NO.: 149) | 1 | 10 | VL | NEG | ND | 2 |
| 2-1080 | 1-8 | 6-19 | 5 | 1 | GRLLMQWPPRGGFDP (SEQ ID NO.: 96) | 1 | 15 | κ | 3-20 | 2 | QYYGSSPPST (SEQ ID NO.: 150) | 0 | 10 | VL | NEG | ND | 1 |
| 2-1025 | 1-8 | 6-19 | 5 | 1 | GRLLMQWPPRGGFDP (SEQ ID NO.: 97) | 1 | 15 | κ | 3-20 | 2 | QYYGSSPPST (SEQ ID NO.: 151) | 0 | 10 | VL | NEG | ND | 3 |
| 2-1037 | 1-8 | 6-19 | 5 | 1 | GRLLMQWPPRGGFDP (SEQ ID NO.: 98) | 1 | 15 | κ | 3-20 | 2 | QYYGSSPPST (SEQ ID NO.: 152) | 0 | 10 | VL | NEG | ND | 1 |
| 2-1021 | 1-8 | 6-19 | 5 | 1 | GRLLMQWPPRGGFDP (SEQ ID NO.: 99) | 1 | 15 | κ | 3-20 | 2 | QYYGISPPST (SEQ ID NO.: 153) | 0 | 10 | VL | NEG | ND | 2 |

Figure 16

| | | | | | | | | | | | | | |
|---|---|---|---|---|---|---|---|---|---|---|---|---|---|
| 2-59 | 3-7 | 5-24/3-9/2-8 | 6 | 5 | ERVLVPDGDADYYYFFDV (SEQ ID NO.:100) | 1 | 20 | κ | 1-5 | 2 | 0 | LFAGT (SEQ ID NO.: 154) | V3 | + | 7 |
| 2-1034 | 3-7 | 5-24/2-8/4-17 | 6 | 5 | ERVLVFPDGDADYYYFFDV (SEQ ID NO.:101) | 1 | 20 | κ | 1-5 | 2 | 0 | LFAGT (SEQ ID NO.: 155) | V3 | + | 13 |
| 2-1092 | 3-7 | 2-8/5-24/4-4 | 6 | 6 | ENVLMESDDYNDYYYYMDV (SEQ ID NO.:102) | 0 | 20 | κ | 1-5 | 2 | 0 | LFAGT (SEQ ID NO.: 156) | V3 | + | 3 |
| 2-69 | 4-39 | 1-1/1-7/1-20 | 3 | 1 | LPRTTGIRNAFDF (SEQ ID NO.:103) | 2 | 13 | λ | 2-8 | 3 | 0 | SSYAATNHWV (SEQ ID NO.:157) | VL | + | 3 |
| 2-1055 | 4-39 | 1-1/1-7/1-20 | 3 | 1 | LPRTTGIRNAFDI (SEQ ID NO.:104) | 2 | 13 | λ | 2-8 | 2/3 | 0 | SSYAGTNHWV (SEQ ID NO.:158) | VL | + | 3 |
| 2-234 | 3-64 | 4-17/4-23 | 6 | 5 | DSEDYVDYYYMDV (SEQ ID NO.:105) | 0 | 13 | κ | 3-11 | 4 | 0 | QQRTSWPLALS (SEQ ID NO.:159) | VL | - | 2 |
| 2-1042 | 4-31 | 2-21 | 4 | 3 | WVVTAAEEYFDY (SEQ ID NO.:106) | 0 | 12 | κ | 3-20 | 5 | 0 | QQYRYSVII (SEQ ID NO.:160) | VL | - | 4 |
| 2-1252 | 4-31 | 2-21 | 4 | 3 | WVVTAAEEYFDY (SEQ ID NO.:107) | 0 | 12 | κ | 3-20 | 5 | 0 | QQYRYSVII (SEQ ID NO.:161) | VL | ND | 1 |
| 2-1280 | 4-31 | 2-21 | 4 | 3 | WVVTAAEEYFDY (SEQ ID NO.:108) | 0 | 12 | κ | 3-20 | 5 | 0 | QQYRYSVII (SEQ ID NO.:162) | VL | ND | 1 |
| 2-1261 | 3-33/3-30 | 4-23/4-17/4-4 | 4 | 2 | HYDALDY (SEQ ID NO.:109) | 1 | 7 | κ | 2-28 | 1 | 1 | MQALETLG (SEQ ID NO.:163) | V3 | + | 1 |

| | | | | | | | | | | | | | |
|---|---|---|---|---|---|---|---|---|---|---|---|---|---|
| 2-55 | 1-46 | 4-23/3-9/2-8 | 4/5 | 1 | TRNTGNSLPYWFDL (SEQ ID NO.:110) | 1 | 14 | κ | 3-11 | 4 | 0 | QQRGHWPLT (SEQ ID NO.:164) | gp41 | - | 3 |
| 2-321 | 1-46 | 4-23/3-9/2-8 | 5 | 1 | TRNTGNSLPYWFDL (SEQ ID NO.:111) | 1 | 14 | κ | 3-11 | 4 | 0 | QQRGHWPLT (SEQ ID NO.:165) | gp41 | ND | 3 |
| 2-378 | 4-39 | 3-10/2-15 | 1/4 | 3 | HGASANYGPGSYSAEHFQH (SEQ ID NO.:112) | 3 | 19 | κ | 1-5 | 2 | 1 | QEYNNYN (SEQ ID NO.:166) | gp41 | IMMUNO DOM | 1 |
| 2-116 | 4-39 | 3-10/1-26 | 1/4 | 2 | HGASENYGPGSYSAEHFQH (SEQ ID NO.:113) | 3 | 19 | κ | 1-5 | 2 | 1 | QEYNTYT (SEQ ID NO.:167) | gp41 | ND | 1 |
| 2-1240 | 4-39 | 3-10/1-26 | 1/4 | 1 | HGASANYGPGSYSAEHFQH (SEQ ID NO.:114) | 3 | 19 | κ | 1-5 | 2 | 0 | QEYNTYT (SEQ ID NO.:168) | gp41 | ND | 2 |
| 2-150 | 1-58 | 3-10/1-26 | 4 | 1 | RGHSFSLPFDS (SEQ ID NO.:115) | 2 | 11 | κ | 3-20 | 4 | 0 | QKYGSSLT (SEQ ID NO.:169) | gp41 | IMMUNO DOM | 1 |
| 2-566 | 1-58 | 3-10/1-26 | 4 | 1 | RGHSFSLPFDS (SEQ ID NO.:116) | 2 | 11 | κ | 3-20 | 4 | 0 | QKYGSSLT (SEQ ID NO.:170) | gp41 | NEG | 3 |
| 2-1104 | 1-58 | 6-13/6-25/6-19 | 4 | 1 | RGHSFSLPFDS (SEQ ID NO.:117) | 2 | 11 | κ | 3-20 | 4 | 0 | QKYGSSLT (SEQ ID NO.:171) | gp41 | NEG | 2 |
| 2-275 | 4-23/4-4/4-59 | 4-23/4-4/4-11 | 4 | 1 | GAINSSPSYFDS (SEQ ID NO.:118) | 0 | 12 | κ | 3-11 | 2 | 1 | QQRVNWPPN (SEQ ID NO.:172) | gp41 | NEG | 1 |
| 2-1209 | 4-61/4-4/4-59 | 6-13/3-16/6-6 | 4 | 2 | GDITSSPLYFDF (SEQ ID NO.:119) | 0 | 12 | κ | 3-11 | 2 | 0 | QQR-TWPPI (SEQ ID NO.:173) | gp41 | ND | 1 |
| 2-354 | 4-61/4-4/4-59 | 4-23/3-16 | 4 | 1 | GAINSSPLYFDS (SEQ ID NO.:120) | 0 | 12 | κ | 3-11 | 2 | 0 | QQRVNWPPN (SEQ ID NO.:174) | gp41 | NEG | 1 |
| 2-474 | 3-23 | 3-9/7-27/3-16 | 4/5 | 1 | RNWGNFDH (SEQ ID NO.:121) | 2 | 8 | κ | 3-11 | 2 | 0 | LQCGSSPPYT (SEQ ID NO.:175) | gp41 | NEG | 3 |
| 2-512 | 1-2 | 1-1/5-24/1-7 | 4/5 | 2 | DRLSFSVQVEQGVLQF (SEQ ID NO.:122) | 1 | 16 | κ | 3-11 | 4 | 0 | QQRYSWPSLT (SEQ ID NO.:176) | gp41 | - | 2 |
| 2-1059 | 1-2 | 6-6/6-25/6-19 | 4 | 2 | DRLSFSVQVEQGVLDY (SEQ ID NO.:123) | 1 | 16 | κ | 3-11 | 4 | 0 | QQRYSWPSLT (SEQ ID NO.:177) | gp41 | ND | 4 |
| 2-149 | 1-69 | 3-22 | 4 | 3 | MALPSGPLDRSGYYFDD (SEQ ID NO.:124) | 0 | 17 | κ | 1-27 | 1 | 0 | QKYNNAPWT (SEQ ID NO.:178) | gp41 | - | 2 |
| 2-529 | 1-69 | 3-22 | 4 | 2 | MALASGPYDVSGYYFDY (SEQ ID NO.:125) | 1 | 17 | κ | 1-27 | 1 | 0 | QKYNGAPWT (SEQ ID NO.:179) | gp41 | ND | 1 |

Figure 16 (continued)

| | | | | | | | | | | | | |
|---|---|---|---|---|---|---|---|---|---|---|---|---|
| 2-1061 | 1-69 | 3-22 | 4 | 2 | MALASGPYDVSGYYFDY (SEQ ID NO.: 126) | 0 | 17 | κ | 1-27 | 1 | 0 | QKYNGAPWT (SEQ ID NO.: 180) | 1 | 9 | gp41 | NEG | ND | 3 |
| 2-37 | 1-69 | 3-22 | 4 | 2 | MALTSGPYDVSGYYFDY (SEQ ID NO.: 127) | 0 | 17 | κ | 1-27 | 1 | 0 | QKYNGAPWT (SEQ ID NO.: 181) | 1 | 9 | gp41 | NEG | ND | 1 |
| 2-1007 | 4-39 | 6-19/6-25/6-13 | 4 | 3 | HIAVGGREEE (SEQ ID NO.: 128) | 2 | 10 | κ | 3-11 | 2 | 1 | QQRSTTRPPEYT (SEQ ID NO.: 182) | 1 | 11 | gp41 | IMMUNO DOM | - | 1 |
| 2-1139 | 4-39 | 6-19/6-25/6-13 | 4 | 2 | HIAVGGSEDH (SEQ ID NO.: 129) | 2 | 10 | κ | 3-11 | 2 | 1 | QGRTTRPPDYT (SEQ ID NO.: 183) | 1 | 11 | gp41 | IMMUNO DOM | ND | 1 |
| 2-1288 | 4-39 | 6-19/6-25/6-13 | 4 | 2 | HIAVGGSEEH (SEQ ID NO.: 130) | 2 | 10 | κ | 3-11 | 2 | 1 | QQRTTRPPDYT (SEQ ID NO.: 184) | 1 | 11 | gp41 | IMMUNO DOM | ND | 1 |
| 2-557 | 4-39 | 6-19/6-25/6-13 | 4 | 3 | HIAVGGREEE (SEQ ID NO.: 131) | 1 | 10 | κ | 3-11 | 2 | 1 | QQRTTRPPEYT (SEQ ID NO.: 185) | 1 | 11 | gp41 | IMMUNO DOM | ND | 2 |
| 2-1290 | 1-46 | 1-26/2-15/4-23 | 4 | 1 | PAQAGVGPRFDY (SEQ ID NO.: 132) | 1 | 12 | λ | 2-11 | 2 | 0 | CSYAGSYTYV (SEQ ID NO.: 186) | 0 | 10 | gp41 | NEG | - | 2 |

Figure 16 (continued)

Supplementary Table 2c. Repertoire and reactivity of gp140 binding antibodies, patient 3

| Ab name | VH | D | JH | (±) | CDR3 (aa) | (±) | Length | κ/λ | Vκ/λ | Jκ/λ | (±) | CDR3 (aa) | (±) | Length | Binding | Peptide | NEUT | # of |
|---|---|---|---|---|---|---|---|---|---|---|---|---|---|---|---|---|---|---|
| 3-869 | 4-4/4-59 | 6-19/5-12/1-26 | 4 | 2 | EKGQWLTVPPYYFDS (SEQ ID NO.:187) | 1 | 15 | κ | 1D-39 | 5 | 0 | QQSHSPS (SEQ ID NO.:226) | 1 | 7 | CD4bs | NEG | + | 1 |
| 3-779 | 4-4/4-59 | 1-26/6-19/5-24 | 4 | 2 | EKGQWVTLPPYYFDS (SEQ ID NO.:188) | 1 | 15 | κ | 1D-39 | 5 | 0 | QQSHSPS (SEQ ID NO.:227) | 1 | 7 | CD4bs | NEG | ND | 2 |
| 3-613 | 4-59 | 3-10/3-22 | 4 | 2 | HKSVLLWFRELDY (SEQ ID NO.:189) | 3 | 13 | κ | 3-20 | 3 | 0 | QQYGSSPFT (SEQ ID NO.:228) | 0 | 9 | CD4bs | NEG | + | 1 |
| 3-124 | 3-23 | 3-3/3-22 | 4 | 1 | VGGTWSGYSNYLDY (SEQ ID NO.:190) | 0 | 15 | κ | 3-11 | 5 | 0 | QQRSNWAIT (SEQ ID NO.:229) | 1 | 9 | Core | NEG | + | 1 |
| 3-518 | 4-31 | 2-8/1-14/2-2 | 4 | 2 | DYTASGRHFFDY (SEQ ID NO.:191) | 2 | 12 | κ | 1D-39 | 4 | 0 | QQSSSKP (SEQ ID NO.:230) | 1 | 7 | Core | NEG | - | 1 |
| 3-256 | 4-31 | 6-19/1-26 | 4 | 2 | DYTASGRHFFDY (SEQ ID NO.:192) | 2 | 12 | κ | 1D-39 | 4 | 0 | QQSAGTP (SEQ ID NO.:231) | 0 | 7 | Core | NEG | ND | 1 |
| 3-366 | 4-31 | 2-8 | 4 | 3 | DYTARGRHFFDY (SEQ ID NO.:193) | 2 | 12 | κ | 1D-39 | 4 | 0 | QQSSSTP (SEQ ID NO.:232) | 0 | 7 | Core | NEG | ND | 1 |
| 3-966 | 4-31 | 6-13/6-25/6-6 | 4 | 2 | DYSAAGRHLFDS (SEQ ID NO.:194) | 2 | 12 | κ | 1D-39 | 4 | ND | ND | ND | ND | ND | NEG | ND | 2 |
| 3-978 | 4-31 | 2-8 | 4 | 3 | DYTARGRHFFDY (SEQ ID NO.:195) | 2 | 12 | κ | 1D-39 | 4 | ND | ND | ND | ND | ND | NEG | ND | 1 |
| 3-228 | 5-51 | 3-3/2-2 | 6 | 1 | TRCFGANCFNFMDV (SEQ ID NO.:196) | 1 | 14 | κ | 4-1 | 3 | 0 | QQYISP (SEQ ID NO.:233) | 0 | 7 | VL | NEG | + | 18 |
| 3-539 | 3-23 | 3-3/3-9/3-16 | 6 | 1 | TGGLLRFPEV (SEQ ID NO.:197) | 1 | 10 | λ | 2-14 | 1 | 0 | SSYSSTNTVV (SEQ ID NO.:234) | 0 | 10 | VL | NEG | - | 1 |
| 3-584 | 3-21 | 3-10/6-19/3-3 | 4 | 1 | SGPGLLRGFDY (SEQ ID NO.:198) | 1 | 11 | λ | 2-14 | 2/3 | 0 | SSYTSSSTLGVV (SEQ ID NO.:235) | 0 | 12 | VL | NEG | - | 1 |
| 3-637 | 4-31 | 5-18/3-3/1-1 | 3 | 1 | VPRTTATRNAFDI (SEQ ID NO.:199) | 2 | 13 | λ | 2-8 | 2/3 | 0 | SSYAGINN (SEQ ID NO.:236) | 0 | 8 | VL | NEG | - | 1 |
| 3-239 | 4-31 | 2-8 | 4 | 2 | DYTARGRHFFDY (SEQ ID NO.:200) | 3 | 12 | κ | 1D-39 | 4 | 0 | QCSSSTPFT (SEQ ID NO.:237) | 0 | 9 | CD4i | NEG | - | 1 |
| 3-596 | 1-2 | 3-3/3-9 | 4 | 2 | GPDDFWSGYPKY (SEQ ID NO.:201) | 1 | 12 | κ | 3-20 | 1 | 0 | QQYGSSWT (SEQ ID NO.:238) | 0 | 8 | CD4i | NEG | - | 1 |
| 3-383 | 1-69 | 3-22/6-19/5-12 | 6 | 5 | GEFDSSGFDYESWYPYYMDV (SEQ ID NO.:202) | 0 | 20 | κ | 3-20 | 3 | 0 | QQYASSPFT (SEQ ID NO.:239) | 0 | 9 | CD4i | NEG | + | 3 |
| 3-67 | 1-24 | 3-16/3-3 | 4 | 3 | DNPVLQLGELSSSLDY (SEQ ID NO.:203) | 0 | 16 | κ | 3-11 | 5 | 1 | QQRGIWPLQIT (SEQ ID NO.:240) | 0 | 11 | CD4i | NEG | + | 2 |
| 3-576 | 1-69 | 3-9/5-12/2-15 | 4 | 3 | AQGDILTEGYFDY (SEQ ID NO.:204) | 0 | 13 | λ | 1-44/1-47 | 1 | 2 | AAWDDSLHV (SEQ ID NO.:241) | 1 | 9 | CD4i | NEG | + | 2 |
| 3-381 | 1-69 | 3-9/5-12/1-26 | 4 | 3 | AQGDILTEGYFDY (SEQ ID NO.:205) | 0 | 13 | κ | 1-12 | 2/5 | 0 | QKATT (SEQ ID NO.:242) | 1 | 5 | CD4i | NEG | ND | 2 |
| 3-461 | 1-46 | 2-2 | 4 | 1 | PEPSSIVAPLYY (SEQ ID NO.:206) | 0 | 12 | κ | 3-20 | 1 | 0 | QQYGTLHPRT (SEQ ID NO.:243) | 2 | 10 | gp41 | NEG | - | 1 |
| 3-746 | 1-46 | 2-2 | 4 | 1 | PEPSSIVGALYY (SEQ ID NO.:207) | 0 | 12 | κ | 3-20 | 1 | 0 | QWYGTLHPRT (SEQ ID NO.:244) | 2 | 10 | gp41 | NEG | ND | 1 |
| 3-18 | 1-69 | 3-10/5-24 | 3 | 3 | DPQVEVRGNAFDI (SEQ ID NO.:208) | 1 | 13 | κ | 1D-39 | 5 | 0 | QQTYTSPIT (SEQ ID NO.:245) | 0 | 9 | gp41 | NEG | - | 1 |

Figure 17

| | | | | | | | | | | | |
|---|---|---|---|---|---|---|---|---|---|---|---|
| 3-144 | 1-69 | 3-10/5-24 | 3 | 3 | DPQIEIRGNAFDI (SEQ ID NO.: 209) | 13 | κ | 1D-39 | 5 | 0 | QQTFTDPVT (SEQ ID NO.: 246) | 0 | 9 | gp41 | NEG | ND | 1 |
| 3-384 | 1-69 | 2-8/2-2 | 4/5 | 2 | DPQVNRRGNCFDH (SEQ ID NO.: 210) | 13 | κ | 1D-39 | 2 | 0 | QQTYRSVT (SEQ ID NO.: 247) | 1 | 8 | gp41 | NEG | - | 1 |
| 3-419 | 1-69 | 4-4/1-14/4-11 | 4/5 | 2 | DPQVNRRGNCFDH (SEQ ID NO.: 211) | | κ | 1D-39 | 2 | 0 | QQTYSSVT (SEQ ID NO.: 248) | 0 | 8 | gp41 | NEG | ND | 1 |
| 3-64 | 1-69 | 5-24/2-15/3-3 | 4 | 2 | GRREGLNFLLDY (SEQ ID NO.: 212) | 12 | κ | 1-16 | 5 | 0 | QQYNYYPIT (SEQ ID NO.: 249) | 0 | 9 | gp41 | NEG | - | 1 |
| 3-160 | 4-59/4-61 | 3-16/3-9 | 5 | 4 | ADYDNIWDSRGGFDL (SEQ ID NO.: 213) | 15 | κ | 1-27 | 5 | 2 | QKYDTDPMT (SEQ ID NO.: 250) | 1 | 9 | gp41 | NEG | - | 1 |
| 3-204 | 1-46 | 3-3/3-9 | 6 | 2 | AHHDFWRAPVDV (SEQ ID NO.: 214) | 12 | κ | 3-20 | 2 | 0 | QQYATSSLYT (SEQ ID NO.: 251) | 0 | 10 | gp41 | NEG | - | 1 |
| 3-125 | 1-46 | 1-20/1-7/3-10 | 3 | 2 | PQYNLGRDPLDV (SEQ ID NO.: 215) | 12 | κ | 3-20 | 1 | 0 | QQYGLSPWT (SEQ ID NO.: 252) | 0 | 9 | gp41 | NEG | - | 1 |
| 3-816 | 1-46 | 1-14/1-7/1-20 | 3 | 1 | PQYNLGREPLNV (SEQ ID NO.: 216) | 12 | κ | 3-20 | 1 | 0 | HQYALSPWT (SEQ ID NO.: 253) | 1 | 9 | gp41 | NEG | ND | 14 |
| 3-296 | 4-59 | 5-12/5-24/3-3 | 4 | 3 | RRGQRLLAYFDY (SEQ ID NO.: 217) | 12 | κ | 3-15 | 1 | 0 | QQYNNWPPA (SEQ ID NO.: 254) | 0 | 9 | gp41 | NEG | - | 1 |
| 3-474 | 3-23 | 5-12/2-8/2-2 | 3 | 1 | RSPGGGYAFDI (SEQ ID NO.: 218) | 11 | κ | 3-20 | 1 | 0 | HQYGSSQR (SEQ ID NO.: 255) | 2 | 8 | gp41 | ND | - | 1 |
| 3-255 | 4-59 | 3-3/3-9 | 4 | 3 | ADYDLLTSSYHFDS (SEQ ID NO.: 219) | 14 | λ | 7-43 | 3 | 0 | LLLPYYGGPWI (SEQ ID NO.: 256) | 0 | 11 | gp41 | NEG | - | 1 |
| 3-244 | 4-59 | 3-9/3-3 | 4 | 3 | GDYDILTSSYQFDY (SEQ ID NO.: 220) | | λ | 7-43 | 3 | 0 | LLLLYYGGPWI (SEQ ID NO.: 257) | 0 | 11 | gp41 | NEG | ND | 2 |
| 3-233 | 4-59 | 3-3/4-17 | 4 | 3 | LDGEAFRYYLDL (SEQ ID NO.: 221) | 12 | λ | 2-14 | 2/3 | 0 | SSFTPTNTLV (SEQ ID NO.: 258) | 0 | 10 | gp41 | NEG | - | 3 |
| 3-93 | 4-59 | 4-17/3-16 | 4 | 3 | LDGEAFRYYFDS (SEQ ID NO.: 222) | 12 | λ | 2-14 | 2/3 | 0 | GSFTTSLTLV (SEQ ID NO.: 259) | 0 | 10 | gp41 | NEG | ND | 1 |
| 3-334 | 1-2 | 7-27/1-1/1-7 | 6 | 1 | DLRPMRGNWAMHV (SEQ ID NO.: 223) | 13 | λ | 2-8 | 1 | 0 | SSYAGSNNFV (SEQ ID NO.: 260) | 0 | 10 | gp41 | NEG | - | 2 |
| 3-140 | 3-21/3-48 | 1-14/3-9/3-10 | 5 | 1 | TFITASWFDS (SEQ ID NO.: 224) | 10 | λ | 2-11/2-8 | 1 | 0 | CSYAGTYSYV (SEQ ID NO.: 261) | 0 | 10 | gp41 | NEG | ND | 1 |
| 3-650 | 1-46 | 6-6/2-2/3-16 | 4 | 1 | PHSPTNIPSRPLDY (SEQ ID NO.: 225) | 14 | λ | 2-11 | 3 | 0 | CSYAGSYIWV (SEQ ID NO.: 262) | 0 | 10 | gp41 | NEG | - | 1 |

Figure 17 (continued)

Supplementary Table 2d. Repertoire and reactivity of gp140 binding antibodies, patient 4

| Ab name | VH | D | JH | (-) | CDR3 (aa) | (+) | Length | κ/λ | Vκλ | Jκλ | (+) | CDR3 (aa) | (+) | Length | Binding | Peptide | NEUT | # of |
|---|---|---|---|---|---|---|---|---|---|---|---|---|---|---|---|---|---|---|
| 4-208 | 3-30/3-33 | 3-10/5-5/5-18 | 5 | 2 | EGGSLWFGGANWLDP (SEQ ID NO.:263) | 0 | 15 | κ | 3-20 | 3 | 0 | QHYGNSPRVT (SEQ ID NO.:298) | 2 | 10 | CD4bs | NEG | + | 4 |
| 4-392 | 3-30 | 5-5/5-18 | 5 | 2 | EGGSLWFGGANWLDP (SEQ ID NO.:264) | 0 | 15 | κ | 3-20 | 3/4 | 0 | QHYGNSPRVT (SEQ ID NO.:299) | 2 | 10 | CD4bs | NEG | ND | 1 |
| 4-116 | 1-18 | 3-22/5-12/2-21 | 4 | 2 | GYDNSGPDY (SEQ ID NO.:265) | 0 | 9 | κ | 3-11 | 1 | 0 | QQRANWPPGGT (SEQ ID NO.:300) | 1 | 11 | CD4bs | NEG | + | 1 |
| 4-253 | 1-46 | 5-5/5-18/3-3 | 4/5 | 2 | DQVGRYSFGFATGQQRVSAISD (SEQ ID NO.:266) | 2 | 22 | κ | 1-39 | 2 | 0 | QQTYTPYS (SEQ ID NO.:301) | 0 | 9 | CD4bs | NEG | + | 1 |
| 4-527 | 3-30 | 3-3/3-16 | 3 | 3 | ERSTKYSFWSAVMRPDAFDL (SEQ ID NO.:267) | 2 | 20 | κ | 1-27 | 4 | 0 | QQYDSAPVT (SEQ ID NO.:302) | 0 | 9 | CD4bs | NEG | + | 2 |
| 4-630 | 4-30 | 3-3/3-9 | 5 | 2 | GGSALTIFGVDPKFDP (SEQ ID NO.:268) | 0 | 17 | λ | 1-44/1-47 | 3 | 3 | AAWDDSLDGFWV (SEQ ID NO.:303) | 0 | 12 | CD4bs | NEG | + | 1 |
| 4-341 | 3-11 | 3-10/3-16 | 6 | 2 | RVKFPLWFGETTYYYGMDV (SEQ ID NO.:269) | 2 | 20 | λ | 1-51 | 2/3 | 1 | GTWDSSLSAVV (SEQ ID NO.:304) | 0 | 11 | CD4bs | NEG | + | 1 |
| 4-133 | 3-15 | 3-9/3-3 | 4 | 2 | KYPAYYDILTGYYRNYYFDY (SEQ ID NO.:270) | 2 | 20 | λ | 2-14 | 2/3 | 1 | CSHTGSSDTLV (SEQ ID NO.:305) | 1 | 10 | Core | NEG | + | 5 |
| 4-419 | 3-15 | 3-3/3-9 | 4 | 2 | KYPAYYDILTANYRSYYFDY (SEQ ID NO.:271) | 2 | 20 | λ | 2-14 | 2/3 | 0 | CSYTSSATVV (SEQ ID NO.:306) | 0 | 10 | Core | NEG | ND | 1 |
| 4-77 | 1-69 | 5-12/5-24/3-3 | 4 | 1 | LRATIAGFDY (SEQ ID NO.:272) | 1 | 10 | κ | 1-17 | 4 | 0 | LQYNAYPLT (SEQ ID NO.:307) | 0 | 9 | Core | NEG | + | 3 |
| 4-207 | 1-69 | 5-12/5-24/3-3 | 4 | 1 | LRATTPGFDY (SEQ ID NO.:273) | 1 | 10 | κ | 1-17 | 4 | 0 | LQYNAYPLT (SEQ ID NO.:308) | 0 | 9 | Core | NEG | + | 2 |
| 4-578 | 1-69 | 5-12/2-15/5-24 | 4 | 1 | LRATTPGFDY (SEQ ID NO.:274) | 1 | 10 | κ | 1-17 | 4 | 0 | LQYSTVPLT (SEQ ID NO.:309) | 0 | 9 | Core | NEG | ND | 1 |
| 4-53 | 3-9 | 3-3/3-9 | 6 | 3 | DGKGKAYDFWSGYRNQKYYGLDV (SEQ ID NO.:275) | 4 | 24 | κ | 3-15 | 1 | 0 | QQYNDWPA (SEQ ID NO.:310) | 0 | 8 | Core | NEG | + | 7 |
| 4-57 | 1-69 | 3-22/3-21 | 4 | 2 | LRRGYFDSGGDH (SEQ ID NO.:276) | 3 | 12 | κ | 1-17 | 1 | 1 | LQHNNYPWT (SEQ ID NO.:311) | 1 | 9 | Core | NEG | + | 3 |
| 4-327 | 1-69 | 3-22/2-21/3-22 | 4 | 2 | LRRGYYDSGEDY (SEQ ID NO.:277) | 2 | 12 | κ | 1-17 | 1 | 0 | LQHNRYPWT (SEQ ID NO.:312) | 2 | 9 | Core | NEG | ND | 1 |
| 4-221 | 4-61 | 3-3/2-15 | 6 | 3 | ELSGEYHFWSGTYRYGVDV (SEQ ID NO.:278) | 2 | 19 | κ | 3-20 | 4 | 0 | QQYGSSPRT (SEQ ID NO.:313) | 1 | 9 | Core | NEG | + | 2 |
| 4-32 | 4-61 | 3-3/3-9 | 6 | 4 | DRVSDYDFWSGKRGYGMDV (SEQ ID NO.:279) | 3 | 19 | κ | 3-15 | 2 | ND | ND | ND | ND | Core | NEG | ND | 2 |
| 4-214 | 4-31 | 3-3/3-9 | 6 | 4 | EQKDYDFWNGLYKYGMDV (SEQ ID NO.:280) | 2 | 18 | κ | 3-15 | 1 | 1 | QQYNDWPRT (SEQ ID NO.:314) | 1 | 9 | Core | NEG | + | 2 |
| 4-252 | 3-33 | 3-3/1-1 | 3 | 3 | GQRNVLHFLERKNDAFDI (SEQ ID NO.:281) | 4 | 18 | κ | 1-39 | 2 | 0 | QQSFGTPRT (SEQ ID NO.:315) | 1 | 9 | Core | NEG | + | 2 |
| 4-459 | 3-11 | 3-22/6-19/3-3 | 1/4 | 1 | GPRVFFESSGYYFRN (SEQ ID NO.:282) | 2 | 15 | κ | 3-20 | 3 | 0 | QQYGRSSPL (SEQ ID NO.:316) | 0 | 9 | Core | NEG | + | 2 |
| 4-345 | 3-11/3-48 | 3-22/3-3 | 4/5 | 2 | GPRVLFESSGHYLRD (SEQ ID NO.:283) | 2 | 15 | κ | 3-20 | 3/4 | 0 | QQYGRSPL (SEQ ID NO.:317) | 1 | 8 | Core | NEG | + | 1 |
| 4-455 | 3-11 | 3-3/3-22 | 4/5 | 2 | GPRVFFESSGYYFRD (SEQ ID NO.:284) | 2 | 15 | λ | 3-7 | 2 | 0 | HLYVSRPV (SEQ ID NO.:318) | 2 | 8 | Core | NEG | ND | 1 |
| 4-79 | 1-69 | 3-3/3-9 | 4 | 3 | GTRYDFWSGFSNRDGRALAGYFDY (SEQ ID NO.:285) | 3 | 24 | κ | 1-5 | 2 | 1 | QQYNSDYT (SEQ ID NO.:319) | 0 | 8 | Core | NEG | + | 1 |

Figure 18

| 4-256 | 3-11 | 6-19/3-22 | 4 | 1 | ARPRSPWDSTGWSVGY (SEQ ID NO.: 286) | 2 | 16 | κ | 3-20 | 2 | 1 | QQYGGSPPDT (SEQ ID NO.: 320) | 0 | 10 | Core | NEG | + | 1 |
| 4-263 | 3-30/3-33 | 3-3/2-8 | 4/5 | 2 | DFVSIYGVAYFTGGGPSSPDI (SEQ ID NO.: 287) | 0 | 21 | λ | 1-47 | 2/3 | 2 | AAWDDSLGGVV(SEQ ID NO.: 321) | 0 | 11 | Core | NEG | + | 3 |
| 4-328 | 4-B/4-39 | 3-3/3-9 | 4 | 2 | KRVTIFGVVDTPRGYFDY (SEQ ID NO.: 288) | 3 | 18 | κ | 3-20 | 2 | 0 | QYYGSSPYT (SEQ ID NO.: 322) | 0 | 9 | Core | NEG | + | 1 |
| 4-277 | 1-46 | 5-5/5-18/5-12 | 1/4 | 2 | DQLGRYSFGFVTGQNKVSAISD (SEQ ID NO.: 289) | 2 | 22 | κ | 1-39 | 2 | 0 | QQSYTFPYI (SEQ ID NO.: 323) | 0 | 9 | Core | NEG | + | 1 |
| 4-45 | 1-46 | 5-5/5-18/3-3 | 4/5 | 2 | DQRGRYSFGFVTGQTKVSAIS (SEQ ID NO.: 290) | 3 | 22 | κ | 1-39 | 2 | 0 | QQTFTFPYT (SEQ ID NO.: 324) | 0 | 9 | Core | NEG | ND | 1 |
| 4-649 | 3-11/3-48 | 3-10/3-3 | 5 | 1 | GALWFGQLRGLDP (SEQ ID NO.: 291) | 1 | 13 | κ | 3-15 | 5 | 1 | QQYNDWPIT (SEQ ID NO.: 325) | 0 | 9 | Core | NEG | + | 1 |

| 4-182 | 3-30 | 3-10/3-16 | 6 | 1 | GPGSMVRGLIVTSYGMDV (SEQ ID NO.: 292) | 1 | 18 | κ | 1-17 | 4 | 0 | LQHNSYPLT (SEQ ID NO.: 326) | 1 | 9 | VL | NEG | + | 2 |
| 4-150 | 1-2 | 3-9/2-21/2-2 | 3 | 1 | RGRLNIPSPSAILTAFDV (SEQ ID NO.: 293) | 2 | 18 | κ | 1-39 | 4 | 0 | QQSYNTRPLT (SEQ ID NO.: 327) | 1 | 10 | VL | NEG | + | 1 |
| 4-366 | 1-69 | 6-19/5-12/3-3 | 4 | 1 | GPKSVASLSYFDK (SEQ ID NO.: 294) | 2 | 13 | κ | 3-11 | 5 | 0 | QQRSNWPPKIT (SEQ ID NO.: 328) | 2 | 11 | VL | NEG | + | 1 |
| 4-324 | 4-39 | 3-16/3-10 | 4 | 3 | REIRFGELSFYFDY (SEQ ID NO.: 295) | 2 | 14 | κ | 1-5 | 4 | 0 | QQYKSYSPLT (SEQ ID NO.: 329) | 1 | 10 | VL | NEG | + | 1 |
| 4-195 | 4-39 | 3-16/3-10 | 4 | 3 | REIKFGELSFYFDS (SEQ ID NO.: 296) | 2 | 14 | κ | 1-5 | 4 | 0 | QQYKSYSPLT (SEQ ID NO.: 330) | 1 | 10 | VL | NEG | ND | 1 |
| 4-395 | 1-2 | 5-24 | 6 | 2 | DAFVSSAMDV (SEQ ID NO.: 297) | 0 | 10 | κ | 1-9 | 2 | 0 | QHLNSYPRMYT (SEQ ID NO.: 331) | 2 | 11 | VL | NEG | ND | 1 |

Figure 18 (continued)

Supplementary Table 2d. Repertoire and reactivity of gp140 binding antibodies, patient 4 (continued)

| | | | | | | | | | | | | |
|---|---|---|---|---|---|---|---|---|---|---|---|---|
| 4-42 | 1-18 | 6-19/6-13/1-26 | 4 | 3 | ENYSDGWYEVGHFDL (SEQ ID NO.: 332) | 1 | 15 | κ | 1-39 | 3 | 0 | QQTYASVT (SEQ ID NO.: 375) | 8 | 0 | NEG | + | 1 |
| 4-405 | 1-18 | 6-19/5-24/1-20 | 4 | 3 | ENYSDGWNEVGHFDF (SEQ ID NO.: 333) | 1 | 15 | κ | 1-39 | 3/4 | 0 | QQSHTSVT (SEQ ID NO.: 376) | 8 | 1 | NEG | ND | 1 |
| 4-90 | 1-18 | 6-19/5-24/6-25 | 4 | 4 | ENYSDGWEEVGHFDS (SEQ ID NO.: 334) | 1 | 15 | κ | 1-39 | 3/4 | 0 | QQTYSSVT (SEQ ID NO.: 377) | 8 | 0 | NEG | ND | 1 |
| 4-265 | 1-18 | 6-19/5-24/6-25 | 4 | 4 | ENYSDGWEEVGHFDY (SEQ ID NO.: 335) | 1 | 15 | κ | 1-39 | 3/4 | 0 | QQSYSSVT (SEQ ID NO.: 378) | 8 | 0 | NEG | ND | 2 |
| 4-8 | 1-69 | 2-15/5-24 | 6 | 7 | DEGSWVEAADEWDEHLFREMAV (SEQ ID NO.: 336) | 2 | 22 | κ | 3-20 | 2 | 0 | HQYGSSPQS (SEQ ID NO.: 379) | 9 | 1 | NEG | + | 1 |
| 4-653 | 1-69 | 2-15/5-24 | 6 | 7 | DEVSWVEAADEWDEHLFREMAV (SEQ ID NO.: 337) | 2 | 22 | κ | 3-20 | 2 | 0 | HQYGSSPQS (SEQ ID NO.: 380) | 9 | 1 | NEG | + | 1 |
| 4-663 | 1-69 | 5-24/2-15/5-5 | 6 | 7 | DEASWVEAADEWDEHLFREMAV (SEQ ID NO.: 338) | 2 | 22 | κ | 3-20 | 2 | 0 | HQYGSSPQT (SEQ ID NO.: 381) | 9 | 1 | NEG | ND | 1 |
| 4-174 | 3-23 | 2-15/2-8/2-2 | 6 | 2 | HLVVAAAGPDYFSYGMDV (SEQ ID NO.: 339) | 1 | 19 | κ | 3-20 | 2 | 0 | QQFGSSPGT (SEQ ID NO.: 382) | 9 | 0 | NEG | - | 8 |
| 4-31 | 1-24 | 3-22/5-12/3-16 | 5 | 2 | SRGYAYDSGGHYFPTWFDP (SEQ ID NO.: 340) | 2 | 19 | κ | 1-39 | 1 | 1 | QQSYDTPRT (SEQ ID NO.: 383) | 9 | 0 | NEG | - | 1 |
| 4-288 | 1-69 | 6-19/6-25/6-13 | 4 | 4 | LDSSSGWEEVGYFDR (SEQ ID NO.: 341) | 1 | 15 | κ | 1-39 | 1 | 0 | QQSNSSPWT (SEQ ID NO.: 384) | 9 | 0 | NEG | + | 1 |
| 4-433 | 1-24 | 3-16/3-10 | 4/5 | 1 | SLTGRLHLGELSSGIGP (SEQ ID NO.: 342) | 2 | 17 | κ | 3-11 | 4 | 0 | QQRSIWPPSLT (SEQ ID NO.: 385) | 11 | 1 | NEG | + | 1 |
| 4-441 | 1-69 | 3-10/3-3 | 6 | 5 | CSIVGNGDFLEEDSHYPAMDV (SEQ ID NO.: 343) | 1 | 21 | κ | 1-33 | 4 | 0 | QQCTLPLT (SEQ ID NO.: 386) | 8 | 0 | NEG | + | 1 |
| 4-554 | 1-69 | 5-12/5-24/4-4 | 6 | 5 | NYLIESRYDEKDYYAMDV (SEQ ID NO.: 344) | 2 | 19 | κ | 1-33 | 5 | 1 | QQYDILPLT (SEQ ID NO.: 387) | 9 | 0 | NEG | + | 1 |
| 4-103 | 1-69 | 3-22/4-17/2-8 | 4 | 6 | DSGFDLDYDTNELYFGFDY (SEQ ID NO.: 345) | 0 | 20 | λ | 1-51 | 2/3 | 1 | GTWDSSLRAAL (SEQ ID NO.: 388) | 11 | 1 | NEG | + | 3 |
| 4-92 | 1-69 | 3-22/4-17/2-8 | 4 | 6 | DSGFDLDYDTNELYFGFDY (SEQ ID NO.: 346) | 0 | 20 | λ | 1-51 | 2/3 | 1 | ATWDSSLRTAL (SEQ ID NO.: 389) | 11 | 1 | NEG | + | 3 |
| 4-164 | 1-69 | 6-6/2-2 | 6 | 4 | QNIAARTAERLYENDYYFYGMDV (SEQ ID NO.: 347) | 2 | 23 | κ | 1-33 | 3 | 1 | QQYDNLPT (SEQ ID NO.: 390) | 8 | 0 | NEG | + | 1 |
| 4-295 | 1-69 | 6-6/6-25/6-13 | 6 | 4 | QNIAARAAEKLYENDYYFYGMDV (SEQ ID NO.: 348) | 2 | 23 | κ | 1-33 | 1/3 | 1 | QQYDNLPT (SEQ ID NO.: 391) | 8 | 0 | NEG | ND | 1 |
| 4-652 | 4-31 | 2-15/1-26/6-19 | 4 | 1 | CYSGRSRYFFDS (SEQ ID NO.: 349) | 1 | 12 | κ | 1-39 | 2 | 2 | QQSQRTPHT (SEQ ID NO.: 392) | 9 | 0 | NEG | - | 1 |
| 4-357 | 3-23 | 4-22/2-21 | 4 | 3 | DLARYGVTSIVPEFGFDF (SEQ ID NO.: 350) | 1 | 18 | κ | 3-20 | 5 | 0 | QQYPST (SEQ ID NO.: 393) | 6 | 0 | NEG | - | 3 |
| 4-104 | 3-11 | 5-24/3-10/4-23 | 6 | 3 | DRWVRPQFPSMDFQYNGLDV (SEQ ID NO.: 351) | 2 | 20 | κ | 1-9 | 1 | 0 | QQLGT (SEQ ID NO.: 394) | 5 | 0 | NEG | - | 1 |
| 4-283 | 3-11/3-48 | 3-11/3-3/3-9 | 1/2 | 1 | GFHFWSGTGTPRNWYFDL (SEQ ID NO.: 352) | 3 | 19 | κ | 3-20 | 2 | 0 | QQYGSSPST (SEQ ID NO.: 395) | 9 | 0 | NEG | - | 1 |
| 4-20 | 1-69 | 3-3/5-12 | 3 | 1 | VAISYAGLIVVPGPFDV (SEQ ID NO.: 353) | 0 | 17 | κ | 1-27 | 3 | 1 | QKYDTAP (SEQ ID NO.: 396) | 7 | 1 | IMMUNODOM | - | 1 |

Figure 19

| | | | | | | | | | | | |
|---|---|---|---|---|---|---|---|---|---|---|---|
| 4-225 | 1-69 | 3 | 1 | VSITYAGLIVVPGAFDV (SEQ ID NO.: 354) | 0 | 17 | κ | 1-27 | 1 | QKYDTAP (SEQ ID NO.: 397) | 1 | 7 | gp41 | IMMUNO DOM | ND | 1 |
| 4-157 | 1-69 | 6 | 3 | VLTDLDQGNPRMDV (SEQ ID NO.: 355) | 1 | 14 | κ | 1-5 | 1 | QQYETYPWT (SEQ ID NO.: 398) | 0 | 9 | gp41 | NEG | - | 1 |
| 4-196 | 1-69 | 6 | 3 | VLTDLDQGNPRMDV (SEQ ID NO.: 356) | 1 | 14 | κ | 1-5 | 1/4 | QQYETYPWT (SEQ ID NO.: 399) | 0 | 9 | gp41 | NEG | ND | 1 |
| 4-95 | 4-30 | 6 | 1 | GRGSTFPSAQFSYFGLDV (SEQ ID NO.: 357) | 1 | 18 | κ | 1-9 | 3 | QQLGT (SEQ ID NO.: 400) | 0 | 5 | gp41 | NEG | - | 1 |
| 4-66 | 4-30 | 6 | 2 | GRGSFTGFDQYHYGMDV (SEQ ID NO.: 358) | 2 | 18 | κ | 1-9 | 2/3 | QQLGT (SEQ ID NO.: 401) | 0 | 5 | gp41 | NEG | ND | 2 |
| 4-480 | 4-30 | 6 | 1 | GRGYSHGFGQYNYYGMDV (SEQ ID NO.: 359) | 2 | 18 | κ | 1-9/1-17 | 1/3 | QQLGT (SEQ ID NO.: 402) | 0 | 5 | gp41 | NEG | ND | 1 |
| 4-529 | 4-30 | 6 | 2 | GRGSFQGFGQYEYYGMDV (SEQ ID NO.: 360) | 1 | 18 | κ | 1-33/1-5 | 4 | ND | ND | ND | gp41 | NEG | ND | 1 |
| 4-531 | 4-30 | 6 | 2 | GRGSFQGFGQYEYYGMDV (SEQ ID NO.: 361) | 1 | 18 | κ | 1-33/1-5 | 4 | ND | ND | ND | gp41 | NEG | - | 1 |
| 4-63 | 4-4/4-59 | 6 | 1 | GGGYAVVGPKYGLDV (SEQ ID NO.: 362) | 1 | 15 | λ | 2-18 | 3 | GAYTTSTLV (SEQ ID NO.: 403) | 0 | 10 | gp41 | NEG | ND | 1 |
| 4-553 | 4-4/4-59 | 6 | 1 | GGGYAVVGPKYGLDV (SEQ ID NO.: 363) | 1 | 15 | λ | 2-18 | 3 | GAYTTSTLV (SEQ ID NO.: 404) | 0 | 10 | gp41 | NEG | - | 1 |
| 4-147 | 5-51 | 4 | 1 | QVRAPTLRFRHGGYFET (SEQ ID NO.: 364) | 4 | 17 | λ | 1-40 | 3 | QSYDTSLSDTGV (SEQ ID NO.: 405) | 0 | 12 | gp41 | NEG | - | 1 |
| 4-367 | 5-51 | 4 | 1 | QLRAPTTRFRHGGYFEN (SEQ ID NO.: 365) | 4 | 17 | λ | 1-40 | 3 | QSYDTSLTDTGV (SEQ ID NO.: 406) | 0 | 12 | gp41 | NEG | ND | 1 |
| 4-153 | 1-2 | 4/5 | 2 | SDPAIAAAGSLDL (SEQ ID NO.: 366) | 0 | 13 | κ | 1-9 | 4 | HQLDS (SEQ ID NO.: 407) | 1 | 5 | gp41 | IMMUNO DOM | - | 1 |
| 4-43 | 1-2 | 4/5 | 2 | SDPAIAAAGSLDL (SEQ ID NO.: 367) | 0 | 13 | κ | 1-9 | 4 | HQLDS (SEQ ID NO.: 408) | 1 | 5 | gp41 | IMMUNO DOM | ND | 1 |
| 4-576 | 1-2 | 4/5 | 2 | SDPAIAAAGSLDL (SEQ ID NO.: 368) | 0 | 13 | κ | 1-9 | 4 | HQLDS (SEQ ID NO.: 409) | 1 | 5 | gp41 | IMMUNO DOM | ND | 1 |
| 4-615 | 1-2 | 4/5 | 2 | SDPAIAAAGSLDL (SEQ ID NO.: 369) | 0 | 13 | κ | 1-9 | 4 | HQLDT (SEQ ID NO.: 410) | 1 | 5 | gp41 | IMMUNO DOM | ND | 1 |
| 4-251 | 1-69 | 4/5 | 3 | RDKYQYIDSSGDYPFDR (SEQ ID NO.: 370) | 3 | 17 | κ | 1-33 | 4 | QQYDNLPRVT (SEQ ID NO.: 411) | 1 | 10 | gp41 | NEG | - | 1 |
| 4-431 | 4-39 | 4 | 1 | HIGAGGPYSEY (SEQ ID NO.: 371) | 1 | 11 | κ | 3-11 | 2 | QQRTTWPPEYT (SEQ ID NO.: 412) | 1 | 11 | gp41 | NEG | ND | 2 |
| 4-342 | 3-23 | 3 | 1 | RTTLVNFGVFDL (SEQ ID NO.: 372) | 1 | 12 | κ | 3-20 | 1 | QHYGNSRWT (SEQ ID NO.: 413) | 2 | 9 | gp41 | NEG | ND | 1 |
| 4-380 | 1-2 | 4/5 | 2 | DKDASIYGYRILNH (SEQ ID NO.: 373) | 3 | 14 | κ | 1-33 | 5 | QYYDHRPAIA (SEQ ID NO.: 414) | 2 | 10 | gp41 | NEG | - | 1 |
| 4-613 | 3-23 | 5 | 2 | DQGGYPVSPVGPKWFDP (SEQ ID NO.: 374) | 1 | 17 | λ | 2-11 | 1 | CSYAGSYT (SEQ ID NO.: 415) | 0 | 7 | gp41 | NEG | - | 1 |

Figure 19 (continued)

Supplementary Table 2e. Repertoire and reactivity of gp140 binding antibodies, patients 5 and 6

| Ab name | VH | D | JH | (-) | CDR3 (aa) | (+) | Length | κ/λ | Vκ/λ | Jκ/λ | CDR3 (aa) | (+) | Length | Binding | Peptide Library | NEUT | # of relatives |
|---|---|---|---|---|---|---|---|---|---|---|---|---|---|---|---|---|---|
| 5-146 | 3-23 | 6 | 4/5 | 2 | DVRLVAVPGAD (SEQ ID NO.: 416) | 1 | 11 | κ | 2-14 | 3 | SSYTSSLTLV (SEQ ID NO.: 434) | 0 | 10 | CD4i | NEG | + | 3 |
| 5-10 | 4-31 | 2-2 | 5 | 2 | EHRLPPPTGRRTRNWFDP (SEQ ID NO.: 417) | 5 | 18 | λ | 1-40 | 2/3 | QSYDSSVSVV (SEQ ID NO.: 435) | 0 | 10 | CD4i | NEG | - | 1 |
| 5-165 | 1-24 | 3 | 4 | 3 | DRVGRRLGELSAGFDY (SEQ ID NO.: 418) | 3 | 16 | κ | 3-11 | 4 | QQRSIWPPSLT (SEQ ID NO.: 436) | 1 | 11 | CD4i | NEG | + | 1 |
| 5-174 | 4-34 | 4 | 6 | 4 | GSLYDYRDNADLKPSYYYAMD V (SEQ ID NO.: 419) | 2 | 22 | λ | 2-14 | 3 | SSYSATGVA (SEQ ID NO.: 437) | 0 | 9 | CD4i | NEG | - | 1 |
| 5-216 | 4-31 | 5 | 6 | 2 | YEGKRSGMDV (SEQ ID NO.: 420) | 2 | 10 | κ | 1-33 | 1 | QQYDNLPLA (SEQ ID NO.: 438) | 0 | 9 | CD4i | ND | ND | 1 |
| 5-269 | 1-69 | 1 | 6 | 5 | SVITDLHTFGDYESGDPSYYYM DV (SEQ ID NO.: 421) | 1 | 24 | κ | 1-27 | 4 | QRYNRDPYI (SEQ ID NO.: 439) | 2 | 9 | CD4i | NEG | + | 1 |
| 5-580 | 3-30 | 3-22 | 3 | 6 | DWIGYDYDGSGSHLRDESFDI (SEQ ID NO.: 422) | 2 | 21 | κ | 2-30 | 3 | MQATHWPPG (SEQ ID NO.: 440) | 1 | | VL | NEG | + | 1 |
| 5-25 | 1-69 | 1 | 4 | 2 | RYKYLPGDQHMPWDY (SEQ ID NO.: 423) | 3 | 15 | κ | 1-33 | 3 | QQYDNLPPRVT (SEQ ID NO.: 441) | 1 | 11 | gp41 | NEG | - | 1 |
| 5-287 | 1-69 | 5 | 4 | 2 | RYKYLPGDQHMPWDN (SEQ ID NO.: 424) | 3 | 15 | κ | 1-33 | 3 | ND | ND | ND | gp41 | NEG | ND | 2 |

| Ab name | VH | D | JH | (-) | CDR3 (aa) | (+) | Length | κ/λ | Vκ/λ | Jκ/λ | CDR3 (aa) | (+) | Length | Binding | Peptide Library | NEUT | # of relatives |
|---|---|---|---|---|---|---|---|---|---|---|---|---|---|---|---|---|---|
| 6-187 | 4-39 | 3-3 | 5 | 2 | HRANYDFWGGSNLRGYFDP (SEQ ID NO.: 425) | 3 | 19 | κ | 3-20 | 3 | QQYGTSPT (SEQ ID NO.: 442) | 0 | 9 | CD4bs | NEG | + | 1 |
| 6-103 | 4-39 | 3-3 | 5 | 3 | HRADYDFWNGSNLRGYFDP (SEQ ID NO.: 426) | 3 | 19 | κ | 3-20 | 3 | QQYGSSPTT (SEQ ID NO.: 443) | 0 | 9 | CD4bs | NEG | ND | 2 |
| 6-155 | 4-39 | 3-3 | 5 | 3 | HRANYDFWGGSNLRGYFDP (SEQ ID NO.: 427) | 3 | 19 | κ | 3-20 | 3 | QQYGTSPGT (SEQ ID NO.: 444) | 0 | 9 | CD4bs | NEG | ND | 1 |
| 6-179 | 3-7 | 3-10 | 6 | 4 | DRYEAAWFGADKVYGMDV (SEQ ID NO.: 428) | 2 | 18 | κ | 1D-17 | 1 | LQHHSYPWT (SEQ ID NO.: 445) | 0 | 9 | Core | NEG | + | 1 |
| 6-91 | 3-30 | 3-3/2-8 | 6 | 3 | DQRDCSTNRGFGVFGYYMDV (SEQ ID NO.: 429) | 2 | 20 | κ | 3-11 | 4 | QHRSSWPLT (SEQ ID NO.: 446) | 2 | 9 | gp41 | NEG | + | 1 |
| 6-129 | 4-b/39 | 6-13 | 1 | 0 | RGIAAAGFYFQN (SEQ ID NO.: 430) | 1 | 12 | κ | 1-5 | 1 | HHYKSDCQT (SEQ ID NO.: 447) | 3 | 9 | gp41 | NEG | - | 1 |
| 6-137 | 4-b/39 | 6-13 | 1 | 0 | RGIAAAAFYFQT (SEQ ID NO.: 431) | 1 | 12 | κ | 1-5 | 1 | HHYSSSSHT (SEQ ID NO.: 448) | 3 | 9 | gp41 | NEG | ND | 1 |
| 6-161 | 4-b/39 | 6-13 | 1 | 0 | RGIAAAGFYFQH (SEQ ID NO.: 432) | 2 | 12 | κ | 1-5 | 1 | HHYMSDLQT (SEQ ID NO.: 449) | 3 | 9 | gp41 | NEG | ND | 1 |
| 6-182 | 3-15 | 3-3/-22 | 5/1 | 2 | EIGVAEH (SEQ ID NO.: 433) | 1 | 7 | κ | 1-NL1 | 5 | QQYFTSVIT (SEQ ID NO.: 450) | 0 | 9 | gp41 | ND | ND | 1 |

Figure 20

Supplementary Table 2f. Repertoire and reactivity of gp140 non binding antibodies, patient 2

| Ab name | VH | D | JH | (-) | CDR3 (aa) | (+) | Length | κ/λ | Vκ/λ | Jκ/λ | (-) | CDR3 (aa) | (+) | Length | Binding |
|---|---|---|---|---|---|---|---|---|---|---|---|---|---|---|---|
| 2N124 | 3-30 | 1-26 | 3 | 3 | DEIVGALLGAFDI (SEQ ID NO.: 451) | 0 | 13 | κ | 1-16 | 4 | 0 | QQYNTYPLT (SEQ ID NO.: 496) | 0 | 9 | ND |
| 2N-126 | 3-48 | 3-22 | 5 | 1 | SAYYRNWFDS (SEQ ID NO.: 452) | 1 | 10 | κ | 1-13 | 4 | 0 | QQFNSYPPLT (SEQ ID NO.: 497) | 0 | 10 | gp140- |
| 2N-130 | 3-23 | 2-15 | 6 | 3 | GVWEAPDGSSYYYMAD (SEQ ID NO.: 453) | 0 | 17 | κ | 1D-39 | 4 | 0 | QQGFSAPFT (SEQ ID NO.: 498) | 0 | 9 | gp140- |
| 2N-132 | 4-31 | 6-13 | 6 | 2 | DSRPQALVAALDV (SEQ ID NO.: 454) | 1 | 13 | κ | 2-30 | 1 | 0 | MQGTYWLWT (SEQ ID NO.: 499) | 0 | 9 | ND |
| 2N-166 | 1-8 | 6-19/-25 | 4 | 1 | VRRGSSYPDY (SEQ ID NO.: 455) | 2 | 10 | κ | 3-15 | 4 | 0 | QQYHNWPPS (SEQ ID NO.: 500) | 1 | 9 | gp140- |
| 2N-167 | 4-61 | 2-8/3-16 | 6 | 1 | LFGAKRLGVAPSGYYMDV (SEQ ID NO.: 456) | 2 | 18 | κ | 1D-39 | 5 | 0 | QQSYTTPL (SEQ ID NO.: 501) | 0 | 8 | gp140- |
| 2N-169 | 4-34 | 3-16/1-26 | 4 | 1 | RGSLLIKYFDY (SEQ ID NO.: 457) | 2 | 11 | κ | 3-11 | 4 | 0 | QCRSNWPPGLT (SEQ ID NO.: 502) | 1 | 11 | ND |
| 2N-176 | 3-49 | 3-3 | 4 | 3 | TYYNFWSDQSQGLDFDY (SEQ ID NO.: 458) | 0 | 17 | κ | 1-5 | 1 | 0 | QQYNSYFRT (SEQ ID NO.: 503) | 1 | 9 | gp140- |
| 2N-177 | 4-39 | 6-13 | 5 | 0 | HLIAPTAGNYFYP (SEQ ID NO.: 459) | 1 | 13 | λ | 2-23 | 3 | 1 | CSYAGRDTSWV (SEQ ID NO.: 504) | 1 | 11 | gp140- |
| 2N-178 | 4-39 | 6-19/ | 4 | 1 | KVYSDGWSPPTGFVV (SEQ ID NO.: 460) | 1 | 15 | κ | 3-20 | 1 | 0 | QQYGSSRRWT (SEQ ID NO.: 505) | 2 | 10 | ND |
| 2N-179 | 1-8 | 3-10 | 6 | 1 | GGSMRGVPSPFYYGMDV (SEQ ID NO.: 461) | 1 | 18 | κ | 3-20 | 3 | 0 | HQCGSSPRT (SEQ ID NO.: 506) | 2 | 9 | gp140- |
| 2N-182 | 3-11 | 3-3 | 5 | 1 | FGRTPWFDP (SEQ ID NO.: 462) | 1 | 9 | κ | 2-30 | 1 | 0 | MQGTHWPWT (SEQ ID NO.: 507) | 1 | 9 | gp140- |
| 2N-189 | 3-33 | 6-19/5-12/3-22 | 4 | 2 | GDSGPTGFDY (SEQ ID NO.: 463) | 0 | 10 | κ | 3-15 | 3 | 0 | QQYWPPFT (SEQ ID NO.: 508) | 0 | 9 | gp140- |
| 2N-256 | 3-33 | 4-17 | 6 | 6 | DKPAYDEYAEETIAPHNYHAMDL (SEQ ID NO.: 464) | 3 | 23 | κ | 4-1 | 4 | 0 | QQYSTPVT (SEQ ID NO.: 509) | 0 | 9 | ND |
| 2N-259 | 3-30 | 1-26 | 3 | 2 | DVIVGALLGAFDI (SEQ ID NO.: 465) | 0 | 13 | κ | 1-16 | 4 | 0 | QQYKTYPVT (SEQ ID NO.: 510) | 1 | 9 | gp140- |
| 2N-338 | 1-18 | 3-22 | 4 | 2 | SFYDNGGYYLGLDY (SEQ ID NO.: 466) | 0 | 14 | κ | 3-15 | 2 | 1 | HQYNKWDT (SEQ ID NO.: 511) | 2 | 8 | ND |
| 2N-339 | 3-7 | 2-8/3-16/7-27 | 4 | 0 | SIYSTGPAPVY (SEQ ID NO.: 467) | 0 | 11 | λ | 3-10 | 3 | 1 | YSTDNSGKQHWV (SEQ ID NO.: 512) | 1 | 12 | gp140- |
| 2N-341 | 4-61 | 3-9 | 4/5 | 2 | DLID (SEQ ID NO.: 468) | 0 | 4 | κ | 1D-39 | 2 | 0 | QQSYSTPYT (SEQ ID NO.: 513) | 0 | 9 | ND |
| 2N-342 | 3-15 | 5-24/2-8 | 4 | 0 | IKGPPRGNFGVAFVF (SEQ ID NO.: 469) | 2 | 15 | κ | 1D-33 | 3 | 1 | QQHDTFPFT (SEQ ID NO.: 514) | 1 | 9 | gp140- |
| 2N-343 | 3-23 | 6-19/3-16 | 5 | 1 | GTCSYSAVAPGWFDP (SEQ ID NO.: 470) | 0 | 15 | κ | 4-1 | 4 | 0 | QQYYSSPLT (SEQ ID NO.: 515) | 0 | 9 | gp140- |
| 2N-345 | 3-74 | 5-12 | 6 | 3 | GGYDYGDHYYYYMDV (SEQ ID NO.: 471) | 1 | 15 | κ | 3-20 | 5 | 0 | QQYGSSIT (SEQ ID NO.: 516) | 0 | 8 | ND |
| 2N-347 | 1-18 | 3-10 | 6 | 5 | DVVERPGFGDFRYDYYGMDV (SEQ ID NO.: 472) | 2 | 20 | κ | 2D-29 | 2 | 0 | MQSLHLPYT (SEQ ID NO.: 517) | 1 | 9 | gp140- |

Figure 21

| | | | | | | | | | | |
|---|---|---|---|---|---|---|---|---|---|---|
| 2N-349 | 4-31 | 6-19 | 4/5 | 2 | DRLSSFWSGGIDQ (SEQ ID NO.: 473) | 1 | 13 | κ | 1-27 | 5 | 1 | QSYNGDPPVT (SEQ ID NO.: 518) | 0 | 10 | gp140- |
| 2N-350 | 3-74 | 6-19 | 4 | 1 | APYISSSHLDYW (SEQ ID NO.: 474) | 1 | 12 | λ | 3-25 | 1 | 1 | LSADSSSTYQV (SEQ ID NO.: 519) | 0 | 11 | gp140- |
| 2N-352 | 4-31 | 4-23 | 4 | 2 | QRWETIDY (SEQ ID NO.: 475) | 1 | 8 | λ | 1-51 | 1 | 1 | GSWDGSLNAGV (SEQ ID NO.: 520) | 0 | 11 | ND |
| 2N-354 | 4-31 | 4-23 | 6 | 3 | AREGRWFSDNYYAMDV (SEQ ID NO.: 476) | 2 | 16 | κ | 3-20 | 4 | 0 | QQYGFSLPVT (SEQ ID NO.: 521) | 0 | 10 | gp140- |
| 2N-355 | 4-b/4-39 | 3-9/-16/2-21 | 4 | 1 | GVGTRYYVYFDS (SEQ ID NO.: 477) | 1 | 12 | λ | 1-40 | 3 | 1 | QSYDSSLSGWV (SEQ ID NO.: 522) | 0 | 11 | ND |
| 2N-357 | 3-11 | 6-19 | 5 | 2 | DRGSSGWYGWLDP (SEQ ID NO.: 478) | 1 | 13 | κ | 1-5 | 4 | 1 | QQYDVWPLT (SEQ ID NO.: 523) | 0 | 9 | ND |
| 2N-359 | 3-11 | 5-24 | 3 | 3 | EMAATSDAFDI (SEQ ID NO.: 479) | 0 | 11 | κ | 3-15 | 1 | 0 | QQYKKWPPWT (SEQ ID NO.: 524) | 2 | 10 | ND |
| 2N-361 | 3-20 | 6-13 | 6 | 3 | SIAADDYYYYMDV (SEQ ID NO.: 480) | 0 | 14 | κ | 3-20 | 5 | 0 | QQYGSSPIT (SEQ ID NO.: 525) | 0 | 9 | ND |
| 2N-364 | 4-59 | 3-9/-10 | 4 | 2 | LEGTDY (SEQ ID NO.: 481) | 0 | 6 | κ | 1D-33 | 5 | 1 | QQYDRLPIT (SEQ ID NO.: 526) | 1 | 9 | gp140- |
| 2N-366 | 3-30 | 3-22 | 4 | 1 | AQFHNSGYYYSGLDY (SEQ ID NO.: 482) | 1 | 15 | κ | 3-20 | 1 | 0 | QHHGSSPTWT (SEQ ID NO.: 527) | 2 | 10 | gp140- |
| 2N-367 | 3-48 | 3-3/2-2 | 4 | 2 | APPPGSTEWAYYFDY (SEQ ID NO.: 483) | 0 | 15 | κ | 3-15 | 2 | 0 | QHYNNWPYT (SEQ ID NO.: 528) | 1 | 9 | ND |
| 2N-368 | 3-h/3-48 | 6-6 | 3 | 1 | REGSQGAFDI (SEQ ID NO.: 484) | 1 | 10 | λ | 3-1 | 3 | 1 | QAWDSSTAV (SEQ ID NO.: 529) | 0 | 9 | gp140- |
| 2N-370 | 1-46 | 3-3 | 5 | 2 | AAIPIGDSKYSYFDS (SEQ ID NO.: 485) | 1 | 15 | κ | 4-1 | 4 | 0 | QQYTVPS (SEQ ID NO.: 530) | 0 | 8 | ND |
| 2N-371 | 5-51 | 1-26 | 4 | 1 | GVRSIVGAHFDY (SEQ ID NO.: 486) | 2 | 12 | κ | 2D-28 | 4 | 0 | MQALQTSLT (SEQ ID NO.: 531) | 0 | 9 | ND |
| 2N-376 | 4-31 | 6-13 | 5 | 0 | GHSSSWTKFNWFGP (SEQ ID NO.: 487) | 2 | 14 | κ | 1-5 | 4 | 1 | QQYSGPLT (SEQ ID NO.: 532) | 0 | 8 | gp140- |
| 2N-377 | 4-4/-34 | 1-7 | 6 | 2 | RDRYNWKYYYLDV (SEQ ID NO.: 488) | 3 | 13 | κ | 1-9 | 1 | 1 | QQLNSDPPWT (SEQ ID NO.: 533) | 0 | 10 | ND |
| 2N-378 | 3-43 | 4-23 | 3 | 2 | GLTVATLYDAFDV (SEQ ID NO.: 489) | 0 | 13 | κ | 2D-29 | 4 | 0 | MQSIQLPLT (SEQ ID NO.: 534) | 0 | 9 | ND |
| 2N-379 | 4-39 | 3-10 | 4 | 1 | HSRPGAPPHYFDY (SEQ ID NO.: 490) | 3 | 13 | κ | 3-20 | 2 | 0 | QQYGSSAPYT (SEQ ID NO.: 535) | 0 | 10 | ND |
| 2N-382 | 4-34 | 3-3 | 5 | 2 | LYYNFGSGYDTGIGDH (SEQ ID NO.: 491) | 1 | 16 | κ | 1-27 | 4 | 0 | QNYNKPPRT (SEQ ID NO.: 536) | 2 | 9 | ND |
| 2N-383 | 3-72 | 3-3 | 4 | 2 | VKQFLEWLYLDY (SEQ ID NO.: 492) | 1 | 12 | κ | 1D-39 | 1 | 0 | QQSYIAGT (SEQ ID NO.: 537) | 0 | 9 | ND |
| 2N-389 | 1-69 | 5-12 | 4 | 3 | PSYGGYDDQGWYFEY (SEQ ID NO.: 493) | 0 | 15 | λ | 3-21 | 3 | 2 | QVWDSGRDSWV (SEQ ID NO.: 538) | 0 | 11 | ND |
| 2N-391 | 1-2 | 5-5/-18/3-9 | 5 | 1 | KGRGYGYWFDS (SEQ ID NO.: 494) | 2 | 11 | κ | 3-15 | 5 | 0 | QQYYKWPPIT (SEQ ID NO.: 539) | 1 | 10 | ND |
| 2N-392 | 3-30 | 3-10 | 6 | 2 | AFQASMVRGVIVDPYGMDV (SEQ ID NO.: 495) | 1 | 19 | κ | 4-1 | 4 | 0 | QQYSTPHT (SEQ ID NO.: 540) | 1 | 9 | ND |

Figure 21 (continued)

Supplementary Table 2g. Repertoire and reactivity of gp140 non binding antibodies, patient 3

| Ab name | VH | D | JH | (-) | CDR3 (aa) | (+) | Length | κ/λ | Vκ/λ | Jκ/λ | (-) | CDR3 (aa) | (+) | Length | Binding |
|---|---|---|---|---|---|---|---|---|---|---|---|---|---|---|---|
| 3N-105 | 3-23 | 3-3 | 4 | 3 | EGGYSDFWSGYSGFDY (SEQ ID NO.: 541) | 0 | 17 | λ | 2-14 | 3 | 0 | SSYTISSPRV (SEQ ID NO.: 588) | 1 | 10 | gp140- |
| 3N-109 | 3-48 | 3-22 | 3 | 2 | ANYDSSGYGLDI (SEQ ID NO.: 542) | 0 | 13 | λ | 1-40 | 2/3 | 1 | QSYDSSLSG (SEQ ID NO.: 589) | 0 | 9 | gp140- |
| 3N-113 | 5-51 | 3-10 | 6 | 3 | HYYGSGLTKDYYEYIDV (SEQ ID NO.: 543) | 2 | 17 | λ | 1-40 | 1 | 1 | QSYDSSLGVEV (SEQ ID NO.: 590) | 0 | 11 | ND |
| 3N-116 | 3-30 | 1-1 | 4 | 3 | DRFNWNDGGYFFDS (SEQ ID NO.: 544) | 1 | 14 | λ | 1-5 | 4 | 0 | QQYNSYPLT (SEQ ID NO.: 591) | 0 | 9 | ND |
| 3N-117 | 5-51 | 5-24 | 6 | 1 | RMATLTGGYYYYMDV (SEQ ID NO.: 545) | 1 | 16 | κ | 2D-28 | 5 | 0 | MQSLQTPIT (SEQ ID NO.: 592) | 0 | 9 | gp140- |
| 3N-118 | 4-39 | 6-13/2-2 | 6 | 2 | RISSSSWYMVDNSHTLHFYYM DV (SEQ ID NO.: 546) | 3 | 23 | λ | 1-47 | 3 | 2 | AAWDDSLSGLNWV (SEQ ID NO.: 593) | 0 | 13 | gp140- |
| 3N-120 | 3-7 | 6-6/-13 | 6 | 1 | AARRAFYYYMDV (SEQ ID NO.: 547) | 2 | 13 | κ | 1-5 | 2 | 0 | QQFNTYSQT (SEQ ID NO.: 594) | 0 | 9 | gp140- |
| 3N-127 | 4-30 | 3-22 | 3 | 2 | GATYYYDSSGHQSRRAFDI (SEQ ID NO.: 548) | 3 | 19 | κ | 2-30 | 5 | 0 | MQGTYWPPSIT (SEQ ID NO.: 595) | 0 | 11 | gp140- |
| 3N-129 | 3-23 | 3-10 | 6 | 1 | ASGSYILGTMDV (SEQ ID NO.: 549) | 0 | 12 | κ | 3-11 | 2 | 0 | QQRTSWPQT (SEQ ID NO.: 596) | 1 | 9 | gp140- |
| 3N-130 | 3-30 | 2-15/-21 | 6 | 1 | MNPPWFRGGSNNPYSYYYMD V (SEQ ID NO.: 550) | 1 | 21 | κ | 2-29 | 1/5 | ND | ND | ND | ND | gp140- |
| 3N-134 | 5-51 | 6-19 | 1 | 2 | QTTDEGRQWLVGFQH (SEQ ID NO.: 551) | 2 | 15 | κ | 3-15 | 4 | 1 | QQYENWLT (SEQ ID NO.: 597) | 0 | 8 | gp140- |
| 3N-135 | 5-51 | 3-22 | 4 | 2 | IYDGRGYYSYFFDL (SEQ ID NO.: 552) | 1 | 14 | κ | 1-27 | 1 | 0 | QLYNSVPQT (SEQ ID NO.: 598) | 0 | 9 | gp140- |
| 3N-138 | 4-b/4-59 | 2-15 | 4/5 | 2 | LGCSGGSCYEDS (SEQ ID NO.: 553) | 0 | 12 | κ | 3-20 | 1 | 0 | QQYSTTPRT (SEQ ID NO.: 599) | 0 | 9 | ND |
| 3N-142 | 4-61 | 3-3/-16 | 4 | 3 | LTKNPSQDFWGSYLYFFED (SEQ ID NO.: 554) | 1 | 19 | κ | 1D-39 | 1 | 0 | QQGYSTPWT (SEQ ID NO.: 600) | 0 | 9 | gp140- |
| 3N-143 | 3-72 | 5-24 | 5 | 2 | AGREGWFDP (SEQ ID NO.: 555) | 1 | 9 | κ | 1D-39 | 5 | 0 | HQSYSTPPT (SEQ ID NO.: 601) | 1 | 9 | gp140- |
| 3N-144 | 5-51 | 3-22/2-2 | 4 | 2 | QVSSYSSSGYRRFFDY (SEQ ID NO.: 556) | 2 | 16 | κ | 4-1 | 1 | 0 | QQYYSIPPWTF (SEQ ID NO.: 602) | 0 | 11 | gp140- |
| 3N-145 | 4-61 | 3-22 | 6 | 1 | SGVHYMDV (SEQ ID NO.: 557) | 1 | 8 | κ | 1D-39 | 1 | 0 | QQSFSTLWT (SEQ ID NO.: 603) | 0 | 9 | gp140- |
| 3N-150 | 3-23 | 3-22 | 4 | 1 | FTQRQGGFDY (SEQ ID NO.: 558) | 1 | 10 | λ | 1-40 | 3 | 1 | QSYDNSLSGWV (SEQ ID NO.: 604) | 0 | 11 | ND |
| 3N-169 | 3-21 | 3-3 | 6 | 1 | HGRTVFGVVRNYYYMDV (SEQ ID NO.: 559) | 3 | 17 | κ | 1D-39 | 5 | ND | ND | ND | ND | ND |
| 3N-170 | 3-30 | 3-16 | 1 | 1 | NGHSALGGEYFQH (SEQ ID NO.: 560) | 2 | 13 | κ | 1D-33 | 4 | 1 | HQCDNLIAR (SEQ ID NO.: 605) | 2 | 9 | ND |
| 3N-177 | 1-46 | 3-22 | 4 | 5 | DHGIKPDNYYDISGYNLDYFDY (SEQ ID NO.: 561) | 2 | 22 | κ | 3-20 | 4 | 0 | QQYGSSPPT (SEQ ID NO.: 606) | 0 | 9 | gp140- |
| 3N-190 | 3-30 | 3-16 | 1 | 0 | NGHSLGGGYFPH (SEQ ID NO.: 562) | 2 | 13 | κ | 1D-33 | 4 | 0 | QQYDNLLAH (SEQ ID NO.: 607) | 1 | 9 | ND |
| 3N-194 | 1-2 | 2-2 | 3 | 1 | AGHCSSTSSVYCPPFDM (SEQ ID NO.: 563) | 1 | 16 | κ | 4-1 | 2 | 1 | QEYILPCS (SEQ ID NO.: 608) | 0 | 9 | ND |
| 3N-305 | 4-34 | 3-3/-9 | 4 | 2 | TNWANDFVTGYYRFDF (SEQ ID NO.: 564) | 0 | 16 | λ | 1-51 | 3 | 1 | GTWDGSLTTGV (SEQ ID NO.: 609) | 0 | 11 | ND |
| 3N-317 | 3-73 | 3-22 | 4 | 1 | GLYDSSGYFGY (SEQ ID NO.: 565) | 0 | 12 | λ | 2-11 | 2/3 | 0 | YSYAGNSLGV (SEQ ID NO.: 610) | 0 | 10 | gp140- |

Figure 22

| | | | | | | | | | | | | | |
|---|---|---|---|---|---|---|---|---|---|---|---|---|---|
| 3N-319 | 5-51 | 4 | 2 | TLDGNFHWDF (SEQ ID NO.: 566) | 1 | 10 | λ | 2-14 | 1 | 0 | CSFTYVNPTYL (SEQ ID NO.: 611) | 0 | 11 | ND |
| 3N-320 | 3-33 | 3 | 3 | DRAPYGAFEPFDF (SEQ ID NO.: 567) | 1 | 13 | λ | 1-5 | 2 | 0 | QQYNRYSYT (SEQ ID NO.: 612) | 1 | 9 | gp140 |
| 3N-325 | 3-23 | 4 | 1 | RYCSSTICYRGHFDY (SEQ ID NO.: 568) | 3 | 15 | κ | 2-8 | 1 | 2 | SSYADTNDFGV (SEQ ID NO.: 613) | 0 | 11 | ND |
| 3N-326 | 4-59 | 5 | 2 | LTGPSGYCDSSGCYWFDP (SEQ ID NO.: 569) | 0 | 18 | λ | 2-23 | 3 | ND | ND | ND | ND | ND |
| 3N-328 | 3-h/-48 | 4 | 6 | DRDYDEDFDF (SEQ ID NO.: 570) | 1 | 10 | λ | 2-11 | 1 | 0 | CSYAGSYSYV (SEQ ID NO.: 614) | 0 | 10 | ND |
| 3N-330 | 1-69 | 5 | 3 | DLVSVSPPYGNYGPDNNWFDF (SEQ ID NO.: 571) | 0 | 21 | κ | 3-15 | 4 | 0 | QQYNNLPVT (SEQ ID NO.: 615) | 0 | 9 | gp140 |
| 3N-333 | 4-61 | 4 | 2 | DFGRAYAIGYFEY (SEQ ID NO.: 572) | 1 | 13 | κ | 1-5 | 1 | 1 | QQYDSFSWT (SEQ ID NO.: 616) | 0 | 9 | gp140 |
| 3N-345 | 3-48 | 3 | 1 | LIPVSGAFDV (SEQ ID NO.: 573) | 0 | 10 | κ | 3-11 | 3 | 0 | QQRSTWPPT (SEQ ID NO.: 617) | 1 | 9 | gp140 |
| 3N-347 | 4-4 | 5 | 1 | GGSPEH (SEQ ID NO.: 574) | 1 | 6 | κ | 1D-39 | 3 | ND | ND | ND | ND | ND |
| 3N-352 | 1-3 | 6 | 4 | DGRYSGDDQYYYHYYYMDV (SEQ ID NO.: 575) | 1 | 19 | κ | 3-20 | 4 | 0 | QYYGMSVT (SEQ ID NO.: 618) | 0 | 8 | gp140 |
| 3N-354 | 3-48 | 6 | 3 | ESWLYSNGDYYYMDV (SEQ ID NO.: 576) | 0 | 15 | κ | 3-15 | 1 | 0 | QQYHNWPRT (SEQ ID NO.: 619) | 2 | 9 | gp140 |
| 3N-356 | 4-34/-61 | 4 | 2 | EAGSVTATGPFDS (SEQ ID NO.: 577) | 0 | 13 | κ | 1-5 | 1 | 0 | QQYSHYRT (SEQ ID NO.: 620) | 2 | 8 | gp140 |
| 3N-364 | 3-9 | 3 | 2 | LYFDWAPHAFDI (SEQ ID NO.: 578) | 1 | 12 | κ | 1D-33 | 5 | ND | ND | ND | ND | ND |
| 3N-375 | 4-34 | 4 | 3 | QEWELQPFDY (SEQ ID NO.: 579) | 0 | 10 | κ | 3-20 | 2 | 0 | QQYGSSLLYT (SEQ ID NO.: 621) | 0 | 10 | gp140 |
| 3N-376 | 3-10/1-26 | 3 | 4 | EEPRDAFDL (SEQ ID NO.: 580) | 1 | 9 | λ | 1-27P | 6 | 3 | STWDYSLSAHEDV (SEQ ID NO.: 622) | 1 | 13 | ND |
| 3N-379 | 5-5/-18 | 4 | 1 | SQGNTAIDY (SEQ ID NO.: 581) | 0 | 9 | κ | 2-30 | 4 | 0 | MQGTYWPPLT (SEQ ID NO.: 623) | 0 | 10 | gp140 |
| 3N-380 | 4-17/6-6 | 4 | 4 | DLLPDYPYSSAPEDF (SEQ ID NO.: 582) | 0 | 15 | κ | 3-11 | 3 | 0 | QQRHNWPIS (SEQ ID NO.: 624) | 1 | 9 | gp140 |
| 3N-381 | 4-39 | 4 | 2 | LPKSRMVGGDHLPFYPDF (SEQ ID NO.: 583) | 3 | 18 | λ | 1-44 | 1 | 2 | AAWDDSLNGHGV (SEQ ID NO.: 625) | 1 | 12 | ND |
| 3N-391 | 3-30 | 6 | 2 | DLNFGVVTPYYYYLDV (SEQ ID NO.: 584) | 0 | 17 | κ | 3-15 | 1 | 0 | QSKT (SEQ ID NO.: 626) | 1 | 4 | gp140 |
| 3N-392 | 3-3 | 4 | 2 | DNTISGVVPRWFDY (SEQ ID NO.: 585) | 1 | 14 | κ | 3-15 | 4 | 0 | QQYNNWPPFT (SEQ ID NO.: 627) | 0 | 10 | gp140 |
| 3N-395 | 1-46 | 5 | 1 | PGYCNNNICTHWFDT (SEQ ID NO.: 586) | 1 | 15 | λ | 2-8 | 2 | ND | ND | ND | ND | ND |
| 3N-396 | 4-39 | 4 | 2 | LSSDRIVVGPDY (SEQ ID NO.: 587) | 1 | 13 | κ | 3-11 | 4 | 0 | QQRSNWPRLT (SEQ ID NO.: 628) | 2 | 10 | ND |

Figure 22 (continued)

Affinity measurements by surface plasmon resonance

| antibody | epitope | gp140 ka (1/Ms) | gp140 kd (1/s) | gp140 KD (M) | gp120 ka (1/Ms) | gp120 kd (1/s) | gp120 KD (M) | gp120^core ka (1/Ms) | gp120^core kd (1/s) | gp120^core KD (M) |
|---|---|---|---|---|---|---|---|---|---|---|
| 1-64 | CD4BS | 2.4E+04 | 8.2E-07 | 3.3E-11* | 6.7E+04 | 2.3E-05 | 3.4E-10* | 2.0E+05 | 5.0E-05 | 2.5E-10* |
| 1-154 | CD4BS | 2.1E+04 | 3.5E-04 | 1.7E-08* | 5.5E+04 | 3.2E-04 | 5.9E-09* | 1.8E+05 | 3.9E-04 | 2.2E-09* |
| 1-577 | CD4BS | 3.7E+04 | 5.0E-04 | 1.3E-08* | 3.9E+04 | 4.2E-04 | 1.1E-08* | 1.3E+05 | 1.3E-04 | 9.7E-10* |
| 4-341 | CD4BS | 9.8E+03 | 1.3E-04 | 1.3E-08* | 4.4E+04 | 8.3E-04 | 1.9E-08 | 2.0E+05 | 3.5E-03 | 1.7E-08 |
| 1-74 | Core | 2.9E+07 | 1.4E-05 | 4.8E-10* | | | | | | |
| 1-479 | Core | 1.7E+04 | 2.5E-05 | 1.4E-09* | 3.7E+04 | 2.1E-05 | 5.8E-09* | 1.5E+05 | 1.1E-06 | 7.4E-12* |
| 2-491 | Core | 5.3E+04 | 2.2E-04 | 6.9E-09* | 5.8E+04 | 7.0E-05 | 1.2E-09* | 3.7E+05 | 7.5E-05 | 2.1E-10* |
| 4-133 | Core | 5.1E+04 | 9.8E-04 | 2.0E-08 | 5.2E+04 | 2.2E-04 | 4.3E-09* | 1.4E+05 | 5.7E-05 | 4.0E-10* |
| 4-221 | Core | 3.3E+04 | 1.1E-05 | 4.1E-10* | 8.0E+04 | 4.1E-05 | 5.2E-10* | 3.6E+05 | 9.2E-05 | 2.5E-10* |
| 4-649 | Core | 3.0E+04 | 1.9E-04 | 5.2E-09* | 3.1E+04 | 1.3E-03 | 4.3E-08 | 1.7E+05 | 7.8E-04 | 4.6E-09 |
| 4-8 | CD4i | 1.4E+04 | 5.7E+05 | 4.4E-09* | | | | | | |
| 2-52 | VL | 1.4E+04 | 2.1E-05 | 1.3E-09* | | | | | | |
| 2-59 | VL | 7.7E+04 | 4.2E-05 | 5.2E-10* | | | | | | |
| b12 | CD4BS | 4.1E+04 | 4.9E-04 | 1.2E-8 | | | | | | |

Figure 23

Competition ELISA experiments a — Competing Gp120^Core Antibodies (non-biotinylated)

| biotinylated antibodies | 1-74 | 1-479 | 1-664 | 1-695 | 1-732 | 2-491 | 3-124 | 4-53 | 4-57 | 4-77 | 4-79 | 4-133 | 4-221 | 4-214 | 4-252 | 4-459 | 4-649 |
|---|---|---|---|---|---|---|---|---|---|---|---|---|---|---|---|---|---|
| Gp120^Core | 6.7 | 4.5 | 5.5 | 8.5 | 5.7 | 5.4 | 8.2 | 6.6 | 19.8 | 11.2 | 14.9 | 10.3 | 3.0 | 5.6 | 5.8 | 10.5 | 10.5 |
| CD4bs | 6.0 | 6.4 | 6.2 | 17.3 | 8.5 | 6.5 | 10.8 | 5.7 | 9.5 | 8.8 | 10.5 | 7.8 | 4.4 | 5.6 | 8.0 | 26.6 | 20.3 |
| B12 | 3.9 | 4.8 | 6.1 | 18.2 | 4.7 | 6.5 | 6.1 | 6.9 | 21.2 | 19.3 | >100.0 | 10.8 | 3.3 | 4.3 | 6.5 | 79.4 | 30.3 |
| CD4i | 3.3 | 5.0 | 5.2 | 8.3 | 6.0 | 4.6 | 8.7 | 3.8 | 4.9 | 4.7 | 5.4 | 5.3 | 1.6 | 4.1 | 4.6 | 7.8 | 6.6 |
| V3-Loop | >100.0 | >100.0 | >100.0 | >100.0 | 48.3 | 32.7 | >100.0 | 69.1 | 51.1 | >100.0 | 79.9 | 36.9 | >100.0 | >100.0 | >100.0 | 46.6 | >100.0 | b — Competing CD4bs Antibodies (non-biotinylated)

| biotinylated antibodies | 1-64 | 1-154 | 1-577 | 1-863 | 2-470 | 2-1207 | 2-1262 | 3-613 | 3-869 | 4-116 | 4-208 | 4-253 | 4-341 | 4-527 | 4-630 | B12 |
|---|---|---|---|---|---|---|---|---|---|---|---|---|---|---|---|---|
| Gp120^Core | 6.4 | 10.5 | 6.0 | 3.2 | 9.5 | 16.8 | 6.8 | 16.0 | 12.8 | 25.7 | 8.5 | 6.4 | 10.0 | 15.3 | 7.0 | 10.7 |
| CD4bs | 4.6 | 19.8 | 10.2 | 7.9 | 11.5 | 21.1 | 6.6 | 10.1 | 8.4 | 11.7 | 7.8 | 11.6 | 14.8 | 16.5 | 14.2 | 8.3 |
| B12 | 4.7 | 13.2 | 10.4 | 4.2 | 38.1 | 24.6 | 6.8 | >100.0 | >100.0 | 18.5 | 1.8 | 12.4 | 14.3 | >100.0 | 13.3 | 5.0 |
| CD4i | 3.8 | 6.8 | 4.8 | 5.1 | 7.3 | 8.5 | 5.6 | 7.2 | 6.2 | 6.0 | 1.6 | 4.9 | 4.9 | 6.2 | 5.5 | 7.5 |
| V3-Loop | >100.0 | >100.0 | 53.6 | 83.8 | >100.0 | >100.0 | >100.0 | >100.0 | >100.0 | 82.6 | >100.0 | >100.0 | 88.8 | >100.0 | >100.0 | >100.0 | c — Competing CD4i Antibodies (non-biotinylated)

| biotinylated antibodies | 1-182 | 2-73 | 2-301 | 3-67 | 3-383 | 3-576 | 4-8 | 4-42 | 4-103 | 4-164 | 4-433 | 4-441 | 4-554 |
|---|---|---|---|---|---|---|---|---|---|---|---|---|---|
| Gp120^Core | >100.0 | >100.0 | >100.0 | >100.0 | >100.0 | >100.0 | >100.0 | >100.0 | >100.0 | >100.0 | 19.7 | 41.8 | 16.2 |
| CD4bs | >100.0 | >100.0 | 75.0 | 45.5 | >100.0 | 88.9 | >100.0 | 33.6 | >100.0 | >100.0 | 43.4 | >100.0 | >100.0 |
| B12 | >100.0 | >100.0 | >100.0 | >100.0 | >100.0 | >100.0 | >100.0 | >100.0 | >100.0 | >100.0 | >100.0 | >100.0 | >100.0 |
| CD4i | 9.2 | >100.0 | >100.0 | 12.7 | >100.0 | 28.2 | 11.4 | 5.8 | >100.0 | 6.0 | 7.1 | 24.7 | >100.0 |
| V3-Loop | >100.0 | >100.0 | 49.5 | >100.0 | >100.0 | >100.0 | >100.0 | 43.7 | 78.5 | 90.0 | 42.1 | >100.0 | >100.0 | d — Competing VL antibodies (non-biotinylated)

| biotinylated antibodies | 1-79 | 2-59 | 2-1261 | 3-228 | 4-150 | 4-366 | 447-52D |
|---|---|---|---|---|---|---|---|
| Gp120^Core | >100.0 | >100.0 | >100.0 | >100.0 | >100.0 | >100.0 | >100.0 |
| CD4bs | >100.0 | >100.0 | 86.3 | >100.0 | >100.0 | >100.0 | 33.3 |
| B12 | >100.0 | >100.0 | >100.0 | >100.0 | >100.0 | >100.0 | >100.0 |
| CD4i | >100.0 | >100.0 | >100.0 | >100.0 | 36.0 | 5.9 | >100.0 |
| V3-Loop | 7.5 | 5.2 | 28.8 | 59.4 | >100.0 | 56.1 | 5.7 |

Figure 24

In vitro Tzm-bl neutralization assay a

| TIER | CLADE | STRAIN | CD4BS 1-64 | 1-676 | 1-154 | 1-695 | 1-711 | 1-732 | 1-863 | 1-74 | CORE 1-621 | 1-479 | 1-705 | 1-795 | 1-809 | 1-664 | 1-687 | 1-752 | CD4i 1-68 | 1-693 | VL 1-79 |
|---|---|---|---|---|---|---|---|---|---|---|---|---|---|---|---|---|---|---|---|---|---|
| 1 | C | MW965.23 | >50 | >50 | >50 | >50 | >50 | >50 | >50 | >50 | 9.8 | <0.02 | <0.02 | <0.02 | <0.02 | >50 | >50 | >25 | >50 | >50 | 2.84 |
| 1 | A | DJ263.8 | 33.1 | >50 | 0.88 | 2.5 | >50 | 4.3 | 1.9 | 0.16 | >50 | 0.7 | 0.9 | 0.9 | 1.0 | 2.9 | >50 | 1.7 | >50 | >50 | >50 |
| 1 | B | SF162.LS | 0.45 | 2.1 | 0.9 | 9.3 | 4.0 | 3.5 | 2.2 | >50 | >50 | 1.1 | 3.2 | 2.8 | 3.0 | 1.1 | >50 | 2.9 | 0.4 | >50 | <0.023 |
| 1 | B | SS1196.1 | ND | >50 | >50 | >50 | >50 | >50 | 38.4 | 13 | >50 | 30.4 | 45.8 | 34.7 | 26.3 | >50 | >50 | >25 | 5.2 | >50 | 1 |
| 1 | B | BaL.26 | 1.64 | 2.7 | 17.7 | >50 | 46.3 | 50 | 7.9 | 2.75 | >50 | 12.2 | 14.7 | 22.6 | 17.1 | 19.2 | >50 | >25 | 13.2 | >50 | 0.08 |
| 2 | B | 6535.3 | >50 | >50 | >50 | ND | >50 | >50 | >50 | 42.3 | >50 | 24.2 | 33.4 | 12 | 11.8 | 19.60 | >50 | >25 | >50 | >50 | >50 |
| 2 | B | RHPA4259.7 | >50 | >50 | >50 | >50 | >50 | >50 | >50 | >50 | >50 | >50 | >50 | >50 | >50 | >50 | >50 | >25 | >50 | >50 | >50 |
| 2 | B | TRO.11 | >50 | >50 | >50 | >50 | >50 | >50 | >50 | >50 | >50 | >50 | >50 | >50 | >50 | >50 | >50 | >25 | >50 | >50 | >50 |
| 2 | B | SC422661.8 | >50 | >50 | >50 | ND | >50 | >50 | >50 | >50 | >50 | >50 | >50 | >50 | >50 | >50 | >50 | >25 | >50 | >50 | >50 |
| 2 | B | PVO.4 | >50 | >50 | >50 | >50 | >50 | >50 | >50 | >50 | >50 | >50 | >50 | >50 | >50 | >50 | >50 | >25 | >50 | >50 | >50 |

| TIER | CLADE | STRAIN | gp41 1-11 | 1-27 | 1-96 | 1-167 | 1-491 | 1-696 | 1-763 | pt1 IGG | POOL | controls b12 | 2g12 | 2F5 | 4E10 | 447-52D |
|---|---|---|---|---|---|---|---|---|---|---|---|---|---|---|---|---|
| 1 | C | MW965.23 | >50 | >38 | >50 | >50 | ND | >50 | >50 | 8 | 0.4 | 0.2 | >25 | >25 | 0.01 | 0.05 |
| 1 | A | DJ263.8 | >50 | >38 | >50 | >50 | ND | >50 | >50 | 212 | 5.5 | >25 | 1.9 | >25 | 0.2 | 20.5 |
| 1 | B | SF162.LS | >50 | >38 | >50 | >50 | ND | >50 | >50 | 5 | 0.5 | 0.01 | 0.6 | 0.1 | 0.3 | <0.02 |
| 1 | B | SS1196.1 | ND | ND | ND | ND | ND | >50 | >50 | 57 | 66.4 | 0.3 | 12 | 24 | 0.3 | 0.4 |
| 1 | B | BaL.26 | >50 | >38 | >50 | >50 | ND | >50 | >50 | 34 | 8.5 | 0.2 | 0.9 | 0.8 | 0.7 | 0.04 |
| 2 | B | 6535.3 | ND | ND | ND | ND | ND | >50 | >50 | 88 | 100 | 1.4 | 2 | 1.9 | 0.2 | 0.1 |
| 2 | B | RHPA4259.7 | ND | ND | ND | ND | ND | >50 | >50 | 113 | 1082 | 0.1 | >50 | 12 | 6.9 | 48.9 |
| 2 | B | TRO.11 | ND | ND | >40 | >40 | >40 | >50 | >50 | 72 | 1077 | >50 | 0.4 | >50 | 0.3 | >25 |
| 2 | B | SC422661.8 | ND | ND | ND | ND | >40 | >50 | >50 | 49 | 1697 | 0.2 | 2.1 | 0.7 | 0.9 | >25 |
| 2 | B | PVO.4 | ND | ND | ND | ND | ND | >50 | >50 | 89 | 1243 | >50 | 1.2 | >50 | 6.5 | >25 | b

| TIER | CLADE | STRAIN | CD4BS 2-470 | 2-1262 | 2-1207 | CORE 2-491 | 2-876 | CD4i 2-901 | 2-73 | VL 2-52 | 2-59 | 2-1092 | 2-1034 | 2-69 | 2-1055 | 2-234 | 2-1042 | 2-1261 |
|---|---|---|---|---|---|---|---|---|---|---|---|---|---|---|---|---|---|---|
| 1 | C | MW965.23 | 0.1 | <0.01 | 16.8 | <0.01 | >100 | 3.5 | 24.9 | >50 | 1.2 | 2.5 | 0.6 | >50 | >23 | >25 | >30 | >35 |
| 1 | A | DJ263.8 | 1.2 | 0.1 | 3.3 | 0.3 | >100 | >25 | >25 | >50 | 26.5 | >50 | 35.1 | >50 | >23 | >25 | >30 | >35 |
| 1 | B | SF162.LS | 12.4 | 0.98 | >25 | 1.6 | >100 | 2.2 | 10.9 | >50 | <0.01 | <0.02 | 0.04 | >50 | >23 | >25 | >30 | 0.03 |
| 1 | B | SS1196.1 | >25 | 6 | >25 | 21.4 | >100 | 10.5 | 5.35 | >50 | 1.16 | 3 | 4.8 | >50 | >23 | >25 | >30 | 0.86 |
| 1 | B | BaL.26 | >25 | 1.9 | >25 | 8.2 | >100 | 22.7 | 17.2 | >50 | 0.25 | 0.3 | 0.6 | >50 | >23 | >25 | ND | 0.5 |
| 2 | B | 6535.3 | 99 | 0.97 | >50 | 4.6 | ND | >25 | >25 | >50 | >50X | >50 | >50X | >50 | >23 | >25 | >30 | 0.92 |
| 2 | B | RHPA4259.7 | >100 | >25X | >25 | >25 | ND | >25 | >25 | >50 | >50X | >50 | >50X | >50 | >23 | >25 | >30 | 35 |
| 2 | B | CAAN5342.A2 | >100 | >25 | >25 | >25 | ND | >25 | >25 | >50 | >50 | >50 | >50 | >50 | >23 | >25 | >30 | >35 |
| 2 | B | THRO4156.18 | >25X | >25 | >25 | >25X | ND | >25X | >25X | >50 | >50 | >50 | >50 | >50 | >23 | >25 | >30 | >35 |
| 2 | B | SC422661.8 | 73.5 | >25X | >25 | 79.1 | ND | >25X | >25 | >50 | >50X | >50X | >50 | >50 | >23 | >25 | ND | >50 |

| TIER | CLADE | STRAIN | gp41 2-55 | 2-378 | 2-150 | 2-275 | 2-512 | 2-149 | 2-1007 | pt2 IGG | POOL |
|---|---|---|---|---|---|---|---|---|---|---|---|
| 1 | C | MW965.23 | >25 | >50 | >23 | >45 | >40 | >20 | >23 | >40 | 2 | 0.07 |
| 1 | A | DJ263.8 | >25 | >50 | >23 | >45 | >40 | >20 | >23 | >40 | 72 | 7.7 |
| 1 | B | SF162.LS | >25 | >50 | >23 | >45 | >40 | >20 | >23 | >40 | 6 | 0.2 |
| 1 | B | SS1196.1 | >25 | >50 | >23 | >45 | >40 | >20 | >23 | >40 | 104 | 38.8 |
| 1 | B | BaL.26 | >25 | >50 | >23 | >45 | >40 | >20 | >23 | >40 | 24 | 10.5 |
| 2 | B | 6535.3 | >25 | >50 | >23 | >45 | >40 | >20 | >23 | >40 | 152 | 55 |
| 2 | B | RHPA4259.7 | >25 | >50 | >23 | >45 | >40 | >20 | >23 | >40 | 259 | >1500 |
| 2 | B | CAAN5342.A2 | >25 | >50 | >23 | >45 | >40 | >20 | >23 | >40 | 236 | >1500 |
| 2 | B | THRO4156.18 | >25 | >50 | >23 | >45 | >40 | >20 | >23 | >40 | 1258 | >1500 |
| 2 | B | SC422661.8 | >25 | >50 | >23 | >45 | >40 | >20 | >23 | >40 | 495 | >1500 |

Figure 25 c

| TIER | CLADE | STRAIN | CD4BS | | CORE | | CD4i | | | | VL | | | |
|---|---|---|---|---|---|---|---|---|---|---|---|---|---|---|
| | | | 3-869 | 3-613 | 3-124 | 3-518 | 3-67 | 3-383 | 3-596 | 3-259 | 3-228 | 3-637 | 3-584 | 3-539 |
| 1 | C | MW965.23 | >25 | >25 | >25 | >25 | 0.1 | >50 | 0.5 | >25 | >50 | >30 | >50 | >25 | >25 |
| 1 | A | DJ263.8 | 8.4 | >25X | >25 | >25 | >50 | >50 | >25 | >25 | >50 | >30 | >50 | >25 | >25 |
| 1 | B | SF162.LS | 5 | 11.7 | 0.2 | >25 | 1.4 | 3 | >25 | >25 | >50 | >30 | >50 | >25 | >25 |
| 1 | B | SS1196.1 | >25 | >25 | >25 | >25 | 10.7 | 43 | 5 | >25 | >50 | 8.2 | >50 | >25 | >25 |
| 1 | B | BaL.26 | 25 | 18.5 | >25 | >25 | 19.2 | 27 | 5.3 | >25 | >50 | 3.9 | >50 | >25 | >25 |
| 2 | B | 6535.3 | >25 | >25 | ND | >25 | >50 | >50 | ND | ND | >50 | >30 | ND | ND | ND |
| 2 | B | RHPA4259.7 | >25 | >25 | ND | >25 | >50 | >50 | ND | ND | >50 | >30 | ND | ND | ND |
| 2 | B | TRO.11 | >25 | >25 | ND | >25 | >50 | >50 | ND | ND | >50 | >30 | ND | ND | ND |
| 2 | B | SC422661.8 | >25 | >25 | ND | >25 | >50 | >50 | ND | ND | >50 | >30 | ND | ND | ND |
| 2 | B | PVO.4 | >25 | >25 | ND | >25 | >50 | >50 | ND | ND | >50 | >30 | ND | ND | ND |

| TIER | CLADE | STRAIN | gp41 | | | | | | | | | | | | pt3 | |
|---|---|---|---|---|---|---|---|---|---|---|---|---|---|---|---|---|
| | | | 3-140 | 3-474 | 3-296 | 3-296 | 3-204 | 3-650 | 3-160 | 3-18 | 3-125 | 3-259 | 3-334 | 3-384 | 3-64 | 3-233 | IGG | POOL |
| 1 | C | MW965.23 | >30 | >30 | >25 | >25 | >25 | >25 | >25 | >25 | >25 | >25 | >25 | >25 | >50 | >50 | 7 | 3.3 |
| 1 | A | DJ263.8 | >30 | >30 | >25 | >25 | >25 | >25 | >25 | >25 | >25 | >25 | >25 | >25 | >50 | >50 | 35 | 248.4 |
| 1 | B | SF162.LS | >30 | >30 | >25 | >25 | >25 | >25 | >25 | >25 | >25 | >25 | >25 | >25 | >50 | >50 | 18 | 13.2 |
| 1 | B | SS1196.1 | >30 | >30 | >25 | >25 | >25 | >25 | >25 | >25 | >25 | >25 | >25 | >25X | >50 | >50 | 69 | 81.2 |
| 1 | B | BaL.26 | >30 | >30 | >25 | >25 | >25 | >25 | >25 | >25 | >25 | >25 | >25 | >25 | >50 | >50 | 21 | 25.6 |
| 2 | B | 6535.3 | ND | ND | ND | ND | ND | ND | ND | >25 | >25 | >25 | >25 | >25 | ND | ND | 689 | >1500 |
| 2 | B | RHPA4259.7 | ND | ND | ND | ND | ND | ND | ND | >25 | >25 | >25 | >25 | >25 | ND | ND | 71 | >1500 |
| 2 | B | TRO.11 | ND | ND | ND | ND | ND | ND | ND | >25 | >25 | >25 | >25 | >25 | ND | ND | 117 | >1500 |
| 2 | B | SC422661.8 | ND | ND | ND | ND | ND | ND | ND | >25 | >25 | >25 | >25 | >25 | ND | ND | 65 | >1500 |
| 2 | B | PVO.4 | ND | ND | ND | ND | ND | ND | ND | >25 | >25 | >25 | >25 | >25 | ND | ND | 193 | >1500 | d

| TIER | CLADE | STRAIN | CD4BS | | | | | | |
|---|---|---|---|---|---|---|---|---|---|
| | | | 4-116 | 4-253 | 4-341 | 4-527 | 4-630 | 4-208 | 4-233 |
| 1 | C | MW965.23 | 5.9 | >50 | 5.2 | >50 | >50 | 2.9 | ND |
| 1 | A | DJ263.8 | >50 | >50 | 0.6 | >50 | 1.9 | >25 | ND |
| 1 | B | SF162.LS | >50 | 1.3 | 2.3 | 0.7 | 1.7 | >25 | ND |
| 1 | B | SS1196.1 | >50 | >50 | >50 | >50 | >50X | >25 | ND |
| 1 | B | BaL.26 | >50 | 8 | 22.1 | >50 | 28 | 17.2 | ND |
| 2 | B | 6535.3 | >100 | >100X | 9.6 | 18.3 | ND | 15.4 | ND |
| 2 | B | RHPA4259.7 | >100 | >100 | >100 | >100 | >50 | >25 | >25 |
| 2 | B | TRO.11 | >100 | >100 | >100 | >100 | >50 | >25 | >25X |
| 2 | B | SC422661.8 | >100 | >100X | >100 | >100 | ND | >25 | >25 |
| 2 | B | PVO.4 | >100 | >100 | >100 | >100 | >50 | >25 | ND |

| TIER | CLADE | STRAIN | CORE | | | | | | | | | | | |
|---|---|---|---|---|---|---|---|---|---|---|---|---|---|---|
| | | | 4-17 | 4-79 | 4-79 | 4-649 | 4-252 | 4-459 | 4-13 | 4-221 | 4-214 | 4-57 | 4-263 | 4-277 | 4-256 | 4-328 |
| 1 | C | MW965.23 | >25 | >25 | >25 | 0.1 | 0.06 | >30 | 1.1 | >100 | >25 | 0.1 | >25 | >25 | 4.5 | >25X |
| 1 | A | DJ263.8 | 0.76 | 0.5 | 0.85 | 6.3 | 0.8 | >30 | 0.7 | 0.6 | 0.6 | 1.6 | >25 | 0.7 | 2.4 | 3.8 |
| 1 | B | SF162.LS | 7.7 | 0.4 | 12.7 | 6.8 | 1.7 | 1.3 | 1.9 | 0.2 | 1 | 3.5 | 3.2 | 1.3 | 8.3 | >25 |
| 1 | B | SS1196.1 | >25 | >25X | >25 | >25 | >50 | >30 | >50 | >100 | >25 | 75.4 | >25X | >25 | >25 | >25 |
| 1 | B | BaL.26 | >25X | 1.4 | >25X | 41.9 | 7.5 | >30 | 6.9 | 2 | 4.7 | 35.7 | >25X | 4.6 | >25X | >25 |
| 2 | B | 6535.3 | >25X | >25X | >25X | 42.9 | >30 | 18.5 | 22.7 | >100 | >25 | 14.5 | 23.5 | >25X | >25X | >25 |
| 2 | B | RHPA4259.7 | >25 | >25 | >25 | >100 | >30 | >30 | >50 | >100 | >25 | >100 | >25 | >25 | >25 | >25 |
| 2 | B | TRO.11 | >25 | >25 | >25 | >100 | >30 | >30 | >50 | >100 | >25 | >100 | >25 | >25 | >25 | >25 |
| 2 | B | SC422661.8 | >25X | >25 | >25X | >100 | >30 | >30 | >50X | >100X | >25 | >100 | >25 | >25 | >25 | >25 |
| 2 | B | PVO.4 | >25 | >25 | >25 | >100 | >30 | >30 | >50 | >100 | >25 | >100 | >25 | >25 | >25 | >25 |

| TIER | CLADE | STRAIN | VL | | | | | CD4i | | | | | | | | | |
|---|---|---|---|---|---|---|---|---|---|---|---|---|---|---|---|---|---|
| | | | 4-150 | 4-366 | 4-117 | 4-251 | 4-395 | 4-42 | 4-8 | 4-653 | 4-554 | 4-441 | 4-433 | 4-164 | 4-174 | 4-103 | 4-31 | 4-288 | 4-652 |
| 1 | C | MW965.23 | 0.04 | 0.09 | >25X | 0.1 | >50 | 0.05 | 0.3 | 0.4 | >30 | 12.8 | 0.7 | >25 | >100 | >100 | >25 | 9.1 | >50 |
| 1 | A | DJ263.8 | 4.4 | 2.6 | >25X | 3.1 | >50 | 15.2 | >25X | >25X | >30 | >30 | >50 | >25X | >100 | >100 | >25 | >25 | >50 |
| 1 | B | SF162.LS | 6.3 | >30 | >25 | 15.3 | >50 | 0.7 | 1.7 | 0.8 | 4.4 | 3.2 | 0.4 | 13 | >100 | 33.5 | >25 | 6.5 | >50 |
| 1 | B | SS1196.1 | >25 | >30 | >25 | >25 | >50 | 8.7 | 6.9 | 5.8 | >30 | >30 | 23.5 | >25 | >100 | >100 | >25 | >25X | >50 |
| 1 | B | BaL.26 | 1.1 | 1.7 | >25X | 3 | >50 | 7.9 | 17.7 | 18.1 | >30 | >30 | 16.1 | >25 | >100 | >100 | >25 | >25 | >50 |
| 2 | B | 6535.3 | >25 | >30X | >25 | >25 | >50 | >50 | >25 | ND | >30 | >50 | >50 | >25 | ND | >100 | ND | >25 | ND |
| 2 | B | RHPA4259.7 | >25 | >30 | >25 | >25 | >50 | >50X | >25X | ND | >30 | >30 | >50 | >50 | ND | >100 | ND | >25 | ND |
| 2 | B | TRO.11 | >25 | >30 | >25 | >25 | >50 | >50X | >25X | >25 | >30 | >30 | >50 | >50 | ND | >100 | ND | >25 | ND |
| 2 | B | SC422661.8 | >25 | >30 | >25 | >25 | >50 | >50 | >25 | ND | >30 | >30 | >50 | >25X | ND | >100 | ND | >25 | ND |
| 2 | B | PVO.4 | >25 | >30 | >25 | >25 | >50 | >50X | >25X | ND | >30 | >30 | >50 | >25 | ND | >100 | ND | >25 | ND |

| TIER | CLADE | STRAIN | gp41 | | | | | | | | | | | | pt4 | |
|---|---|---|---|---|---|---|---|---|---|---|---|---|---|---|---|---|
| | | | 4-20 | 4-163 | 4-613 | 4-357 | 4-380 | 4-95 | 4-157 | 4-104 | 4-63 | 4-147 | 4-251 | 4-283 | 4-342 | IGG | POOL |
| 1 | C | MW965.23 | >25 | >25 | >30 | >30 | >30 | >30 | >50 | >50 | >100 | >25 | >25 | >25 | >50 | 19 | <0.1 |
| 1 | A | DJ263.8 | >25 | >25 | >30 | >30 | >30 | >30 | >50 | >50 | >100 | >25 | >25 | >25 | >50 | 211 | 3.2 |
| 1 | B | SF162.LS | >25 | >25 | >30 | >30 | >30 | >30 | >50 | >50 | >100 | >25 | >25 | >25 | >50 | 99 | 1.4 |
| 1 | B | SS1196.1 | >25 | >25 | >30 | >30 | >30 | >30 | >50 | >50 | >100 | >25 | >25 | >25 | >50 | >250 | 107.1 |
| 1 | B | BaL.26 | >25 | >25 | >30 | >30 | >30 | >30 | >50 | >50 | >100 | >25 | >25 | >25 | >50 | 178 | 14.7 |
| 2 | B | 6535.3 | >25 | >25 | ND | ND | ND | ND | ND | ND | ND | ND | ND | ND | ND | >2000 | 137 |
| 2 | B | RHPA4259.7 | >25 | >25 | ND | ND | ND | ND | ND | ND | ND | ND | ND | ND | ND | 116 | >2000 |
| 2 | B | TRO.11 | >25 | >25 | ND | ND | ND | ND | ND | ND | ND | ND | ND | ND | ND | 88 | 1445 |
| 2 | B | SC422661.8 | >25 | >25 | ND | ND | ND | ND | ND | ND | ND | ND | ND | ND | ND | 298 | 2000 |
| 2 | B | PVO.4 | >25 | >25 | ND | ND | ND | ND | ND | ND | ND | ND | ND | ND | ND | 773 | >2000 |

Figure 26 e

| TIER | CLADE | STRAIN | CD4i | | | | | | VL | gp41 | TIER | CLADE | STRAIN | CD4BS CORE | | gp41 | | |
|---|---|---|---|---|---|---|---|---|---|---|---|---|---|---|---|---|---|---|
| | | | 5-367 | 5-269 | 5-216 | 5-165 | 5-10 | 5-216 | 5-580 | 5-25 | | | | 6-187 | 6-179 | 6-91 | 6-129 | 6-182 |
| 1 | C | MW965.23 | >50 | >25 | >25 | 0.2 | >50 | ND | 1 | >50 | 1 | C | MW965.23 | 0.02 | 0.1 | >50 | >50 | ND |
| 1 | A | DJ263.8 | >50 | >25 | >25 | >25 | >50 | ND | 5.3 | >50 | 1 | A | DJ263.8 | 0.4 | 2.1 | >50 | >50 | ND |
| 1 | B | SF162.LS | >50 | 8.3 | >25 | 2.3 | >50 | ND | <0.01 | >50 | 1 | B | SF162.LS | 1.8 | 1.9 | 12.8 | >50 | ND |
| 1 | B | SS1196.1 | 14.9 | 11 | >25 | 14 | >50 | ND | 15.3 | >50 | 1 | B | SS1196.1 | 14 | >50 | >50 | >50 | ND |
| 1 | B | BaL.26 | >50 | >25 | >25 | >25 | >50 | ND | >25 | >50 | 1 | B | BaL.26 | 16 | 44.1 | >50 | >50 | ND |
| 2 | B | 6535.3 | >50 | >25 | ND | >25 | ND | ND | >25 | >50 | 2 | B | 6535.3 | 7.8 | 27.2 | >50 | ND | ND |
| 2 | B | RHPA4259.7 | >50 | >25 | ND | >25 | ND | ND | >25 | >50 | 2 | B | RHPA4259.7 | >50 | >50 | >50 | >50 | ND |
| 2 | B | TRO.11 | >50 | >25 | ND | >25 | ND | ND | >25 | >50 | 2 | B | TRO.11 | >50 | >50 | >50 | >50 | ND |
| 2 | B | SC422661.8 | >50 | >25 | ND | >25 | ND | ND | >25 | >50 | 2 | B | SC422661.8 | >50 | >50 | >50 | ND | ND |
| 2 | B | PVO.4 | >50 | >25 | ND | >25 | ND | ND | >25 | >50 | 2 | B | PVO.4 | >50 | >50 | >50 | >50 | ND |

Figure 27

Supplementary Table 6. Neutralization screen of plasma samples against standard virus panel. (1)

| | | | | | | | | TZM.bl Neutralization Assay: Plasma ID50 Titer | | | | | | | | |
|---|---|---|---|---|---|---|---|---|---|---|---|---|---|---|---|---|
| Sample ID | Date | Internal Ref | Tier 1 SF162.LS | Tier 1 BaL.26 | Tier 1 SS1196.1 | Tier 2 6535.3 | Tier 2 QH0692.42 | Tier 2 SC422661.8 | Tier 2 PVO.4 | Tier 2 TRO.11 | Tier 2 AC10.0.29 | Tier 2 RHPA4259.8 | Tier 2 THRO4156.18 | Tier 2 REJO4541.67 | Tier 2 TRJO4551.58 | Tier 2 WITO4160.33 | Tier 2 CAAN5342.A2 | Neg. Cont SIVmac251 |
| BWH-2 | 9/8/2010 | WD001 | 20 | 34 | 46 | <20 | <20 | 32 | 41 | <20 | 23 | <20 | 77 | 21 | <20 | 90 | 70 | <20 |
| BWH-7 | 3/16/2011 | WD002 | 45 | 34 | 29 | <20 | 21 | 33 | 32 | 37 | <20 | 32 | 70 | 65 | <20 | 121 | 95 | <20 |
| 01 3587j | 5/11/2011 | WD003 | 1,041 | 73 | 66 | 64 | 27 | 62 | 31 | 31 | 31 | 28 | 54 | 72 | <20 | 69 | 73 | <20 |
| 01 3614l (GAP) | 4/6/2011 | WD004 | 93 | 26 | 67 | 22 | 41 | 94 | 37 | 52 | 33 | 33 | 52 | 88 | 21 | 53 | 96 | <20 |
| CR0462r | 4/14/2011 | WD005 | 339 | 33 | 89 | 24 | 44 | 77 | 39 | 71 | 51 | 31 | 69 | 74 | <20 | 150 | 160 | <20 |
| CRO559 | 12/13/2010 | WD006 | 4,165 | 339 | 113 | 70 | 55 | 249 | 67 | 68 | 1,922 | 76 | 176 | 189 | 30 | 185 | 82 | <20 |
| EH 01 3560C | 10/20/2010 | WD007 | 23 | <20 | 38 | 57 | 34 | 50 | 56 | 39 | 40 | 34 | 81 | 34 | 26 | 92 | 66 | <20 |
| 391368 AG | 10/4/2010 | WD008 | 7,114 | 915 | 165 | 146 | 50 | 1,535 | 470 | 1,050 | 197 | 5,403 | 705 | 401 | 1,535 | 116 | 108 | <20 |
| PMA 373616 | 11/15/2010 | WD009 | 515 | 231 | 81 | 65 | 46 | 78 | 45 | 78 | 44 | 44 | 71 | 74 | <20 | 76 | 73 | <20 |
| 8137 | 2/23/2011 | WD010 | 8,500 | 1,005 | 370 | 184 | 51 | 149 | 51 | 98 | 100 | 105 | 115 | 238 | 21 | 41 | 158 | <20 |
| 8194 | 4/21/2011 | WD011 | 517 | 110 | 118 | 55 | 95 | 127 | 77 | 80 | 43 | 38 | 126 | 94 | 28 | 99 | 93 | <20 |
| 8227 | 10/20/2010 | WD012 | 2,004 | 600 | 166 | 96 | 26 | 44 | <20 | 28 | 27 | 36 | 144 | 393 | <20 | 45 | 59 | <20 |
| 8252 | 3/17/2011 | WD013 | 4,279 | 481 | 159 | 182 | 37 | 118 | 26 | 58 | 21 | 109 | 83 | 839 | <20 | 52 | 164 | <20 |
| 8257 | 1/20/2011 | WD014 | 1,887 | 198 | 103 | 58 | 36 | 67 | 28 | 52 | 52 | 175 | 74 | 107 | <20 | 50 | 67 | <20 |
| 8288 | 11/15/2010 | WD015 | 874 | 99 | 99 | 66 | 52 | 85 | <20 | 65 | 38 | 24 | 63 | 101 | 20 | 32 | 108 | <20 |
| 8293 | 9/14/2010 | WD016 | 1,643 | 172 | 133 | 94 | 78 | 166 | 101 | 86 | 147 | 97 | 150 | 131 | 28 | 115 | 119 | <20 |
| 8333 | 1/20/2011 | WD017 | 6,370 | 1,201 | 296 | 102 | 57 | 198 | 69 | 60 | 37 | 43 | 94 | 214 | 24 | 75 | 55 | <20 |
| FW012 | 9/21/2010 | WD018 | 1,323 | 98 | 40 | <20 | 24 | 43 | 21 | <20 | 37 | 21 | 47 | 45 | <20 | 41 | 26 | <20 |
| FW041 | 1/23/2011 | WD019 | 19,441 | 1,732 | 286 | 242 | 32 | 62 | 27 | 73 | 39 | 104 | 132 | 145 | 20 | 102 | 68 | <20 |
| FW042 | 9/7/2010 | WD020 | 635 | 130 | 157 | 80 | 95 | 173 | 147 | 83 | 62 | 38 | 150 | 115 | 36 | 163 | 130 | <20 |
| FW056 | 11/14/2010 | WD021 | 2,507 | 219 | 94 | 50 | 35 | 43 | 74 | 32 | 35 | 58 | 114 | 83 | <20 | 62 | 69 | <20 |
| FW057 | 11/29/2010 | WD022 | 4,048 | 245 | 144 | 82 | 52 | 112 | 67 | 39 | 37 | 101 | 90 | 115 | 23 | 84 | 80 | <20 |
| CTR 035 | 11/22/2010 | WD023 | 39 | 52 | 32 | <20 | 28 | 69 | 37 | 24 | <20 | 36 | 39 | 55 | <20 | 50 | 32 | <20 |
| CTR 039 | 3/7/2011 | WD024 | 372 | 26 | 57 | 70 | 35 | 121 | <20 | 34 | 35 | 74 | 67 | 95 | 21 | 88 | 60 | <20 |
| CTR 040 JL | 3/9/2011 | WD025 | 1,773 | 113 | 102 | 78 | 47 | 87 | <20 | <20 | 21 | 78 | 99 | 100 | <20 | 76 | <20 | <20 |
| CTR 050 | 9/22/2010 | WD026 | 63 | 37 | 45 | <20 | 69 | 76 | <20 | <20 | <20 | <20 | 83 | 65 | 22 | 85 | 34 | <20 |
| CTR 090 | 8/5/2006 | WD027 | 2,506 | 258 | 71 | 73 | 30 | 80 | 54 | 41 | <20 | <20 | 46 | 66 | 26 | 67 | 56 | <20 |
| CTR 102 | 3/10/2011 | WD028 | 126 | 37 | 43 | <20 | 38 | 89 | 21 | 27 | 26 | 69 | 46 | 33 | <20 | 50 | 32 | <20 |
| CTR 111 | 9/8/2010 | WD029 | 93 | 61 | 65 | 70 | 46 | 110 | <20 | 64 | 27 | 43 | 85 | 95 | 31 | 95 | 89 | <20 |
| CTR 112 | 9/8/2010 | WD030 | 4,161 | 722 | 228 | 132 | 69 | 174 | <20 | 102 | 51 | 26 | 140 | 165 | 37 | 94 | 134 | <20 |
| CTR 113 | 9/13/2010 | WD031 | 24 | 33 | 80 | 45 | 70 | 83 | <20 | 63 | 27 | 28 | 69 | 32 | 40 | 83 | 68 | <20 |
| CTR 116 DS | 9/15/2010 | WD032 | 14,728 | 850 | 397 | 188 | 38 | 59 | <20 | 42 | 23 | 91 | 111 | 157 | <20 | 81 | 121 | <20 |
| CTR 117 MS | 9/15/2010 | WD033 | 1,341 | 122 | 153 | 126 | 46 | 79 | <20 | 64 | <20 | 63 | 183 | 54 | <20 | 134 | 109 | <20 |
| CTR 118 LC | 9/20/2010 | WD034 | 8,395 | 2,151 | 413 | 215 | 20 | 353 | <20 | 101 | 95 | 164 | 133 | 160 | 40 | 133 | 251 | <20 |
| CTR 123 JM | 9/22/2010 | WD035 | 102 | 68 | 30 | 99 | 77 | 123 | <20 | 25 | <20 | 67 | 103 | 58 | <20 | 125 | 108 | <20 |
| CTR 127 RB | 9/28/2010 | WD036 | 262 | 109 | 21 | 20 | <20 | 54 | <20 | <20 | <20 | 31 | 39 | 26 | 26 | 62 | 58 | <20 |
| CTR 132 | 9/29/2010 | WD037 | 62 | 71 | 32 | 53 | 24 | 94 | 41 | <20 | <20 | 39 | 66 | 36 | 23 | 91 | 83 | <20 |
| CTR 133 HML | 10/4/2010 | WD038 | 1,446 | 258 | 100 | 63 | 34 | 141 | 37 | 27 | 26 | 69 | 96 | 49 | <20 | 70 | 103 | <20 |
| CTR 134 JFU | 10/4/2010 | WD039 | 116 | 41 | 32 | 82 | 35 | 132 | <20 | 64 | 41 | 43 | 96 | 92 | 26 | 104 | 104 | <20 |
| CTR 143 VS | 10/12/2010 | WD040 | 5,896 | 362 | 125 | 93 | 41 | 138 | 42 | 78 | 103 | 173 | 110 | 347 | 21 | 94 | 150 | <20 |
| CTR 144 WG | 10/12/2010 | WD041 | 358 | 103 | 62 | 50 | 30 | 121 | <20 | 59 | 47 | 56 | 71 | 93 | 21 | 138 | 78 | <20 |
| CTR 146 ML | 10/18/2010 | WD042 | 189 | 55 | 78 | 74 | 43 | 147 | 26 | 81 | 67 | 59 | 114 | 133 | 36 | 146 | 155 | <20 |
| CTR 147 RC | 10/18/2010 | WD043 | 600 | 200 | 113 | 111 | 53 | 163 | <20 | 65 | 46 | 74 | 166 | 50 | 23 | 217 | 244 | <20 |
| CTR 148 CB | 10/19/2010 | WD044 | 4,395 | 217 | 62 | 82 | 20 | 78 | <20 | 60 | 33 | 75 | 85 | 79 | <20 | 91 | 72 | <20 |
| CTR 149 TZ | 10/19/2010 | WD045 | 1,013 | 298 | 76 | 71 | 35 | 93 | 21 | 44 | 37 | 86 | 80 | 92 | 20 | 86 | 96 | <20 |
| CTR 154 HAG | 11/2/2010 | WD046 | 118 | 76 | 70 | 63 | 40 | 74 | 21 | 52 | 30 | 42 | 75 | 60 | 24 | 88 | 59 | <20 |
| CTR 157 AF | 11/2/2010 | WD047 | 93 | 92 | 43 | 33 | <20 | 65 | <20 | <20 | <20 | 24 | 65 | 59 | <20 | 83 | 60 | <20 |
| CTR 159 KW | 11/10/2010 | WD048 | 2,451 | 287 | 122 | 93 | 63 | 151 | <20 | 64 | 36 | 87 | 167 | 154 | <20 | 119 | 140 | <20 |
| CTR 161 SM | 11/10/2010 | WD049 | 732 | 84 | 183 | 63 | 63 | 105 | <20 | 63 | 66 | 38 | 166 | 146 | 41 | 137 | 107 | <20 |
| CTR 164 | 11/8/2010 | WD050 | 10,723 | 766 | 220 | 124 | 50 | 164 | 90 | 90 | 58 | 135 | 127 | 144 | 50 | 102 | 113 | <20 |

Figure 28A

Supplementary Table 6. Neutralization screen of plasma samples against standard virus panel. (2)

TZM.bl Neutralization Assay: Plasma ID50 Titer

| Sample ID | Date | Internal Ref | Tier 1 SF162.LS | Tier 1 BaL.26 | Tier 1 SS1196.1 | Tier 2 6535.3 | Tier 2 QH0692.42 | Tier 2 SC422661.8 | Tier 2 PVO.4 | Tier 2 TRO.11 | Tier 2 AC10.0.29 | Tier 2 RHPA4259. | Tier 2 THRO4156.1 | Tier 2 REJO4541.67 | Tier 2 TRJO4551.58 | Tier 2 WITO4160.33 | Tier 2 CAAN5342.A | Neg. Cont SIVmac251. |
|---|---|---|---|---|---|---|---|---|---|---|---|---|---|---|---|---|---|---|
| CTR 171 | 12/6/2010 | WD052 | 641 | 54 | 38 | 47 | 21 | 83 | <20 | 41 | 24 | 54 | 116 | 81 | 24 | 70 | 79 | <20 |
| CTR 174 | 12/14/2010 | WD053 | 6,991 | 354 | 175 | 93 | 49 | 119 | <20 | 56 | 45 | 24 | 106 | 169 | 75 | 104 | 87 | <20 |
| CTR 183 | 12/20/2010 | WD054 | 1,071 | 361 | 185 | 213 | 110 | 466 | 33 | 157 | 77 | 225 | 78 | 175 | 47 | 244 | 251 | <20 |
| CTR 184 | 12/20/2010 | WD055 | 6,136 | 676 | 109 | 152 | 61 | 118 | 87 | 72 | 92 | 181 | 78 | 175 | 47 | 120 | 152 | <20 |
| CTR 185 | 12/20/2010 | WD056 | 478 | 64 | 29 | 31 | <20 | 63 | 32 | <20 | <20 | <20 | 51 | 43 | <20 | 87 | 102 | <20 |
| CTR 188 | 12/20/2010 | WD057 | 1,649 | 251 | 72 | 42 | 63 | 125 | 68 | 58 | 41 | 77 | 115 | 95 | 21 | 135 | 178 | <20 |
| CTR 190 | 1/10/2011 | WD058 | 42 | <20 | <20 | 63 | 20 | 53 | 25 | 29 | 66 | <20 | 46 | 44 | <20 | 86 | 77 | <20 |
| CTR 197 | 1/24/2011 | WD059 | 6,568 | 538 | 144 | 132 | 72 | 208 | 39 | 57 | 70 | 124 | 86 | 156 | <20 | 101 | 119 | <20 |
| CTR 199 | 1/24/2011 | WD060 | 4,316 | 464 | 141 | 102 | 37 | 122 | 40 | 70 | 58 | 116 | 91 | 179 | <20 | 123 | 116 | <20 |
| CTR 200 | 1/25/2011 | WD061 | 14,526 | 1,183 | 202 | 111 | 91 | 207 | 44 | 96 | 53 | 106 | 116 | 236 | 26 | 94 | 95 | <20 |
| CTR 203 | 1/25/2011 | WD062 | 9,250 | 756 | 278 | 121 | 36 | 421 | 80 | 77 | <20 | 891 | 129 | 162 | 44 | 228 | 264 | <20 |
| CTR 205 | 2/1/2011 | WD063 | 311 | 109 | 41 | 69 | 33 | 97 | 29 | 46 | 61 | 78 | 66 | 75 | 25 | 207 | 112 | <20 |
| CTR 207 | 2/1/2011 | WD064 | 17,380 | 509 | 233 | 190 | 140 | 2,066 | 186 | 616 | 126 | 2,694 | 205 | 306 | 197 | 169 | 163 | <20 |
| CTR 210 | 2/7/2011 | WD065 | 1,649 | 98 | 71 | 108 | 79 | 87 | 26 | 83 | 85 | 77 | 101 | 49 | 33 | 156 | 98 | <20 |
| CTR 213 | 2/8/2011 | WD066 | 4,092 | 452 | 184 | 195 | 85 | 118 | 45 | 90 | 51 | 73 | 198 | 258 | 27 | 151 | 91 | <20 |
| CTR 215 | 2/8/2011 | WD067 | 1,505 | 93 | 44 | 44 | 36 | 44 | <20 | <20 | <20 | 22 | 65 | 39 | 23 | 125 | 69 | <20 |
| CTR 217 | 2/10/2011 | WD068 | 2,942 | 109 | 44 | 66 | 21 | 50 | <20 | <20 | 26 | 37 | 43 | 32 | <20 | 59 | 92 | <20 |
| CTR 218 | 2/10/2011 | WD069 | 177 | 45 | 40 | 28 | <20 | 36 | 25 | 31 | 30 | <20 | 42 | 57 | 25 | 63 | 111 | <20 |
| CTR 223 | 2/17/2011 | WD070 | 270 | 106 | 82 | 34 | 34 | 34 | 21 | 25 | 32 | <20 | 33 | <20 | <20 | 44 | 76 | <20 |
| CTR 224 | 2/17/2011 | WD071 | 104 | 21 | 39 | 52 | 26 | 51 | 28 | 26 | 48 | 25 | 52 | 40 | <20 | 66 | 94 | <20 |
| CTR 225 | 2/17/2011 | WD072 | 3,379 | 258 | 40 | 89 | 26 | 201 | <20 | 30 | 36 | 32 | 64 | 94 | 23 | 21 | 77 | <20 |
| CTR 226 | 2/20/2011 | WD073 | 605 | 89 | 20 | 76 | <20 | 81 | 21 | 57 | 63 | 48 | 50 | 80 | <20 | 89 | 97 | <20 |
| CTR 228 | 2/22/2011 | WD074 | 1,723 | 283 | 64 | 73 | 39 | 81 | 34 | 69 | 79 | 53 | 51 | 72 | <20 | 112 | 64 | <20 |
| CTR 229 | 2/22/2011 | WD075 | 1,621 | 202 | 32 | 47 | 31 | 135 | <20 | <20 | <20 | 25 | 45 | 86 | <20 | 35 | 56 | <20 |
| CTR 231 | 2/23/2011 | WD076 | 207 | 443 | 88 | 69 | 29 | 94 | 50 | 48 | 58 | 44 | 87 | 152 | 30 | 73 | 101 | <20 |
| CTR 232 | 2/23/2011 | WD077 | 2,682 | 218 | 33 | <20 | <20 | 85 | <20 | <20 | <20 | 24 | 54 | 39 | <20 | <20 | 57 | <20 |
| CTR 235 | 2/28/2011 | WD078 | 2,789 | 170 | 46 | 61 | <20 | 76 | <20 | 33 | 50 | 44 | 55 | 69 | <20 | 75 | 73 | <20 |
| CTR 237 | 3/2/2011 | WD079 | 5,439 | 534 | 136 | 160 | 43 | 156 | <20 | 34 | 49 | 47 | 34 | 104 | 32 | 24 | 103 | <20 |
| CTR 238 | 3/2/2011 | WD080 | 195 | 38 | 31 | 109 | <20 | 109 | 27 | 28 | 60 | 54 | 55 | 90 | 30 | 64 | 89 | <20 |
| CTR 239 | 3/2/2011 | WD081 | 3,472 | 283 | 162 | 463 | 44 | 117 | 41 | 86 | 204 | 96 | 143 | 336 | 61 | 97 | 150 | <20 |
| CTR 240 | 3/2/2011 | WD082 | 3,454 | 305 | 68 | 62 | 33 | 123 | <20 | 32 | <20 | 31 | 56 | 90 | <20 | 65 | 86 | <20 |
| CTR 241 | 3/2/2011 | WD083 | 2,745 | 277 | 65 | 74 | <20 | 110 | <20 | 24 | <20 | 35 | 74 | 154 | <20 | 80 | 114 | <20 |
| CTR 242 | 3/6/2011 | WD084 | 15,329 | 1,033 | 142 | 115 | 29 | 89 | <20 | 34 | 22 | 78 | 86 | 191 | 27 | 64 | 129 | <20 |
| CTR 243 | 3/6/2011 | WD085 | 2,302 | 307 | 66 | 258 | 23 | 190 | 49 | 91 | 179 | 72 | 110 | 251 | 74 | 78 | 232 | <20 |
| CTR 247 | 3/7/2011 | WD086 | 2,470 | 530 | 51 | 51 | <20 | 68 | <20 | 29 | 41 | 28 | 106 | 82 | <20 | 83 | 66 | <20 |
| CTR 253 SP | 3/16/2011 | WD087 | 617 | 402 | 110 | 124 | 64 | 156 | 20 | 71 | 49 | 85 | 89 | 120 | 62 | 85 | 208 | <20 |
| CTR 255 | 3/22/2011 | WD088 | 5,515 | 313 | 43 | 71 | <20 | 64 | <20 | <20 | 75 | 81 | 77 | 52 | <20 | 89 | 45 | <20 |
| CTR 256 | 3/22/2011 | WD089 | 536 | 69 | 30 | 77 | <20 | 41 | 30 | 42 | 72 | 58 | 62 | 62 | <20 | 94 | 75 | <20 |
| CTR 260 | 3/28/2011 | WD090 | 106 | 64 | 27 | 99 | <20 | 34 | <20 | 58 | 76 | 38 | 201 | 77 | <20 | 150 | 91 | <20 |
| CTR 264 | 3/29/2011 | WD091 | 2,341 | 296 | 93 | 54 | <20 | 35 | 55 | 34 | 68 | 31 | 81 | 58 | <20 | 74 | 76 | <20 |
| CTR 265 | 3/29/2011 | WD092 | 83 | 36 | <20 | 60 | <20 | 40 | 23 | 51 | 30 | 31 | 51 | 79 | 32 | 71 | 81 | <20 |
| CTR 268 | 4/6/2011 | WD093 | 158 | 84 | 22 | 103 | 44 | 63 | 36 | 36 | 62 | 64 | 44 | 61 | 24 | 72 | 65 | <20 |
| CTR 272 | 4/12/2011 | WD094 | 1,469 | 100 | 39 | 119 | <20 | 54 | <20 | 24 | <20 | 41 | 74 | 110 | <20 | 78 | 60 | <20 |
| CTR 273 | 4/12/2011 | WD095 | 1,625 | 360 | 69 | 115 | 68 | 120 | <20 | 38 | <20 | 50 | 127 | 120 | 27 | 118 | 138 | <20 |
| CTR 276 | 4/19/2011 | WD096 | 75 | 38 | <20 | 97 | <20 | 81 | 49 | 78 | <20 | 39 | 78 | 64 | 47 | 83 | 126 | <20 |
| CTR 281 | 4/25/2011 | WD097 | 4,845 | 391 | 89 | 207 | 35 | 118 | 56 | 91 | 53 | 54 | 81 | 123 | 32 | 69 | 86 | <20 |
| CTR 283 | 4/26/2011 | WD098 | 1,406 | 330 | 43 | 90 | <20 | <20 | <20 | <20 | 75 | 81 | 38 | 188 | <20 | 38 | 94 | <20 |
| CTR 291 | 5/3/2011 | WD099 | 736 | 48 | 24 | 113 | <20 | 89 | 29 | 67 | 52 | 34 | 95 | 42 | <20 | 63 | 130 | <20 |
| CTR 294 | 5/8/2011 | WD100 | 200 | 43 | 28 | 47 | 36 | 49 | 27 | 56 | 38 | <20 | 82 | 83 | 25 | 105 | 128 | <20 |
| CTR 295 | 5/9/2011 | WD101 | 72 | 46 | 23 | 93 | 67 | 81 | 70 | 49 | 93 | 39 | 73 | 73 | 62 | 102 | 78 | <20 |
| Naive Serum | | Neg. Control | <20 | <20 | <20 | <20 | <20 | <20 | <20 | <20 | <20 | <20 | <20 | <20 | <20 | <20 | <20 | <20 |

Figure 28B

Supplementary Table 6. Neutralization screen of plasma samples against standard virus panel. (3)

TZM.bl Neutralization Assay: Plasma ID50 Titer

| Sample ID | Date | Internal Ref | Tier 1 SF162.LS | Tier 1 BaL.26 | Tier 1 SS1196.1 | Tier 2 6535.3 | Tier 2 QH0692.42 | Tier 2 SC422661.8 | Tier 2 PVO.4 | Tier 2 TRO.11 | Tier 2 AC10.0.29 | Tier 2 RHPA4259.7 | Tier 2 THRO4156.18 | Tier 2 REJO4541.67 | Tier 2 TRJO4551.58 | Tier 2 WITO4160.33 | Tier 2 CAAN5342.A | Neg. Cont MuLV |
|---|---|---|---|---|---|---|---|---|---|---|---|---|---|---|---|---|---|---|
| 8280 | 10/22/2009 | WD102 | 7,052 | 393 | 143 | 44 | <20 | 77 | 39 | 79 | 66 | 38 | 90 | 49 | <20 | 58 | 45 | 63 |
| CTR31 VB HRES | 12/1/2009 | WD103 | 9,448 | 1,409 | 337 | 192 | <20 | 88 | 66 | 107 | 91 | 59 | 146 | 178 | <20 | 98 | 81 | 46 |
| CTR22 | 1/13/2010 | WD104 | 2,490 | 532 | 82 | 26 | <20 | <20 | 54 | 53 | 32 | 22 | 74 | 50 | <20 | 40 | 46 | <20 |
| CTR 20 KH | 1/25/2010 | WD106 | 371 | 67 | 56 | <20 | <20 | <20 | 39 | 51 | 30 | 24 | 52 | 21 | <20 | 32 | 39 | 40 |
| BWH-4-BZ | 3/2/2010 | WD107 | 63 | 81 | 112 | <20 | <20 | 20 | 54 | 59 | 49 | <20 | 62 | 29 | <20 | 76 | 55 | 71 |
| CTR 44 DM | 3/15/2010 | WD108 | 4,471 | 109 | 85 | <20 | <20 | 39 | 38 | <20 | <20 | <20 | 58 | <20 | <20 | <20 | <20 | <20 |
| CTR 45-LD | 3/22/2010 | WD109 | 654 | 78 | 96 | <20 | <20 | 26 | 84 | 44 | 38 | <20 | 75 | 34 | <20 | 67 | 59 | 80 |
| MC CR0030Q | 3/23/2010 | WD110 | 935 | 152 | 116 | <20 | <20 | 53 | 54 | 51 | 53 | 43 | 79 | <20 | <20 | 59 | 32 | 68 |
| CTR 48 NM | 3/29/2010 | WD111 | #### | 1,173 | 192 | 225 | 22 | 54 | 58 | 61 | 54 | 57 | 126 | 170 | <20 | 85 | <20 | 97 |
| CTR 51-DR | 4/7/2010 | WD112 | 25,539 | 2,101 | 452 | 352 | <20 | 61 | 109 | 57 | 38 | 57 | 115 | 80 | <20 | 132 | 50 | 52 |
| CTR 52-HS | 4/13/2010 | WD113 | 6,722 | 429 | 172 | 38 | 22 | 102 | 88 | 67 | 32 | 56 | 83 | 49 | <20 | 74 | 40 | 55 |
| CTR 53-AA | 4/14/2010 | WD114 | 16,471 | 1,136 | 363 | 68 | 32 | 60 | 117 | 97 | 54 | 83 | 163 | 333 | <20 | 412 | <20 | 79 |
| CTR 55-BW | 4/20/2010 | WD115 | 12,552 | 243 | 172 | 58 | <20 | 92 | 67 | 93 | 38 | 59 | 98 | 54 | <20 | 127 | <20 | 56 |
| CTR 63 RR | 5/25/2010 | WD116 | 1,640 | 109 | 72 | <20 | <20 | 75 | 52 | 70 | 37 | 24 | 92 | <20 | <20 | 81 | 23 | 94 |
| CTR 64-JO | 5/26/2010 | WD117 | 18,655 | 1,678 | 243 | 85 | <20 | 262 | 295 | 162 | 71 | 76 | 224 | 138 | 28 | 221 | 225 | 70 |
| CTR 66 RH | 5/26/2010 | WD118 | 12,358 | 928 | 319 | 83 | <20 | 60 | 36 | 87 | 45 | 30 | 77 | 154 | <20 | 50 | 59 | 25 |
| CTR 76 WM | 6/22/2010 | WD119 | >43,740 | 514 | 198 | 26 | 32 | 73 | 81 | 87 | 43 | 35 | 103 | 90 | <20 | 52 | <20 | 73 |
| CTR 80 CC | 7/13/2010 | WD120 | 6,685 | 515 | 179 | 100 | 22 | 107 | 76 | 124 | 95 | 98 | 114 | 154 | 63 | 119 | 113 | 74 |
| CTR 92 | 8/3/2010 | WD122 | 321 | 40 | 118 | <20 | <20 | 161 | 109 | 115 | 149 | 41 | 130 | 166 | <20 | 128 | 109 | 75 |
| CTR 98 MI | 8/10/2010 | WD123 | 653 | 257 | 145 | <20 | 23 | 78 | 65 | 107 | 104 | 46 | 128 | 101 | <20 | 129 | 75 | 52 |
| 8272 | 8/4/2010 | WD124 | 1,205 | 223 | 81 | 26 | <20 | 54 | 30 | 62 | 50 | 35 | 102 | 76 | 25 | 82 | 32 | 51 |
| CTR 106 KP | 8/24/2010 | WD125 | 2,144 | 242 | 149 | <20 | <20 | 67 | 33 | 71 | 104 | 61 | 147 | 101 | <20 | 72 | 52 | 62 |
| CTR 109 | 9/1/2010 | WD126 | 16,595 | 627 | 220 | 76 | <20 | <20 | 26 | 41 | <20 | <20 | 135 | 28 | <20 | <20 | <20 | <20 |
| CTR 130 | 9/29/2010 | WD127 | 1,603 | 62 | 110 | <20 | 24 | 61 | 69 | 94 | 22 | 52 | 85 | 61 | <20 | 72 | 68 | 71 |
| CTR 220(UCLA 120) | 2/14/2011 | WD128 | 10,023 | 480 | 294 | 79 | 29 | 97 | 43 | 106 | 24 | 36 | 140 | 113 | <20 | 71 | 39 | 24 |
| CTR 299 | 5/15/2011 | WD129 | 7,181 | 544 | 323 | 152 | 29 | 160 | 92 | 158 | 61 | 66 | 233 | 206 | 48 | 200 | 156 | 65 |
| CTR 300 | 5/17/2011 | WD130 | 11,385 | 277 | 176 | 140 | 48 | 250 | 77 | 115 | 100 | 92 | 141 | 139 | <20 | 177 | 54 | 56 |
| CTR 302 | 5/17/2011 | WD131 | 557 | 31 | <20 | <20 | <20 | <20 | <20 | 39 | <20 | <20 | 70 | 30 | <20 | 80 | 36 | <20 |
| CTR 311 | 5/23/2011 | WD133 | 365 | 36 | 122 | <20 | 37 | <20 | 39 | 54 | 64 | <20 | 85 | 35 | <20 | 65 | 39 | 82 |
| GS 0131966 | 5/18/2011 | WD134 | 510 | <20 | 85 | <20 | 28 | <20 | 34 | 33 | 38 | 31 | 73 | 35 | <20 | 69 | 31 | 73 |
| CTR 312 | 5/23/2011 | WD135 | 6,522 | 197 | 107 | 93 | 68 | 61 | 45 | 67 | 60 | 51 | 105 | 112 | <20 | 87 | 92 | 94 |
| CTR 313 | 5/23/2011 | WD136 | 1,097 | <20 | 42 | <20 | 24 | 82 | 82 | 131 | 49 | 37 | 56 | 47 | <20 | 72 | 35 | 76 |
| CTR 316 | 5/31/2011 | WD137 | 3,142 | 86 | 96 | 57 | 44 | 70 | 32 | 50 | 23 | 38 | 60 | 54 | <20 | 75 | 49 | 89 |
| CTR 323 | 6/14/2011 | WD140 | 1,471 | 225 | 112 | 40 | 46 | 90 | 52 | 65 | 50 | 57 | 96 | 143 | 30 | 94 | 49 | 70 |
| CTR 325 | 6/15/2011 | WD141 | 5,762 | 104 | 196 | 51 | 44 | 86 | 106 | 117 | 56 | 66 | 97 | 143 | <20 | 170 | 44 | 85 |
| CTR 326 | 6/19/2011 | WD142 | 3,137 | 152 | 122 | 27 | 38 | 116 | 74 | 71 | 28 | 55 | 65 | 76 | <20 | 113 | 39 | 34 |
| CTR335 | 6/26/2011 | WD143 | <20 | <20 | <20 | <20 | <20 | <20 | 21 | 30 | <20 | <20 | 40 | 25 | <20 | <20 | 29 | <20 |
| CTR 340 | 6/10/2011 | WD144 | 6,800 | 141 | 297 | 66 | 30 | 105 | 66 | 79 | 60 | 154 | 111 | 171 | <20 | 64 | 44 | <20 |
| CTR 342 | 6/11/2011 | WD145 | 13,975 | 222 | 331 | 150 | 96 | 264 | 110 | 147 | 108 | 120 | 168 | 135 | 33 | 124 | 103 | 49 |
| CTR 343 | 6/12/2011 | WD146 | 3,038 | 252 | 601 | 114 | 173 | 858 | 554 | 374 | 114 | 527 | 267 | 983 | 138 | 282 | 145 | 38 |
| CTR 347 | 7/18/2011 | WD148 | 354 | <20 | 57 | <20 | <20 | 21 | <20 | 31 | <20 | <20 | 61 | 31 | <20 | 31 | <20 | <20 |
| CTR 348 | 7/19/2011 | WD149 | 587 | 98 | 176 | 54 | 50 | 27 | 22 | 49 | 78 | <20 | 99 | 71 | <20 | 33 | 46 | 57 |
| CTR 351 | 8/1/2011 | WD150 | 7,352 | 439 | 176 | 195 | 49 | 195 | 46 | 74 | 95 | 127 | 115 | 171 | <20 | 98 | 64 | 56 |
| CTR 353 | 8/1/2011 | WD151 | 468 | <20 | 62 | <20 | 25 | 65 | 30 | 36 | 115 | 37 | 61 | 44 | <20 | 59 | 52 | 44 |

Figure 28C

Supplementary Table 6. Neutralization screen of plasma samples against standard virus panel. (4)

| | | | | | | TZM.bl Neutralization Assay: Plasma ID50 Titer | | | | | | | | | | |
|---|---|---|---|---|---|---|---|---|---|---|---|---|---|---|---|---|
| | | Tier 1 | Tier 1 | Tier 1 | Tier 1 | Tier 2 | Tier 2 | Tier 2 | Tier 2 | Tier 2 | Tier 2 | Tier 2 | Tier 2 | Tier 2 | Tier 2 | Neg. Cont |
| Sample ID | Date | Internal Ref | SF162.LS | Bal.26 | SS1196.1 | 6535.3 | QH0692.42 | SC422661.8 | PVO.4 | TRO.11 | AC10.0.29 | RHPA4259.7 | THRO4156.18 | REJO4541.67 | TRJO4551.58 | WITO4160.33 | CAAN5342.A1 | MuLV |
| CTR 352 | 8/1/2011 | WD152 | 1,337 | 410 | 122 | 76 | 34 | 78 | 34 | 46 | 55 | <20 | 53 | 92 | <20 | 36 | 25 | <20 |
| CTR 354 | 8/2/2011 | WD153 | 1,493 | 82 | 171 | 98 | 49 | 85 | 64 | 42 | <20 | <20 | 74 | 110 | <20 | 69 | 63 | 22 |
| CTR 356 | 8/2/2011 | WD154 | 8,215 | 710 | 216 | 167 | 63 | 156 | 39 | 202 | 150 | 51 | 166 | 175 | <20 | 138 | 119 | 54 |
| CTR 360 | 8/8/2011 | WD155 | 3,075 | 41 | 108 | 43 | 69 | 65 | 47 | 48 | 33 | 30 | 99 | 65 | <20 | 72 | 54 | 43 |
| CTR 365 | 8/17/2011 | WD156 | 11,712 | <20 | 29 | <20 | <20 | <20 | <20 | <20 | <20 | <20 | 40 | <20 | <20 | 45 | 36 | <20 |
| CTR 369 | 8/22/2011 | WD157 | 22 | <20 | 44 | <20 | 24 | <20 | 25 | <20 | <20 | <20 | 41 | <20 | <20 | 26 | 39 | 24 |
| CTR 368 | 8/22/2011 | WD158 | 438 | 623 | 155 | 106 | 61 | 32 | <20 | 27 | 28 | 22 | 116 | 77 | <20 | 65 | 45 | 48 |
| CTR 373 | 8/28/2011 | WD159 | 3,760 | 477 | 90 | 66 | <20 | 52 | <20 | 56 | 48 | <20 | 112 | 39 | <20 | 37 | 72 | <20 |
| MEF 407V07001474 | 8/24/2011 | WD160 | 1,047 | 167 | 82 | 20 | 64 | 33 | <20 | 38 | 50 | <20 | 79 | 37 | <20 | 51 | 63 | 41 |
| CTR 374 | 8/29/2011 | WD161 | 2,686 | 628 | 231 | 31 | 45 | 105 | <20 | 90 | 84 | 46 | 74 | 67 | <20 | 53 | 62 | 25 |
| CTR 376 | 8/30/2011 | WD162 | 836 | 84 | 135 | 25 | 32 | 27 | <20 | 57 | 83 | 21 | 59 | 29 | <20 | 80 | 116 | 42 |
| CTR 377 | 8/31/2011 | WD163 | 6,131 | 639 | 157 | 51 | 53 | <20 | <20 | 51 | 24 | 34 | 65 | 67 | <20 | 38 | 52 | 49 |
| CTR 379 | 9/5/2011 | WD164 | 310 | <20 | 36 | 26 | 37 | <20 | <20 | <20 | <20 | <20 | 56 | 29 | <20 | 79 | 38 | 63 |
| CTR 386 | 9/11/2011 | WD165 | 779 | 263 | 84 | 56 | 44 | 41 | <20 | 35 | <20 | <20 | 89 | 93 | <20 | 46 | 50 | <20 |
| CTR 390 | 9/12/2011 | WD166 | 7,627 | 284 | 161 | 65 | 100 | 31 | <20 | 41 | 57 | 50 | 108 | 65 | <20 | 68 | 73 | 31 |
| CTR 394 | 9/14/2011 | WD167 | 13,541 | 1,406 | 392 | 126 | 110 | 257 | <20 | 211 | 231 | 111 | 169 | 277 | 64 | 143 | 220 | 35 |
| CTR 395 | 9/14/2011 | WD168 | 2,986 | 134 | 89 | 65 | <20 | <20 | <20 | 49 | 109 | 37 | 62 | 70 | <20 | 56 | 53 | 35 |
| FCH2000-03-FW057 | 10/10/2011 | WD170 | 8,411 | 349 | 193 | 101 | 58 | 98 | 26 | 40 | <20 | 78 | 58 | 129 | <20 | 52 | 50 | 70 |
| CTR 405 | 10/10/2011 | WD171 | 5,099 | 781 | 590 | 323 | 162 | 401 | 87 | 932 | 450 | 71 | 93 | 82 | <20 | 246 | 97 | 46 |
| CTR 409 | 10/12/2011 | WD172 | 9,227 | 383 | 150 | 80 | 42 | <20 | <20 | <20 | <20 | 34 | 73 | 43 | <20 | 84 | 44 | <20 |
| CTR 410 | 10/12/2011 | WD173 | 3,812 | 245 | 163 | 134 | 56 | 87 | <20 | 115 | 70 | 122 | 136 | 159 | 39 | 109 | 71 | 50 |
| CTR 414 | 10/16/2011 | WD174 | 63 | <20 | 30 | <20 | 33 | <20 | <20 | 50 | 21 | 56 | 68 | <20 | <20 | 104 | 58 | <20 |
| CR0559M ESR | 10/18/2011 | WD175 | 9,924 | 1,302 | 291 | 117 | 133 | 278 | <20 | 97 | 1,869 | 70 | 86 | 141 | 34 | 110 | 73 | 29 |
| CTR 416 | 10/16/2011 | WD176 | 6,036 | 257 | 100 | 195 | 97 | 51 | <20 | 67 | 38 | 58 | 137 | 82 | <20 | 72 | 90 | <20 |
| CTR 417 | 10/17/2011 | WD177 | 2,501 | 487 | 124 | 106 | 332 | 66 | <20 | 83 | 24 | 106 | 92 | 114 | <20 | 75 | 50 | 47 |
| CTR 418 | 10/18/2011 | WD178 | 1,669 | 165 | 140 | 85 | <20 | 102 | <20 | 41 | <20 | 113 | 107 | 139 | <20 | 93 | 55 | 38 |
| CTR 420 | 10/23/2011 | WD179 | 367 | 78 | 98 | <20 | 60 | 107 | <20 | 106 | 61 | 59 | 108 | 160 | <20 | 92 | 127 | 50 |
| CTR 422 | 10/23/2011 | WD180 | 7,522 | 94 | 129 | <20 | 43 | 53 | <20 | 45 | <20 | 75 | 75 | 21 | <20 | 26 | 87 | <20 |
| CTR 423 | 10/25/2011 | WD181 | 243 | 135 | 74 | 26 | 52 | 81 | <20 | 50 | 34 | 45 | 85 | 44 | <20 | 56 | 59 | <20 |
| CTR 401 | 10/30/2011 | WD182 | 793 | 64 | 84 | 31 | 83 | 79 | <20 | 33 | <20 | 54 | 106 | 98 | <20 | 115 | 75 | <20 |
| CTR 426 | 10/30/2011 | WD183 | >43,740 | 1,913 | 571 | 280 | 67 | 822 | 110 | 338 | 263 | 113 | 153 | 263 | 23 | 221 | 115 | <20 |
| CTR 428 | 11/7/2011 | WD184 | 770 | 87 | 101 | 65 | 46 | 77 | <20 | 68 | 27 | 61 | 77 | 122 | <20 | 92 | 52 | 63 |
| BWH-3 SP | 11/9/2011 | WD185 | 7,640 | <20 | 41 | <20 | 40 | 36 | <20 | 22 | <20 | 47 | 49 | 40 | <20 | 93 | 38 | 45 |
| CTR 436 | 11/20/2011 | WD186 | 2,123 | 157 | 95 | 26 | 100 | 74 | <20 | 49 | 27 | 52 | 66 | 64 | <20 | <20 | 61 | 38 |
| CTR 437 | 11/21/2011 | WD187 | 243 | <20 | 39 | <20 | 94 | 50 | <20 | 44 | <20 | 31 | 72 | 34 | <20 | 68 | 66 | <20 |
| CTR 439 | 11/27/2011 | WD188 | 433 | 44 | 77 | <20 | 64 | 130 | <20 | 99 | 40 | 75 | 155 | 138 | <20 | 108 | 108 | 35 |
| CTR 440 | 11/29/2011 | WD189 | 963 | 243 | 102 | <20 | 94 | 124 | <20 | 91 | 21 | 62 | 173 | 79 | <20 | 110 | 107 | <20 |

Figure 28D

| | | anti-core antibodies | | | | | | | | | | | |
|---|---|---|---|---|---|---|---|---|---|---|---|---|---|
| Strain | Tier/Clade | 1-74 | 6-179 | 1-479 | 1-621 | 1-664 | 1-687 | 1-752 | 2-491 | 3-124 | 3-518 | 4-53 | 4-57 |
| MW965.23 | 1/C | >50 | 0.1 | <0.02 | 9.8 | >50 | >50 | >25 | <0.01 | >25 | >25 | >25 | 0.1 |
| DJ263.8 | 1/A | 0.16 | 2.1 | 0.7 | >50 | 2.9 | >50 | 1.7 | 0.3 | >25 | >25 | 0.5 | 1.6 |
| SF162.LS | 1/B | >50 | 1.9 | 1.1 | >50 | 1.1 | >50 | 2.9 | 1.6 | 0.2 | >25 | 0.4 | 3.5 |
| SS1196.1 | 1/B | 13 | >50 | 30.4 | >50 | >50 | >50 | >25 | 21.4 | >25 | >25 | >25X | 75.4 |
| BaL.26 | 1/B | 2.75 | 44.1 | 12.2 | >50 | 19.2 | >50 | >25 | 8.2 | >25 | >25 | 1.4 | 35.7 |
| 6535.3 | 2/B | 42.3 | 27.2 | 24.2 | >50 | 19.6 | >50 | >25 | 4.6 | ND | >25 | >25X | 14.5 |
| RHPA4259.7 | 2/B | >50 | >50 | >50 | >50 | >50 | >50 | >25 | >25 | ND | >25 | >25 | >100 |
| TRO.11 | 2/B | >50 | >50 | >50 | >50 | >50 | >50 | >25 | ND | ND | >25 | >25 | >100 |
| CAAN5342.A2 | 2/B | ND | ND | ND | ND | ND | ND | ND | >25 | ND | ND | ND | ND |
| SC422661.8 | 2/B | >50 | >50 | >50 | >50 | >50 | >50 | >25 | 79.1 | ND | >25 | >25 | >100 |
| THRO4156.18 | 2/B | ND | ND | ND | ND | ND | ND | ND | >25X | ND | ND | ND | ND |
| PVO.4 | 2/B | >50 | >50 | >50 | >50 | >50 | >50 | >25 | ND | ND | >25 | >25 | >100 |

| | | anti-core antibodies | | | | | | | | | | | | |
|---|---|---|---|---|---|---|---|---|---|---|---|---|---|---|
| Strain | Tier/Clade | 4-77 | 4-79 | 4-133 | 4-214 | 4-221 | 4-252 | 4-256 | 4-263 | 4-277 | 4-328 | 4-459 | 4-649 | b12 |
| MW965.23 | 1/C | >25 | >25 | 1.1 | >25 | >100 | 0.06 | 4.5 | >25 | >25 | >25X | >30 | 0.1 | 0.2 |
| DJ263.8 | 1/A | 0.76 | 0.85 | 0.7 | 0.6 | 0.6 | 0.8 | 2.4 | >25 | 0.7 | 3.8 | >30 | 6.3 | >25 |
| SF162.LS | 1/B | 7.7 | 12.7 | 1.9 | 1 | 0.2 | 1.7 | 8.3 | 3.2 | 1.3 | >25 | 1.3 | 6.8 | 0.01 |
| SS1196.1 | 1/B | >25 | >25 | >50 | >25 | >100 | >30 | >25 | >25X | >25 | >25 | >30 | >50 | 0.3 |
| BaL.26 | 1/B | >25X | >25X | 6.9 | 4.7 | 2 | 7.5 | >25X | >25X | 4.6 | >25 | >30 | 41.9 | 0.2 |
| 6535.3 | 2/B | >25X | >25X | 22.7 | >25 | >100 | >30 | >25X | 23.5 | >25X | >25 | 18.5 | 42.9 | 1.4 |
| RHPA4259.7 | 2/B | >25 | >25 | >50 | >25 | >100 | >30 | >25 | >25 | >25 | >25 | >30 | >100 | 0.1 |
| TRO.11 | 2/B | >25 | >25 | >50 | >25 | >100 | >30 | >25 | >25 | >25 | >25 | >30 | >100 | >50 |
| CAAN5342.A2 | 2/B | ND | ND | ND | ND | ND | ND | ND | ND | ND | ND | ND | ND | ND |
| SC422661.8 | 2/B | >25X | >25X | >50X | >25 | >100X | >30 | >25 | >25 | >25 | >25 | >30 | >100 | 0.2 |
| THRO4156.18 | 2/B | ND | ND | ND | ND | ND | ND | ND | ND | ND | ND | ND | ND | ND |
| PVO.4 | 2/B | >25 | >25 | >50 | >25 | >100 | >30 | >25 | >25 | >25 | >25 | >30 | >100 | >50 |

Figure 31A

| mAb | F176A | I184A | E172A | H374A | T373A | L288A | G380A | I449A |
|---|---|---|---|---|---|---|---|---|
| | | V2 | | | | not on surface | | |
| 1-74 | 133 | 138 | 162 | 99 | 102 | 14 | 107 | 48 |
| 1-479 | 87 | 70 | 84 | 130 | 97 | 26 | 89 | 26 |
| 1-621 | 36 | 106 | 160 | 94 | 110 | 28 | 75 | 79 |
| 1-664 | 108 | 154 | 130 | 145 | 99 | 24 | 81 | 57 |
| 1-687 | 92 | 182 | 112 | 65 | 96 | 26 | 42 | 65 |
| 1-752 | 82 | 117 | 132 | 122 | 86 | 17 | 52 | 43 |
| 2-491 | 79 | 76 | 82 | 122 | 104 | 17 | 92 | 31 |
| 3-124 | 85 | 66 | 70 | 87 | 71 | 24 | 72 | 34 |
| 3-518 | 103 | 131 | 83 | 53 | 66 | 17 | 34 | 58 |
| 4-53 | 87 | 110 | 95 | 137 | 107 | 22 | 82 | 53 |
| 4-57 | 129 | 69 | 75 | 149 | 121 | 25 | 101 | 31 |
| 4-77 | 126 | 116 | 90 | 130 | 104 | 20 | 76 | 52 |
| 4-79 | 89 | 124 | 124 | 99 | 101 | 19 | 105 | 57 |
| 4-133 | 127 | 101 | 122 | 114 | 93 | 16 | 74 | 49 |
| 4-214 | 77 | 85 | 95 | 147 | 115 | 16 | 87 | 39 |
| 4-221 | 95 | 164 | 157 | 97 | 88 | 9 | 94 | 62 |
| 4-252 | 102 | 110 | 117 | 101 | 91 | 20 | 89 | 47 |
| 4-256 | 130 | 145 | 141 | 110 | 108 | 29 | 98 | 48 |
| 4-263 | 100 | 101 | 92 | 132 | 106 | 26 | 69 | 59 |
| 4-277 | 103 | 98 | 96 | 124 | 98 | 19 | 80 | 51 |
| 4-328 | 96 | 106 | 105 | 122 | 96 | 24 | 59 | 53 |
| 4-459 | 102 | 126 | 101 | 113 | 138 | 31 | 64 | 55 |
| 4-649 | 112 | 73 | 60 | 136 | 94 | 20 | 70 | 19 |
| 6-179 | 94 | 54 | 84 | 111 | 88 | 15 | 50 | 46 |
| b12 | 110 | 111 | 89 | 96 | 61 | 14 | 70 | 33 |
| 1-79 | 96 | 82 | 91 | 132 | 127 | 102 | 94 | 93 |

| mAb | origin K350A | origin V489A | origin V488A | origin K487A | origin K490A | origin I491A | origin E492A | turned y,-90 D402A | turned x,-90 W400A | origin R273A |
|---|---|---|---|---|---|---|---|---|---|---|
| 1-74 | 87 | 100 | 127 | 107 | 120 | 83 | 104 | 124 | 113 | 70 |
| 1-479 | 87 | 72 | 54 | 59 | 90 | 64 | 68 | 91 | 69 | 42 |
| 1-621 | 56 | 95 | 144 | 125 | 133 | 78 | 127 | 117 | 71 | 81 |
| 1-664 | 82 | 128 | 128 | 99 | 127 | 78 | 109 | 112 | 78 | 75 |
| 1-687 | 63 | 80 | 111 | 80 | 115 | 63 | 98 | 114 | 91 | 59 |
| 1-752 | 69 | 94 | 101 | 83 | 109 | 77 | 94 | 81 | 54 | 52 |
| 2-491 | 67 | 63 | 54 | 65 | 85 | 70 | 96 | 86 | 71 | 46 |
| 3-124 | 57 | 61 | 57 | 46 | 82 | 61 | 94 | 94 | 81 | 37 |
| 3-518 | 51 | 52 | 80 | 81 | 101 | 65 | 104 | 122 | 76 | 48 |
| 4-53 | 100 | 95 | 81 | 55 | 100 | 117 | 102 | 109 | 80 | 65 |
| 4-57 | 80 | 52 | 46 | 55 | 77 | 72 | 96 | 142 | 105 | 34 |
| 4-77 | 99 | 89 | 87 | 89 | 105 | 111 | 140 | 88 | 67 | 75 |
| 4-79 | 79 | 110 | 79 | 69 | 95 | 88 | 117 | 100 | 81 | 71 |
| 4-133 | 85 | 77 | 83 | 87 | 94 | 96 | 127 | 77 | 78 | 84 |
| 4-214 | 75 | 79 | 71 | 125 | 148 | 77 | 97 | 88 | 87 | 63 |
| 4-221 | 77 | 152 | 141 | 82 | 95 | 122 | 131 | 96 | 77 | 83 |
| 4-252 | 65 | 101 | 99 | 79 | 123 | 101 | 117 | 83 | 71 | 69 |
| 4-256 | 66 | 98 | 114 | 72 | 104 | 109 | 108 | 109 | 92 | 54 |
| 4-263 | 66 | 93 | 98 | 68 | 79 | 134 | 143 | 106 | 117 | 81 |
| 4-277 | 62 | 80 | 78 | 74 | 86 | 85 | 114 | 109 | 77 | 52 |
| 4-328 | 64 | 77 | 82 | 66 | 113 | 117 | 125 | 91 | 95 | 73 |
| 4-459 | 49 | 81 | 76 | 37 | 58 | 107 | 122 | 103 | 65 | 50 |
| 4-649 | 63 | 40 | 49 | 46 | 70 | 61 | 74 | 85 | 64 | 20 |
| 6-179 | 65 | 52 | 63 | 60 | 95 | 71 | 101 | 80 | 61 | 48 |
| b12 | 39 | 72 | 80 | 58 | 95 | 115 | 142 | 92 | 58 | 54 |
| 1-79 | 113 | 95 | 97 | 94 | 96 | 81 | 93 | 89 | 94 | 90 |

Figure 31D

HIV-1 ANTI-CORE NEUTRALIZING ANTIBODIES THAT TARGET A CONFORMATIONAL EPITOPE WITHIN THE ALPHA5-HELIX OF GP120

FIELD

This invention relates to antibodies directed to epitopes of Human Immunodeficiency Virus, or HIV, especially the preparation and use of highly neutralizing antibodies directed to HIV gp120 envelope protein, in the vaccination and treatment of HIV-infected patients.

BACKGROUND

Acquired immunodeficiency syndrome (AIDS) is caused by a retrovirus identified as the human immunodeficiency virus (HIV). The immune response to HIV infection in long-term non-progressors suggests that specific viral immunity may limit infection and the symptoms of disease. Rare HIV infected individuals show broadly neutralizing IgG antibodies in their serum but little is known regarding the specificity and activity of these antibodies despite their potential importance in designing effective vaccines. No single characteristic yet correlates with protective immunity. In animal models, passive transfer of neutralizing antibodies can also contribute to protection against virus challenge. Neutralizing antibody responses can also be developed in HIV-infected individuals and are associated with lower viral loads in long-term non-progressors. Though this neutralizing antibody response is uncommon, it is directed largely against the Env protein of the virus.

A number of immunologic abnormalities have been described in AIDS including abnormalities in B-cell function, abnormal antibody response, defective monocyte cell function, impaired cytokine production, depressed natural killer and cytotoxic cell function, and defective ability of lymphocytes to recognize and respond to soluble antigens. Other immunologic abnormalities associated with AIDS have been reported. Among the more important immunologic defects in patients with AIDS is the depletion of the T4 helper/inducer lymphocyte population.

The HIV env protein has been extensively described, and the amino acid and RNA sequences encoding HIV env from a number of HIV strains are known (Modrow, S. et al., J. Virology 61(2): 570 (1987). The HIV virion is covered by a membrane or envelope derived from the outer membrane of host cells. The membrane contains a population of envelope glycoproteins (gp 160) anchored in the membrane bilayer at their carboxyl terminal region. Each glycoprotein contains two segments. The N-terminal segment, called gp120 by virtue of its relative molecular weight of about 120 kD, protrudes into the aqueous environment surrounding the virion. The C-terminal segment, called gp41, spans the membrane. gp120 and gp 41 are covalently linked by a peptide bond that is particularly susceptible to proteolytic cleavage. McCune et al., EPO Application No. 0 335 635, priority 28 Mar. 88 and references cited therein, herein incorporated by reference.

Several approaches to an AIDS vaccine have been proposed, including inactivated and attenuated virus vaccines, subunit vaccines from virus-infected cells, recombinantly produced viral antigens, vaccines based on synthetic peptides, anti-idiotypic vaccines, and viral carrier-based vaccines, however no vaccination study published to date has provided protection against challenge with virus. Several reviews of HIV vaccine development have been published, e.g. Lasky, (1989), Newmark, (Jun. 23, 1988), and Fauci et al., (1 Mar. 1989).

However, there have been problems including reversion of attenuated virus vaccines; soliciting partial immune response; not eliciting cellular immunity; and the variability and mutability of HIV itself. These problems have frustrated the development of HIV therapies.

Other approaches to HIV therapeutic and prophylactic treatments have included making highly neutralized antibodies for HIV treatment. There have been many years of extensive HIV research in cloning and making monoclonal antibodies by various techniques for targeting CD4 and for neutralizing HIV. These techniques usually involve self-fusion or phage display techniques. A limited number of monoclonal antibodies produced so far are broadly neutralizing to HIV. Among those broadly neutralizing monoclonal antibodies is the phage display antibody, B12. Typically, in making HIV neutralizing antibodies using phage display techniques, random combinations of heavy and light chains are combined and a random pair is selected; in this instance, B12 was shown effective. Monoclonal antibody B12 is a broadly neutralizing antibody which prevents HIV infection in Macaques. Another broadly neutralizing antibody includes 2G12, which, atypically, has a structure which has yet to be seen in any other antibody with three combining sites. The structure of 2G12 has yet to be reproduced.

It has been found that certain people develop antibodies to HIV, which are broadly neutralizing antibodies, which means that their antibodies can neutralize many strains of HIV in their sera. While such patients do not cure their own infection, they are able to inhibit it. When the antibody sees the virus, the virus mutates away from the antibody. These people continue to make antibodies even as the virus keeps mutating. Antibodies can be protective against initial HIV infection in passive transfer experiments in non-human primates and can modulate viral load during infection. Mascola, 2000; Shibata, 1999; Veazey, 2003; Parren, 2001; Mascola, 1999; Trkola, 2005; Wei, 2003; Frost, 2005. Based on these observations, it has been proposed that such antibodies may be important components of a preventative vaccine. Burton, 2004; Mascola, 2007; Karlsson Hedestam, 2008; McMichael, 2006; Zolla-Pazner, 2004.

These Rare HIV infected patients develop high titers of broadly neutralizing antibodies. But, despite intensive study over two decades, only a small number of well-characterized monoclonal antibodies broadly neutralize HIV efficiently in vitro and only a fraction of these prevent infection of non-human primates, as discussed herein, Mascola, 2000; Shibata, 1999, Veazey, 2003; Parren, 2001; Mascola, 1999. At present, broadly neutralizing antibodies from non-progressor patients and/or slow progressor patients have not been made or isolated. It is therefore a continuing need to identify and produce neutralizing antibodies for the development of HIV therapeutics and vaccines.

Citation of the above documents or any references cited herein is not intended as an admission that any of the foregoing is pertinent prior art. All statements as to the date or representation as to the contents of these documents is based on the information available to the applicant and does not constitute any admission as to the correctness of the dates or contents of these documents.

SUMMARY

The invention described herein provides for neutralizing antibodies to HIV and method of using and making such HIV neutralizing antibodies ("HIV neutralizing antibodies"). In certain embodiments, these HIV neutralizing antibodies can be derived from non-progressor and slow-progressor HIV patients.

This invention is particularly directed to HIV neutralizing antibodies comprising at least one of an antibody, or antigen binding portion thereof, which comprises a binding region binds to an antigenic epitope on gp120, or a portion of the antigenic epitope, wherein the antigenic epitope is on the same face of gp120 as a CD4 binding site. The antigenic epitope may also be on the same face as the binding site for a b12 antibody. An aspect of the invention provides for antibodies, or an antigen binding portion thereof, which binds to a new the antigenic epitope comprises gp120$^{core}$, which binds to the same face of gp120 as b12 and CD4.

It is an aspect of the invention to provide for an antibody, or antigen binding portion thereof, comprising a binding region which comprises a CDR3 region comprising at least one of SEQ ID NOs: 1-630, or fragments or derivatives thereof. The antibodies which bind to a CDR3 region further may bind to epitopes, or portions of epitopes, comprising V3, gp41, VL, CD4i or CD4bs. In yet another aspect, the invention provides for a vaccine comprising at least one antibody of the invention and a pharmaceutically acceptable carrier.

Another aspect of the invention provides for a method of inhibiting virus replication or spread to additional host cells or tissues comprising contacting a mammalian cell with at least one antibody of the invention. An aspect of the invention further provides for a method for treating a mammal with infected with HIV administering to said mammal a pharmaceutical composition comprising at least one antibody according to the invention.

It is a further aspect of the invention to provide for a method for vaccinating a mammal from HIV infection. The vaccines or antibody pharmaceutical compositions of this invention may be administered alone or in combination with other HIV antigens, and in one or several immunization doses. It is further an aspect of the invention to vaccinate a mammal by administering epitopes that bind the antibodies, comprising any one of SEQ. ID No. 1-630, or any combination thereof.

The objects of this invention are accomplished by the preparation and administration an HIV antibody preparation which is suitable for administration to a human or non-human primate patient having or at risk of having HIV infection, in an amount and according to an immunization schedule sufficient to induce a protective immune response against HIV.

It is therefore an object of this invention to provide for compositions of broadly neutralizing antibodies that can elicit a protective immune response against HIV infection. It is a further object of this invention to provide methods for preparing and administering such compositions.

These and other objects of some exemplary embodiments will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments without departing from the spirit thereof. Additional features may be understood by referring to the accompanying drawings, which should be read in conjunction with the following detailed description and examples.

A) Flow cytometry plots of peripheral blood monocular cells from four HIV patients stained with anti-CD 19 and biotin-gp140. B) Distribution of gp140 binders and non-binders among all antibodies cloned. C) Igκ and Igλ expression among all gp140 binding antibodies. The number in the center of the pie charts indicates total number of antibodies analyzed, each pie slice represents a unique Ig heavy and light chain pair and the size of the slice is proportional to the number of clonal members. Each clonal family shaded throughout and unique antibodies that are not members of clones are not shaded. D) gp140 binding ELISA results for a set of representative antibodies cloned from gp140 binding memory B cells from patient 1 (left), patient 2 (middle), and from IgG B cells that did not bind to gp140 from patient 2 as control (right). Each line represents an individual antibody. One line shows the binding characteristics of the anti-gp140 antibody b12, (Burton, 1991), another line is a negative control antibody mGO53 (Wardemann, 2003). Antibody concentration in µg/ml is on the X-axis and optical density values on the Y-axis.

Figure 2:
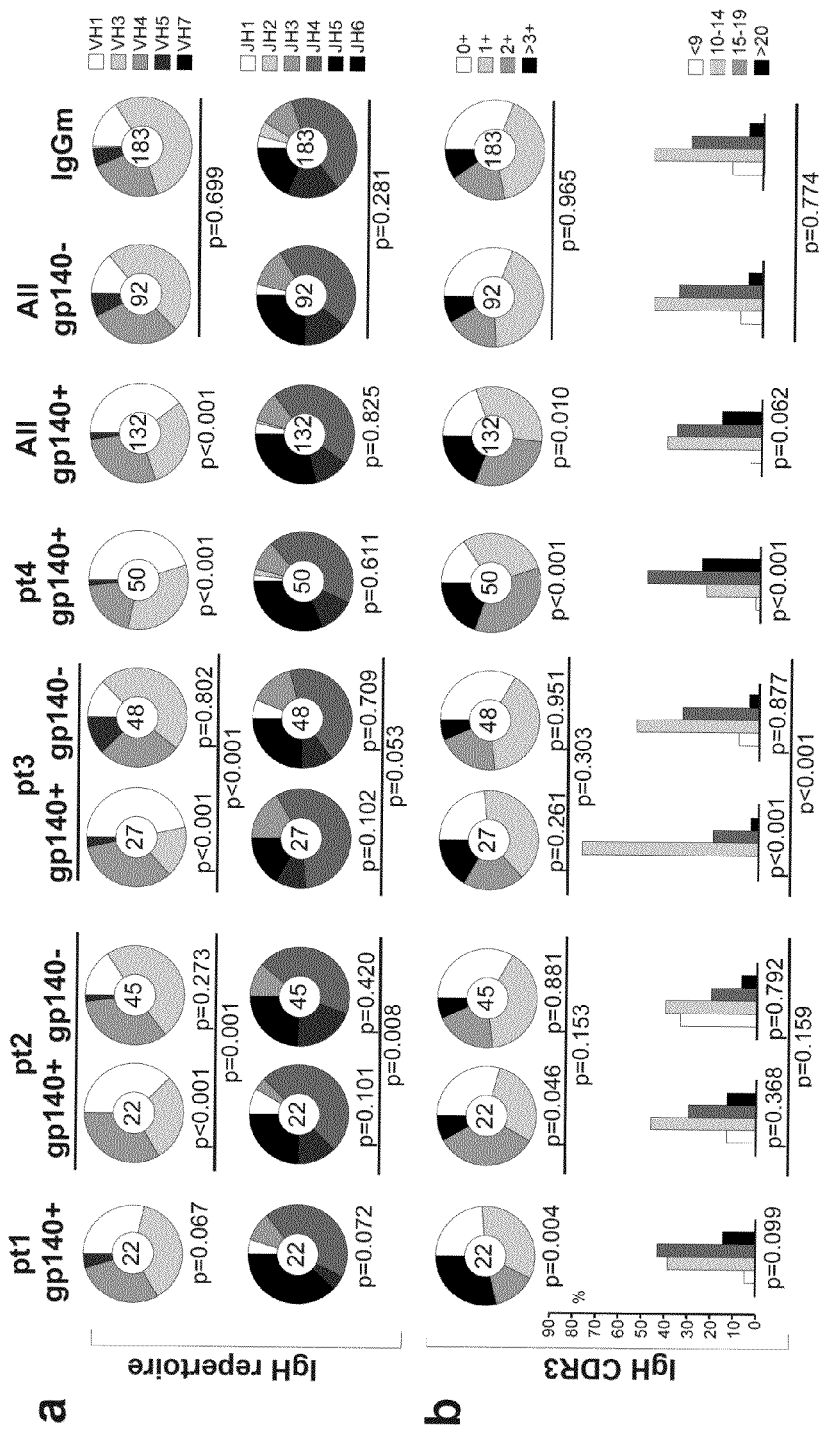
Figure 2:
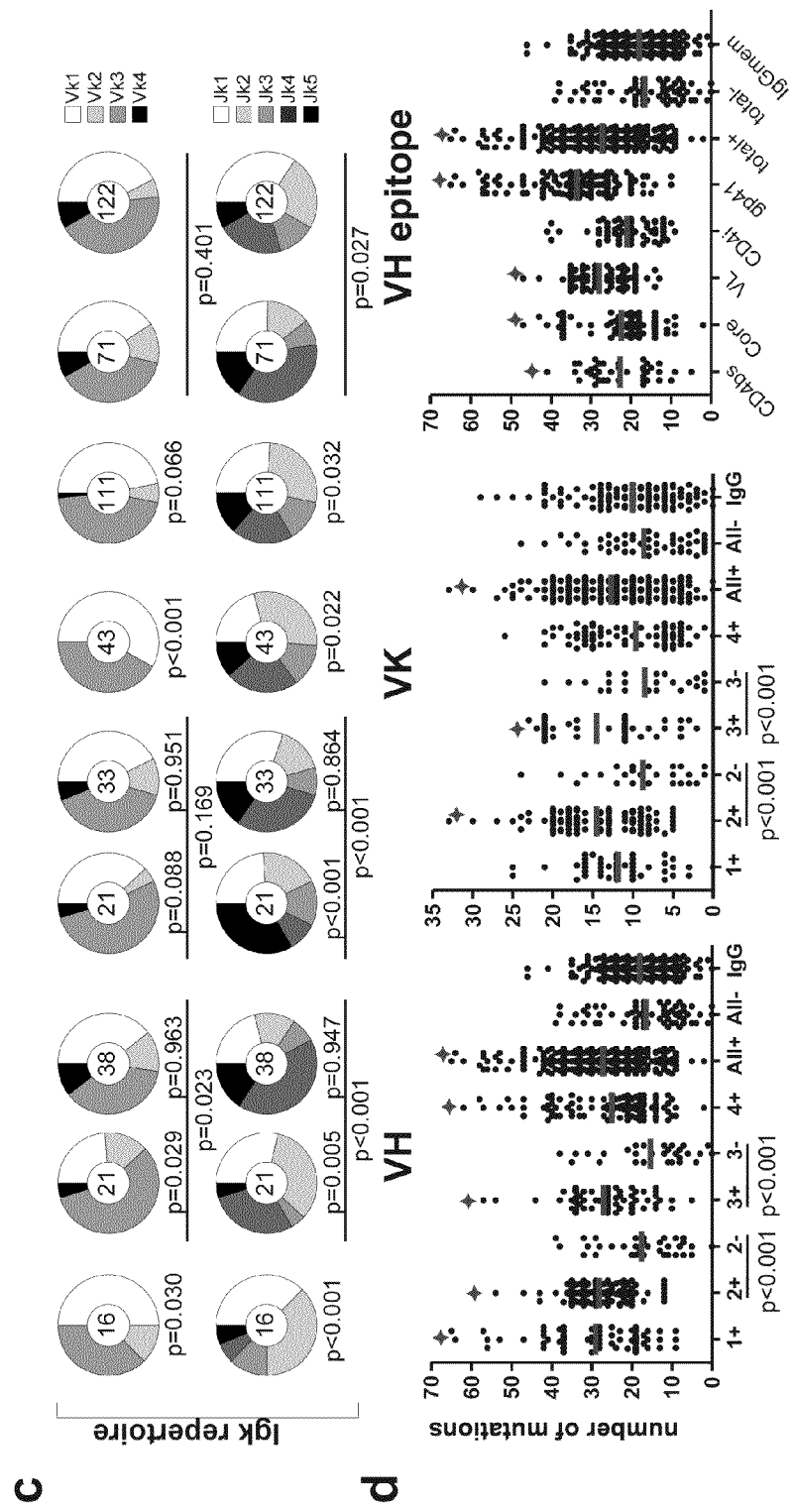

FIG. 2. Anti-gp140 Antibody Repertoire.

Top line indicates patient number and whether the antibodies bind to gp140. IgGm are previously published IgG memory antibody controls {Tiller, 2007}. Each clone is represented once irrespective of clone size, and somatic variants are not considered. A) IgH repertoire analysis comparing $V_H$ (top) and $J_H$ (bottom). Each slice represents a $V_H$ family or $J_H$ as indicated at right. B) IgH CDR3 positive charges (top, pies) and length (bottom, histograms). Each pie slice or histogram bar is shaded to indicate number of positive charges or amino acids as indicated. C) Igκ repertoire comparing Vκ (top) and Jκ (bottom). Each slice represents a Vκ family or Jκ as indicated. D) Graphs show numbers of mutations per antibody for $V_H$ (left) grouped by patient, Vκ (middle) grouped by patient, and $V_H$ (right) for all antibodies to a specific epitope as indicated. Stars indicate p values ≤0.001. P values were calculated by comparison to the pool of gp140 non-reactive antibodies except those below the lines, which refer to the paired samples. P values for Ig gene repertoire analyses were calculated by 2×5 Fisher's Exact Test and Chi-Square test. Statistical analyses for mutation numbers were performed using non-paired two-tailed Student's t test.

Figure 3:
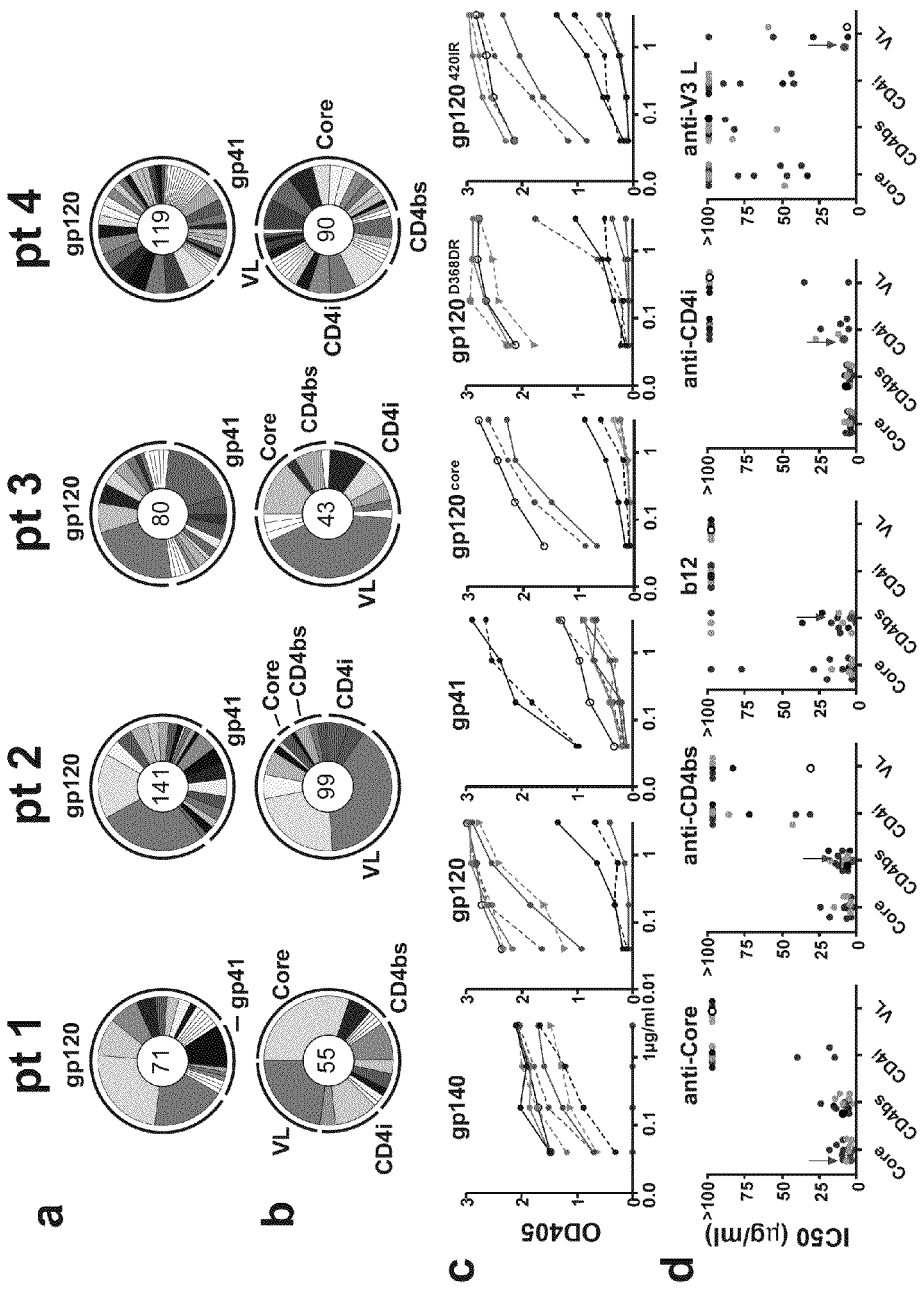

FIG. 3. Anti.gp140 Mapping by ELISA.

Figure 6:
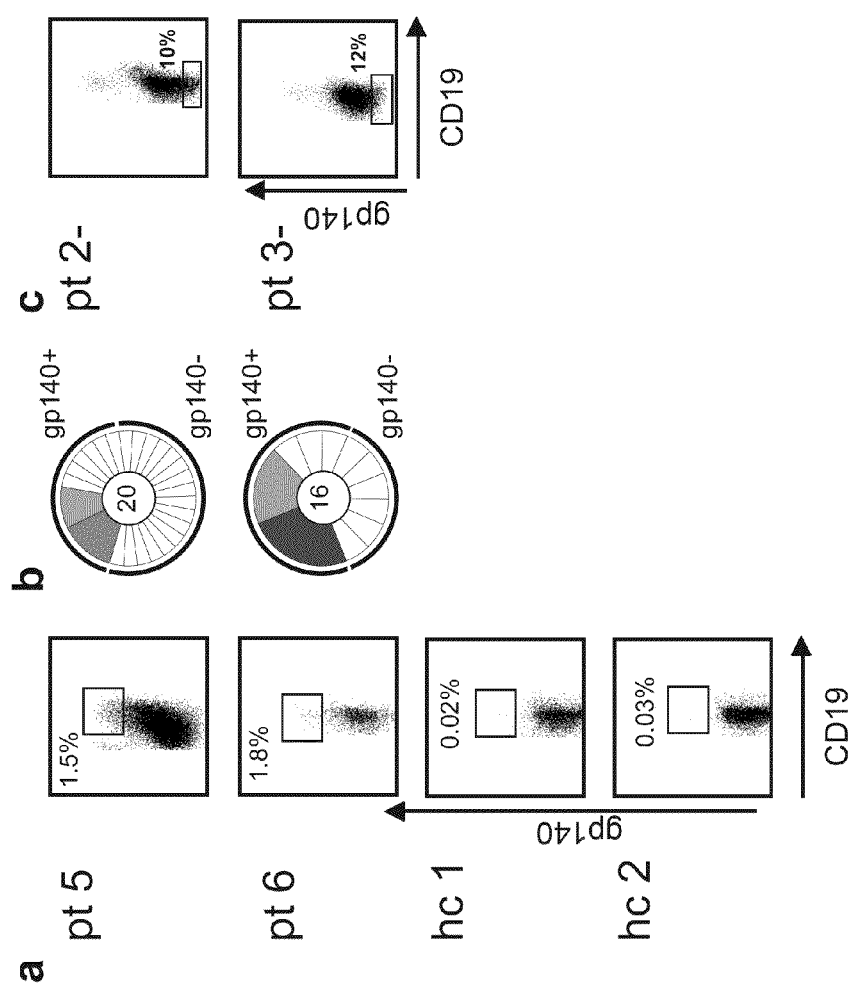

A) Pie charts show relative distribution of anti-gp120 and anti-gp41 antibodies among all anti-gp140 antibodies cloned from patients 1-4 (see also FIG. 6 an FIGS. 15-22 for additional patients). B) Pie charts show relative distribution of antibodies binding to gp120, gp120$^{core}$, gp120$^{1420R}$ but not to gp120$^{D368R}$ (CD4bs), gp120, gp120$^{D368R}$ but not to gp120$^{1420R}$ (C04i), gp120, gp120$^{D368R}$, gp120$^{1420R}$ but not gp120$^{core}$ (VL), and gp120, gp120$^{D368R}$, gp120$^{1420R}$ and gp120$^{core}$ (Core). C) Representative ELISA results for binding to gp140, gp120, gp41, gp120$^{core}$, gp120$^{D368R}$, and gp120$^{1420R}$. Solid lines show 447-52D (anti-VL, {Gorny, 1992}), 2F5 (anti-gp41, {Buchacher, 1994}), b12 (anti-CD4gs, {Burton, 1991}), neg. control antibody mGO53 {Wardemann, 2003}, 4-221 (anti-Core), dashed lines show 2-59 (anti-VL), 3-384 (anti-gp41), 2-1262 (anti-CD4bs). D) Competition ELISA for reactivity with gp120. b12, 1-64 anti-CD4bs, 2-491 anti-Core, 1-182 anti-CD41, and 1-79 anti-V3L were biotin labeled. Inhibition of binding 10 gp120 was measured by ELISA in competition experiments with unlabeled antibodies from patient 1, 2, 3, and 4. Each dot indicates the IC50 for an individual antibody (see also Supplementary Table 4 for the exact concentrations and IC50s). The arrows show the self-inhibitory activity of the biotinylated antibody. Non-biotinylated b12 is indicated as black, 447-52D as open circle. The blocking antibodies are grouped according to their epitopes. The IC50 for unlabeled antibody that corresponds precisely to the biotin labeled indicator was 5 µg/ml for b12, 4.6 µg/ml for 1-64, 5.4 µg/ml for 2-491, 9.2 µg/ml for 1-182, and 7.5 µg/ml for 1-79 (each indicated with arrows). Antibodies at the top of each graph did not inhibit binding.

Figure 4:
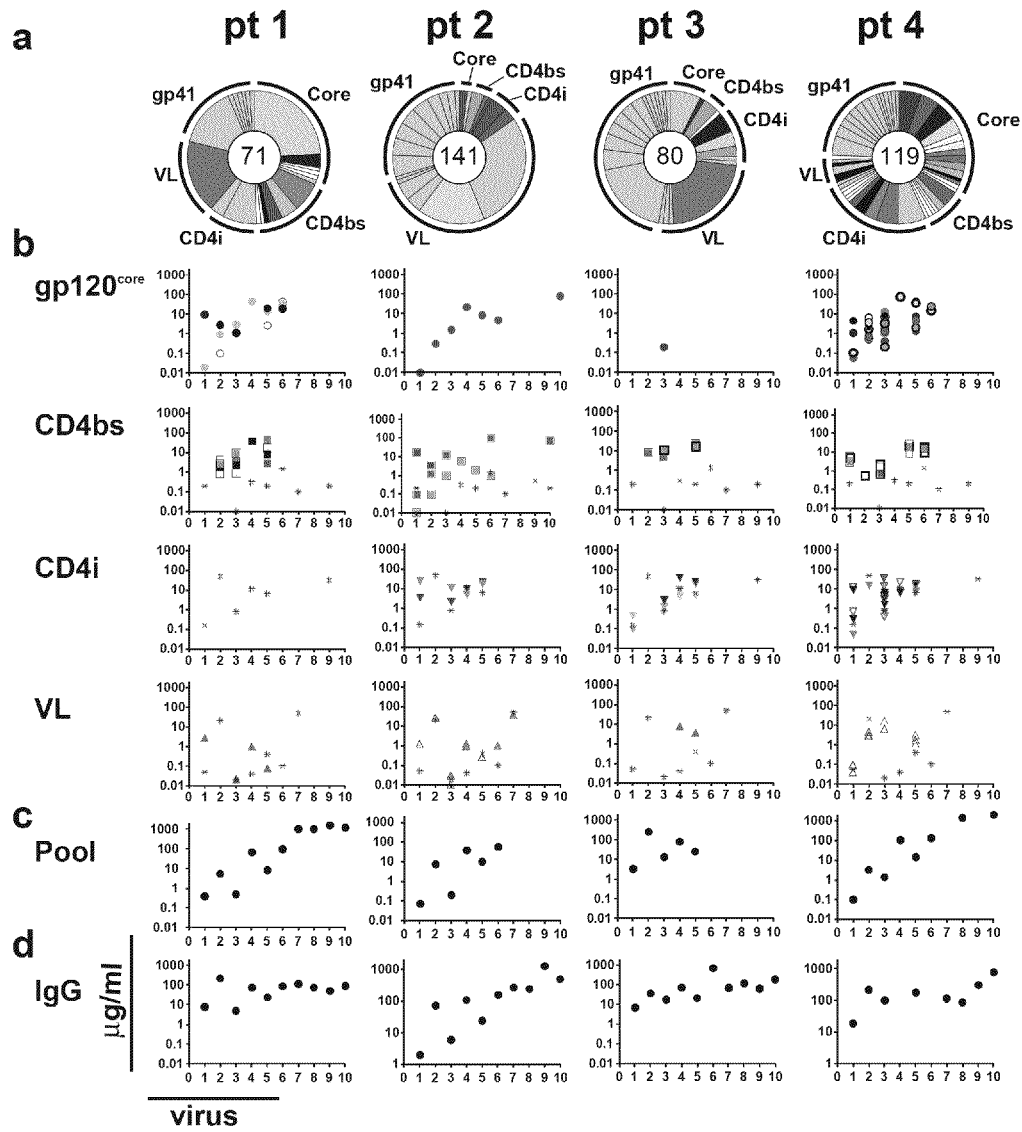

FIG. 4. Neutralizing Activity in TZM•bl Cells.

Source of antibodies from patients 1-4 is indicated at the top. A) Pie charts show neutralizing antibodies in color and non-neutralizers in grey as well as the epitopes they recognize. The size of the slice is proportional to the clone size (see also FIGS. 15-20). Number in the center indicates the total number of tested antibodies. B) Graphs show neutralizing IC50 in µg/ml of individual antibodies specific for gp41, CD4bs, CD4i, $gp120^{core}$, VLs as indicated. The dots in the graphs correspond to the pie charts above. C) Neutralizing activity of all of the pooled anti-gp 140 antibodies (pool), irrespective of their individual neutralizing activity (top). D) Neutralizing activity of purified serum IgG from each of the patients. In b, c, and d, Y axis shows the antibody concentration in µg/ml required to achieve IC50. The numbers on the X axis represent individual viruses all of which are Clade-B unless otherwise stated; For patients 1, 3, 4: 1. MW965.23 (Clade C tier-1), 2. DJ263.8 (Clade A tier-1), 3. SF162.LS (tier-1), 4. SS1196.1 (tier-1), 5. Bal.26 (tier-1), 6. 6535.3 (tier-2). 7. RHPA4259.7 (tier-2), 8. TR0.11 (tier-2), 9. SC422661.8 (tier-2), 10. PVO.4 (tier-2). For patient2: 1. MW965.23 (Clade C tier-1), 2. DJ263.8 (Clade A tier-1), 3. SFI62.LS (tier-1), 4. SS1196.1 (tier-1), 5. Bal.26 (tier-1), 6. 6535.3 (tier-2), 7. RHPA4259.7 (tier-2), 8. CAAN5342.A2 (tier-2), 9. THRO4156.18 (tier-2), 10. SC422661.8 (tier-2) (see also FIG. 25 for IC50s for individual antibodies and pools).

Figure 5:
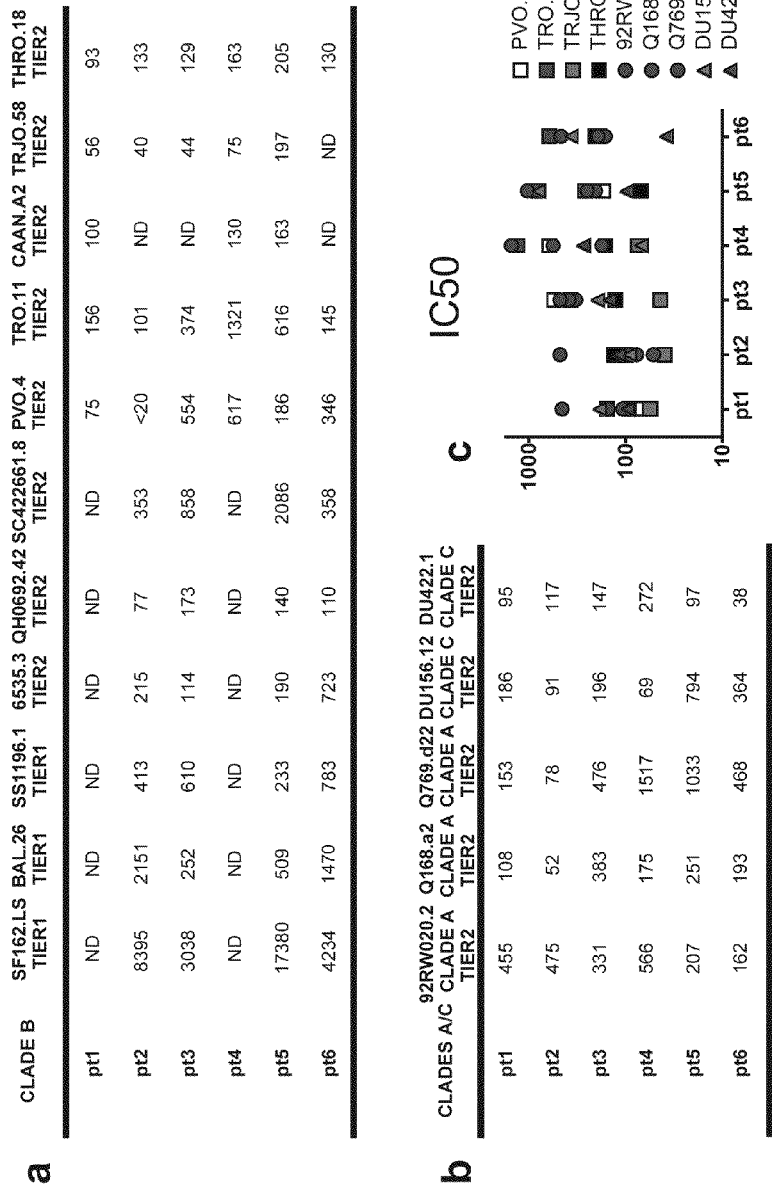

FIG. 5. Neutralizing Activity of Patient Serum in TZM•bl Assays.

A) Table shows serum dilution IC50 for all six patients on selected Clade-B tier-1 and tier-2 viruses. B) Table shows serum dilution IC50s for all six patients on selected clade A/C tier-2 viruses. C) The graph summarizes each patients' tier-2 serologic activity. The Y axis shows the serum dilution IC50, each virus is represented by a different colored symbol (right), and the X axis indicates the source of the serum.

FIG. 6. Anti-gp140 Antibody Cloning.

Figure 1:
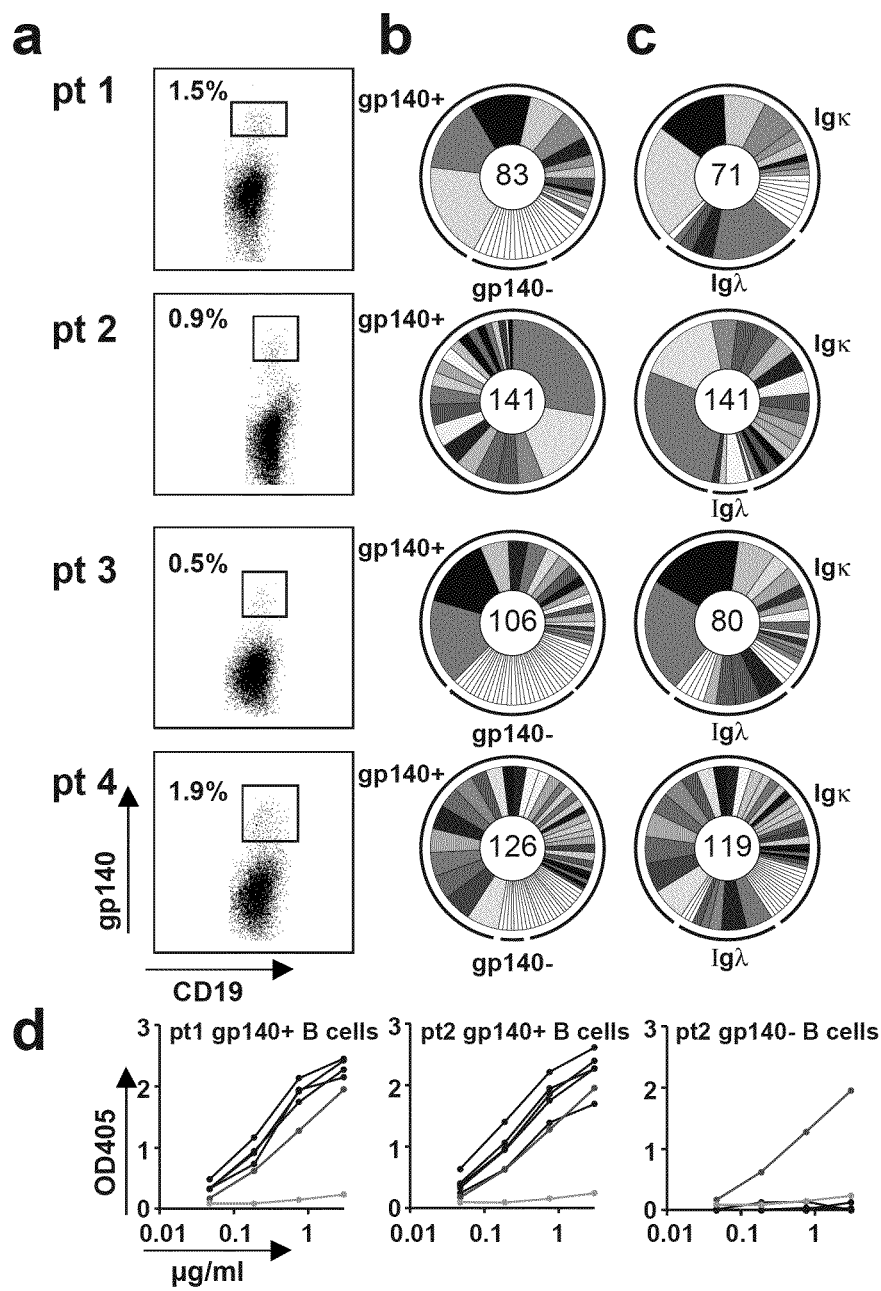
FIG. 1 Anti-gp140 Antibody Cloning.

A) Dot plots show gp140 biotin and anti-CD19 staining on blood mononuclear cells pre-gated for IgG and CD19 expression from patients 5 and 6 (pt 5 and 6) and healthy controls (hc 1 and 2). See FIG. 14 for participant profiles. Healthy controls (hc 1 and 2) were healthy HIV negative men with no known medical problems and normal blood counts. B) Pie charts show the distribution of gp140 binders and non-binders among all antibodies cloned. The number in the center indicates total number of antibodies analyzed, each pie slice represents a clonal family and the size of the slice is proportional to the number of clonal members better: relatives. Each clonal family is represented by the same shade throughout and unique antibodies that are not members of clones are not shaded. C) Dot plots show gp140 and CD19 staining of blood mononuclear cells from patient 2 and 3 as in FIG. 1. Gated non-gp140-binding cells were sorted as negative control (See also FIGS. 20 and 21).

Figure 7:
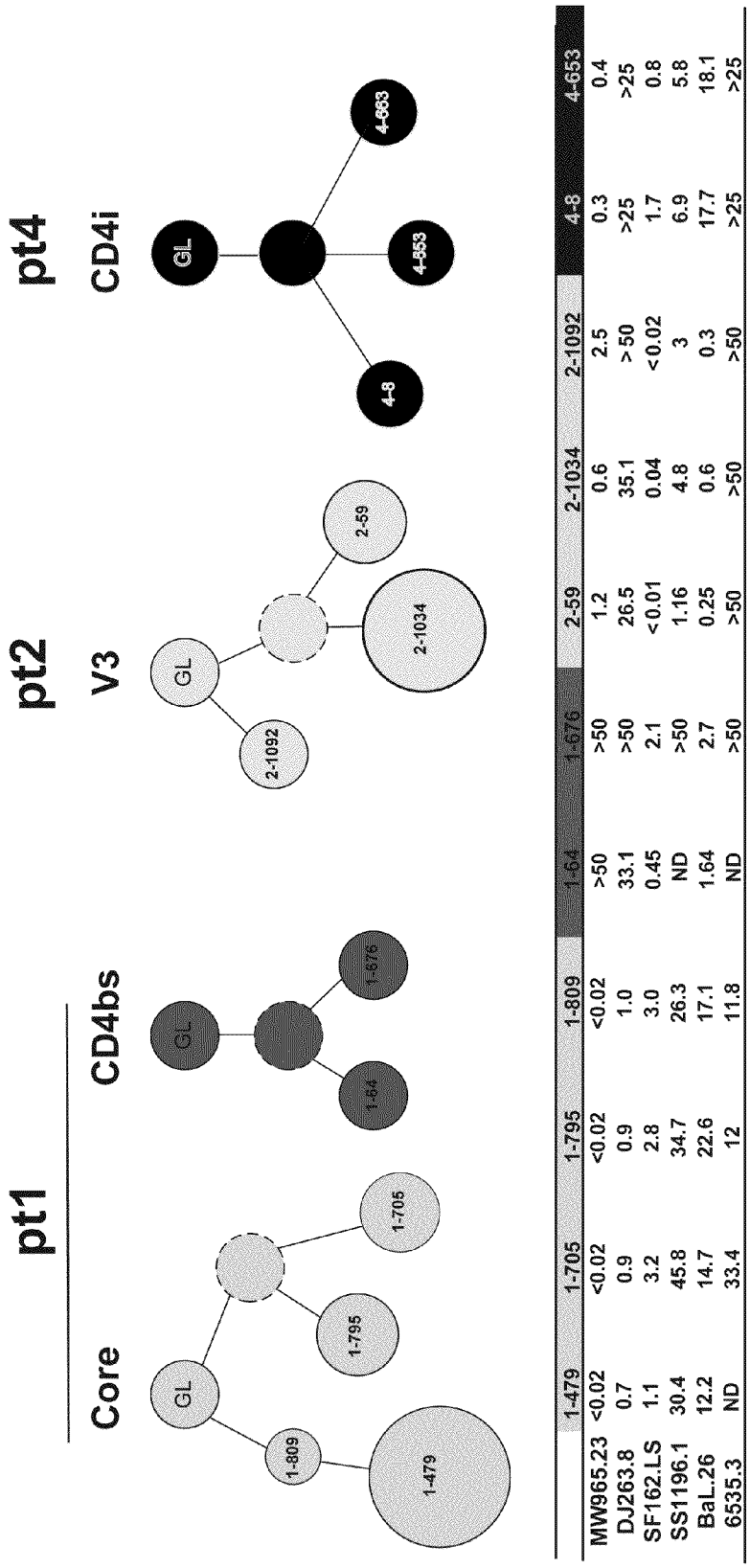

FIG. 7. Sample Mutational Trees Showing Clonal Relationships Between Members of gp140 Binding Antibodies.

Clones showed identical IgH and IgL chain rearrangements with variations in somatic mutations as indicated by individual circles. Each clone is represented separately. The size of the circle is proportional to the number of clone members with identical somatic mutation patterns. The name of the clone members that are part of a given branch is indicated in the center of each circle. Blank circles represent uncloned intermediates.

Figure 8:
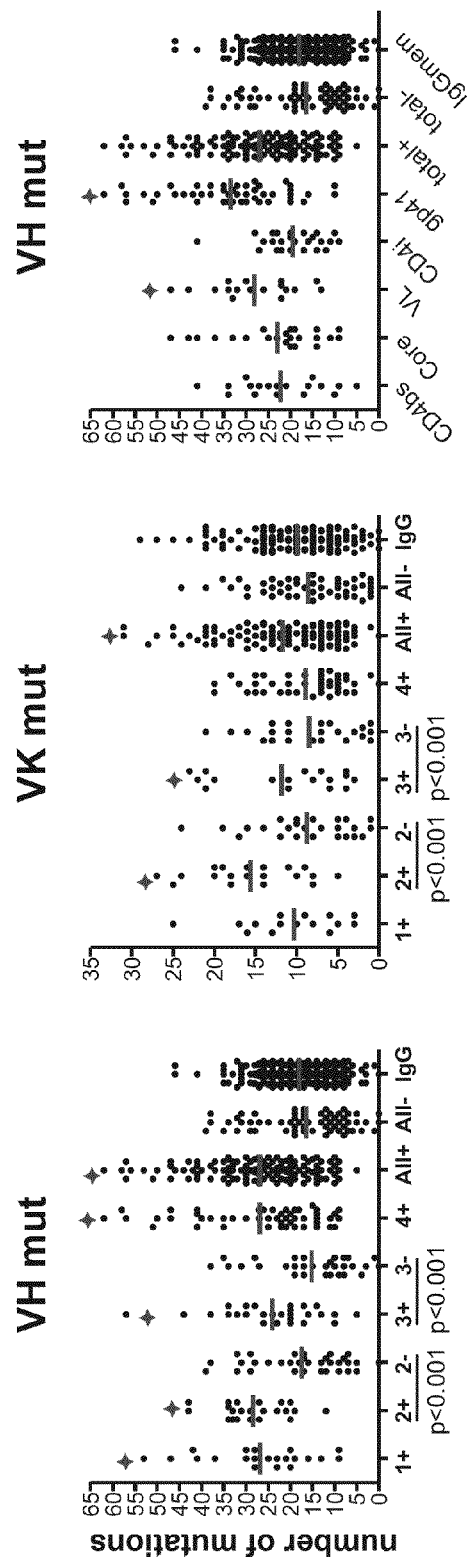

FIG. 8. Somatic Hypermutation.

Graphs show numbers of mutations per antibody for $V_H$ (left) grouped by patient. Vκ (middle) grouped by patient, and $V_H$ (right) for all antibodies to a specific epitope as indicated. Stars indicate P values ≤0.001. P values were calculated by comparison to the pool of gp140 non-reactive antibodies except those below the lines, which refer to the paired samples. Each antibody clone is represented once by a single randomly selected clone member. Statistical analyses for mutation numbers were performed using non-paired two tailed Student's t test.

Figure 9:
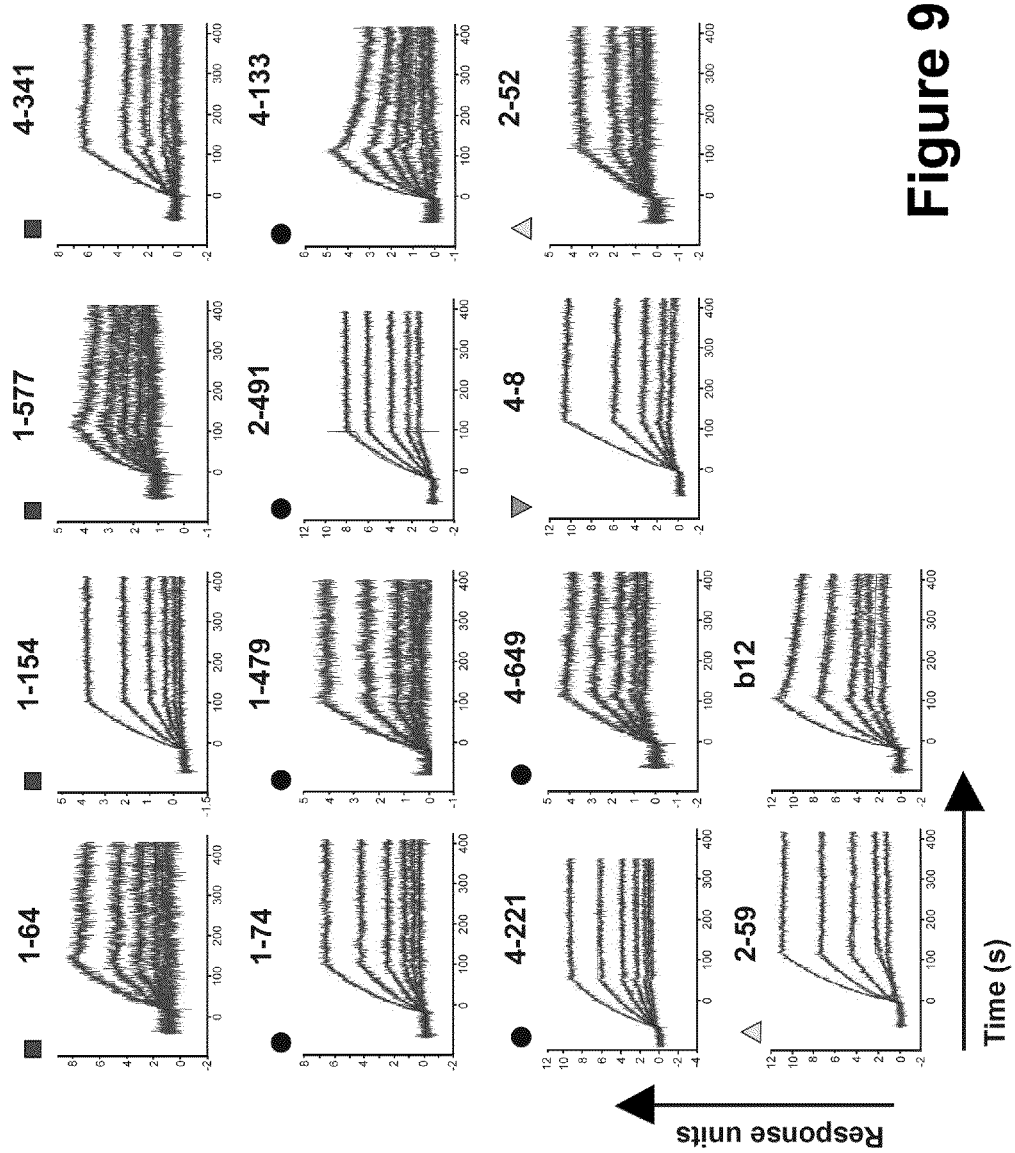

FIG. 9. Surface Plasmon Resonance Measurements for Interaction Between Selected Antibodies and gp140.

Graphs show antibody dissociation curves over time. The starting concentration of gp140 was 25-50 µg/ml and the different curves represent 1:2 dilutions of the starting material. The X-axis shows time in seconds and the Y-axis shows the response rate. The antibodies are indicated above each graph. Squares indicate anti-CD4bs, circles anti-$gp120^{core}$, triangle (point down) anti-CD4i and triangle (point up) anti-VL antibodies.

Figure 10:
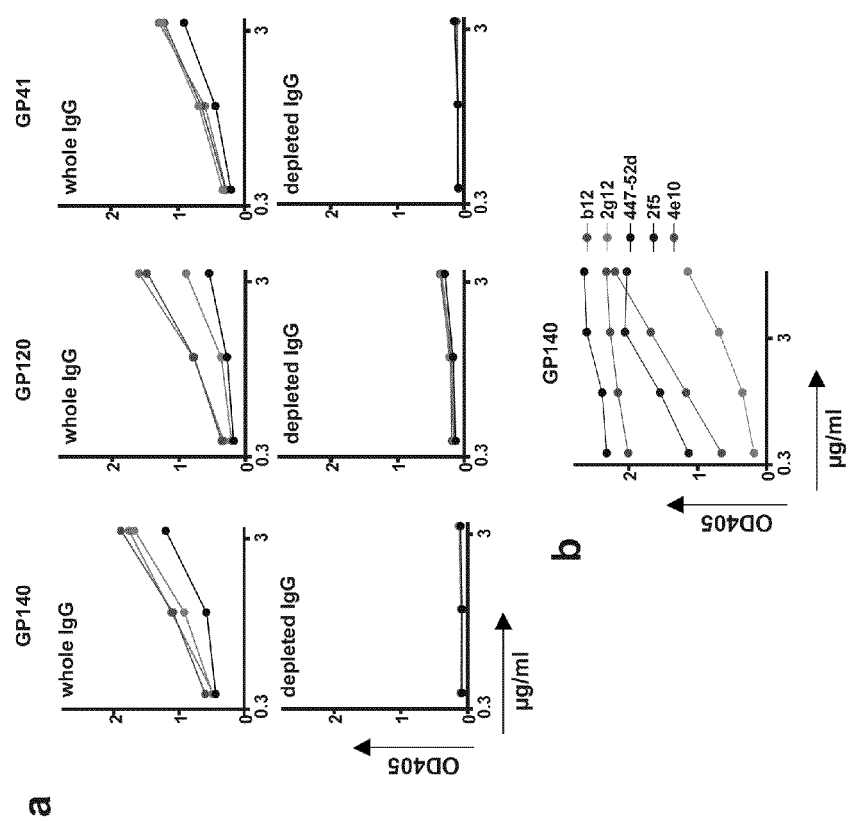

FIG. 10. Effect of Deglycosylation on gp120 Binding.

A) Gel electrophoresis and Coomassie blue staining or Western blot with LCA and DCA lectin of gp120 and aglyco-gp120. B) Representative ELISA results comparing binding to gp120 and aglyco-gp120 for two antibodies that are sensitive (3-42) to or not-sensitive to (3-133) gp120 deglycosylation. Lines indicate gp120 binding and aglyco-gp120 reactivity. Antibody concentration is shown on the X-axis and $OD_{405}$ on the Y axis. C) Binding to gp120 (red) or aglyco-gp120 as measured by ELISA under saturation conditions for all neutralizing antibodies from patients 1-4. Epitopes, patient source, antibody number and relative (see above) $OD_{405}$ are indicated. Stars show antibodies sensitive to deglycosylation. D) as in c, except for a selected group of $gp120^{core}$ non-neutralizers. Deglycosylation was accomplished by treating 150 ug of GP120 with PNGase F (New England Biolabs) and O-glycosidase (QA Bio) in 50 mM sodium phosphate without denaturing agents at 37° C. overnight. For lectin blotting 10 ug of protein was resolved on an SDS-PAGE gel under non-reducing conditions, transferred to polyvinylidene difluoride membranes, blocked with Western Blocking Reagent (Roche), and incubated with biotinylated *Lens culinaris* agglutinin (Le A, 15 ug/ml, Vector Laboratories) to detect N-linked glycans or *Datura stramonium* lectin (DSA, 5 ug/ml, Vector Laboratories) to detect N- and O-linked glycans. The membrane was next incubated with alkaline phosphatase-conjugated goat anti-biotin antibody, and visualized with 4-nitro bluetetrazolium chloride/5-bromo-4-chloro-3-indolylphosphate (Roche).

FIG. 10: Serum Absorption by YU2-gp140 Trimer and Binding to Control Monoclonal Antibodies.

a, ELISA results of serum IgG tested for binding to gp140, gp120 and gp41 before and after absorption with YU2 gp140 trimer. Patients 1-4 are represented in red, green, brown and blue respectively. b, binding of b12, 2G12, 447-52d, 2F5, and 4E10 to trimerized gp140.

Figure 11:
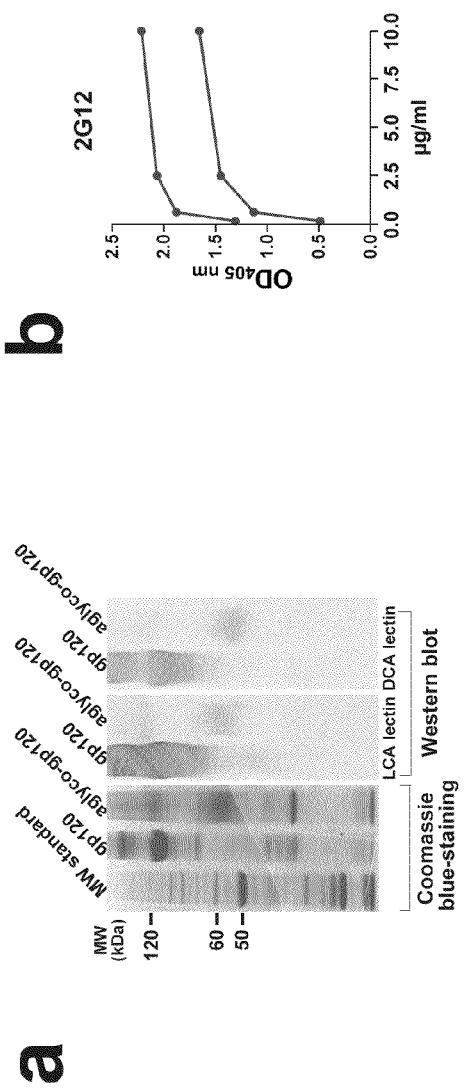
Figure 11:
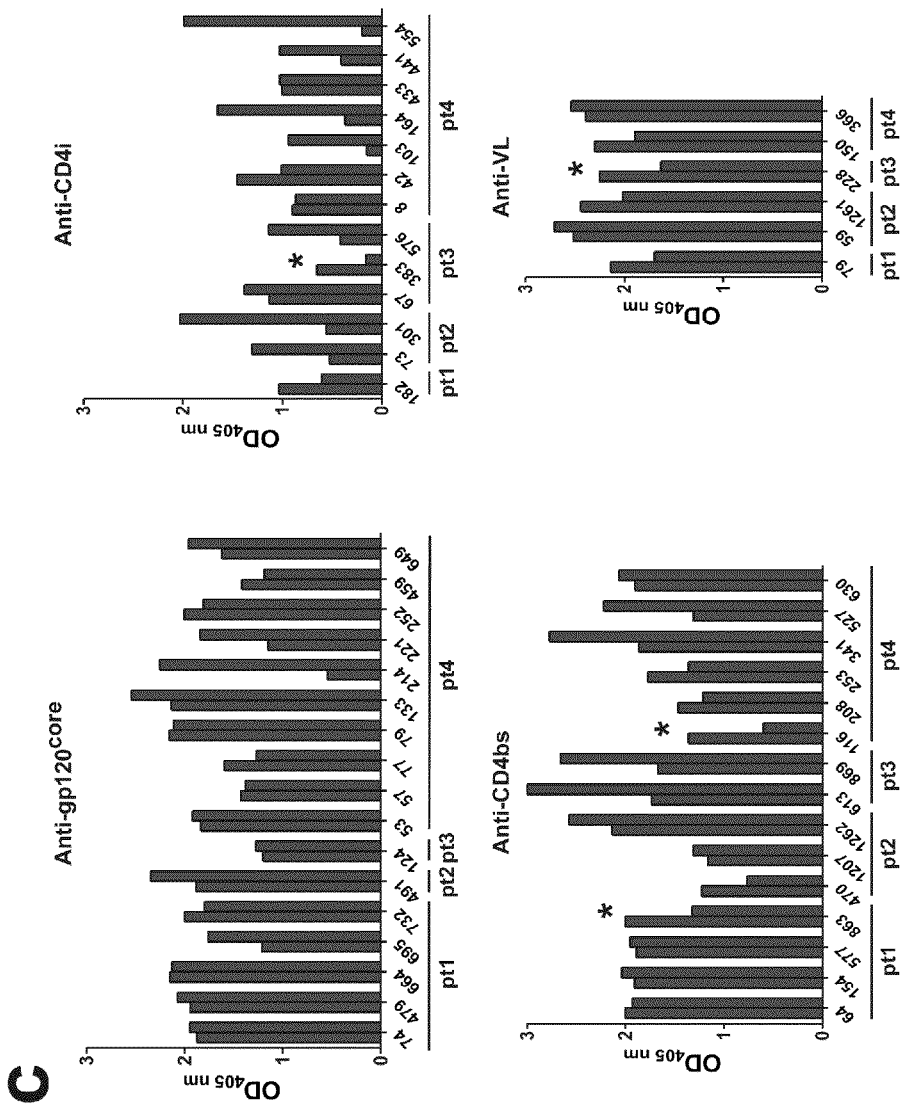

FIG. 11: Effect of Deglycosylation on BAL gp120 Binding.

a, Gel electrophoresis and Coomassie blue staining or Western blot with LCA and DCA lectin of BAL gp120 and aglyco-BAL-gp120. b, Representative ELISA results comparing binding to gp120 and aglyco-gp120 for control antibody 2g12[67]. The red line indicates gp120 binding and green lines indicate aglyco-gp120 reactivity. Antibody concentration is shown on the X axis and $OD_{405}$ on the Y axis. c, Binding to gp120 (red) or aglyco-gp120 (green) as measured by ELISA under saturation conditions for all neutralizing antibodies from patients 1-4. Epitopes, patient source, antibody number and relative (see above) $OD_{405}$ are indicated. Stars show antibodies sensitive to deglycosylation. Deglycosylation was accomplished by treating 150 µg of gp120 with PNGase F (New England Biolabs) and O-glycosidase (QA Bio) in 50 mM sodium phosphate without denaturing agents at 37° C. overnight. For lectin blotting 10 µg of protein was resolved on an SDS-PAGE gel under non-reducing conditions, transferred to polyvinylidene difluoride membranes, blocked with Western Blocking Reagent (Roche), and incubated with biotinylated *Lens culinaris* agglutinin (LCA, 15 µg/ml, Vector Laboratories) to detect N-linked glycans or *Datura stramonium* lectin (DSA, 5 µg/ml, Vector Laboratories) to detect N- and O-linked glycans. The membrane was next incubated with alkaline phosphatase-conjugated goat anti-biotin antibody, and visualized with 4-nitro blue tetrazolium chloride/5-bromo-4-chloro-3-indolyl phosphate (Roche).

Figure 12:
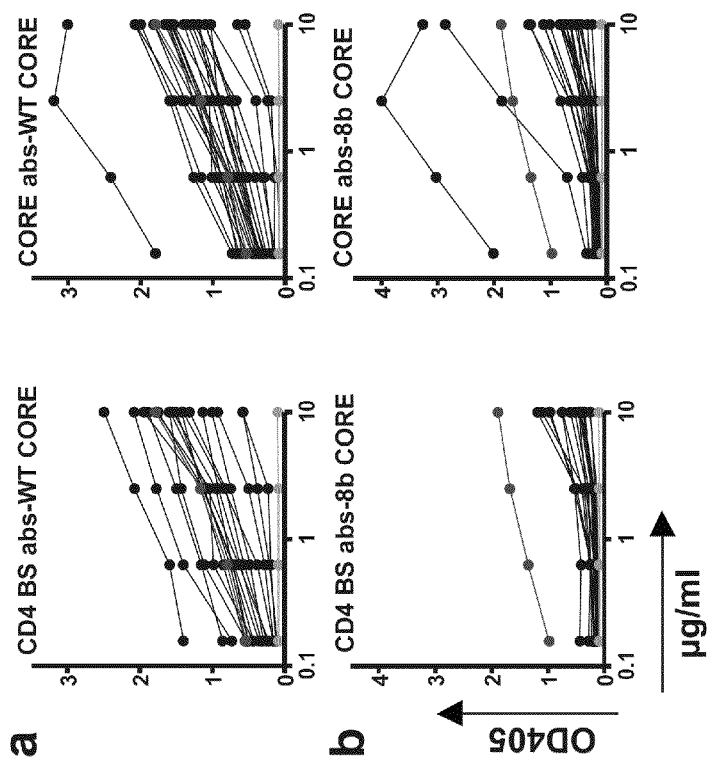

FIG. 12. Binding of Anti-gp120$^{core}$ Anti-CD4Bs Antibodies to gp120 Core and Stabilized Core.

Graphs show the ELISAs for binding to YU2 gp120$^{core}$(a), and the 8b mutant YU2 gp120 core that was stabilized in the CD4 bound state[54] (b). AntiCD4bs and anti-Core antibodies from patients 1-6 were tested for binding to both forms of gp120 at a starting concentration of 100 g/ml. Control antibody b12 is shown[65], negative control antibody mgo53[70].

Figure 13:
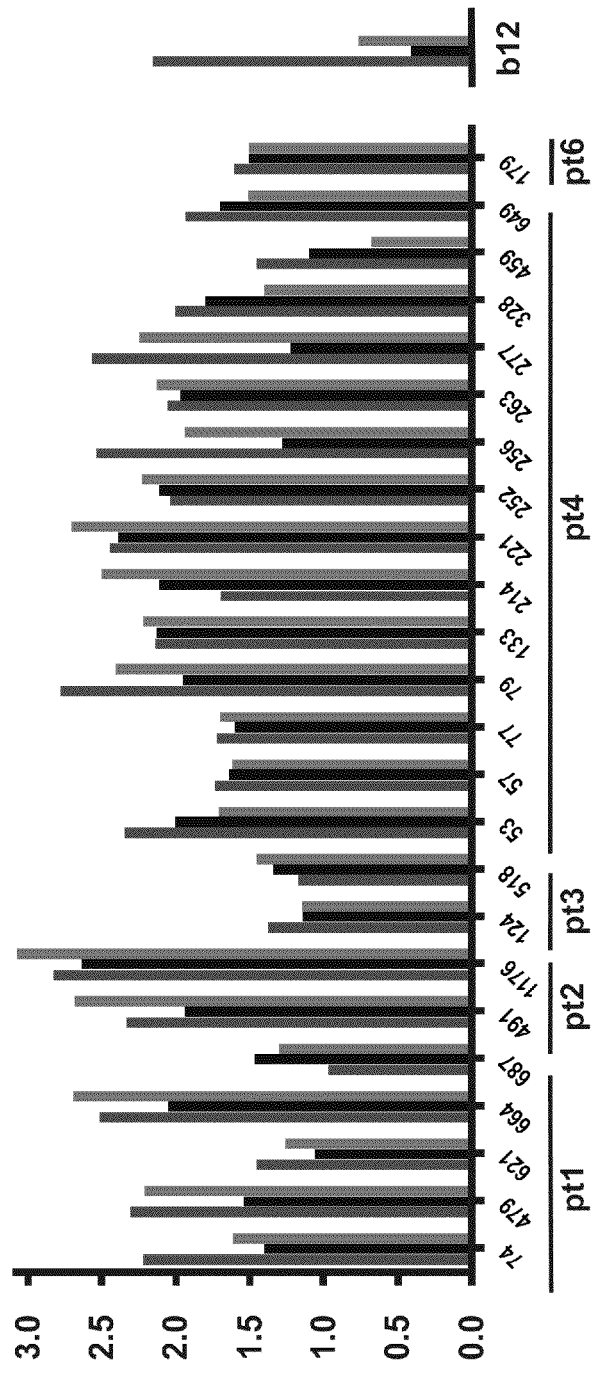

FIG. 13. Binding of anti-gp120$^{core}$ antibodies to gp120, gp120$^{D368R}$ and gp120$^{368/370AA}$.

Anti-Core antibodies from patients 1-4 and 6 were tested in ELISA for their binding to YU2 gp120, gp120$^{D368R}$ and gp120$^{368/370AA}$45-48. Lines indicate binding to gp120, to gp120$^{D368R}$ and to gp120$^{368/370AA}$. B12 is shown as a control.

FIG. 14. Patient and Control Information.

A table showing the clinical information of patients providing sera for the methods disclosed herein and clinical status.

FIG. 15. Repertoire and Reactivity of gp140 Binding Antibodies, Patient 1.

A table showing IgH and IgL chain gene sequence information and antibody reactivity and neutralization assay results of cloned antibodies. ND indicates not determined. The number of clone members with 100% IgH and IgL chain gene sequence homology is indicated and clonal relatives with various degrees of somatic mutations are shown. Antibodies from gp140-reactive IgG B cells form patients 1-6.

FIG. 16. Repertoire and Reactivity of gp140 Binding Antibodies, Patient 2.

A table showing IgH and IgL chain gene sequence information and antibody reactivity and neutralization assay results of cloned antibodies. ND indicates not determined. The number of clone members with 100% IgH and IgL chain gene sequence homology is indicated and clonal relatives with various degrees of somatic mutations are shown. Antibodies from gp140-reactive IgG B cells form patients 1-6.

FIG. 17. Repertoire and Reactivity of gp140 Binding Antibodies, Patient 3.

A table showing IgH and IgL chain gene sequence information and antibody reactivity and neutralization assay results of cloned antibodies. ND indicates not determined. The number of clone members with 100% IgH and IgL chain gene sequence homology is indicated and clonal relatives with various degrees of somatic mutations are shown. Antibodies from gp140-reactive IgG B cells form patients 1-6.

FIG. 18. Repertoire and Reactivity of gp140 Binding Antibodies, Patient 4.

A table showing IgH and IgL chain gene sequence information and antibody reactivity and neutralization assay results of cloned antibodies. ND indicates not determined. The number of clone members with 100% IgH and IgL chain gene sequence homology is indicated and clonal relatives with various degrees of somatic mutations are shown. Antibodies from gp140-reactive IgG B cells form patients 1-6.

FIG. 19. Repertoire and Reactivity of gp140 Binding Antibodies, Patient 4.

A table showing IgH and IgL chain gene sequence information and antibody reactivity and neutralization assay results of cloned antibodies. ND indicates not determined. The number of clone members with 100% IgH and IgL chain gene sequence homology is indicated and clonal relatives with various degrees of somatic mutations are shown. Antibodies from gp140-reactive IgG B cells form patients 1-6.

FIG. 20. Repertoire and Reactivity of gp140 Binding Antibodies, Patient 5 and 6.

A table showing IgH and IgL chain gene sequence information and antibody reactivity and neutralization assay results of cloned antibodies. ND indicates not determined. The number of clone members with 100% IgH and IgL chain gene sequence homology is indicated and clonal relatives with various degrees of somatic mutations are shown. Antibodies from gp140-reactive IgG B cells form patients 1-6.

FIG. 21. Repertoire and Reactivity of gp140 Binding Antibodies, Patient 2.

A table showing IgH and IgL chain gene sequence information and antibody reactivity and neutralization assay results of cloned antibodies. ND indicates not determined. The number of clone members with 100% IgH and IgL chain gene sequence homology is indicated and clonal relatives with various degrees of somatic mutations are shown. Antibodies from gp140 non-reactive IgG B cells form patients 2 and 3.

FIG. 22. Repertoire and Reactivity of gp140 Binding Antibodies, Patient 2.

A table showing IgH and IgL chain gene sequence information and antibody reactivity and neutralization assay results of cloned antibodies. ND indicates not determined. The number of clone members with 100% IgH and IgL chain gene sequence homology is indicated and clonal relatives with various degrees of somatic mutations are shown. Antibodies from gp140 non-reactive IgG B cells form patients 2 and 3.

FIG. 23. Affinity Measurements of b12 and Selected Antibodies by Surface Plamon Resonance.

Stars indicated cases in which the sensorgrams are virtually flat during the dissociation phase. Off-rates might therefore be even slower than the ones listed. Epitopes against which the affinities were measured are indicated above. (M=Mol/liter; s=seconds)

FIG. 24. Summary of gp140 Competition ELISA Experiments.

Numbers indicate IC50s for the specific antibody in ELISA assays measuring the blocking of the binding of the indicated biotinylated antibody (indicated at right) to gp120. a, anti-gp120 core antibodies. B, anti-CD4bs antibodies. c, anti-CD4i antibodies. d, anti-VL antibodies. Biotinylated antibodies are: b12, 1-64 anti-CD4bs, 2-491 anti-Core, 1-182 anti-CD41, and 1-79 antiV3L.

FIG. 25. In Vitro Tzm-Bl Neutralization Assay.

Showing tables a and b whereby Numbers indicate IC50s for the specific monoclonal antibody, serum IgG or pooled antibodies in the Tzm-bl assay measuring inhibition of infection by the indicated viral strains. X indicates activity that did not reach IC50 values at the concentration tested for patients 1-4 and previously described control antibodies.

FIG. 26. In Vitro Tzm-Bl Neutralization Assay.

Showing tables c and d whereby Numbers indicate IC50s for the specific monoclonal antibody, serum IgG or pooled antibodies in the Tzm-bl assay measuring inhibition of infection by the indicated viral strains. X indicates activity that did not reach IC50 values at the concentration tested for patients 1-4 and previously described control antibodies.

FIG. 27. In Vitro Tzm-Bl Neutralization Assay.

Showing tables e whereby Numbers indicate IC50s for the specific monoclonal antibody, serum IgG or pooled antibodies in the Tzm-bl assay measuring inhibition of infection by the indicated viral strains. X indicates activity that did not reach IC50 values at the concentration tested for patients 5 and 6.

FIGS. 28A, 28B, 28C, 28D. Neutralization Screen of Plasma Samples Against Standard Virus Panel.

Screen of 1818 plasma samples from a cohort of HIV-1 infected elite controllers against a standard panel of HIV isolates. Shown are the reciprocal dilutions needed to achieve a 50% inhibition in the TZM•bl neutralization assay. Samples were tested primary at a 1:20 dilution and then titrated 3-fold seven times in duplicate wells. HIVIG was used as appositive control at a starting concentration of 2500 µg/ml. Negative controls were normal naïve human plasma and Murine Leukemia pseudovirus. Patients 2, 3, and 5 correspond to CTR118, CTR34 and CTR207 respectively. Patients with broad activity against tier-2 viruses are shaded.

Figure 29A:
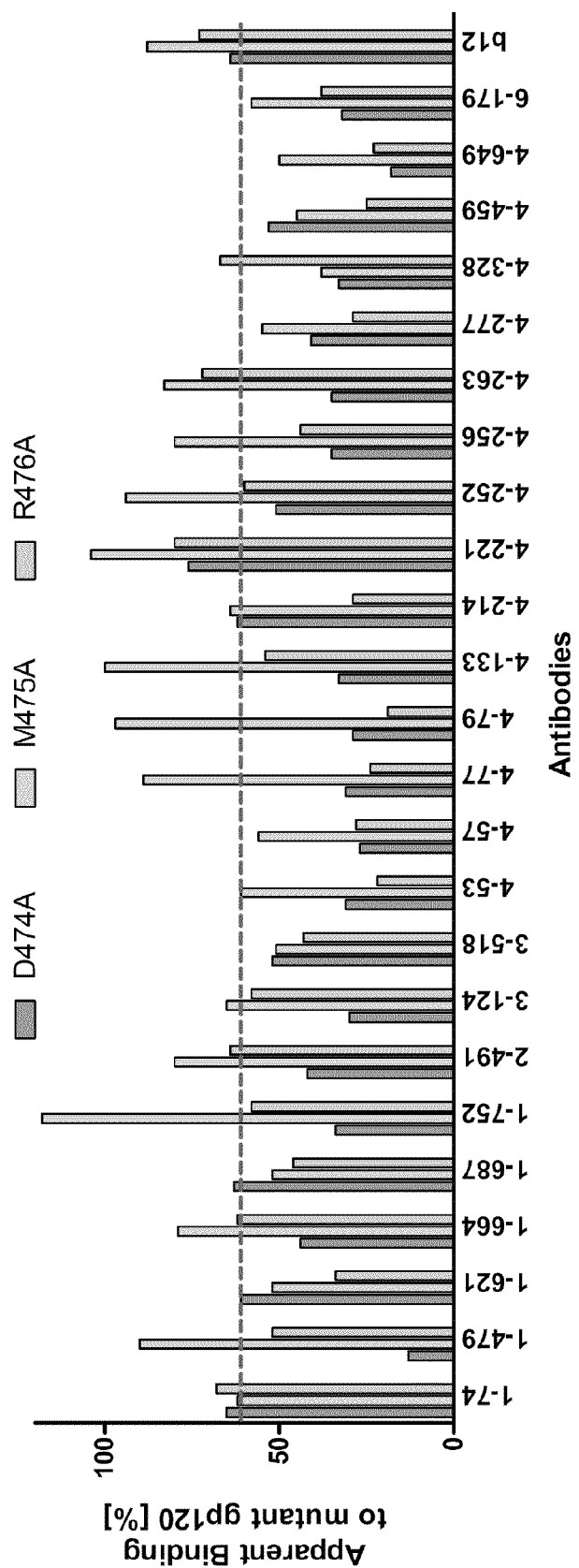
Figure 29B:
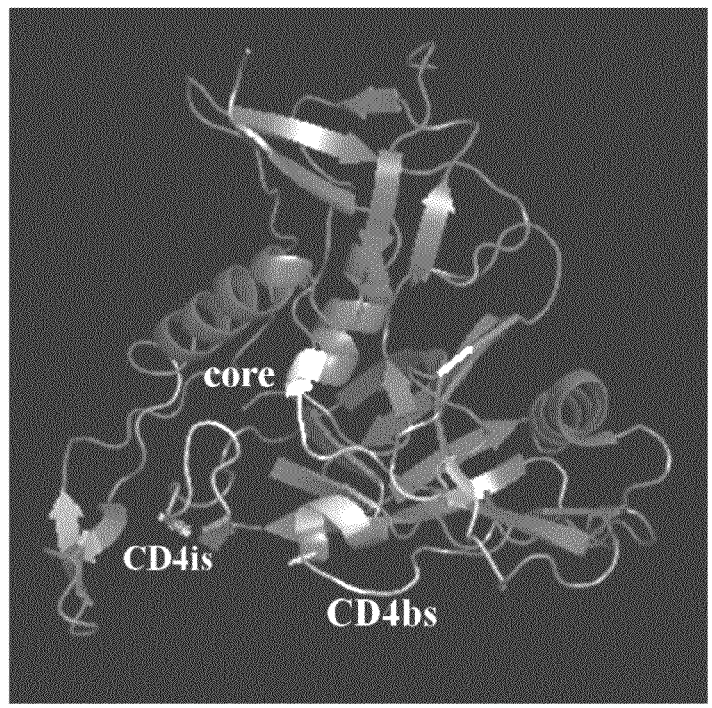
Figure 29C:
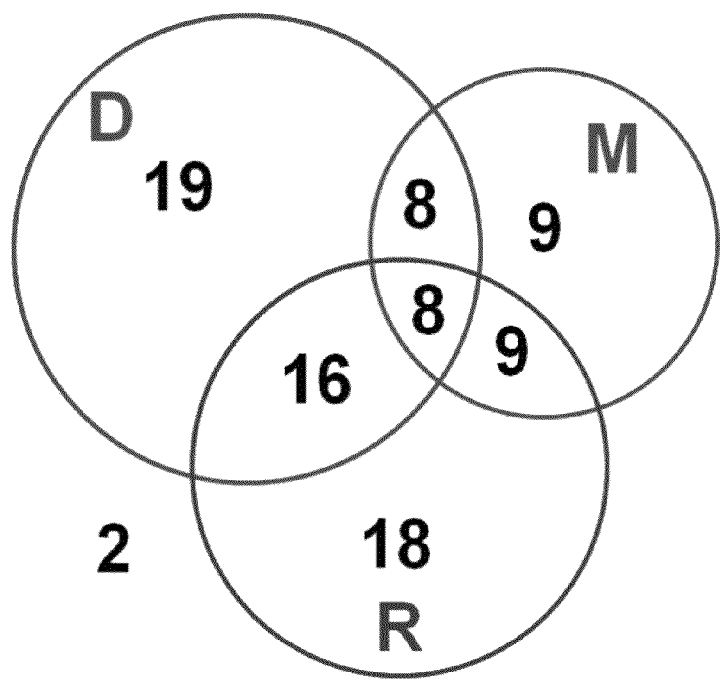

FIG. 29. Mapping of the Core Epitope.

(A) Bar diagram shows the percental apparent binding of anti-core antibodies and b12 to mutant gp120 (D474A, M475A, R476A) relative to gp120 wildtype. Relative binding below 60% was considered to be significant decrease. (B) Ribbon diagram of gp120 (PDB ID: 3DNO {Liu J, 2008 #45}) that shows the CD4bs, the CD4is and the defined core epitope. (C) Venn diagram summarizes the sensitivity for anti-core antibodies to bind to D474A, M475A and R476A. E.g., two anti-core antibodies showed an insensitive binding to any of the three mutants, whereas 16 antibodies were sensitive for D474A and R476A.

Figure 30A:
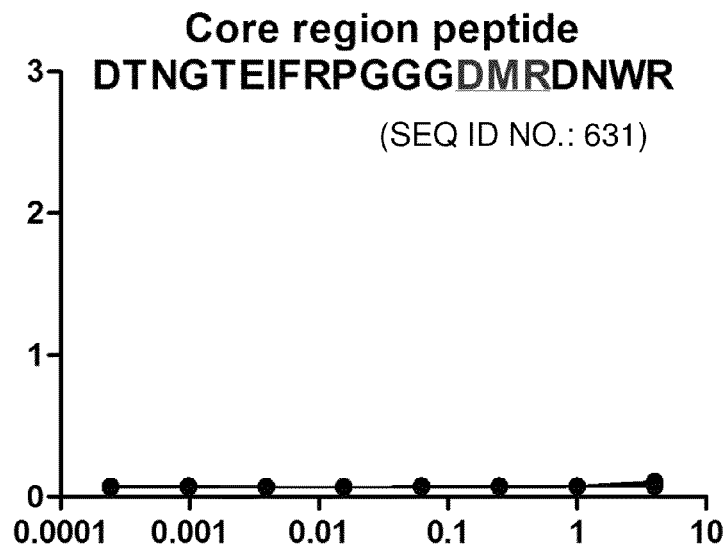
Figure 30B:
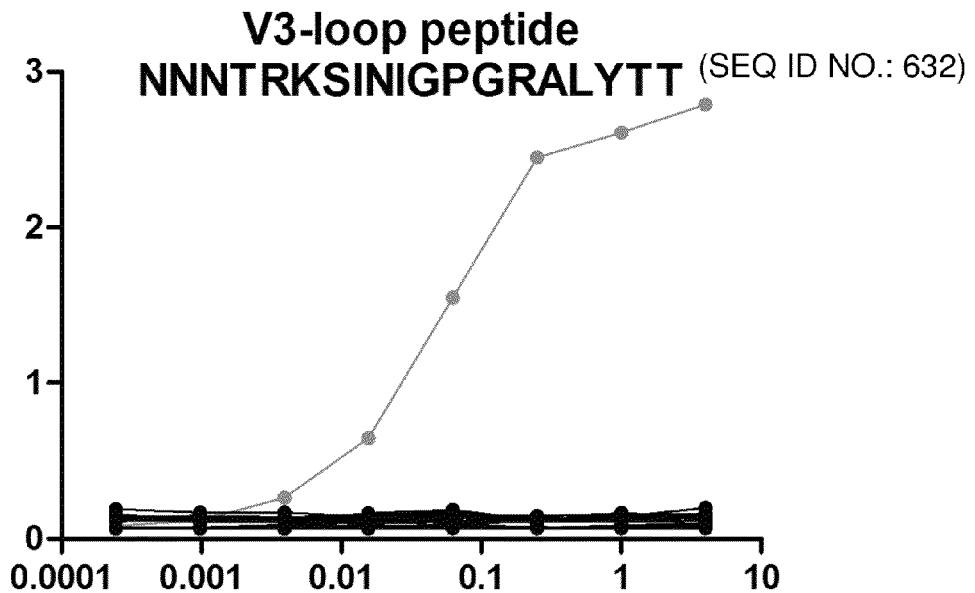
Figure 31B:
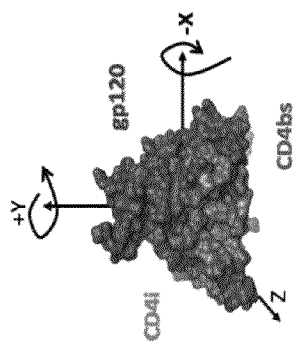
Figure 31B:
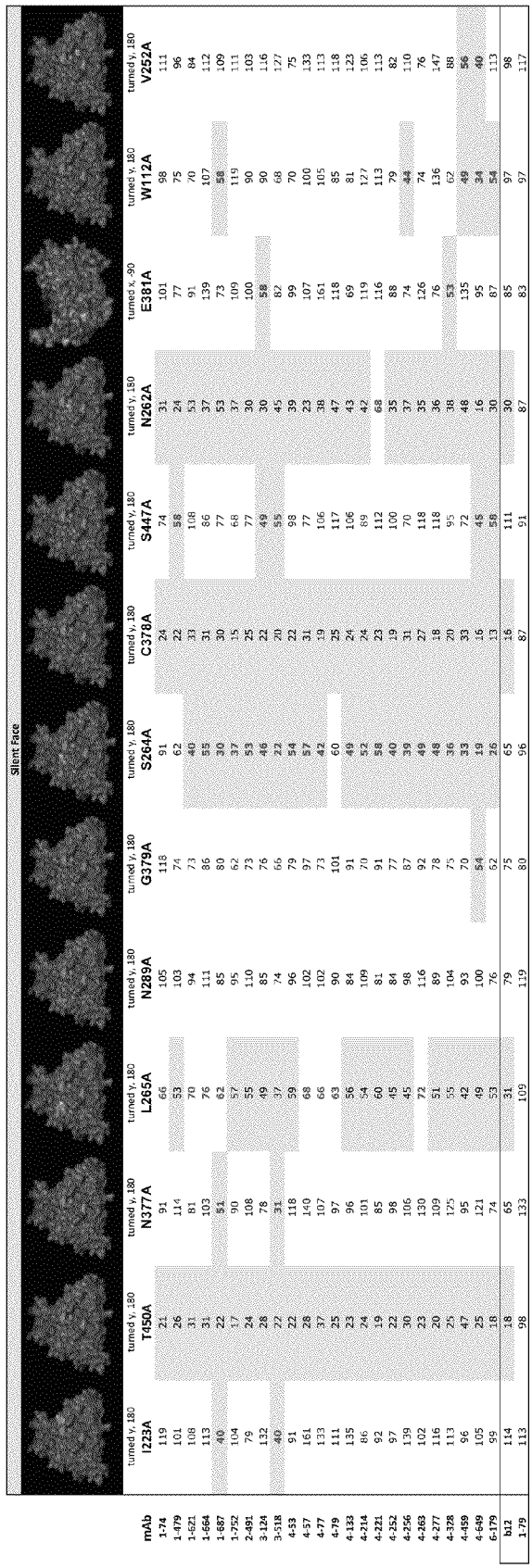
Figure 31C:
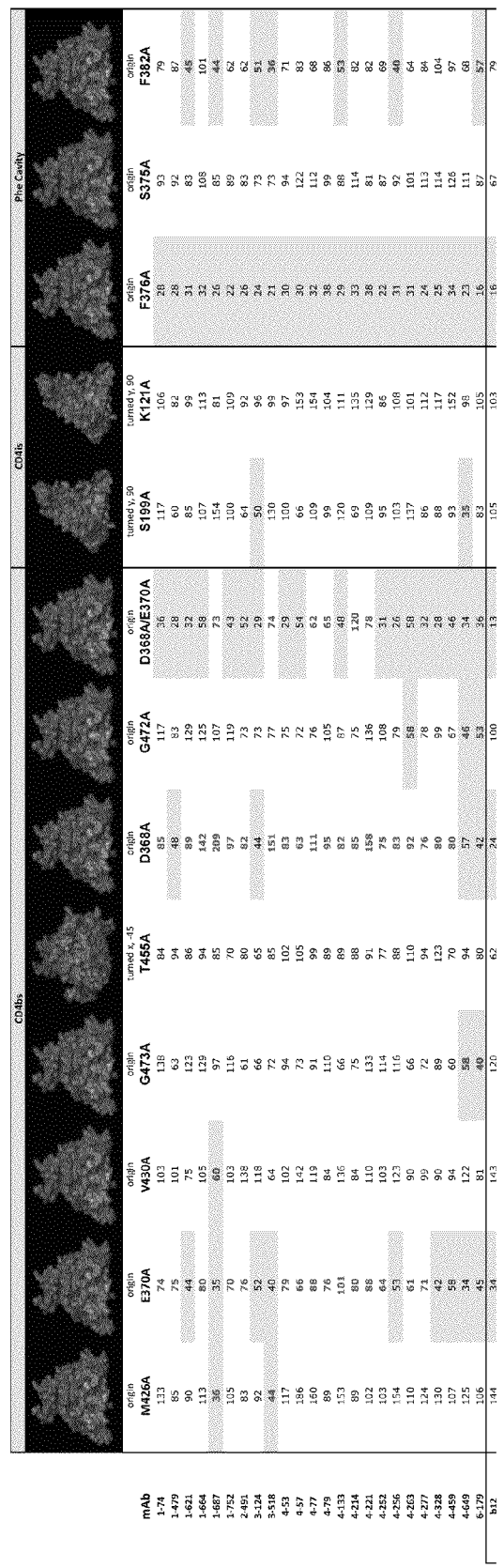
Figure 31C:
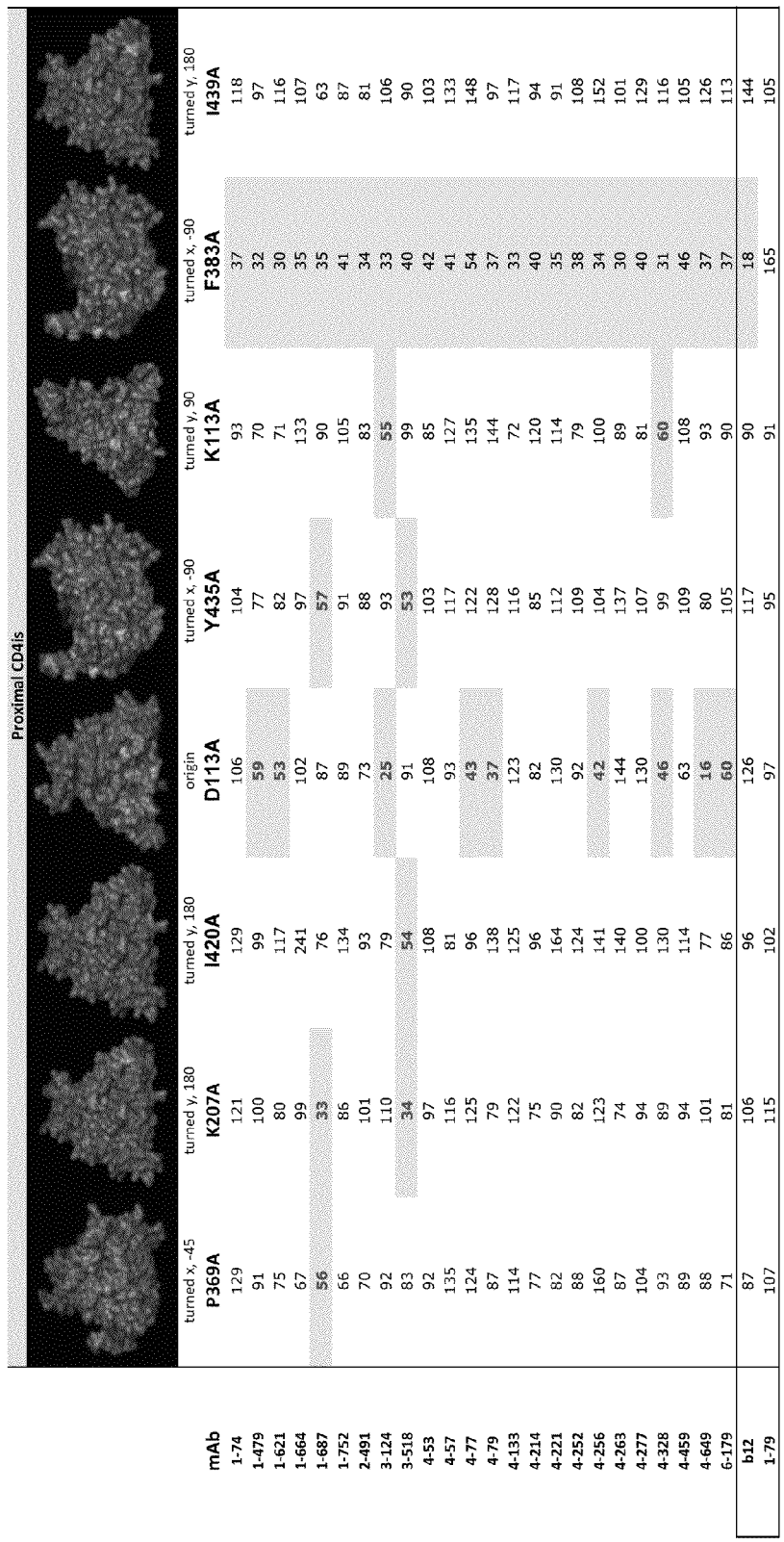
Figure 31D:
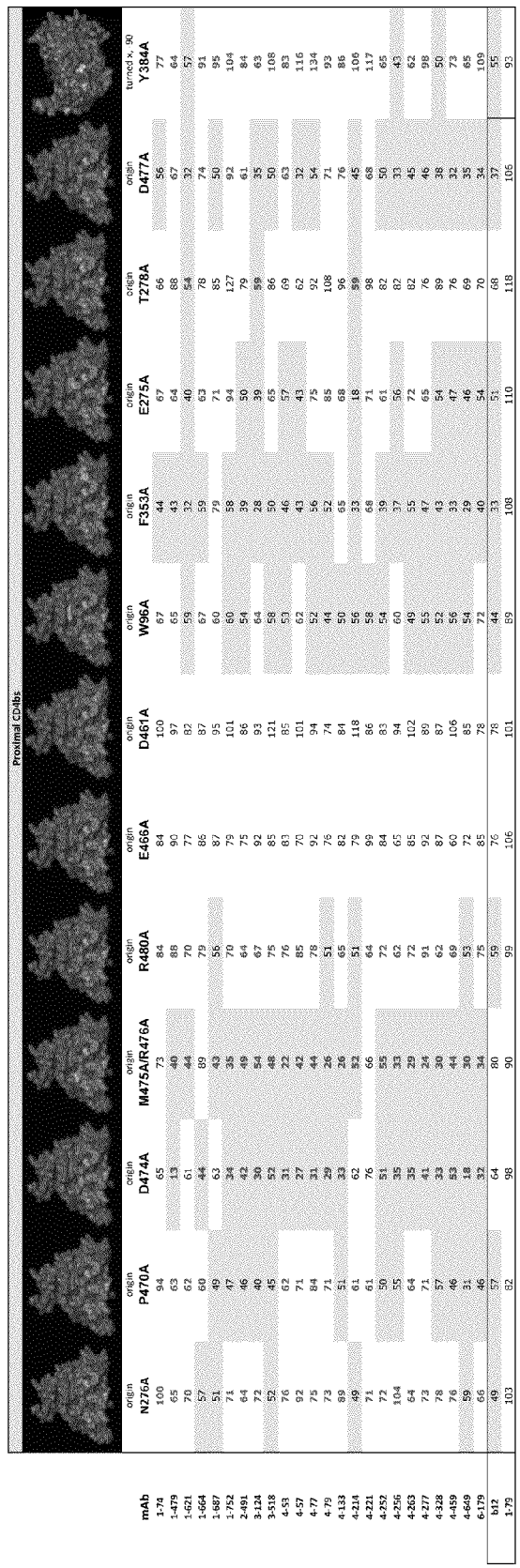
Figure 31E:
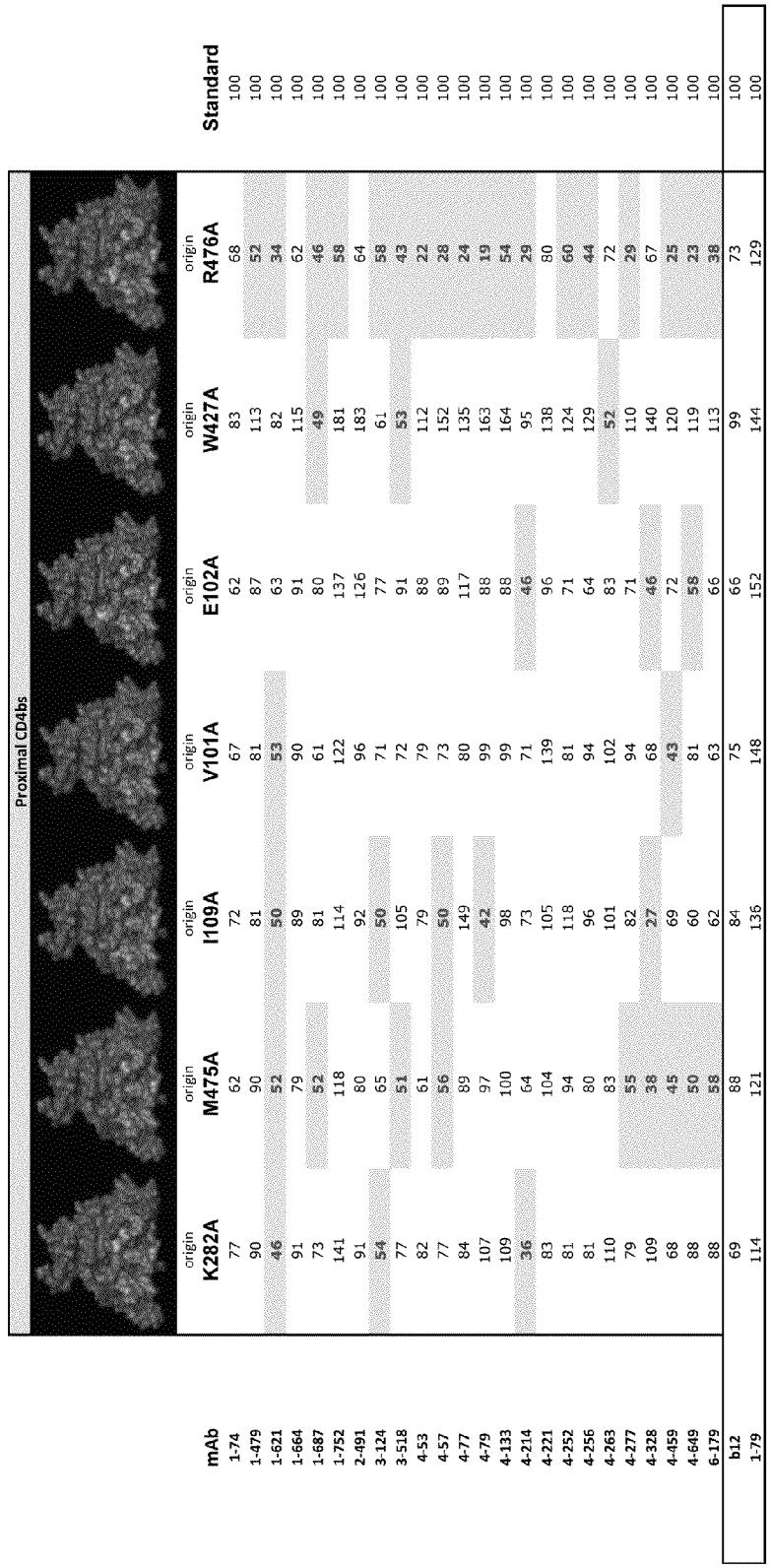

FIG. 30. Peptide ELISA.

(A) Anti-core antibodies (black lines) do not bind the core region peptide. (B) Positive control V3-loop peptide was recognized by an anti-V3-loop antibody (2-59, {Scheid JF, 2009 #25}) (inclining line).

FIGS. 31A-E. TZMbl Neutralization Data.

(A) Values represent $IC_{50}$ s in µg/ml for anti-core antibodies and b12 in an TZMbl-based neutralization assay. Values in red show inhibition at the concentrations tested. X indicates that this given antibody almost reached an $IC_{50}$ at the highest concentration tested {Scheid JF, 2009 #25}. (B-E) Numbers indicate the apparent binding [%] of the anti-core antibodies to the different gp120 mutant proteins. Shaded fields indicate a significant decrease (below 60%) in binding. Bolded text highlight differences in binding properties compared to anti-CD4bs antibody b12.

DETAILED DESCRIPTION

Long-lived memory antibody responses are a key feature of successful immune responses and the basis of many vaccines. This type of memory resides in circulating post germinal center memory B cells and in long-lived plasma cells {Zinkernagel, 1996; Maruyama, 2000; Maclennan, 2000; Radbruch, 2006}. Antigen-specific memory B cells are rare, non-cycling cells that do not require stimulation by antigen in order to persist for long periods of time {Schittek, 1990; Maruyama, 2000}. However, they expand rapidly in response to antigen and develop into plasma cells that reside in the bone marrow and produce large quantities of antibodies for prolonged periods of time {Manz, 1997; Slifka, 1998; Radbruch, 2006}.

Provided herein are HIV neutralizing antibodies, or antigen binding portions thereof, which comprises a binding region that binds to an antigenic epitope on gp120, or a portion of the antigenic epitope, wherein the antigenic epitope is on the same face of gp120 as a CD4 binding site or on the same face as the binding site for a b12 antibody. The antigenic epitope comprises gp120$^{core}$, also the antigenic epitope comprises conformational epitope on gp120 within the α5-helix. The invention further comprises in other embodiments a vaccine comprising at least one antibody comprising gp120$^{core}$ and a pharmaceutically acceptable carrier.

In yet another embodiment, a method of inhibiting virus replication or spread to additional host cells or tissues comprising contacting a mammalian cell with the antibody, or a portion thereof, as disclosed herein which binds to an antigenic epitope on gp120.

In yet another embodiment, a method for treating a mammal with infected with a virus infection comprising administering to said mammal a pharmaceutical composition comprising the anti-gp120$^{core}$ antibodies disclosed herein. In yet another embodiment, the method provides for the vaccination against HIV comprising administering to a subject the vaccine disclosed herein.

A method for isolating virus neutralizing antibodies comprising: providing a viral surface protein; binding of memory B-cells to said viral surface protein; producing antibodies by said memory B-cells; and isolating antibodies and further comprising providing an artificially trimerized gp140 protein; purifying gp140 binding B-cells; and isolating antibodies. The antibody produced thereby binds to an antigenic epitope comprising gp120$^{core}$, or a portion thereof.

Antibodies can be protective against initial HIV infection in passive transfer experiments in non-human primates and can modulate viral load during infection {Mascola, 2000; Shibata, 1999; Veazey, 2003; Parren, 2001; Mascola, 1999; Trkola, 2005; Wei, 2003; Frost, 2005}. Based on these observations, it has been proposed that such antibodies may be important components of a preventative vaccine {Burton, 2004; Mascola, 2007; Karlsson Hedestam, 2008; McMichael, 2006; Zolla-Pazner, 2004}.

The present invention provides for antibodies, either alone or in combination with other antibodies, having broad neutralizing activity in serum. Neutralization activity can be the result of a single highly effective antibody such as gp120$^{core}$ of the present invention, or a plurality of antibodies as described. Broadly neutralizing serological activity can be elicited by a combination of antibodies that phenocopies the natural anti-HIV immune response in patients as an effective means of protection against a large number of HIV strains.

It is an embodiment of the invention to provide for HIV neutralizing antibodies comprising at least one of an antibody, or antigen binding portion thereof, which comprises a binding region binds to an antigenic epitope on gp120, or a portion of the antigenic epitope, wherein the antigenic epitope is on the same face of gp120 as a CD4 binding site. The antigenic epitope may also be on the same face as the binding site for a b12 antibody. An aspect of the invention provides for antibodies, or an antigen binding portion thereof, which binds to a new the antigenic epitope comprises gp120$^{core}$, which binds to the same face of gp120 as b12 and CD4.

Another embodiment of the invention provides for an antibody, or antigen binding portion thereof, comprising a binding region which binds to a CDR3 region comprising at least one of SEQ ID NOs: 1-630, or fragments or derivatives thereof. The antibodies which bind to a CDR3 region further may bind to epitopes, or portions of epitopes, comprising V3, gp41, VL, CD4i or CD4bs.

In yet another embodiment, the invention provides for a vaccine comprising at least one antibody of the invention and a pharmaceutically acceptable carrier. It is a further embodiment of the invention to provide for a vaccine comprising at least one antibody described herein and a pharmaceutically acceptable carrier. The vaccine can include a plurality of the antibodies having the characteristics described herein in any combination and can further include antibodies neutralizing to HIV as are known in the art.

In another embodiment of the invention a method of inhibiting virus replication or spread to additional host cells or tissues comprising contacting a mammalian cell with an antibody, or a portion thereof, which binds to an antigenic epitope on gp120 is provided. As described the antibody or antibodies of the invention bind to the gp120$^{core}$ epitope which can be found on a separate binding site on the same face of gp120 as a CD4 binding site or a b12 antibody.

The method may further comprise administering to a cell one or more antibodies which bind to a CDR3 region comprising any one of SEQ ID NOs: 1-630, or a fragments thereof.

In a further embodiment, the invention provides for a method for treating a mammal with infected with a virus infection comprising administering to said mammal a pharmaceutical composition comprising an antibody, or a portion thereof, which binds to an antigenic epitope on gp120 is provided. As described the antibody or antibodies of the invention bind to the gp120$^{core}$ epitope which can be found on a separate binding site on the same face of gp120 as a CD4 binding site or a b12 antibody. The method may further comprise administering to the mammal one or more antibodies which bind to a CDR3 region comprising any one of SEQ ID NOs: 1-630, or a fragments thereof. The compositions and vaccines of the invention can include more than one antibody having the characteristics disclosed (e.g. a plurality or pool of antibodies). It may also include other HIV neutralizing antibodies as are known in the art.

It is yet another embodiment of the invention to provide for a method for vaccinating a mammal from HIV infection. The vaccines or antibody pharmaceutical compositions of this invention may be administered alone or in combination with other HIV antigens, and in one or several immunization doses.

The present invention also provides for methods of producing and isolating virus neutralizing antibodies comprising: providing a viral surface protein; binding of memory B-cells to said viral surface protein; producing antibodies by said memory B-cells; and isolating antibodies.

For isolating HIV neutralizing antibodies the method further includes providing an artificially trimerized gp140 protein; purifying gp140 binding B-cells; and isolating antibodies. An antibody, or antigen binding portion thereof, produced by the method comprising providing an artificially trimerized gp140 protein; binding of said trimerized gp140 to B-cells; purifying gp140 binding B-cells; and isolating antibodies produced by the memory B-cells. It is yet another embodiment of the invention to provide for antibodies produced by the methods disclosed.

The above described antibodies and antibody compositions or vaccine compositions, comprising at least one or a combination of the antibodies described herein, may be administered for the prophylactic and therapeutic treatment of HIV viral infection, as well as for other reasons described herein.

A "cell" can be any cell, and, preferably, is of a eukaryotic, multicellular species (e.g., as opposed to a unicellular yeast cell), and, even more preferably, is a mammalian, e.g., human cell.

A cell can be present as a single entity, or can be part of a larger collection of cells. Such a "larger collection of cells" can comprise, for instance, a cell culture (either mixed or pure), a tissue (e.g., endothelial, epithelial, mucosa or other tissue), an organ (e.g., lung, liver, muscle and other organs), an organ system (e.g., circulatory system, respiratory system, gastrointestinal system, urinary system, nervous system, integumentary system or other organ system), or an organism (e.g., a bird, mammal, or the like). Preferably, the organs/tissues/cells being targeted are of the circulatory system (e.g., including, but not limited to blood, including white blood cells). The target cells need not be normal cells and can be diseased cells. Such diseases cells can be, but are not limited to, HIV infected cells.

In one embodiment, the invention provides for a method for inducing immune responses in a subject said method comprising administering a pharmaceutical composition, including vaccines or antibody compositions, comprising HIV neutralizing antibodies disclosed herein. Such induced immune response include cellular and humoral responses.

It is to be understood that compositions may a single or a combination of antibodies disclosed herein, which may be the same or different, in order to prophylactically or therapeutically treat the progression of various subtypes of human immunodeficiency virus infection after vaccination. Such combinations may be selected according to the desired immunity. When a an antibody vaccine is administered to an animal or a human, it can be combined with one or more pharmaceutical acceptable carriers, excipients or adjuvants as are known to one of ordinary skilled in the art. The composition may further included broadly neutralizing antibodies known in the art, including but not limited to, b12, 2F5, 4E10 and 2G12.

As used in this specification and the appended claims, the singular forms "a", "an" and "the" include plural referents unless the content clearly dictates otherwise. Thus, for example, reference to "a cell" may include a combination of two or more cells; reference to "DNA" may include mixtures of DNA, and the like.

Vaccine formulations may conveniently be presented in unit dosage form and may be prepared by conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials. Extemporaneous injection solutions and suspensions may be prepared from purified nucleic acid preparations for the DNA plasmid priming compounds and/or purified viral vector compounds commonly used by one of ordinary skill in the art. Preferred unit dosage formulations are those containing a dose or unit, or an appropriate fraction thereof, of the administered ingredient. It should be understood that in addition to the ingredients, particularly mentioned above, the formulations may also include other agents commonly used by one of ordinary skill in the art.

The formulation may be administered through different routes, such as oral, including buccal and sublingual, rectal, aerosol, nasal, intramuscular, subcutaneous, intradermal, and topical. The vaccine may likewise be administered in different forms, including but not limited to solutions, emulsions and suspensions, microspheres, particles, microparticles, nanoparticles, and liposomes. It is expected that from about one to about five dosages (e.g., two dosages—an initial inoculation, the prime of prime/boost, and a booster) may be required per immunization protocol. The initial prime and boost administrations may contain a quantity of antigen sufficient to induce a satisfactory immune response. An appropriate quantity of prime and boost antigen(s) to be administered is determined for any of the prime/boost protocols disclosed herein by one skilled in the art based on a variety of physical characteristics of the subject or patient, including, for example, the patient's age, body mass index (weight), gender, health, immunocompetence, and the like. Similarly, the volume of administration will vary depending on the route of administration. By way of example, intramuscular injections may range from about 0.1 mL to 1.0 mL. Preferably a patient has a normal immune system and is not infected with human immunodeficiency virus, although the vaccine may also be administered after initial HIV infection to ameliorate disease progression, or after initial infection to treat AIDS.

Further, with respect to determining the effective level in a patient for treatment of HIV, in particular, suitable animal models are available and have been widely implemented for evaluating the in vivo efficacy against HIV of various gene therapy protocols (Sarver et al. (1993b), supra). These models include mice, monkeys and cats. Even though these animals are not naturally susceptible to HIV disease, chimeric mice models (e.g., SCID, bg/nu/xid, NOD/SCID, SCID-hu, immunocompetent SCID-hu, bone marrow-ablated BALB/c) reconstituted with human peripheral blood mononuclear cells (PBMCs), lymph nodes, fetal liver/thymus or other tissues can be infected with lentiviral vector or HIV, and employed as models for HIV pathogenesis. Similarly, the simian immune deficiency virus (SIV)/monkey model can be employed, as can the feline immune deficiency virus (FIV)/cat model. The pharmaceutical composition can contain other pharmaceuticals, in conjunction with a vector according to the invention, when used to therapeutically treat AIDS. These other pharmaceuticals can be used in their traditional fashion (i.e., as agents to treat HIV infection).

Since the discovery of HIV, numerous monoclonal antibodies to the envelope protein have been produced by random cloning of heavy and light chains in phage display libraries or by selection of antibody secreting hybridomas, but only a few highly active broad neutralizing antibodies have been obtained {Pantophlet, 2006; Burton, 2005; Mascola, 2007; Zolla-Pazner, 2004; Karlsson Hedestam, 2008}. Among these b12 anti-CD4bs {Burton, 1991}, 2F5 and 4E10 anti-gp41 {Buchacher, 1994; Zwick, 2001}, and 2G12 anti-glycan {Trkola, 1996} antibodies have received the greatest attention because of their unique breadth and potency in vitro and in vivo. Ideally, a vaccine that induces such antibodies might be protective against HIV. However, to date, it has not been possible to re-isolate such antibodies from patients, or induce them by immunization in experimental animals {Karlsson-Hedestam, 2008; Zolla-Pazner, 2004; Burton, 2005; Burton, 2004; Mascola, 2007}.

The invention further provides for identifying and isolating antibodies from the memory compartment of B cells containing many different neutralizing antibodies with diverse activity. Therefore, broad serologic neutralizing activity can involve a combination of antibodies.

In embodiments discussed herein, the invention provides for a new core epitope to gp120 (gp120$^{core}$). Antibodies to gp120$^{core}$ differ from B 12 and can be a very potent neutralizer in that it works as well as the CD4 binding site antibodies in neutralization studies. In this embodiment, the invention provides for a collection of antibodies that neutralize various strains and clades of HIV with different antibodies neutralizing different viruses. An embodiment of the invention is a vaccine comprising the epitopes identified by the antibodies disclosed.

The present invention provides for vaccines, either alone or in combination with other antigens, and epitopes, that elicit broad neutralizing activity in serum. Neutralization activity can be the result of a single epitope such as gp120$^{core}$ of the present invention, or a plurality of epitopes identified by the antibodies as described. Broadly neutralizing serological activity can be elicited by a combination of antigens that phenocopies the natural anti-HIV immune response in patients as an effective means of protection against a large number of HIV strains.

To characterize memory antibody responses to HIV, antibodies from HIV envelope binding memory B cells cloned from six HIV infected patients with high titers of broadly neutralizing antibodies. The human B cell memory response to HIV can be composed of independent, expanded B cell clones can express high affinity neutralizing antibodies to the gp120 variable loops, the CD4 binding site, the co-receptor biding site, and to a new neutralizing epitope that is on the same face of gp120 as the CD4 binding site, gp120$^{core}$. The IgG memory B cell compartment in humans with serum neutralizing activity to HIV can thus be comprised of multiple individual clonal responses each with more limited anti-viral activity that in aggregate, therefore resulting in broad neutralizing activity. Effective vaccination to HIV may require a strategy that elicits a broad repertoire of antibodies to provide protection against the large number of HIV strains and the neutrability of the virus.

The antibodies produced by memory B cells purified from the blood of six patients with high serum titers of broadly neutralizing anti-HIV antibodies (FIG. 5). One of the patients was a non progressor, three were elite controllers, one a slow progressor, and one had been infected two years ago (Supplementary Table 1 {Walker, 2007}). Artificially trimerized gp 140 protein, which is a fusion of the gp120 and gp41 envelope proteins, can be used to identify and purify HIV specific B cells because this molecule resembles the native trimer in that it can bind to the broadly neutralizing anti-HIV antibodies {Scheid, 2009; Yang, 2000}. Small numbers of B cells that bind the gp140 trimer can readily detected in the IgG memory B cell compartment in the samples from patients but not in uninfected controls (FIG. 14 and FIG. 6). Individual gp140 binding memory B cells can also be purified by cell sorting, and Ig heavy and light chains can be cloned from single cell cDNA libraries {Tiller, 2008; Scheid J., 2009}. Ig heavy and light chain genes can be amplified from samples from each of four HIV infected individuals (FIG. 1a) and smaller numbers from two other samples (FIG. 6).

In embodiments discussed herein, the invention provides for a new core epitope to gp120 (gp120$^{core}$) Antibodies to gp120$^{core}$ differ from B12 and can be a very potent neutralizer in that it works as well as the CD4 binding site antibodies in neutralization studies. Provided herein is the conserved epitope on gp120 that is frequently recognized by high affinity, neutralizing monoclonal antibodies cloned from HIV-1 infected individuals with broadly neutralizing serologic activity and low to intermediate viral loads. gp120$^{core}$ epitope to D474A, M475A, R476A, thus to the outer domain/inner domain junction of gp120.

The antibodies disclosed herein bind to a conformational epitope recognized by neutralizing human monoclonal anti-gp120-$^{core}$ antibodies. These antibodies target a conformational epitope on gp120 (D474A, M475A, R476A) found within the α5-helix of the molecule, that is highly conserved across different HIV-1 clades. Anti-core antibodies bind to a conformational three-dimentional structure of the linear epitope TNGTEIFRPGGGDMRDNWR (SEQ ID NO: 629) however the anti-core antibodies do not recognize the linear peptide epitope. Thus, anti-core antibodies do not recognize a linear epitope.

Addressing the induction of an immune response against the gp120 core epitope, anti-core antibodies show a higher affinity (one order of magnitude) to gp120$_{core}$ than to gp120 {Scheid JF, 2009 #25}, which can be related to the absence of the variable loops 1 to 3 in gp120$^{core}$ that may interfere with anti-core antibody binding.

In an embodiment, the invention provides for a collection of antibodies that neutralize various strains and clades of HIV with different antibodies neutralizing different viruses. An embodiment of the invention is a vaccine comprising the epitopes identified by the antibodies disclosed.

The present invention provides for vaccines, either alone or in combination with other antigens, and epitopes, that elicit broad neutralizing activity in serum. Neutralization activity can be the result of a vaccine comprising a single epitope or antigen such as gp120$^{core}$ of the present invention, or a plurality of epitopes or antigens identified by the antibodies as described. Broadly neutralizing serological activity can be elicited by a combination of antigens or epitopes that phenocopies the natural anti-HIV immune response in patients as an effective means of protection against a large number of HIV strains. The way forward for a vaccine is to phenocopy the human as revealed by the following examples.

Examples

Characteristics of Anti-gp140 Memory Antibodies

In contrast to random antibody cloning from memory B cells {Mietzner, 2008; Tiller, 2007}, and to the antibodies isolated from B cells that did not bind to gp140 from the same subjects, many clonally related antibodies in the gp140 binding B cells can be formed (FIG. 1*b* and FIG. 6, FIG. 7 and FIGS. 15-22). Each clone was expanded to varying degrees ranging from 1-39 family members (FIG. 1*b*). The majority of the antibodies derived from gp140 binding memory cells belonged to clones with more than one member and in patient sample #2 all of the 141 antibodies were members of 22 expanded families related by somatic mutations. The finding that most of the antibodies isolated from the four more complete patients belonged to expanded clones suggested that a significant fraction of the gp140-reactive memory B cell repertoire was captured.

Individual antibodies were expressed by transfection and tested for reactivity to gp140 by ELISA. Eighty-six percent of all of the antibodies cloned from sorted gp140 binding B cells were gp140 reactive (FIG. 1*b*, *d*, and FIGS. 15-22). In contrast, none of the 51 antibodies obtained from the non-gp 140 binding memory B cells from two of the same patients were gp140 specific (FIG. 1*b*, *d*, and FIGS. 15-22). Overall, 432 individual anti-gp140 antibodies were obtained belonging to 132 different clones (FIGS. 15-22). The expanded clones of gp140 binding B cells contained antibodies that were related by mutation with a maximum number of 66 mutations separating the individual clonal relatives (FIG. 7 and FIGS. 15-22).

When compared to IgG antibodies derived from non-gp 140 binding B cells from the same patients or IgG memory B cells from historical controls {Tiller, 2007} the gp140 binding antibodies were enriched for $V_H$I {Huang, 2004}, Igκvs. Igλ, and Jκ2 or Jκ5 (FIGS. 1*c* and 2*a*, *b* and *c*). Individual samples showed longer or more charged IgH CDR3s but these features were not found in all of the samples (FIG. 2*b*). An unexpected finding was that anti-gp 140 antibodies were highly mutated when compared to non-gp140 binding antibodies from the same patient samples or randomly cloned IgG memory antibodies from historical controls (FIG. 2*d*). This difference in mutation frequency was found for both $V_H$ and Vκ and was highly significant whether all antibodies were included or counted individual clones only a single time (FIG. 2*d* and FIG. 8). Anti-gp140 memory B cells can be highly selected post-germinal center cells skewed to Igκ and $V_H$1 usage. The exceptionally high level of mutation found in these antibodies may reflect chronic B cell immune responses to HIV with persistent somatic hypermutation and selection.

Epitopes Recognized by Anti-gp140 Memory Antibodies

To map the antigenic specificity of the gp140 binding antibodies performed ELISA experiments with purified gp120 and gp41 were performed. Seventy percent (70%) of the gp140 antibodies bound to gp120 and 30% were gp41 specific (FIG. 3*a*). Thus, the majority of the anti-gp140 antibodies in patient samples with broadly neutralizing anti-HIV antibodies are directed to gp120.

Anti-gp41 antibodies were further screened against a peptide library consisting of overlapping 15mers including the membrane proximal region that binds to two broadly neutralizing anti-gp41 monoclonal antibodies 2F5 and 4E10 {Muster, 1993; Zwick, 2001}. None of the 131 anti-gp41 antibodies assayed bound to the membrane proximal peptides and only one antibody bound to peptides corresponding to the previously reported immunodominant region of gp41 {Xu, 1991}. The majority of the gp41 antibodies produced by memory B cells in patients with broad serum neutralizing activity recognize conformational determinants and antibodies to the membrane proximal region can be difficult to detect in the gp140 trimer binding B cells despite the fact that both 2F5 and 4E10 bind to the trimer.

The specificity of the anti-gp120 binding antibodies was further mapped using a collection of mutant proteins: gp120$^{D368R}$ interferes with binding to CD4 and nearly all known anti-CD4 binding site (anti-CD4bs) antibodies including b12 {Pantophlet, 2003; Olshevsky, 1990; Roben, 1994; Thali, 1991}; gp120$^{142R}$ interferes with CD4 induced coreceptor binding site antibodies (anti-CD41) including 17b {Thali, 1993}; gp120$^{core}$ lacks the variable loops (VLs) and interferes with anti-VL and CD4i antibodies {Kwong, 2000; Wyatt, 1998; Kwong, 1998}. Antibodies that bound to gp120, gp120$^{core}$, gp120$^{142OR}$ but not to gp120$^{D368R}$ were classified as CD4bs directed. Similarly, those that bound to gp120 but not to gp120$^{core}$ were classified as anti-VL antibodies, and those that bound to gp120, and gp120$^{D368R}$, but not to gp120$^{1420R}$ were classified as anti-CD4i antibodies. Anti-CD4bs, -CD4i, and -VL antibodies were found in all 4 of the more complete patients but their relative representation varied significantly between patients (FIG. 3b). Among all anti-gp140 antibodies anti-CD4bs made up 9%, anti-CD4i 16% and anti-VL 27% (FIG. 3b). All of these antibodies were also screened for binding to a library of overlapping 15mer peptides covering all of gp120. Only three of the anti-gp120 antibodies bound to the linear peptides and all of these bound to the region within the V3 loop that is also targeted by a previously described antibody 447-52D {Gorny, 1992}.

To examine the kinetic binding properties of the anti-CD4bs, -CD4i and -VL antibodies to gp140, surface plasmon resonance experiments were performed with gp140 trimer comparing the binding of 7 such antibodies to the b12 anti-CD4bs monoclonal (FIG. 9 and FIG. 23). The antibodies had rapid association and slow dissociation constants with Kds ranging from $10^{-8}$-$10^{-11}$ with b12 at the lower end of the spectrum with a Kd of $1.2 \times 10^{-8}$ (FIG. 9 and FIG. 23). Thus, the IgG memory B cells obtained from humans that produce broad serum neutralizing activity expressed high affinity antibodies specific for the CD4bs, the CD4i site and the VLs and there was no single immunodominant epitope.

In addition to anti-CD4bs, -CD4l, and -VL antibodies a group of antibodies that bound to gp120, gp120$^{core}$, gp120$^{368R}$, and gp120$^{1420R}$ were found which are referred to as anti-gp120$^{core}$. These antibodies make up 18% of all anti-gp 140 antibodies varying between patients from about 3% to about 35% of the repertoire (FIG. 3b). Only one of the 24 anti-gp120$^{core}$ antibodies was directed to an epitope that was sensitive to gp120 -, whereas 4 out of 13 neutralizing anti-CD4i tested showed sensitivity to deglycosylation (FIG. 4 and FIG. 10) and therefore the anti-gp120$^{core}$ antibodies are not predominantly directed to glycosylation dependent epitopes. In addition, none of the anti-gp120$^{core}$ antibodies bound to a peptide library consisting of overlapping 15mers of gp120. The affinity of the anti-gp120$^{core}$ antibodies was comparable to the other antibodies as measured by surface plasmon resonance for 6 selected antibodies in this group (Kds of $2 \times 10^{-8}$-$4.8 \times 10^{-10}$, FIG. 9 and FIG. 23).

To further examine the properties of the anti-gp120$^{core}$ antibodies inhibition ELISA experiments were performed using biotin labeled neutralizing antibodies to the CD4bs (b12 and 1-64), or CD4i (1-68), or the V3L (1-79) or a representative member of the gp120$^{core}$ specific group (2-491) {Binley, 2004} (FIG. 3d, FIG. 4, FIGS. 15-22, FIG. 26). As expected the results for the two anti-CD4bs antibodies, b12 and 1-64, were similar and both were inhibited by other neutralizing anti-CD4bs antibodies but not by CD4i or VL specific antibodies (FIG. 3d and Supplementary Table 2, 4, and 5). In contrast, neutralizing anti-CD4i, 1-182, was inhibited by all of the neutralizing anti-CD4bs antibodies, but only by 50% of the other anti-CD4i and 29% of the anti-VL antibodies (FIG. 3d and Supplementary Table 2, 4, and 5). The selected neutralizing anti-V3L antibody was strongly inhibited by the other anti-V3L antibodies and not by anti-CD4bs, anti-CD4i, or other neutralizing anti-VLs that were not V3L-NNNTRKSINIGPGRA (SEQ ID NO. 630) peptide specific (FIG. 3, FIG. 4 FIGS. 15-22, FIG. 26 and). The CD4bs may be in close proximity to the CD4i site and that the conformation of the CD4i site is dependent on the CD4bs {Lin, 2008; Thali, 1993; Wyatt, 1998; Rizzuto, 1998; Kwong, 1998}.

Anti-gp120$^{core}$ antibodies resembled b12 and CD4bs antibodies in that they inhibited the binding of the selected anti-gp120$^{core}$, anti-CD4bs, and anti-CD4i, but they did not inhibit binding of the anti-V3L antibody. Conversely, the 2-491 anti-gp120$^{core}$ antibody was inhibited by the other anti-gp120$^{core}$ and the anti-CD4bs antibodies (FIG. 3d, FIGS. 15-22, FIG. 26 and). However, only three out of thirteen of the anti-CD4i antibodies and none of the seven anti-VL antibodies inhibited binding of the anti-gp120$^{core}$ (FIG. 3d, FIGS. 15-22, FIG. 26 and). Anti-gp120$^{core}$ antibodies can recognize an immunogenic epitope in the vicinity of the CD4bs and CD4i sites, but these antibodies differ from CD4, b12 and b17 because they bind gp-120 and gp120$^{1420R}$ and therefore the epitope they recognize must be different from that recognized by CD4 and most CD4bs and CD4i antibodies. This group of antibodies shares some of the features of anti-CD4bs antibodies, and can recognize one or more epitopes on the conserved face of HIV gp120 that interacts with CD4 and the co-receptor.

HIV Neutralizing Activity

To examine the neutralizing activity of the memory antibodies, the ability to inhibit infection of TZM-b1 cells by Env pseudovirus variants {Montefiori, 2005} including isolates from clades A, B, and C (FIG. 4 and) was measured. The panel of clade B viruses was expanded to contain viruses with different levels of resistance to known neutralizing antibodies {Monrefiori, 2005} ranging from tier-1 strains like SFI62.LS that can be easily neutralized to tier-2 strains like TRO.11 which are not neutralized even by potent broadly neutralizing anti-CD4bs antibody b12 {Li, 2005}. To determine whether there was intraclonal variation in neutralizing activity, many of the somatic variants of the anti-CD4bs antibodies were assayed (FIG. 7). Finally, purified serum IgG from the patients was assayed on the same viruses for comparison (FIG. 4, FIG. 5). The breadth of neutralizing activity and the relative sensitivity of different viral strains was similar for serum and purified IgG indicating that most of the neutralizing activity was in the IgG fraction. Purified IgG neutralized viruses from all 3 clades, but the activity was most pronounced for the more easily neutralized tier-1 HIV variants while high concentrations of serum IgG were required for the more resistant strains (FIG. 4).

Seventy-six percent (76%) of all anti-gp120s and none of the anti-gp41 clonal families showed neutralizing activity (FIG. 4 and). Consistent with this finding the anti-gp41 antibodies were the most highly somatically mutated of the anti gp140 antibodies (FIG. 2d, anti-gp41 average number of mutations 34 vs. 24 for anti-gp120 p<0.001) suggesting that B cells producing these antibodies may be persistently recruited to germinal centers and therefore did not exert significant selective pressure on the virus when compared to anti-gp120 antibodies.

All anti-CD4bs and 88% of all anti-gp120$^{core}$ antibodies showed some neutralizing activity (FIG. 4). Of a total of 64 independent clonal families of neutralizing antibodies 22 were anti-gp120$^{core}$, 18 were anti-CD4bs, 16 were anti-CD41, and 8 were anti-VL including all three of anti-V3L antibodies (FIG. 4). As a group, the antibodies to the CD4bs and gp120$^{core}$ showed the highest levels of broad cross-clade and intra-clade B activity with rare antibodies covering the more resistant tier-2 viruses (FIG. 4). Although the anti-V3L antibodies showed cross-clade neutralizing activity, and one of them neutralized tier-2 viruses at high concentrations, most of the anti-VL antibodies were more restricted (FIG. 4). Cross-clade neutralizing activity was also found in the anti-CD4i antibodies but only three of these antibodies showed activity against the more difficult to neutralize tier-2 viruses (FIG. 4 and FIG. 27).

Serum antibody absorption studies found that neutralization of tier-2 viruses was predominantly achieved by anti-CD4bs with a smaller variable contribution from anti-CD4i and unidentified antibodies, however, the resolution in such studies is limited and they cannot define the nature or number of antibodies to a specific site {Li, 2008; Li, 2007; Dhillon, 2007}. No case where a single monoclonal antibody or class of antibodies in memory B cells accounts for all of the neutralizing activity in serum was found (FIG. 4). Individual antibodies showed variable levels of activity against different viruses. For example in patient #1, the Clade-C virus MW965.23 was neutralized by CD4bs 1-621, gp120$^{core}$ 1-705 and VL antibody 1-79, with anti-gp120$^{core}$ 1-705 showing the highest activity (FIG. 4). In contrast, 1-621 did not neutralize the clade-B virus Bal.26, whereas 1•79 did and was superior to 1-705 (FIG. 4). Similarly in patient #2, the clade-A virus DJ263.8 is neutralized by anti-CD4bs 2-470, anti-VL 2-59 but not anti-VL antibody 2-1261, whereas the same anti-VL antibody neutralized the clade-B tier-2 virus RHPA4259.7, but neither 2-470 nor 2-59 reached IC50 against this virus (FIG. 4). Some degree of neutralizing activity was common among gp120 specific memory antibodies. These antibodies recognized a broad array of epitopes and neutralizing activity was heterogeneous for different viral isolates.

Memory B cells are long-lived cells and their antibodies reflect an individuals immune responses over time. Some of these cells differentiate into plasma cells that secrete antibodies but the relative contribution of any given memory B cell to the plasma cell compartment is unknown and therefore a pool of cloned memory B cell antibodies cannot be compared directly to serum. Pools of all antibodies for each individual patient were created and compared the pools to purified serum IgG for neutralization (FIG. 4 and FIG. 27). The pools contained equal concentrations of each of the anti-gp140 clones irrespective of clone size or neutralizing activity.

Purified IgGs from samples of all of the four persons studied neutralized nearly all of the tier1 viruses including clades A, B and C at concentrations ranging from 1-212 μg/ml. The corresponding pools of the recombinant antibodies were active against these viruses and in some cases neutralized viruses that were not neutralized by the serum IgG. For example purified IgG from patient 4 did not reach an IC50 against SS1196.1 or 6535.3 (tier-2), but these viruses were neutralized by recombinant antibodies 4-42, 4-8 and 4-433 and by pooled antibodies from this patient (FIG. 4 and FIG. 27).

Consistent with the more stringent requirements for tier-2 neutralization, only the pooled monoclonal antibodies from patient 1 and 4 completely and 2 and 3 partially reconstituted this type of activity (FIG. 4 and FIG. 27). In each case the activity of the pool was greater than that of any single antibody. For example, RHPA4259.7, TRO.11 and PVO.4 were neutralized by 1-1.24 mg/ml of the patient 1 pool (pool of 21 antibodies), but none of the individual antibodies were able to neutralize these viruses (FIG. 4 and FIG. 27). Similarly the TRO.11 virus was neutralized by the pooled antibodies from patient 4 at 1.4 mg/ml (pool of 50 antibodies). The memory antibody compartment contains a large mixture of anti-HIV neutralizing antibodies combinations of which can increase the breadth of neutralization activity.

Fine Mapping of Anti-Core Antibody Binding Site on gp120.

In order to map the epitope recognized by anti-core antibodies, assayed were anti-core antibodies for binding to 72 different alanine mutants of the HIV-1 envelope protein gp120 by capture ELISA. Controls included the anti-CD4bs antibody b12 and an anti-variable-loop antibody (1-79) {Burton DR, 1994 #10; Saphire EO, 2001 #11}; Scheid JF, 2009 #25}. Mutations that altered antibody binding by 40% or more compared to the wild type protein were considered positive. The mutated residues were initially spread across gp120 to cover a broad range of candidate binding sites and then refined based on initial binding results. In particular, included were residues from the variable-loop 2 (VL2), the silent face, the CD4bs, the CD4 is, the Phe 43-cavity {Kwong PD, 1998 #32}, but also residues that lie proximal or distal to these sites (FIG. S1).

Ten mutations were found that altered the binding of nearly all anti-core antibodies and b12 despite their being physically distant from the CD4bs recognized by b12. Based on their position and chemical characteristics, these residues (L288, I449, T450, L265A, 5264, C378, N262, F376, F383, F353) appear to be required to maintain structural integrity of the molecule.

As previously demonstrated, alanine substitutions in the CD4bs (E370A, D368A, D368A/E370A), or the Phe 43-cavity (F376A), or in close proximity to the CD4bs (N276A, P470A, R480A, W96A, E275A, D477A, Y384A) reduce binding by the anti-CD4bs antibody b12. In addition, found was a slight decrease in b12 binding to W400A, R273A, K350A all of which are not thought to contribute directly to the CD4bs. These mutations had little effect on anti-core antibody binding. Among the 72 mutants, three mutants were found (D474A, M475A, R476A) that inhibited the binding of anti-core antibodies, but had no significant effect on b12 (FIG. 1A). These adjacent residues are in close proximity to the CD4bs and cover a stretch from the CD4bs (D474) down to the α5 helix at the outer-domain/inner-domain junction of gp120 (M475, R476) (FIG. 1B). Among the 24 anti-core antibodies, only two were insensitive to these three mutations. Of the remaining 22, 16 were sensitive to both D474A and R476A (FIG. 1C), and in addition only eight of these showed altered binding to M475A (FIG. 1C).

Methods Summary

Participants.

Samples were derived from patients identified as elite controllers, long term non progressors and slow progressors based on previously described criteria {Walker, 2007; Deeks, 2007}. The controls were samples from uninfected patients. All work with human samples was performed in accordance with approved Institutional Review Board protocols.

Staining, Single Cell Sorting and Antibody Cloning.

Biotinylated YU2-gp140 was produced and used for staining and sorting of single memory B cells as previously described {Yang, 2000; Schei, 2009; Wardemann, 2003; Tiller, 2008}. cDNA synthesis and amplification were performed as described previously {Wardemann, 2003}.

ELISA.

For ELISA-testing individual antigens were coated on 96 well plates overnight as described previously {Tiller, 2008}. For competition ELISAs YU2-gp120 {Kwong, 2000} coatedplates were washed and incubated with pre-mixed biotinylated antibody and inhibiting antibody. Binding of the biotinylated antibody was detected using streptavidin conjugated HRP (Serotec) and Horseradish Peroxidase Substrate Kit (Biorad).

Neutralization Screen.

Neutralization screens were performed as described {Montefiori, 2005; Li, 2005}. In brief, neutralization was detected as reduction in luciferase reporter gene expression after single round infection in Tzm-bl cells. In order to rule out unspecific antiviral activity in plasma and antibody samples SIVmac251.WY5 was used as a negative control.

Ig Gene Sequence Analysis.

Aliquots of the $V_H$, Vκ and Vλ chain second PCR products were sequenced and analyzed by Ig BLAST as described previously {Wardemann, 2003}.

Recombinant Antibody Production and Purification.

Monoclonal antibodies were produced by transient transfection of suspension cultured 293T cells with "293 fectin" according to the manufacturer's suggestion (Invitrogen). Supernatants from transfected cells were collected after about 4 days of culture. Recombinant protein was purified with Protein G beads (GE Healthcare) according to the manufacturer's instructions, dialysed against PBS in Slide-A-Lyzer Dialysis Cassettes (Pierce) and stored at 4° C.

Deglycosylation of gp120.

For deglycosylation 150 ug of GPI20 was treated with PNGase F (New England Biolabs) and O-glycosidase (QA Bio) in 50 mM sodium phosphate without denaturing agents and incubated overnight at 37° C. to ensue maximal deglycosylation. Lectin blots were preformed to verify glycan removal as previously described {Kaneko. 2006).

Surface Plasmon Resonance.

All experiments were performed with a Biacore T100 instrument (Hiacore, Inc) in HBS-EP+ running buffer (Biacore, Inc) at 25C. Samples were analyzed in kinetic experiments performed in duplicates. Antibodies were immobilized to the surface of CM5 chips (Biacore, Inc.) by standard amine coupling with final immobilization levels of 250 to 500 RU. For kinetic measurement gp140 {Yang, 2000} was injected through flow cells in 5 different concentrations (357-22 nM) in HBS–EP+ running buffer (Biaccre, Inc.) at a flow rate of 50 µl/min, with 2 min association and 5 min dissociation. $k_d$, $k_a$, and $K_D$ values were calculated after subtraction of background binding to a control flow cell using Biacore T100 Evaluation software using the kinetic analysis and the 1:1 binding model. The sensor surface was regenerated between each experiment with a 30 second injection of 10 mM glycine-HCl pH 2.5 at a flow rate of 50 µl/min.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein.

Each of the applications and patents cited in this text, as well as each document or reference, patient or non-patient literature, cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference in their entirety. More generally, documents or references are cited in this text, either in a Reference List before the claims; or in the text itself; and, each of these documents or references ("herein-cited references"), as well as each document or reference cited in each of the herein-cited references (including any manufacturer's specifications, instructions, etc.), is hereby expressly incorporated herein by reference.

The invention claimed is:

1. An isolated or purified antibody, or antigen binding portion thereof, wherein said antibody binds specifically to a conformational HIV-1 gp120 α5-helix epitope comprising the amino acids D474, M475, and R476, wherein said antibody, or binding portion thereof, does not bind specifically to a linear peptide consisting of SEQ ID NO.: 628, and further wherein said binding is contingent upon the presence of amino acid residues L288, I449, T450, L265, S264, C378, N262, F383, and F376 in gp120, wherein said numbering scheme is based upon the prototypic HIV-1 isolate YU-2.

2. The antibody, or antigen binding portion thereof of claim 1, wherein said antibody, or antigen binding portion thereof neutralizes at least two different isolates of the HIV-1 virus selected from the group consisting of clade A, clade B, or clade C.

3. The antibody of claim 2, wherein the antibody binds to a clade A HIV-1 virus isolate, and said antibody neutralizes a titer consisting of said clade A HIV-1 virus isolate with an IC50 less than 25.

4. A method of inhibiting HIV-1 viral replication in a host comprising administering an effective amount of a composition comprising the antibody of claim 1 to said host.

* * * * *

SEQUENCE LISTING

```
<160> NUMBER OF SEQ ID NOS: 632

<210> SEQ ID NO 1
<211> LENGTH: 20
<212> TYPE: PRT
<213> ORGANISM: Homo sapiens

<400> SEQUENCE: 1

His Glu Ala Pro Arg Tyr Ser Tyr Ala Phe Arg Arg Tyr Tyr His Tyr
1               5                   10                  15

Gly Leu Asp Val
            20

<210> SEQ ID NO 2
<211> LENGTH: 20
<212> TYPE: PRT
<213> ORGANISM: Homo sapiens

<400> SEQUENCE: 2

His Glu Ala Pro Arg Tyr Ser Tyr Ala Phe Arg Asn Tyr Tyr His Tyr
1               5                   10                  15

Gly Leu Asp Val
            20
```

<210> SEQ ID NO 3
<211> LENGTH: 15
<212> TYPE: PRT
<213> ORGANISM: Homo sapiens

<400> SEQUENCE: 3

Asp Arg Arg Arg Phe Leu Glu Trp Ser Leu Tyr Gly Met Asp Val
1               5                   10                  15

<210> SEQ ID NO 4
<211> LENGTH: 19
<212> TYPE: PRT
<213> ORGANISM: Homo sapiens

<400> SEQUENCE: 4

Ala Gly Leu Asp Tyr Asn Phe Trp Asn Gly Lys Gly Arg Lys Gly Ala
1               5                   10                  15

Phe Asp Val

<210> SEQ ID NO 5
<211> LENGTH: 14
<212> TYPE: PRT
<213> ORGANISM: Homo sapiens

<400> SEQUENCE: 5

Gly Thr Leu Trp Phe Gly Glu Ser Gly Leu Arg Leu Asp His
1               5                   10

<210> SEQ ID NO 6
<211> LENGTH: 14
<212> TYPE: PRT
<213> ORGANISM: Homo sapiens

<400> SEQUENCE: 6

Gly Ser Leu Trp Phe Gly Glu Ser Gly Leu Arg Leu Asp His
1               5                   10

<210> SEQ ID NO 7
<211> LENGTH: 18
<212> TYPE: PRT
<213> ORGANISM: Homo sapiens

<400> SEQUENCE: 7

Asn Arg Arg Val Ala Met Pro Glu Ala Met Ile Leu Ser Phe Tyr Met
1               5                   10                  15

Asp Val

<210> SEQ ID NO 8
<211> LENGTH: 17
<212> TYPE: PRT
<213> ORGANISM: Homo sapiens

<400> SEQUENCE: 8

Gly Ile Gln Glu Asp Tyr Asp Phe Trp Arg Glu Tyr Arg Glu Leu Asp
1               5                   10                  15

Tyr

<210> SEQ ID NO 9
<211> LENGTH: 18
<212> TYPE: PRT
<213> ORGANISM: Homo sapiens

<400> SEQUENCE: 9

Val Val Pro Met Phe Ser Ile Phe Gly Val Val Lys Ala Asn Tyr Phe
1               5                   10                  15

Asp Tyr

<210> SEQ ID NO 10
<211> LENGTH: 16
<212> TYPE: PRT
<213> ORGANISM: Homo sapiens

<400> SEQUENCE: 10

Val Ile Ser Gly Arg Ile Thr Ile Phe Tyr Tyr Asn Tyr Ile Asp Val
1               5                   10                  15

<210> SEQ ID NO 11
<211> LENGTH: 16
<212> TYPE: PRT
<213> ORGANISM: Homo sapiens

<400> SEQUENCE: 11

Val Leu Ser Gly Arg Ile Thr Ile Phe Tyr Tyr Tyr Met Asp Val
1               5                   10                  15

<210> SEQ ID NO 12
<211> LENGTH: 16
<212> TYPE: PRT
<213> ORGANISM: Homo sapiens

<400> SEQUENCE: 12

Gly Phe Arg Gly Ser Pro Phe Ser Ser Gly Ser Leu Tyr Phe Asp Ser
1               5                   10                  15

<210> SEQ ID NO 13
<211> LENGTH: 16
<212> TYPE: PRT
<213> ORGANISM: Homo sapiens

<400> SEQUENCE: 13

Gly Phe Arg Gly Ser Pro Phe Ser Ser Gly Ser Leu Tyr Phe Asp Ser
1               5                   10                  15

<210> SEQ ID NO 14
<211> LENGTH: 16
<212> TYPE: PRT
<213> ORGANISM: Homo sapiens

<400> SEQUENCE: 14

Gly Phe Arg Gly Asn Val Phe Ser Thr Gly Trp Phe Tyr Leu Asp Phe
1               5                   10                  15

<210> SEQ ID NO 15
<211> LENGTH: 16
<212> TYPE: PRT
<213> ORGANISM: Homo sapiens

<400> SEQUENCE: 15

Gly Phe Arg Gly Ser Pro Leu Ser Ser Gly Ser Leu Tyr Phe Asp Ser
1               5                   10                  15

<210> SEQ ID NO 16
<211> LENGTH: 16
<212> TYPE: PRT
<213> ORGANISM: Homo sapiens

<400> SEQUENCE: 16

Gly Phe Arg Gly Ser Pro Phe Ser Ser Gly Ser Met Tyr Phe Asp Ser

```
<210> SEQ ID NO 17
<211> LENGTH: 27
<212> TYPE: PRT
<213> ORGANISM: Homo sapiens

<400> SEQUENCE: 17

Asp Phe Pro Arg Phe His Arg Leu Val Gly Asn Tyr Asp Phe Trp Arg
1               5                   10                  15

Gly Thr Leu Asp Arg Phe Ser Tyr Met Asp Leu
            20                  25

<210> SEQ ID NO 18
<211> LENGTH: 14
<212> TYPE: PRT
<213> ORGANISM: Homo sapiens

<400> SEQUENCE: 18

Ser Thr Pro Leu Val Trp Pro Pro Ala Asn Gly Leu Asp Val
1               5                   10

<210> SEQ ID NO 19
<211> LENGTH: 15
<212> TYPE: PRT
<213> ORGANISM: Homo sapiens

<400> SEQUENCE: 19

Asp Asn Arg Asp Gln Trp Leu Val Leu Arg Ser Trp Phe Asp Pro
1               5                   10                  15

<210> SEQ ID NO 20
<211> LENGTH: 24
<212> TYPE: PRT
<213> ORGANISM: Homo sapiens

<400> SEQUENCE: 20

Ser Val Ile Thr Asp Leu His Thr Phe Gly Asp Tyr Glu Ser Gly Asp
1               5                   10                  15

Pro Ser Tyr Tyr Tyr Met Asp Val
            20

<210> SEQ ID NO 21
<211> LENGTH: 24
<212> TYPE: PRT
<213> ORGANISM: Homo sapiens

<400> SEQUENCE: 21

Ala Val Ile Thr Asp Leu His Thr Phe Ala Asp Tyr Glu Leu Gly Asp
1               5                   10                  15

Pro Ser Tyr Phe Tyr Met Asp Val
            20

<210> SEQ ID NO 22
<211> LENGTH: 24
<212> TYPE: PRT
<213> ORGANISM: Homo sapiens

<400> SEQUENCE: 22

Ala Val Ile Thr Asp Leu His Thr Phe Gly Asp Tyr Glu Leu Glu Asp
1               5                   10                  15

Pro Ser Tyr Tyr Tyr Met Asp Val
            20
```

```
<210> SEQ ID NO 23
<211> LENGTH: 9
<212> TYPE: PRT
<213> ORGANISM: Homo sapiens

<400> SEQUENCE: 23

Arg Gly Arg Arg Gln Ile Gly Asp Tyr
1               5

<210> SEQ ID NO 24
<211> LENGTH: 9
<212> TYPE: PRT
<213> ORGANISM: Homo sapiens

<400> SEQUENCE: 24

Arg Gly Arg Arg Gln Ile Gly Asp Tyr
1               5

<210> SEQ ID NO 25
<211> LENGTH: 16
<212> TYPE: PRT
<213> ORGANISM: Homo sapiens

<400> SEQUENCE: 25

Ser Tyr Tyr Asp Phe Ser Ile Gly Asp Gly Asn Asp Ala Phe Asp Val
1               5                   10                  15

<210> SEQ ID NO 26
<211> LENGTH: 16
<212> TYPE: PRT
<213> ORGANISM: Homo sapiens

<400> SEQUENCE: 26

Ser Tyr Tyr Asp Phe Gln Thr Asp Ser Gly Asn Asp Ala Phe Asp Val
1               5                   10                  15

<210> SEQ ID NO 27
<211> LENGTH: 16
<212> TYPE: PRT
<213> ORGANISM: Homo sapiens

<400> SEQUENCE: 27

Ser Tyr Tyr Asp Phe Arg Ser Asp Ser Gly Asn Asp Ala Phe Asp Ile
1               5                   10                  15

<210> SEQ ID NO 28
<211> LENGTH: 11
<212> TYPE: PRT
<213> ORGANISM: Homo sapiens

<400> SEQUENCE: 28

Gly Gly Gly Tyr Pro Arg Gly Asn Met Asp Val
1               5                   10

<210> SEQ ID NO 29
<211> LENGTH: 19
<212> TYPE: PRT
<213> ORGANISM: Homo sapiens

<400> SEQUENCE: 29

Asp Thr Thr Thr Phe Thr Thr Phe Gly Gly Pro Asn Met Gly Gly
1               5                   10                  15

Phe Asp Pro
```

```
<210> SEQ ID NO 30
<211> LENGTH: 19
<212> TYPE: PRT
<213> ORGANISM: Homo sapiens

<400> SEQUENCE: 30

Asp Thr Thr Thr Phe Ser Ser Phe Gly Ser Pro Pro His Met Gly Gly
1               5                   10                  15

Leu Asp Pro

<210> SEQ ID NO 31
<211> LENGTH: 19
<212> TYPE: PRT
<213> ORGANISM: Homo sapiens

<400> SEQUENCE: 31

Asp Thr Thr Thr Phe Thr Ser Phe Gly Ser Pro Pro Arg Met Gly Gly
1               5                   10                  15

Leu Asp Pro

<210> SEQ ID NO 32
<211> LENGTH: 19
<212> TYPE: PRT
<213> ORGANISM: Homo sapiens

<400> SEQUENCE: 32

Asp Thr Thr Thr Phe Gly Ala Phe Gly Gly Gly Ala Asn Met Gly Gly
1               5                   10                  15

Leu Asp Pro

<210> SEQ ID NO 33
<211> LENGTH: 19
<212> TYPE: PRT
<213> ORGANISM: Homo sapiens

<400> SEQUENCE: 33

Asp Thr Thr Thr Phe Ser Ser Phe Gly Ser Pro Pro Asn Met Gly Gly
1               5                   10                  15

Leu Asp Pro

<210> SEQ ID NO 34
<211> LENGTH: 19
<212> TYPE: PRT
<213> ORGANISM: Homo sapiens

<400> SEQUENCE: 34

Asp Thr Thr Thr Phe Gly Ala Phe Gly Gly Ser Pro Asn Met Gly Gly
1               5                   10                  15

Leu Asp Pro

<210> SEQ ID NO 35
<211> LENGTH: 13
<212> TYPE: PRT
<213> ORGANISM: Homo sapiens

<400> SEQUENCE: 35

Pro Tyr Val Gln Thr Val Ala Thr Thr Thr Phe Asp Phe
1               5                   10

<210> SEQ ID NO 36
<211> LENGTH: 12
<212> TYPE: PRT
<213> ORGANISM: Homo sapiens
```

```
<400> SEQUENCE: 36

Pro Val Val Asn Thr Ile Leu Pro Tyr Cys Asp Val
1               5                   10

<210> SEQ ID NO 37
<211> LENGTH: 11
<212> TYPE: PRT
<213> ORGANISM: Homo sapiens

<400> SEQUENCE: 37

Arg Gly His Ser Phe Thr Ser Pro Phe Asp Ser
1               5                   10

<210> SEQ ID NO 38
<211> LENGTH: 11
<212> TYPE: PRT
<213> ORGANISM: Homo sapiens

<400> SEQUENCE: 38

Glu Phe Gln Thr Ser Gly Val Val Arg Glu Gly
1               5                   10

<210> SEQ ID NO 39
<211> LENGTH: 11
<212> TYPE: PRT
<213> ORGANISM: Homo sapiens

<400> SEQUENCE: 39

Arg Arg Arg Ser Ala Trp Ser Pro Phe Asp Ser
1               5                   10

<210> SEQ ID NO 40
<211> LENGTH: 11
<212> TYPE: PRT
<213> ORGANISM: Homo sapiens

<400> SEQUENCE: 40

Ala Ser Trp Asp Asp Ser Leu Ser Gly Trp Val
1               5                   10

<210> SEQ ID NO 41
<211> LENGTH: 11
<212> TYPE: PRT
<213> ORGANISM: Homo sapiens

<400> SEQUENCE: 41

Ala Ala Trp Asp Asp Ser Leu Asn Gly Trp Val
1               5                   10

<210> SEQ ID NO 42
<211> LENGTH: 10
<212> TYPE: PRT
<213> ORGANISM: Homo sapiens

<400> SEQUENCE: 42

Gln Gln Tyr Gly Ser Ser Pro Glu Tyr Thr
1               5                   10

<210> SEQ ID NO 43
<211> LENGTH: 5
<212> TYPE: PRT
<213> ORGANISM: Homo sapiens

<400> SEQUENCE: 43
```

```
Gln Gln Tyr Asp Ser
1               5

<210> SEQ ID NO 44
<211> LENGTH: 9
<212> TYPE: PRT
<213> ORGANISM: Homo sapiens

<400> SEQUENCE: 44

Gln Gln Tyr Asn Ser Phe Pro Pro Thr
1               5

<210> SEQ ID NO 45
<211> LENGTH: 9
<212> TYPE: PRT
<213> ORGANISM: Homo sapiens

<400> SEQUENCE: 45

Gln Gln Tyr Asn Ser Phe Pro Pro Thr
1               5

<210> SEQ ID NO 46
<211> LENGTH: 7
<212> TYPE: PRT
<213> ORGANISM: Homo sapiens

<400> SEQUENCE: 46

Gln Gln Tyr Gly Arg Ser Pro
1               5

<210> SEQ ID NO 47
<211> LENGTH: 9
<212> TYPE: PRT
<213> ORGANISM: Homo sapiens

<400> SEQUENCE: 47

Met Gln Gly Thr His Trp Pro Arg Thr
1               5

<210> SEQ ID NO 48
<211> LENGTH: 11
<212> TYPE: PRT
<213> ORGANISM: Homo sapiens

<400> SEQUENCE: 48

Gly Thr Trp Asp Ser Ser Leu Ser Ala Val Leu
1               5                   10

<210> SEQ ID NO 49
<211> LENGTH: 11
<212> TYPE: PRT
<213> ORGANISM: Homo sapiens

<400> SEQUENCE: 49

Ala Ser Trp Asp Asn Ser Leu Ser Gly Pro Val
1               5                   10

<210> SEQ ID NO 50
<211> LENGTH: 11
<212> TYPE: PRT
<213> ORGANISM: Homo sapiens

<400> SEQUENCE: 50

Ala Ser Trp Asp Asn Ser Leu Ser Gly Pro Val
1               5                   10
```

```
<210> SEQ ID NO 51
<211> LENGTH: 9
<212> TYPE: PRT
<213> ORGANISM: Homo sapiens

<400> SEQUENCE: 51

His Gln Tyr Ala Tyr Ser Pro Arg Thr
1               5

<210> SEQ ID NO 52
<211> LENGTH: 9
<212> TYPE: PRT
<213> ORGANISM: Homo sapiens

<400> SEQUENCE: 52

His Gln Tyr Ala Ser Ser Pro Arg Thr
1               5

<210> SEQ ID NO 53
<211> LENGTH: 9
<212> TYPE: PRT
<213> ORGANISM: Homo sapiens

<400> SEQUENCE: 53

Gln Gln Tyr Ser Ser Ser Pro Arg Thr
1               5

<210> SEQ ID NO 54
<211> LENGTH: 9
<212> TYPE: PRT
<213> ORGANISM: Homo sapiens

<400> SEQUENCE: 54

His Gln Tyr Ala Ser Ser Pro Arg Thr
1               5

<210> SEQ ID NO 55
<211> LENGTH: 9
<212> TYPE: PRT
<213> ORGANISM: Homo sapiens

<400> SEQUENCE: 55

His Gln Tyr Ala Ser Ser Pro Arg Thr
1               5

<210> SEQ ID NO 56
<211> LENGTH: 5
<212> TYPE: PRT
<213> ORGANISM: Homo sapiens

<400> SEQUENCE: 56

Met Gln Ser Ile Gln
1               5

<210> SEQ ID NO 57
<211> LENGTH: 10
<212> TYPE: PRT
<213> ORGANISM: Homo sapiens

<400> SEQUENCE: 57

Gln Glu Tyr Gly Arg Ser Pro Pro Phe Pro
1               5                   10

<210> SEQ ID NO 58
<211> LENGTH: 9
```

```
<212> TYPE: PRT
<213> ORGANISM: Homo sapiens

<400> SEQUENCE: 58

Gln Gln Ser Tyr Thr Thr Pro Val Thr
1               5

<210> SEQ ID NO 59
<211> LENGTH: 9
<212> TYPE: PRT
<213> ORGANISM: Homo sapiens

<400> SEQUENCE: 59

Gln Gln Tyr Asn Ser Tyr Ser Gly Thr
1               5

<210> SEQ ID NO 60
<211> LENGTH: 9
<212> TYPE: PRT
<213> ORGANISM: Homo sapiens

<400> SEQUENCE: 60

Gln Gln Tyr Lys Ser Tyr Ser Gly Thr
1               5

<210> SEQ ID NO 61
<211> LENGTH: 9
<212> TYPE: PRT
<213> ORGANISM: Homo sapiens

<400> SEQUENCE: 61

Gln Gln Tyr Lys Ser Tyr Ser Gly Thr
1               5

<210> SEQ ID NO 62
<211> LENGTH: 10
<212> TYPE: PRT
<213> ORGANISM: Homo sapiens

<400> SEQUENCE: 62

Gln Gln Ser Phe Gly Ile Pro Pro Trp Thr
1               5                   10

<210> SEQ ID NO 63
<211> LENGTH: 10
<212> TYPE: PRT
<213> ORGANISM: Homo sapiens

<400> SEQUENCE: 63

Gln His Ser Phe Gly Ser Pro Pro Trp Thr
1               5                   10

<210> SEQ ID NO 64
<211> LENGTH: 10
<212> TYPE: PRT
<213> ORGANISM: Homo sapiens

<400> SEQUENCE: 64

Ala Ala Trp Asp Asp Ser Phe Asp Tyr Val
1               5                   10

<210> SEQ ID NO 65
<211> LENGTH: 10
<212> TYPE: PRT
<213> ORGANISM: Homo sapiens
```

```
<400> SEQUENCE: 65

Ala Ala Trp Asp Asp Ser Leu Asp Tyr Val
1               5                   10

<210> SEQ ID NO 66
<211> LENGTH: 10
<212> TYPE: PRT
<213> ORGANISM: Homo sapiens

<400> SEQUENCE: 66

Ala Ala Trp Asp Asp Ser Leu Asp Tyr Val
1               5                   10

<210> SEQ ID NO 67
<211> LENGTH: 9
<212> TYPE: PRT
<213> ORGANISM: Homo sapiens

<400> SEQUENCE: 67

Gln Gln Tyr Thr Asn Tyr Pro Trp Thr
1               5

<210> SEQ ID NO 68
<211> LENGTH: 5
<212> TYPE: PRT
<213> ORGANISM: Homo sapiens

<400> SEQUENCE: 68

Gln Gln Leu Arg Thr
1               5

<210> SEQ ID NO 69
<211> LENGTH: 5
<212> TYPE: PRT
<213> ORGANISM: Homo sapiens

<400> SEQUENCE: 69

Gln Gln Leu Arg Thr
1               5

<210> SEQ ID NO 70
<211> LENGTH: 5
<212> TYPE: PRT
<213> ORGANISM: Homo sapiens

<400> SEQUENCE: 70

Gln Gln Leu Arg Thr
1               5

<210> SEQ ID NO 71
<211> LENGTH: 5
<212> TYPE: PRT
<213> ORGANISM: Homo sapiens

<400> SEQUENCE: 71

Gln Gln Leu Arg Thr
1               5

<210> SEQ ID NO 72
<211> LENGTH: 5
<212> TYPE: PRT
<213> ORGANISM: Homo sapiens

<400> SEQUENCE: 72

Gln Gln Leu Arg Thr
```

```
<210> SEQ ID NO 73
<211> LENGTH: 5
<212> TYPE: PRT
<213> ORGANISM: Homo sapiens

<400> SEQUENCE: 73

Gln Gln Leu Arg Thr
1               5

<210> SEQ ID NO 74
<211> LENGTH: 10
<212> TYPE: PRT
<213> ORGANISM: Homo sapiens

<400> SEQUENCE: 74

Cys Ser Tyr Ala Gly Gly Arg Thr Val Val
1               5                   10

<210> SEQ ID NO 75
<211> LENGTH: 9
<212> TYPE: PRT
<213> ORGANISM: Homo sapiens

<400> SEQUENCE: 75

Gln Gln Tyr Gly Arg Ser Pro Tyr Thr
1               5

<210> SEQ ID NO 76
<211> LENGTH: 8
<212> TYPE: PRT
<213> ORGANISM: Homo sapiens

<400> SEQUENCE: 76

Gln Gln Tyr Gly Ser Ser Leu Arg
1               5

<210> SEQ ID NO 77
<211> LENGTH: 9
<212> TYPE: PRT
<213> ORGANISM: Homo sapiens

<400> SEQUENCE: 77

Gln Gln Tyr Tyr Ser Asp Ser Ile Thr
1               5

<210> SEQ ID NO 78
<211> LENGTH: 6
<212> TYPE: PRT
<213> ORGANISM: Homo sapiens

<400> SEQUENCE: 78

Gln Leu Leu Gln Ser Asn
1               5

<210> SEQ ID NO 79
<211> LENGTH: 13
<212> TYPE: PRT
<213> ORGANISM: Homo sapiens

<400> SEQUENCE: 79

Asp Arg Met Phe Trp Gln Gln Leu Ala Lys Tyr Asp Ser
1               5                   10
```

```
<210> SEQ ID NO 80
<211> LENGTH: 13
<212> TYPE: PRT
<213> ORGANISM: Homo sapiens

<400> SEQUENCE: 80

Asp Arg Met Phe Trp Gln Gln Leu Ala Lys Tyr Asp Ser
1               5                   10

<210> SEQ ID NO 81
<211> LENGTH: 8
<212> TYPE: PRT
<213> ORGANISM: Homo sapiens

<400> SEQUENCE: 81

Gly Pro Leu Gly Asp Tyr Asp Phe
1               5

<210> SEQ ID NO 82
<211> LENGTH: 17
<212> TYPE: PRT
<213> ORGANISM: Homo sapiens

<400> SEQUENCE: 82

Gly Arg Asp Tyr Asn Phe Trp Ser Gly Gly Arg Tyr Tyr Phe Asp
1               5                   10                  15

Phe

<210> SEQ ID NO 83
<211> LENGTH: 16
<212> TYPE: PRT
<213> ORGANISM: Homo sapiens

<400> SEQUENCE: 83

Gly Arg Asp Tyr Asn Phe Trp Gly Gly Gly Lys Ile Asn Phe Pro
1               5                   10                  15

<210> SEQ ID NO 84
<211> LENGTH: 18
<212> TYPE: PRT
<213> ORGANISM: Homo sapiens

<400> SEQUENCE: 84

Ser Arg Gly Asp Tyr Asn Phe Trp Ser Gly Tyr Pro Glu Tyr His Phe
1               5                   10                  15

Asp Arg

<210> SEQ ID NO 85
<211> LENGTH: 12
<212> TYPE: PRT
<213> ORGANISM: Homo sapiens

<400> SEQUENCE: 85

Glu Tyr Arg Phe Asp Asp Trp Gly Pro Leu Asp His
1               5                   10

<210> SEQ ID NO 86
<211> LENGTH: 19
<212> TYPE: PRT
<213> ORGANISM: Homo sapiens

<400> SEQUENCE: 86

Leu Asp Trp Val Arg Gly Val Met Asn Leu Val Glu Asn His Tyr Ala
1               5                   10                  15
```

Met Asp Val

<210> SEQ ID NO 87
<211> LENGTH: 20
<212> TYPE: PRT
<213> ORGANISM: Homo sapiens

<400> SEQUENCE: 87

Gly Asp Leu Leu Gly Tyr Thr Asp Ser Trp Tyr Glu Phe Asp Tyr
1               5                   10                  15

Tyr Met Asp Val
            20

<210> SEQ ID NO 88
<211> LENGTH: 15
<212> TYPE: PRT
<213> ORGANISM: Homo sapiens

<400> SEQUENCE: 88

Gly Arg Leu Phe Val Gln Trp Pro Pro Gln Gly Gly Phe Asp Thr
1               5                   10                  15

<210> SEQ ID NO 89
<211> LENGTH: 15
<212> TYPE: PRT
<213> ORGANISM: Homo sapiens

<400> SEQUENCE: 89

Gly Arg Leu Phe Met Gln Trp Pro Pro Gln Gly Gly Phe Asp Pro
1               5                   10                  15

<210> SEQ ID NO 90
<211> LENGTH: 15
<212> TYPE: PRT
<213> ORGANISM: Homo sapiens

<400> SEQUENCE: 90

Gly Arg Leu Phe Val Gln Trp Pro Pro Gln Gly Gly Phe Asp Thr
1               5                   10                  15

<210> SEQ ID NO 91
<211> LENGTH: 15
<212> TYPE: PRT
<213> ORGANISM: Homo sapiens

<400> SEQUENCE: 91

Gly Arg Leu Phe Val Gln Trp Pro Pro Gln Gly Gly Phe Asp Thr
1               5                   10                  15

<210> SEQ ID NO 92
<211> LENGTH: 15
<212> TYPE: PRT
<213> ORGANISM: Homo sapiens

<400> SEQUENCE: 92

Gly Arg Leu Phe Val Gln Trp Pro Pro Gln Gly Gly Phe Asp Thr
1               5                   10                  15

<210> SEQ ID NO 93
<211> LENGTH: 15
<212> TYPE: PRT
<213> ORGANISM: Homo sapiens

<400> SEQUENCE: 93

Gly Arg Leu Phe Val Gln Trp Pro Pro Gln Gly Gly Phe Asp Thr

```
1               5                   10                  15
```

<210> SEQ ID NO 94
<211> LENGTH: 15
<212> TYPE: PRT
<213> ORGANISM: Homo sapiens

<400> SEQUENCE: 94

```
Gly Arg Leu Phe Val Gln Trp Pro Pro Gln Gly Gly Phe Asp Pro
1               5                   10                  15
```

<210> SEQ ID NO 95
<211> LENGTH: 15
<212> TYPE: PRT
<213> ORGANISM: Homo sapiens

<400> SEQUENCE: 95

```
Gly Arg Leu Phe Met Gln Trp Pro Pro Arg Gly Gly Phe Asp Pro
1               5                   10                  15
```

<210> SEQ ID NO 96
<211> LENGTH: 15
<212> TYPE: PRT
<213> ORGANISM: Homo sapiens

<400> SEQUENCE: 96

```
Gly Arg Leu Leu Met Gln Trp Pro Pro Arg Gly Gly Phe Asp Pro
1               5                   10                  15
```

<210> SEQ ID NO 97
<211> LENGTH: 15
<212> TYPE: PRT
<213> ORGANISM: Homo sapiens

<400> SEQUENCE: 97

```
Gly Arg Leu Leu Met Gln Trp Pro Pro Arg Gly Gly Phe Asp Pro
1               5                   10                  15
```

<210> SEQ ID NO 98
<211> LENGTH: 15
<212> TYPE: PRT
<213> ORGANISM: Homo sapiens

<400> SEQUENCE: 98

```
Gly Arg Leu Leu Met Gln Trp Pro Pro Arg Gly Gly Phe Asp Pro
1               5                   10                  15
```

<210> SEQ ID NO 99
<211> LENGTH: 15
<212> TYPE: PRT
<213> ORGANISM: Homo sapiens

<400> SEQUENCE: 99

```
Gly Arg Leu Leu Met Gln Trp Pro Pro Arg Gly Gly Phe Asp Pro
1               5                   10                  15
```

<210> SEQ ID NO 100
<211> LENGTH: 20
<212> TYPE: PRT
<213> ORGANISM: Homo sapiens

<400> SEQUENCE: 100

```
Glu Arg Val Leu Val Val Pro Asp Gln Asp Ala Asp Tyr Tyr Tyr
1               5                   10                  15

Phe Phe Asp Val
```

20

<210> SEQ ID NO 101
<211> LENGTH: 20
<212> TYPE: PRT
<213> ORGANISM: Homo sapiens

<400> SEQUENCE: 101

Glu Arg Val Leu Val Phe Pro Asp Gln Asp Ala Asp Tyr Tyr Tyr Tyr
1               5                   10                  15

Phe Phe Asp Val
            20

<210> SEQ ID NO 102
<211> LENGTH: 20
<212> TYPE: PRT
<213> ORGANISM: Homo sapiens

<400> SEQUENCE: 102

Glu Asn Val Leu Met Glu Ser Asp Asp Tyr Asn Asp Tyr Tyr Tyr Tyr
1               5                   10                  15

Tyr Met Asp Val
            20

<210> SEQ ID NO 103
<211> LENGTH: 13
<212> TYPE: PRT
<213> ORGANISM: Homo sapiens

<400> SEQUENCE: 103

Leu Pro Arg Thr Thr Gly Ile Arg Asn Ala Phe Asp Phe
1               5                   10

<210> SEQ ID NO 104
<211> LENGTH: 13
<212> TYPE: PRT
<213> ORGANISM: Homo sapiens

<400> SEQUENCE: 104

Leu Pro Arg Thr Thr Gly Ile Arg Asn Ala Phe Asp Ile
1               5                   10

<210> SEQ ID NO 105
<211> LENGTH: 13
<212> TYPE: PRT
<213> ORGANISM: Homo sapiens

<400> SEQUENCE: 105

Asp Ser Glu Asp Tyr Val Asp Tyr Tyr Tyr Met Asp Val
1               5                   10

<210> SEQ ID NO 106
<211> LENGTH: 12
<212> TYPE: PRT
<213> ORGANISM: Homo sapiens

<400> SEQUENCE: 106

Trp Val Val Thr Ala Ala Glu Glu Tyr Phe Asp Tyr
1               5                   10

<210> SEQ ID NO 107
<211> LENGTH: 12
<212> TYPE: PRT
<213> ORGANISM: Homo sapiens

```
<400> SEQUENCE: 107

Trp Val Val Thr Ala Ala Glu Glu Tyr Phe Asp Tyr
 1               5                  10

<210> SEQ ID NO 108
<211> LENGTH: 12
<212> TYPE: PRT
<213> ORGANISM: Homo sapiens

<400> SEQUENCE: 108

Trp Val Val Thr Ala Ala Glu Glu Tyr Phe Asp Tyr
 1               5                  10

<210> SEQ ID NO 109
<211> LENGTH: 7
<212> TYPE: PRT
<213> ORGANISM: Homo sapiens

<400> SEQUENCE: 109

His Tyr Asp Ala Leu Asp Tyr
 1               5

<210> SEQ ID NO 110
<211> LENGTH: 14
<212> TYPE: PRT
<213> ORGANISM: Homo sapiens

<400> SEQUENCE: 110

Thr Arg Asn Thr Gly Asn Ser Leu Pro Tyr Trp Phe Asp Leu
 1               5                  10

<210> SEQ ID NO 111
<211> LENGTH: 14
<212> TYPE: PRT
<213> ORGANISM: Homo sapiens

<400> SEQUENCE: 111

Thr Arg Asn Thr Gly Asn Ser Leu Pro Tyr Trp Phe Asp Leu
 1               5                  10

<210> SEQ ID NO 112
<211> LENGTH: 19
<212> TYPE: PRT
<213> ORGANISM: Homo sapiens

<400> SEQUENCE: 112

His Gly Ala Ser Ala Asn Tyr Gly Pro Gly Ser Tyr Ser Ala Glu His
 1               5                  10                  15

Phe Gln His

<210> SEQ ID NO 113
<211> LENGTH: 19
<212> TYPE: PRT
<213> ORGANISM: Homo sapiens

<400> SEQUENCE: 113

His Gly Ala Ser Glu Asn Tyr Gly Pro Gly Ser Tyr Ser Ala Glu His
 1               5                  10                  15

Phe Gln His

<210> SEQ ID NO 114
<211> LENGTH: 19
<212> TYPE: PRT
```

<400> SEQUENCE: 114

His Gly Ala Ser Ala Asn Tyr Gly Pro Gly Ser Tyr Ser Ala Glu His
1               5                   10                  15

Phe Gln His

<210> SEQ ID NO 115
<211> LENGTH: 11
<212> TYPE: PRT
<213> ORGANISM: Homo sapiens

<400> SEQUENCE: 115

Arg Gly His Ser Phe Ser Leu Pro Phe Asp Ser
1               5                   10

<210> SEQ ID NO 116
<211> LENGTH: 11
<212> TYPE: PRT
<213> ORGANISM: Homo sapiens

<400> SEQUENCE: 116

Arg Gly His Ser Phe Ser Leu Pro Phe Asp Ser
1               5                   10

<210> SEQ ID NO 117
<211> LENGTH: 11
<212> TYPE: PRT
<213> ORGANISM: Homo sapiens

<400> SEQUENCE: 117

Arg Gly His Ser Phe Ser Leu Pro Phe Asp Ser
1               5                   10

<210> SEQ ID NO 118
<211> LENGTH: 12
<212> TYPE: PRT
<213> ORGANISM: Homo sapiens

<400> SEQUENCE: 118

Gly Ala Ile Asn Ser Ser Pro Ser Tyr Phe Asp Ser
1               5                   10

<210> SEQ ID NO 119
<211> LENGTH: 12
<212> TYPE: PRT
<213> ORGANISM: Homo sapiens

<400> SEQUENCE: 119

Gly Asp Ile Thr Ser Ser Pro Leu Tyr Phe Asp Phe
1               5                   10

<210> SEQ ID NO 120
<211> LENGTH: 12
<212> TYPE: PRT
<213> ORGANISM: Homo sapiens

<400> SEQUENCE: 120

Gly Ala Ile Asn Ser Ser Pro Leu Tyr Phe Asp Ser
1               5                   10

<210> SEQ ID NO 121
<211> LENGTH: 8
<212> TYPE: PRT
<213> ORGANISM: Homo sapiens

```
<400> SEQUENCE: 121

Arg Asn Trp Gly Asn Phe Asp His
1               5

<210> SEQ ID NO 122
<211> LENGTH: 16
<212> TYPE: PRT
<213> ORGANISM: Homo sapiens

<400> SEQUENCE: 122

Asp Arg Leu Ser Phe Ser Val Gln Val Glu Gln Gly Val Leu Gln Phe
1               5                   10                  15

<210> SEQ ID NO 123
<211> LENGTH: 16
<212> TYPE: PRT
<213> ORGANISM: Homo sapiens

<400> SEQUENCE: 123

Asp Arg Leu Ser Phe Ser Val Gln Val Glu Gln Gly Val Leu Asp Tyr
1               5                   10                  15

<210> SEQ ID NO 124
<211> LENGTH: 17
<212> TYPE: PRT
<213> ORGANISM: Homo sapiens

<400> SEQUENCE: 124

Met Ala Leu Pro Ser Gly Pro Leu Asp Arg Ser Gly Tyr Tyr Phe Asp
1               5                   10                  15

Asp

<210> SEQ ID NO 125
<211> LENGTH: 17
<212> TYPE: PRT
<213> ORGANISM: Homo sapiens

<400> SEQUENCE: 125

Met Ala Leu Ala Ser Gly Pro Tyr Asp Val Ser Gly Tyr Tyr Phe Asp
1               5                   10                  15

Tyr

<210> SEQ ID NO 126
<211> LENGTH: 17
<212> TYPE: PRT
<213> ORGANISM: Homo sapiens

<400> SEQUENCE: 126

Met Ala Leu Ala Ser Gly Pro Tyr Asp Val Ser Gly Tyr Tyr Phe Asp
1               5                   10                  15

Tyr

<210> SEQ ID NO 127
<211> LENGTH: 17
<212> TYPE: PRT
<213> ORGANISM: Homo sapiens

<400> SEQUENCE: 127

Met Ala Leu Thr Ser Gly Pro Tyr Asp Val Ser Gly Tyr Tyr Phe Asp
1               5                   10                  15

Tyr
```

```
<210> SEQ ID NO 128
<211> LENGTH: 10
<212> TYPE: PRT
<213> ORGANISM: Homo sapiens

<400> SEQUENCE: 128

His Ile Ala Val Gly Gly Arg Glu Glu Glu
1               5                   10

<210> SEQ ID NO 129
<211> LENGTH: 10
<212> TYPE: PRT
<213> ORGANISM: Homo sapiens

<400> SEQUENCE: 129

His Ile Ala Val Gly Gly Ser Glu Asp His
1               5                   10

<210> SEQ ID NO 130
<211> LENGTH: 10
<212> TYPE: PRT
<213> ORGANISM: Homo sapiens

<400> SEQUENCE: 130

His Ile Ala Val Gly Gly Ser Glu Glu His
1               5                   10

<210> SEQ ID NO 131
<211> LENGTH: 10
<212> TYPE: PRT
<213> ORGANISM: Homo sapiens

<400> SEQUENCE: 131

His Ile Ala Val Gly Gly Arg Glu Glu Glu
1               5                   10

<210> SEQ ID NO 132
<211> LENGTH: 12
<212> TYPE: PRT
<213> ORGANISM: Homo sapiens

<400> SEQUENCE: 132

Pro Ala Gln Ala Gly Val Gly Pro Arg Phe Asp Tyr
1               5                   10

<210> SEQ ID NO 133
<211> LENGTH: 9
<212> TYPE: PRT
<213> ORGANISM: Homo sapiens

<400> SEQUENCE: 133

Leu Gln Thr His Ser Tyr Pro Arg Thr
1               5

<210> SEQ ID NO 134
<211> LENGTH: 9
<212> TYPE: PRT
<213> ORGANISM: Homo sapiens

<400> SEQUENCE: 134

Leu Gln Asn His Asn Tyr Pro Arg Thr
1               5

<210> SEQ ID NO 135
<211> LENGTH: 9
<212> TYPE: PRT
```

<213> ORGANISM: Homo sapiens

<400> SEQUENCE: 135

Gln Gln Tyr Thr Ala Tyr Pro Trp Thr
1               5

<210> SEQ ID NO 136
<211> LENGTH: 12
<212> TYPE: PRT
<213> ORGANISM: Homo sapiens

<400> SEQUENCE: 136

Gln Ser Tyr Asp Ser Ser Leu Ser Gly Ser Trp Val
1               5                   10

<210> SEQ ID NO 137
<211> LENGTH: 12
<212> TYPE: PRT
<213> ORGANISM: Homo sapiens

<400> SEQUENCE: 137

Gln Ser Tyr Asp Ser Ser Leu Ser Gly Ser Trp Val
1               5                   10

<210> SEQ ID NO 138
<211> LENGTH: 9
<212> TYPE: PRT
<213> ORGANISM: Homo sapiens

<400> SEQUENCE: 138

Met Gln Pro Leu Gln Thr Pro Tyr Thr
1               5

<210> SEQ ID NO 139
<211> LENGTH: 9
<212> TYPE: PRT
<213> ORGANISM: Homo sapiens

<400> SEQUENCE: 139

Met Lys Ser Gln His Ser Pro Arg Thr
1               5

<210> SEQ ID NO 140
<211> LENGTH: 9
<212> TYPE: PRT
<213> ORGANISM: Homo sapiens

<400> SEQUENCE: 140

Gln Gln Ser Gly Thr Ser Leu Leu Thr
1               5

<210> SEQ ID NO 141
<211> LENGTH: 8
<212> TYPE: PRT
<213> ORGANISM: Homo sapiens

<400> SEQUENCE: 141

Gln Gln Tyr Ala Gly Ser Leu Thr
1               5

<210> SEQ ID NO 142
<211> LENGTH: 10
<212> TYPE: PRT
<213> ORGANISM: Homo sapiens

<400> SEQUENCE: 142

```
Gln Glu Tyr Gly Arg Ala Pro Pro Tyr Pro
1               5                   10

<210> SEQ ID NO 143
<211> LENGTH: 10
<212> TYPE: PRT
<213> ORGANISM: Homo sapiens

<400> SEQUENCE: 143

Gln Glu Tyr Gly Arg Ser Pro Pro Tyr Pro
1               5                   10

<210> SEQ ID NO 144
<211> LENGTH: 10
<212> TYPE: PRT
<213> ORGANISM: Homo sapiens

<400> SEQUENCE: 144

Gln Glu Tyr Gly Arg Ala Pro Pro Tyr Pro
1               5                   10

<210> SEQ ID NO 145
<211> LENGTH: 10
<212> TYPE: PRT
<213> ORGANISM: Homo sapiens

<400> SEQUENCE: 145

Gln Glu Tyr Gly Arg Ala Pro Pro Tyr Pro
1               5                   10

<210> SEQ ID NO 146
<211> LENGTH: 10
<212> TYPE: PRT
<213> ORGANISM: Homo sapiens

<400> SEQUENCE: 146

Gln Glu Tyr Gly Arg Ala Pro Pro Tyr Pro
1               5                   10

<210> SEQ ID NO 147
<211> LENGTH: 10
<212> TYPE: PRT
<213> ORGANISM: Homo sapiens

<400> SEQUENCE: 147

Gln Glu Phe Gly Arg Ala Pro Pro Tyr Pro
1               5                   10

<210> SEQ ID NO 148
<211> LENGTH: 10
<212> TYPE: PRT
<213> ORGANISM: Homo sapiens

<400> SEQUENCE: 148

Gln Glu Tyr Gly Arg Ala Pro Pro Tyr Pro
1               5                   10

<210> SEQ ID NO 149
<211> LENGTH: 10
<212> TYPE: PRT
<213> ORGANISM: Homo sapiens

<400> SEQUENCE: 149

Gln Glu Tyr Gly Arg Ala Pro Pro Tyr Pro
1               5                   10
```

<210> SEQ ID NO 150
<211> LENGTH: 10
<212> TYPE: PRT
<213> ORGANISM: Homo sapiens

<400> SEQUENCE: 150

Gln Tyr Tyr Gly Ser Ser Pro Pro Ser Thr
1               5                   10

<210> SEQ ID NO 151
<211> LENGTH: 10
<212> TYPE: PRT
<213> ORGANISM: Homo sapiens

<400> SEQUENCE: 151

Gln Tyr Tyr Gly Ser Ser Pro Pro Ser Thr
1               5                   10

<210> SEQ ID NO 152
<211> LENGTH: 10
<212> TYPE: PRT
<213> ORGANISM: Homo sapiens

<400> SEQUENCE: 152

Gln Tyr Tyr Gly Ser Ser Pro Pro Ser Thr
1               5                   10

<210> SEQ ID NO 153
<211> LENGTH: 10
<212> TYPE: PRT
<213> ORGANISM: Homo sapiens

<400> SEQUENCE: 153

Gln Tyr Tyr Gly Thr Ser Pro Pro Ser Thr
1               5                   10

<210> SEQ ID NO 154
<211> LENGTH: 5
<212> TYPE: PRT
<213> ORGANISM: Homo sapiens

<400> SEQUENCE: 154

Leu Phe Ala Gly Thr
1               5

<210> SEQ ID NO 155
<211> LENGTH: 5
<212> TYPE: PRT
<213> ORGANISM: Homo sapiens

<400> SEQUENCE: 155

Leu Phe Ala Gly Thr
1               5

<210> SEQ ID NO 156
<211> LENGTH: 5
<212> TYPE: PRT
<213> ORGANISM: Homo sapiens

<400> SEQUENCE: 156

Leu Phe Ala Gly Thr
1               5

<210> SEQ ID NO 157

```
<211> LENGTH: 10
<212> TYPE: PRT
<213> ORGANISM: Homo sapiens

<400> SEQUENCE: 157

Ser Ser Tyr Ala Ala Thr Asn His Trp Val
1               5                   10

<210> SEQ ID NO 158
<211> LENGTH: 10
<212> TYPE: PRT
<213> ORGANISM: Homo sapiens

<400> SEQUENCE: 158

Ser Ser Tyr Ala Gly Thr Asn His Trp Val
1               5                   10

<210> SEQ ID NO 159
<211> LENGTH: 11
<212> TYPE: PRT
<213> ORGANISM: Homo sapiens

<400> SEQUENCE: 159

Gln Gln Arg Thr Ser Trp Pro Leu Ala Leu Ser
1               5                   10

<210> SEQ ID NO 160
<211> LENGTH: 9
<212> TYPE: PRT
<213> ORGANISM: Homo sapiens

<400> SEQUENCE: 160

Gln Gln Tyr Arg Tyr Ser Val Ile Ile
1               5

<210> SEQ ID NO 161
<211> LENGTH: 9
<212> TYPE: PRT
<213> ORGANISM: Homo sapiens

<400> SEQUENCE: 161

Gln Gln Tyr Arg Tyr Ser Val Ile Ile
1               5

<210> SEQ ID NO 162
<211> LENGTH: 9
<212> TYPE: PRT
<213> ORGANISM: Homo sapiens

<400> SEQUENCE: 162

Gln Gln Tyr Arg Tyr Ser Val Ile Ile
1               5

<210> SEQ ID NO 163
<211> LENGTH: 8
<212> TYPE: PRT
<213> ORGANISM: Homo sapiens

<400> SEQUENCE: 163

Met Gln Ala Leu Glu Thr Leu Gly
1               5

<210> SEQ ID NO 164
<211> LENGTH: 9
<212> TYPE: PRT
<213> ORGANISM: Homo sapiens
```

-continued

```
<400> SEQUENCE: 164

Gln Gln Arg Gly His Trp Pro Leu Thr
1               5

<210> SEQ ID NO 165
<211> LENGTH: 9
<212> TYPE: PRT
<213> ORGANISM: Homo sapiens

<400> SEQUENCE: 165

Gln Gln Arg Gly His Trp Pro Leu Thr
1               5

<210> SEQ ID NO 166
<211> LENGTH: 7
<212> TYPE: PRT
<213> ORGANISM: Homo sapiens

<400> SEQUENCE: 166

Gln Glu Tyr Asn Asn Tyr Asn
1               5

<210> SEQ ID NO 167
<211> LENGTH: 7
<212> TYPE: PRT
<213> ORGANISM: Homo sapiens

<400> SEQUENCE: 167

Gln Glu Tyr Asn Thr Tyr Thr
1               5

<210> SEQ ID NO 168
<211> LENGTH: 7
<212> TYPE: PRT
<213> ORGANISM: Homo sapiens

<400> SEQUENCE: 168

Gln Glu Tyr Asn Thr Tyr Thr
1               5

<210> SEQ ID NO 169
<211> LENGTH: 8
<212> TYPE: PRT
<213> ORGANISM: Homo sapiens

<400> SEQUENCE: 169

Gln Lys Tyr Gly Ser Ser Leu Thr
1               5

<210> SEQ ID NO 170
<211> LENGTH: 8
<212> TYPE: PRT
<213> ORGANISM: Homo sapiens

<400> SEQUENCE: 170

Gln Lys Tyr Gly Ser Ser Leu Thr
1               5

<210> SEQ ID NO 171
<211> LENGTH: 8
<212> TYPE: PRT
<213> ORGANISM: Homo sapiens

<400> SEQUENCE: 171
```

```
Gln Lys Tyr Gly Ser Ser Leu Thr
1               5
```

<210> SEQ ID NO 172
<211> LENGTH: 9
<212> TYPE: PRT
<213> ORGANISM: Homo sapiens

<400> SEQUENCE: 172

```
Gln Gln Arg Val Asn Trp Pro Pro Asn
1               5
```

<210> SEQ ID NO 173
<211> LENGTH: 9
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa can be any naturally occurring amino acid

<400> SEQUENCE: 173

```
Gln Gln Arg Xaa Thr Trp Pro Pro Ile
1               5
```

<210> SEQ ID NO 174
<211> LENGTH: 9
<212> TYPE: PRT
<213> ORGANISM: Homo sapiens

<400> SEQUENCE: 174

```
Gln Gln Arg Val Asn Trp Pro Pro Asn
1               5
```

<210> SEQ ID NO 175
<211> LENGTH: 10
<212> TYPE: PRT
<213> ORGANISM: Homo sapiens

<400> SEQUENCE: 175

```
Leu Gln Cys Gly Ser Ser Pro Pro Tyr Thr
1               5                   10
```

<210> SEQ ID NO 176
<211> LENGTH: 10
<212> TYPE: PRT
<213> ORGANISM: Homo sapiens

<400> SEQUENCE: 176

```
Gln Gln Arg Tyr Ser Trp Pro Ser Leu Thr
1               5                   10
```

<210> SEQ ID NO 177
<211> LENGTH: 10
<212> TYPE: PRT
<213> ORGANISM: Homo sapiens

<400> SEQUENCE: 177

```
Gln Gln Arg Tyr Ser Trp Pro Ser Leu Thr
1               5                   10
```

<210> SEQ ID NO 178
<211> LENGTH: 9
<212> TYPE: PRT
<213> ORGANISM: Homo sapiens

<400> SEQUENCE: 178

Gln Lys Tyr Asn Asn Ala Pro Trp Thr
1               5

<210> SEQ ID NO 179
<211> LENGTH: 9
<212> TYPE: PRT
<213> ORGANISM: Homo sapiens

<400> SEQUENCE: 179

Gln Lys Tyr Asn Gly Ala Pro Trp Thr
1               5

<210> SEQ ID NO 180
<211> LENGTH: 9
<212> TYPE: PRT
<213> ORGANISM: Homo sapiens

<400> SEQUENCE: 180

Gln Lys Tyr Asn Gly Ala Pro Trp Thr
1               5

<210> SEQ ID NO 181
<211> LENGTH: 9
<212> TYPE: PRT
<213> ORGANISM: Homo sapiens

<400> SEQUENCE: 181

Gln Lys Tyr Asn Gly Ala Pro Trp Thr
1               5

<210> SEQ ID NO 182
<211> LENGTH: 11
<212> TYPE: PRT
<213> ORGANISM: Homo sapiens

<400> SEQUENCE: 182

Gln Gln Arg Ser Thr Thr Pro Pro Glu Tyr Thr
1               5                   10

<210> SEQ ID NO 183
<211> LENGTH: 11
<212> TYPE: PRT
<213> ORGANISM: Homo sapiens

<400> SEQUENCE: 183

Gln Gly Arg Thr Thr Arg Pro Pro Asp Tyr Thr
1               5                   10

<210> SEQ ID NO 184
<211> LENGTH: 11
<212> TYPE: PRT
<213> ORGANISM: Homo sapiens

<400> SEQUENCE: 184

Gln Gln Arg Thr Thr Arg Pro Pro Asp Tyr Thr
1               5                   10

<210> SEQ ID NO 185
<211> LENGTH: 11
<212> TYPE: PRT
<213> ORGANISM: Homo sapiens

<400> SEQUENCE: 185

Gln Gln Arg Thr Thr Arg Pro Pro Glu Tyr Thr
1               5                   10

```
<210> SEQ ID NO 186
<211> LENGTH: 10
<212> TYPE: PRT
<213> ORGANISM: Homo sapiens

<400> SEQUENCE: 186

Cys Ser Tyr Ala Gly Ser Tyr Thr Tyr Val
1               5                   10

<210> SEQ ID NO 187
<211> LENGTH: 15
<212> TYPE: PRT
<213> ORGANISM: Homo sapiens

<400> SEQUENCE: 187

Glu Lys Gly Gln Trp Leu Thr Val Pro Pro Tyr Tyr Phe Asp Ser
1               5                   10                  15

<210> SEQ ID NO 188
<211> LENGTH: 15
<212> TYPE: PRT
<213> ORGANISM: Homo sapiens

<400> SEQUENCE: 188

Glu Lys Gly Gln Trp Val Thr Leu Pro Pro Tyr Tyr Phe Asp Ser
1               5                   10                  15

<210> SEQ ID NO 189
<211> LENGTH: 13
<212> TYPE: PRT
<213> ORGANISM: Homo sapiens

<400> SEQUENCE: 189

His Lys Ser Val Leu Leu Trp Phe Arg Glu Leu Asp Tyr
1               5                   10

<210> SEQ ID NO 190
<211> LENGTH: 15
<212> TYPE: PRT
<213> ORGANISM: Homo sapiens

<400> SEQUENCE: 190

Val Gly Gly Thr Val Trp Ser Gly Tyr Ser Asn Tyr Leu Asp Tyr
1               5                   10                  15

<210> SEQ ID NO 191
<211> LENGTH: 12
<212> TYPE: PRT
<213> ORGANISM: Homo sapiens

<400> SEQUENCE: 191

Asp Tyr Thr Ala Ser Gly Arg His Phe Phe Asp Tyr
1               5                   10

<210> SEQ ID NO 192
<211> LENGTH: 12
<212> TYPE: PRT
<213> ORGANISM: Homo sapiens

<400> SEQUENCE: 192

Asp Tyr Thr Ala Ser Gly Arg His Phe Phe Asp Tyr
1               5                   10

<210> SEQ ID NO 193
```

```
<211> LENGTH: 12
<212> TYPE: PRT
<213> ORGANISM: Homo sapiens

<400> SEQUENCE: 193

Asp Tyr Thr Ala Arg Gly Arg His Phe Phe Asp Tyr
1               5                   10

<210> SEQ ID NO 194
<211> LENGTH: 12
<212> TYPE: PRT
<213> ORGANISM: Homo sapiens

<400> SEQUENCE: 194

Asp Tyr Ser Ala Ala Gly Arg His Leu Phe Asp Ser
1               5                   10

<210> SEQ ID NO 195
<211> LENGTH: 12
<212> TYPE: PRT
<213> ORGANISM: Homo sapiens

<400> SEQUENCE: 195

Asp Tyr Thr Ala Arg Gly Arg His Phe Phe Asp Tyr
1               5                   10

<210> SEQ ID NO 196
<211> LENGTH: 14
<212> TYPE: PRT
<213> ORGANISM: Homo sapiens

<400> SEQUENCE: 196

Thr Arg Cys Phe Gly Ala Asn Cys Phe Asn Phe Met Asp Val
1               5                   10

<210> SEQ ID NO 197
<211> LENGTH: 10
<212> TYPE: PRT
<213> ORGANISM: Homo sapiens

<400> SEQUENCE: 197

Thr Gly Gly Leu Leu Arg Phe Pro Glu Val
1               5                   10

<210> SEQ ID NO 198
<211> LENGTH: 11
<212> TYPE: PRT
<213> ORGANISM: Homo sapiens

<400> SEQUENCE: 198

Ser Gly Pro Gly Leu Leu Arg Gly Phe Asp Tyr
1               5                   10

<210> SEQ ID NO 199
<211> LENGTH: 13
<212> TYPE: PRT
<213> ORGANISM: Homo sapiens

<400> SEQUENCE: 199

Val Pro Arg Thr Thr Ala Thr Arg Asn Ala Phe Asp Ile
1               5                   10

<210> SEQ ID NO 200
<211> LENGTH: 12
<212> TYPE: PRT
<213> ORGANISM: Homo sapiens
```

```
<400> SEQUENCE: 200

Asp Tyr Thr Ala Arg Gly Arg His Phe Phe Asp Tyr
1               5                   10

<210> SEQ ID NO 201
<211> LENGTH: 12
<212> TYPE: PRT
<213> ORGANISM: Homo sapiens

<400> SEQUENCE: 201

Gly Pro Asp Asp Phe Trp Ser Gly Tyr Pro Lys Tyr
1               5                   10

<210> SEQ ID NO 202
<211> LENGTH: 20
<212> TYPE: PRT
<213> ORGANISM: Homo sapiens

<400> SEQUENCE: 202

Gly Glu Phe Asp Ser Ser Gly Phe Asp Tyr Glu Ser Trp Tyr Pro Tyr
1               5                   10                  15

Tyr Met Asp Val
            20

<210> SEQ ID NO 203
<211> LENGTH: 16
<212> TYPE: PRT
<213> ORGANISM: Homo sapiens

<400> SEQUENCE: 203

Asp Asn Pro Val Leu Gln Leu Gly Glu Leu Ser Ser Ser Leu Asp Tyr
1               5                   10                  15

<210> SEQ ID NO 204
<211> LENGTH: 13
<212> TYPE: PRT
<213> ORGANISM: Homo sapiens

<400> SEQUENCE: 204

Ala Gln Gly Asp Ile Leu Thr Glu Gly Tyr Phe Asp Tyr
1               5                   10

<210> SEQ ID NO 205
<211> LENGTH: 13
<212> TYPE: PRT
<213> ORGANISM: Homo sapiens

<400> SEQUENCE: 205

Ala Gln Gly Asp Ile Leu Thr Glu Gly Tyr Phe Asp Tyr
1               5                   10

<210> SEQ ID NO 206
<211> LENGTH: 12
<212> TYPE: PRT
<213> ORGANISM: Homo sapiens

<400> SEQUENCE: 206

Pro Glu Pro Ser Ser Ile Val Ala Pro Leu Tyr Tyr
1               5                   10

<210> SEQ ID NO 207
<211> LENGTH: 12
<212> TYPE: PRT
<213> ORGANISM: Homo sapiens
```

<400> SEQUENCE: 207

Pro Glu Pro Ser Ser Ile Val Gly Ala Leu Tyr Tyr
1               5                   10

<210> SEQ ID NO 208
<211> LENGTH: 13
<212> TYPE: PRT
<213> ORGANISM: Homo sapiens

<400> SEQUENCE: 208

Asp Pro Gln Val Glu Val Arg Gly Asn Ala Phe Asp Ile
1               5                   10

<210> SEQ ID NO 209
<211> LENGTH: 13
<212> TYPE: PRT
<213> ORGANISM: Homo sapiens

<400> SEQUENCE: 209

Asp Pro Gln Ile Glu Ile Arg Gly Asn Ala Phe Asp Ile
1               5                   10

<210> SEQ ID NO 210
<211> LENGTH: 13
<212> TYPE: PRT
<213> ORGANISM: Homo sapiens

<400> SEQUENCE: 210

Asp Pro Gln Val Asn Arg Arg Gly Asn Cys Phe Asp His
1               5                   10

<210> SEQ ID NO 211
<211> LENGTH: 13
<212> TYPE: PRT
<213> ORGANISM: Homo sapiens

<400> SEQUENCE: 211

Asp Pro Gln Val Asn Arg Arg Gly Asn Cys Phe Asp His
1               5                   10

<210> SEQ ID NO 212
<211> LENGTH: 12
<212> TYPE: PRT
<213> ORGANISM: Homo sapiens

<400> SEQUENCE: 212

Gly Arg Arg Glu Gly Leu Asn Phe Leu Leu Asp Tyr
1               5                   10

<210> SEQ ID NO 213
<211> LENGTH: 15
<212> TYPE: PRT
<213> ORGANISM: Homo sapiens

<400> SEQUENCE: 213

Ala Asp Tyr Asp Asn Ile Trp Asp Ser Arg Gly Gly Phe Asp Leu
1               5                   10                  15

<210> SEQ ID NO 214
<211> LENGTH: 12
<212> TYPE: PRT
<213> ORGANISM: Homo sapiens

<400> SEQUENCE: 214

Ala His His Asp Phe Trp Arg Ala Pro Val Asp Val
1               5                   10

<210> SEQ ID NO 215
<211> LENGTH: 12
<212> TYPE: PRT
<213> ORGANISM: Homo sapiens

<400> SEQUENCE: 215

Pro Gln Tyr Asn Leu Gly Arg Asp Pro Leu Asp Val
1               5                   10

<210> SEQ ID NO 216
<211> LENGTH: 12
<212> TYPE: PRT
<213> ORGANISM: Homo sapiens

<400> SEQUENCE: 216

Pro Gln Tyr Asn Leu Gly Arg Glu Pro Leu Asn Val
1               5                   10

<210> SEQ ID NO 217
<211> LENGTH: 12
<212> TYPE: PRT
<213> ORGANISM: Homo sapiens

<400> SEQUENCE: 217

Arg Arg Gly Gln Arg Leu Leu Ala Tyr Phe Asp Tyr
1               5                   10

<210> SEQ ID NO 218
<211> LENGTH: 11
<212> TYPE: PRT
<213> ORGANISM: Homo sapiens

<400> SEQUENCE: 218

Arg Ser Pro Gly Gly Gly Tyr Ala Phe Asp Ile
1               5                   10

<210> SEQ ID NO 219
<211> LENGTH: 14
<212> TYPE: PRT
<213> ORGANISM: Homo sapiens

<400> SEQUENCE: 219

Ala Asp Tyr Asp Leu Leu Thr Ser Ser Tyr His Phe Asp Ser
1               5                   10

<210> SEQ ID NO 220
<211> LENGTH: 14
<212> TYPE: PRT
<213> ORGANISM: Homo sapiens

<400> SEQUENCE: 220

Gly Asp Tyr Asp Ile Leu Thr Ser Ser Tyr Gln Phe Asp Tyr
1               5                   10

<210> SEQ ID NO 221
<211> LENGTH: 12
<212> TYPE: PRT
<213> ORGANISM: Homo sapiens

<400> SEQUENCE: 221

Leu Asp Gly Glu Ala Phe Arg Tyr Tyr Leu Asp Leu
1               5                   10

```
<210> SEQ ID NO 222
<211> LENGTH: 12
<212> TYPE: PRT
<213> ORGANISM: Homo sapiens

<400> SEQUENCE: 222

Leu Asp Gly Glu Ala Phe Arg Tyr Tyr Phe Asp Ser
1               5                   10

<210> SEQ ID NO 223
<211> LENGTH: 13
<212> TYPE: PRT
<213> ORGANISM: Homo sapiens

<400> SEQUENCE: 223

Asp Leu Arg Pro Met Arg Gly Asn Trp Ala Met His Val
1               5                   10

<210> SEQ ID NO 224
<211> LENGTH: 10
<212> TYPE: PRT
<213> ORGANISM: Homo sapiens

<400> SEQUENCE: 224

Thr Phe Ile Thr Ala Ser Trp Phe Asp Ser
1               5                   10

<210> SEQ ID NO 225
<211> LENGTH: 14
<212> TYPE: PRT
<213> ORGANISM: Homo sapiens

<400> SEQUENCE: 225

Pro His Ser Pro Thr Asn Ile Pro Ser Arg Pro Leu Asp Tyr
1               5                   10

<210> SEQ ID NO 226
<211> LENGTH: 7
<212> TYPE: PRT
<213> ORGANISM: Homo sapiens

<400> SEQUENCE: 226

Gln Gln Ser His Ser Pro Ser
1               5

<210> SEQ ID NO 227
<211> LENGTH: 7
<212> TYPE: PRT
<213> ORGANISM: Homo sapiens

<400> SEQUENCE: 227

Gln Gln Ser His Ser Pro Ser
1               5

<210> SEQ ID NO 228
<211> LENGTH: 9
<212> TYPE: PRT
<213> ORGANISM: Homo sapiens

<400> SEQUENCE: 228

Gln Gln Tyr Gly Ser Ser Pro Phe Thr
1               5

<210> SEQ ID NO 229
<211> LENGTH: 9
```

```
<212> TYPE: PRT
<213> ORGANISM: Homo sapiens

<400> SEQUENCE: 229

Gln Gln Arg Ser Asn Trp Ala Ile Thr
1               5

<210> SEQ ID NO 230
<211> LENGTH: 7
<212> TYPE: PRT
<213> ORGANISM: Homo sapiens

<400> SEQUENCE: 230

Gln Gln Ser Ser Ser Lys Pro
1               5

<210> SEQ ID NO 231
<211> LENGTH: 7
<212> TYPE: PRT
<213> ORGANISM: Homo sapiens

<400> SEQUENCE: 231

Gln Gln Ser Ala Gly Thr Pro
1               5

<210> SEQ ID NO 232
<211> LENGTH: 7
<212> TYPE: PRT
<213> ORGANISM: Homo sapiens

<400> SEQUENCE: 232

Gln Gln Ser Ser Ser Thr Pro
1               5

<210> SEQ ID NO 233
<211> LENGTH: 7
<212> TYPE: PRT
<213> ORGANISM: Homo sapiens

<400> SEQUENCE: 233

Gln Gln Tyr Tyr Ile Ser Pro
1               5

<210> SEQ ID NO 234
<211> LENGTH: 10
<212> TYPE: PRT
<213> ORGANISM: Homo sapiens

<400> SEQUENCE: 234

Ser Ser Tyr Ser Ser Thr Asn Thr Tyr Val
1               5                   10

<210> SEQ ID NO 235
<211> LENGTH: 12
<212> TYPE: PRT
<213> ORGANISM: Homo sapiens

<400> SEQUENCE: 235

Ser Ser Tyr Thr Ser Ser Ser Thr Leu Gly Val Val
1               5                   10

<210> SEQ ID NO 236
<211> LENGTH: 8
<212> TYPE: PRT
<213> ORGANISM: Homo sapiens
```

```
<400> SEQUENCE: 236

Ser Ser Tyr Ala Gly Ile Asn Asn
1               5

<210> SEQ ID NO 237
<211> LENGTH: 9
<212> TYPE: PRT
<213> ORGANISM: Homo sapiens

<400> SEQUENCE: 237

Gln Gln Ser Ser Ser Thr Pro Phe Thr
1               5

<210> SEQ ID NO 238
<211> LENGTH: 8
<212> TYPE: PRT
<213> ORGANISM: Homo sapiens

<400> SEQUENCE: 238

Gln Gln Tyr Gly Ser Ser Trp Thr
1               5

<210> SEQ ID NO 239
<211> LENGTH: 9
<212> TYPE: PRT
<213> ORGANISM: Homo sapiens

<400> SEQUENCE: 239

Gln Gln Tyr Ala Ser Ser Pro Phe Thr
1               5

<210> SEQ ID NO 240
<211> LENGTH: 11
<212> TYPE: PRT
<213> ORGANISM: Homo sapiens

<400> SEQUENCE: 240

Gln Gln Arg Gly Ile Trp Pro Leu Gln Ile Thr
1               5                   10

<210> SEQ ID NO 241
<211> LENGTH: 9
<212> TYPE: PRT
<213> ORGANISM: Homo sapiens

<400> SEQUENCE: 241

Ala Ala Trp Asp Asp Ser Leu His Val
1               5

<210> SEQ ID NO 242
<211> LENGTH: 5
<212> TYPE: PRT
<213> ORGANISM: Homo sapiens

<400> SEQUENCE: 242

Gln Lys Ala Thr Thr
1               5

<210> SEQ ID NO 243
<211> LENGTH: 10
<212> TYPE: PRT
<213> ORGANISM: Homo sapiens

<400> SEQUENCE: 243

Gln Gln Tyr Gly Thr Leu His Pro Arg Thr
```

```
1               5                   10
```

<210> SEQ ID NO 244
<211> LENGTH: 10
<212> TYPE: PRT
<213> ORGANISM: Homo sapiens

<400> SEQUENCE: 244

```
Gln Trp Tyr Gly Thr Leu His Pro Arg Thr
1               5                   10
```

<210> SEQ ID NO 245
<211> LENGTH: 9
<212> TYPE: PRT
<213> ORGANISM: Homo sapiens

<400> SEQUENCE: 245

```
Gln Gln Thr Tyr Thr Ser Pro Ile Thr
1               5
```

<210> SEQ ID NO 246
<211> LENGTH: 9
<212> TYPE: PRT
<213> ORGANISM: Homo sapiens

<400> SEQUENCE: 246

```
Gln Gln Thr Phe Thr Asp Pro Val Thr
1               5
```

<210> SEQ ID NO 247
<211> LENGTH: 8
<212> TYPE: PRT
<213> ORGANISM: Homo sapiens

<400> SEQUENCE: 247

```
Gln Gln Thr Tyr Arg Ser Val Thr
1               5
```

<210> SEQ ID NO 248
<211> LENGTH: 8
<212> TYPE: PRT
<213> ORGANISM: Homo sapiens

<400> SEQUENCE: 248

```
Gln Gln Thr Tyr Ser Ser Val Thr
1               5
```

<210> SEQ ID NO 249
<211> LENGTH: 9
<212> TYPE: PRT
<213> ORGANISM: Homo sapiens

<400> SEQUENCE: 249

```
Gln Gln Tyr Asn Tyr Tyr Pro Ile Thr
1               5
```

<210> SEQ ID NO 250
<211> LENGTH: 9
<212> TYPE: PRT
<213> ORGANISM: Homo sapiens

<400> SEQUENCE: 250

```
Gln Lys Tyr Asp Thr Asp Pro Met Thr
1               5
```

```
<210> SEQ ID NO 251
<211> LENGTH: 10
<212> TYPE: PRT
<213> ORGANISM: Homo sapiens

<400> SEQUENCE: 251

Gln Gln Tyr Ala Thr Ser Ser Leu Tyr Thr
1               5                   10

<210> SEQ ID NO 252
<211> LENGTH: 9
<212> TYPE: PRT
<213> ORGANISM: Homo sapiens

<400> SEQUENCE: 252

Gln Gln Tyr Gly Leu Ser Pro Trp Thr
1               5

<210> SEQ ID NO 253
<211> LENGTH: 9
<212> TYPE: PRT
<213> ORGANISM: Homo sapiens

<400> SEQUENCE: 253

His Gln Tyr Ala Leu Ser Pro Trp Thr
1               5

<210> SEQ ID NO 254
<211> LENGTH: 9
<212> TYPE: PRT
<213> ORGANISM: Homo sapiens

<400> SEQUENCE: 254

Gln Gln Tyr Asn Asn Trp Pro Pro Ala
1               5

<210> SEQ ID NO 255
<211> LENGTH: 8
<212> TYPE: PRT
<213> ORGANISM: Homo sapiens

<400> SEQUENCE: 255

His Gln Tyr Gly Ser Ser Gln Arg
1               5

<210> SEQ ID NO 256
<211> LENGTH: 11
<212> TYPE: PRT
<213> ORGANISM: Homo sapiens

<400> SEQUENCE: 256

Leu Leu Leu Pro Tyr Tyr Gly Gly Pro Trp Ile
1               5                   10

<210> SEQ ID NO 257
<211> LENGTH: 11
<212> TYPE: PRT
<213> ORGANISM: Homo sapiens

<400> SEQUENCE: 257

Leu Leu Leu Leu Tyr Tyr Gly Gly Pro Trp Ile
1               5                   10

<210> SEQ ID NO 258
<211> LENGTH: 10
<212> TYPE: PRT
```

```
<213> ORGANISM: Homo sapiens

<400> SEQUENCE: 258

Ser Ser Phe Thr Pro Thr Asn Thr Leu Val
1               5                   10

<210> SEQ ID NO 259
<211> LENGTH: 10
<212> TYPE: PRT
<213> ORGANISM: Homo sapiens

<400> SEQUENCE: 259

Gly Ser Phe Thr Thr Ser Leu Thr Leu Val
1               5                   10

<210> SEQ ID NO 260
<211> LENGTH: 10
<212> TYPE: PRT
<213> ORGANISM: Homo sapiens

<400> SEQUENCE: 260

Ser Ser Tyr Ala Gly Ser Asn Asn Phe Val
1               5                   10

<210> SEQ ID NO 261
<211> LENGTH: 10
<212> TYPE: PRT
<213> ORGANISM: Homo sapiens

<400> SEQUENCE: 261

Cys Ser Tyr Ala Gly Thr Tyr Ser Tyr Val
1               5                   10

<210> SEQ ID NO 262
<211> LENGTH: 10
<212> TYPE: PRT
<213> ORGANISM: Homo sapiens

<400> SEQUENCE: 262

Cys Ser Tyr Ala Gly Ser Tyr Ile Trp Val
1               5                   10

<210> SEQ ID NO 263
<211> LENGTH: 15
<212> TYPE: PRT
<213> ORGANISM: Homo sapiens

<400> SEQUENCE: 263

Glu Gly Gly Ser Leu Trp Phe Gly Gly Ala Asn Trp Leu Asp Pro
1               5                   10                  15

<210> SEQ ID NO 264
<211> LENGTH: 15
<212> TYPE: PRT
<213> ORGANISM: Homo sapiens

<400> SEQUENCE: 264

Glu Gly Gly Ser Leu Trp Phe Gly Gly Ala Asn Trp Leu Asp Pro
1               5                   10                  15

<210> SEQ ID NO 265
<211> LENGTH: 9
<212> TYPE: PRT
<213> ORGANISM: Homo sapiens

<400> SEQUENCE: 265
```

Gly Tyr Asp Asn Ser Gly Pro Asp Tyr
1               5

<210> SEQ ID NO 266
<211> LENGTH: 22
<212> TYPE: PRT
<213> ORGANISM: Homo sapiens

<400> SEQUENCE: 266

Asp Gln Val Gly Arg Tyr Ser Phe Gly Phe Ala Thr Gly Gln Gln Arg
1               5                   10                  15

Val Ser Ala Ile Ser Asp
            20

<210> SEQ ID NO 267
<211> LENGTH: 20
<212> TYPE: PRT
<213> ORGANISM: Homo sapiens

<400> SEQUENCE: 267

Glu Arg Ser Thr Lys Tyr Ser Phe Trp Ser Ala Val Met Arg Pro Asp
1               5                   10                  15

Ala Phe Asp Leu
            20

<210> SEQ ID NO 268
<211> LENGTH: 17
<212> TYPE: PRT
<213> ORGANISM: Homo sapiens

<400> SEQUENCE: 268

Gly Gly Ser Ala Leu Ile Thr Ile Phe Gly Val Asp Pro Lys Phe Asp
1               5                   10                  15

Pro

<210> SEQ ID NO 269
<211> LENGTH: 20
<212> TYPE: PRT
<213> ORGANISM: Homo sapiens

<400> SEQUENCE: 269

Arg Val Lys Phe Pro Leu Trp Phe Gly Glu Thr Thr Tyr Tyr Tyr Tyr
1               5                   10                  15

Gly Met Asp Val
            20

<210> SEQ ID NO 270
<211> LENGTH: 20
<212> TYPE: PRT
<213> ORGANISM: Homo sapiens

<400> SEQUENCE: 270

Lys Tyr Pro Ala Tyr Tyr Asp Ile Leu Thr Gly Tyr Tyr Arg Asn Tyr
1               5                   10                  15

Tyr Phe Asp Tyr
            20

<210> SEQ ID NO 271
<211> LENGTH: 20
<212> TYPE: PRT
<213> ORGANISM: Homo sapiens

<400> SEQUENCE: 271

Lys Tyr Pro Ala Tyr Tyr Asp Ile Leu Thr Ala Asn Tyr Arg Ser Tyr
1               5                   10                  15

Tyr Phe Asp Tyr
            20

<210> SEQ ID NO 272
<211> LENGTH: 10
<212> TYPE: PRT
<213> ORGANISM: Homo sapiens

<400> SEQUENCE: 272

Leu Arg Ala Thr Ile Ala Gly Phe Asp Tyr
1               5                   10

<210> SEQ ID NO 273
<211> LENGTH: 10
<212> TYPE: PRT
<213> ORGANISM: Homo sapiens

<400> SEQUENCE: 273

Leu Arg Ala Thr Ile Pro Gly Phe Asp Tyr
1               5                   10

<210> SEQ ID NO 274
<211> LENGTH: 10
<212> TYPE: PRT
<213> ORGANISM: Homo sapiens

<400> SEQUENCE: 274

Leu Arg Ala Thr Thr Pro Gly Phe Asp Tyr
1               5                   10

<210> SEQ ID NO 275
<211> LENGTH: 24
<212> TYPE: PRT
<213> ORGANISM: Homo sapiens

<400> SEQUENCE: 275

Asp Gly Lys Gly Lys Ala Tyr Tyr Asp Phe Trp Ser Gly Tyr Arg Asn
1               5                   10                  15

Gln Lys Tyr Tyr Gly Leu Asp Val
            20

<210> SEQ ID NO 276
<211> LENGTH: 12
<212> TYPE: PRT
<213> ORGANISM: Homo sapiens

<400> SEQUENCE: 276

Leu Arg Arg Gly Tyr Phe Asp Ser Gly Gly Asp His
1               5                   10

<210> SEQ ID NO 277
<211> LENGTH: 12
<212> TYPE: PRT
<213> ORGANISM: Homo sapiens

<400> SEQUENCE: 277

Leu Arg Arg Gly Tyr Tyr Asp Ser Gly Glu Asp Tyr
1               5                   10

<210> SEQ ID NO 278
<211> LENGTH: 19
<212> TYPE: PRT

<213> ORGANISM: Homo sapiens

<400> SEQUENCE: 278

Glu Leu Ser Gly Glu Tyr His Phe Trp Ser Gly Thr Tyr Arg Tyr Gly
1               5                   10                  15
Val Asp Val

<210> SEQ ID NO 279
<211> LENGTH: 19
<212> TYPE: PRT
<213> ORGANISM: Homo sapiens

<400> SEQUENCE: 279

Asp Arg Val Ser Asp Tyr Asp Phe Trp Ser Gly Lys Arg Gly Tyr Gly
1               5                   10                  15
Met Asp Val

<210> SEQ ID NO 280
<211> LENGTH: 18
<212> TYPE: PRT
<213> ORGANISM: Homo sapiens

<400> SEQUENCE: 280

Glu Gln Lys Asp Tyr Asp Phe Trp Asn Gly Leu Tyr Lys Tyr Gly Met
1               5                   10                  15
Asp Val

<210> SEQ ID NO 281
<211> LENGTH: 18
<212> TYPE: PRT
<213> ORGANISM: Homo sapiens

<400> SEQUENCE: 281

Gly Gln Arg Asn Val Leu His Phe Leu Glu Arg Lys Asn Asp Ala Phe
1               5                   10                  15
Asp Ile

<210> SEQ ID NO 282
<211> LENGTH: 15
<212> TYPE: PRT
<213> ORGANISM: Homo sapiens

<400> SEQUENCE: 282

Gly Pro Arg Val Phe Phe Glu Ser Ser Gly Tyr Tyr Phe Arg Asn
1               5                   10                  15

<210> SEQ ID NO 283
<211> LENGTH: 15
<212> TYPE: PRT
<213> ORGANISM: Homo sapiens

<400> SEQUENCE: 283

Gly Pro Arg Val Leu Phe Glu Ser Ser Gly His Tyr Leu Arg Asp
1               5                   10                  15

<210> SEQ ID NO 284
<211> LENGTH: 15
<212> TYPE: PRT
<213> ORGANISM: Homo sapiens

<400> SEQUENCE: 284

Gly Pro Arg Val Phe Phe Glu Ser Ser Gly Tyr Tyr Phe Arg Asp
1               5                   10                  15

<210> SEQ ID NO 285
<211> LENGTH: 24
<212> TYPE: PRT
<213> ORGANISM: Homo sapiens

<400> SEQUENCE: 285

Gly Thr Arg Tyr Asp Phe Trp Ser Gly Phe Ser Asn Arg Asp Gly Arg
1               5                   10                  15

Ala Leu Ala Gly Tyr Phe Asp Tyr
            20

<210> SEQ ID NO 286
<211> LENGTH: 16
<212> TYPE: PRT
<213> ORGANISM: Homo sapiens

<400> SEQUENCE: 286

Ala Arg Pro Arg Ser Pro Trp Asp Ser Thr Gly Trp Ser Val Gly Tyr
1               5                   10                  15

<210> SEQ ID NO 287
<211> LENGTH: 21
<212> TYPE: PRT
<213> ORGANISM: Homo sapiens

<400> SEQUENCE: 287

Asp Phe Val Ser Ile Tyr Gly Val Ala Tyr Phe Thr Gly Gly Gly Pro
1               5                   10                  15

Ser Ser Pro Asp Ile
            20

<210> SEQ ID NO 288
<211> LENGTH: 18
<212> TYPE: PRT
<213> ORGANISM: Homo sapiens

<400> SEQUENCE: 288

Lys Arg Val Thr Ile Phe Gly Val Val Asp Thr Pro Arg Gly Tyr Phe
1               5                   10                  15

Asp Tyr

<210> SEQ ID NO 289
<211> LENGTH: 22
<212> TYPE: PRT
<213> ORGANISM: Homo sapiens

<400> SEQUENCE: 289

Asp Gln Leu Gly Arg Tyr Ser Phe Gly Phe Val Thr Gly Gln Asn Lys
1               5                   10                  15

Val Ser Ala Ile Ser Asp
            20

<210> SEQ ID NO 290
<211> LENGTH: 22
<212> TYPE: PRT
<213> ORGANISM: Homo sapiens

<400> SEQUENCE: 290

Asp Gln Arg Gly Arg Tyr Ser Phe Gly Phe Val Thr Gly Gln Thr Lys
1               5                   10                  15

Val Ser Ala Ile Ser Asp
            20

<210> SEQ ID NO 291
<211> LENGTH: 13
<212> TYPE: PRT
<213> ORGANISM: Homo sapiens

<400> SEQUENCE: 291

Gly Ala Leu Trp Phe Gly Gln Leu Arg Gly Leu Asp Pro
1               5                   10

<210> SEQ ID NO 292
<211> LENGTH: 18
<212> TYPE: PRT
<213> ORGANISM: Homo sapiens

<400> SEQUENCE: 292

Gly Pro Gly Ser Met Val Arg Gly Leu Ile Val Thr Ser Tyr Gly Met
1               5                   10                  15

Asp Val

<210> SEQ ID NO 293
<211> LENGTH: 18
<212> TYPE: PRT
<213> ORGANISM: Homo sapiens

<400> SEQUENCE: 293

Arg Gly Arg Leu Asn Ile Pro Ser Pro Ser Ala Ile Leu Thr Ala Phe
1               5                   10                  15

Asp Val

<210> SEQ ID NO 294
<211> LENGTH: 13
<212> TYPE: PRT
<213> ORGANISM: Homo sapiens

<400> SEQUENCE: 294

Gly Pro Lys Ser Val Ala Ser Leu Ser Tyr Phe Asp Lys
1               5                   10

<210> SEQ ID NO 295
<211> LENGTH: 14
<212> TYPE: PRT
<213> ORGANISM: Homo sapiens

<400> SEQUENCE: 295

Arg Glu Ile Arg Phe Gly Glu Leu Ser Phe Tyr Phe Asp Tyr
1               5                   10

<210> SEQ ID NO 296
<211> LENGTH: 14
<212> TYPE: PRT
<213> ORGANISM: Homo sapiens

<400> SEQUENCE: 296

Arg Glu Ile Lys Phe Gly Glu Leu Ser Phe Tyr Phe Asp Ser
1               5                   10

<210> SEQ ID NO 297
<211> LENGTH: 10
<212> TYPE: PRT
<213> ORGANISM: Homo sapiens

<400> SEQUENCE: 297

Asp Ala Phe Val Ser Ser Ala Met Asp Val

```
1               5                   10
```

<210> SEQ ID NO 298
<211> LENGTH: 10
<212> TYPE: PRT
<213> ORGANISM: Homo sapiens

<400> SEQUENCE: 298

```
Gln His Tyr Gly Asn Ser Pro Arg Val Thr
1               5                   10
```

<210> SEQ ID NO 299
<211> LENGTH: 10
<212> TYPE: PRT
<213> ORGANISM: Homo sapiens

<400> SEQUENCE: 299

```
Gln His Tyr Gly Asn Ser Pro Arg Val Thr
1               5                   10
```

<210> SEQ ID NO 300
<211> LENGTH: 11
<212> TYPE: PRT
<213> ORGANISM: Homo sapiens

<400> SEQUENCE: 300

```
Gln Gln Arg Ala Asn Trp Pro Pro Gly Gly Thr
1               5                   10
```

<210> SEQ ID NO 301
<211> LENGTH: 9
<212> TYPE: PRT
<213> ORGANISM: Homo sapiens

<400> SEQUENCE: 301

```
Gln Gln Thr Tyr Thr Phe Pro Tyr Ser
1               5
```

<210> SEQ ID NO 302
<211> LENGTH: 9
<212> TYPE: PRT
<213> ORGANISM: Homo sapiens

<400> SEQUENCE: 302

```
Gln Gln Tyr Asp Ser Ala Pro Val Thr
1               5
```

<210> SEQ ID NO 303
<211> LENGTH: 12
<212> TYPE: PRT
<213> ORGANISM: Homo sapiens

<400> SEQUENCE: 303

```
Ala Ala Trp Asp Asp Ser Leu Asp Gly Phe Trp Val
1               5                   10
```

<210> SEQ ID NO 304
<211> LENGTH: 11
<212> TYPE: PRT
<213> ORGANISM: Homo sapiens

<400> SEQUENCE: 304

```
Gly Thr Trp Asp Ser Ser Leu Ser Ala Val Val
1               5                   10
```

```
<210> SEQ ID NO 305
<211> LENGTH: 10
<212> TYPE: PRT
<213> ORGANISM: Homo sapiens

<400> SEQUENCE: 305

Cys Ser His Thr Ser Ser Asp Thr Leu Val
1               5                   10

<210> SEQ ID NO 306
<211> LENGTH: 10
<212> TYPE: PRT
<213> ORGANISM: Homo sapiens

<400> SEQUENCE: 306

Cys Ser Tyr Thr Ser Ser Ala Thr Val Val
1               5                   10

<210> SEQ ID NO 307
<211> LENGTH: 9
<212> TYPE: PRT
<213> ORGANISM: Homo sapiens

<400> SEQUENCE: 307

Leu Gln Tyr Asn Ala Tyr Pro Leu Thr
1               5

<210> SEQ ID NO 308
<211> LENGTH: 9
<212> TYPE: PRT
<213> ORGANISM: Homo sapiens

<400> SEQUENCE: 308

Leu Gln Tyr Asn Ala Tyr Pro Leu Thr
1               5

<210> SEQ ID NO 309
<211> LENGTH: 9
<212> TYPE: PRT
<213> ORGANISM: Homo sapiens

<400> SEQUENCE: 309

Leu Gln Tyr Ser Thr Tyr Pro Leu Thr
1               5

<210> SEQ ID NO 310
<211> LENGTH: 8
<212> TYPE: PRT
<213> ORGANISM: Homo sapiens

<400> SEQUENCE: 310

Gln Gln Tyr Asn Asp Trp Pro Ala
1               5

<210> SEQ ID NO 311
<211> LENGTH: 9
<212> TYPE: PRT
<213> ORGANISM: Homo sapiens

<400> SEQUENCE: 311

Leu Gln His Asn Asn Tyr Pro Trp Thr
1               5

<210> SEQ ID NO 312
<211> LENGTH: 9
<212> TYPE: PRT
```

<213> ORGANISM: Homo sapiens

<400> SEQUENCE: 312

Leu Gln His Asn Arg Tyr Pro Trp Thr
1               5

<210> SEQ ID NO 313
<211> LENGTH: 9
<212> TYPE: PRT
<213> ORGANISM: Homo sapiens

<400> SEQUENCE: 313

Gln Gln Tyr Gly Ser Ser Pro Arg Thr
1               5

<210> SEQ ID NO 314
<211> LENGTH: 9
<212> TYPE: PRT
<213> ORGANISM: Homo sapiens

<400> SEQUENCE: 314

Gln Gln Tyr Asn Asp Trp Pro Arg Thr
1               5

<210> SEQ ID NO 315
<211> LENGTH: 9
<212> TYPE: PRT
<213> ORGANISM: Homo sapiens

<400> SEQUENCE: 315

Gln Gln Ser Phe Gly Thr Pro Arg Thr
1               5

<210> SEQ ID NO 316
<211> LENGTH: 8
<212> TYPE: PRT
<213> ORGANISM: Homo sapiens

<400> SEQUENCE: 316

Gln Gln Tyr Gly Ser Ser Pro Leu
1               5

<210> SEQ ID NO 317
<211> LENGTH: 8
<212> TYPE: PRT
<213> ORGANISM: Homo sapiens

<400> SEQUENCE: 317

Gln Gln Tyr Gly Arg Ser Pro Leu
1               5

<210> SEQ ID NO 318
<211> LENGTH: 8
<212> TYPE: PRT
<213> ORGANISM: Homo sapiens

<400> SEQUENCE: 318

His Leu Tyr Val Ser Arg Pro Val
1               5

<210> SEQ ID NO 319
<211> LENGTH: 8
<212> TYPE: PRT
<213> ORGANISM: Homo sapiens

<400> SEQUENCE: 319

Gln Gln Tyr Asn Ser Asp Tyr Thr
1               5

<210> SEQ ID NO 320
<211> LENGTH: 10
<212> TYPE: PRT
<213> ORGANISM: Homo sapiens

<400> SEQUENCE: 320

Gln Gln Tyr Gly Gly Ser Pro Pro Asp Thr
1               5                   10

<210> SEQ ID NO 321
<211> LENGTH: 11
<212> TYPE: PRT
<213> ORGANISM: Homo sapiens

<400> SEQUENCE: 321

Ala Ala Trp Asp Asp Ser Leu Gly Gly Val Val
1               5                   10

<210> SEQ ID NO 322
<211> LENGTH: 9
<212> TYPE: PRT
<213> ORGANISM: Homo sapiens

<400> SEQUENCE: 322

Gln Tyr Tyr Gly Ser Ser Pro Tyr Thr
1               5

<210> SEQ ID NO 323
<211> LENGTH: 9
<212> TYPE: PRT
<213> ORGANISM: Homo sapiens

<400> SEQUENCE: 323

Gln Gln Ser Tyr Thr Phe Pro Tyr Ile
1               5

<210> SEQ ID NO 324
<211> LENGTH: 9
<212> TYPE: PRT
<213> ORGANISM: Homo sapiens

<400> SEQUENCE: 324

Gln Gln Thr Phe Thr Phe Pro Tyr Thr
1               5

<210> SEQ ID NO 325
<211> LENGTH: 9
<212> TYPE: PRT
<213> ORGANISM: Homo sapiens

<400> SEQUENCE: 325

Gln Gln Tyr Asn Asp Trp Pro Ile Thr
1               5

<210> SEQ ID NO 326
<211> LENGTH: 9
<212> TYPE: PRT
<213> ORGANISM: Homo sapiens

<400> SEQUENCE: 326

Leu Gln His Asn Ser Tyr Pro Leu Thr
1               5

<210> SEQ ID NO 327
<211> LENGTH: 10
<212> TYPE: PRT
<213> ORGANISM: Homo sapiens

<400> SEQUENCE: 327

Gln Gln Ser Tyr Asn Thr Arg Pro Leu Thr
1               5                   10

<210> SEQ ID NO 328
<211> LENGTH: 11
<212> TYPE: PRT
<213> ORGANISM: Homo sapiens

<400> SEQUENCE: 328

Gln Gln Arg Ser Asn Trp Pro Pro Lys Ile Thr
1               5                   10

<210> SEQ ID NO 329
<211> LENGTH: 10
<212> TYPE: PRT
<213> ORGANISM: Homo sapiens

<400> SEQUENCE: 329

Gln Gln Tyr Lys Ser Tyr Ser Pro Leu Thr
1               5                   10

<210> SEQ ID NO 330
<211> LENGTH: 10
<212> TYPE: PRT
<213> ORGANISM: Homo sapiens

<400> SEQUENCE: 330

Gln Gln Tyr Lys Ser Tyr Ser Pro Leu Thr
1               5                   10

<210> SEQ ID NO 331
<211> LENGTH: 11
<212> TYPE: PRT
<213> ORGANISM: Homo sapiens

<400> SEQUENCE: 331

Gln His Leu Asn Ser Tyr Pro Arg Met Tyr Thr
1               5                   10

<210> SEQ ID NO 332
<211> LENGTH: 15
<212> TYPE: PRT
<213> ORGANISM: Homo sapiens

<400> SEQUENCE: 332

Glu Asn Tyr Ser Asp Gly Trp Tyr Glu Val Gly His Phe Asp Leu
1               5                   10                  15

<210> SEQ ID NO 333
<211> LENGTH: 15
<212> TYPE: PRT
<213> ORGANISM: Homo sapiens

<400> SEQUENCE: 333

Glu Asn Tyr Ser Asp Gly Trp Asn Glu Val Gly His Phe Asp Phe
1               5                   10                  15

<210> SEQ ID NO 334

```
<211> LENGTH: 15
<212> TYPE: PRT
<213> ORGANISM: Homo sapiens

<400> SEQUENCE: 334

Glu Asn Tyr Ser Asp Gly Trp Glu Glu Val Gly His Phe Asp Ser
1               5                   10                  15

<210> SEQ ID NO 335
<211> LENGTH: 15
<212> TYPE: PRT
<213> ORGANISM: Homo sapiens

<400> SEQUENCE: 335

Glu Asn Tyr Ser Asp Gly Trp Glu Glu Val Gly His Phe Asp Tyr
1               5                   10                  15

<210> SEQ ID NO 336
<211> LENGTH: 22
<212> TYPE: PRT
<213> ORGANISM: Homo sapiens

<400> SEQUENCE: 336

Asp Glu Gly Ser Trp Val Glu Ala Ala Asp Glu Trp Asp Glu His Leu
1               5                   10                  15

Phe Arg Glu Met Ala Val
            20

<210> SEQ ID NO 337
<211> LENGTH: 22
<212> TYPE: PRT
<213> ORGANISM: Homo sapiens

<400> SEQUENCE: 337

Asp Glu Val Ser Trp Val Glu Ala Ala Asp Glu Trp Asp Glu His Leu
1               5                   10                  15

Phe Arg Glu Met Ala Val
            20

<210> SEQ ID NO 338
<211> LENGTH: 22
<212> TYPE: PRT
<213> ORGANISM: Homo sapiens

<400> SEQUENCE: 338

Asp Glu Ala Ser Trp Val Glu Ala Ala Asp Glu Trp Asp Glu His Leu
1               5                   10                  15

Phe Arg Glu Met Ala Val
            20

<210> SEQ ID NO 339
<211> LENGTH: 19
<212> TYPE: PRT
<213> ORGANISM: Homo sapiens

<400> SEQUENCE: 339

His Leu Val Val Ala Val Ala Ala Gly Pro Asp Tyr Phe Ser Tyr Gly
1               5                   10                  15

Met Asp Val

<210> SEQ ID NO 340
<211> LENGTH: 19
<212> TYPE: PRT
<213> ORGANISM: Homo sapiens
```

<400> SEQUENCE: 340

Ser Arg Gly Tyr Ala Tyr Asp Ser Gly Gly His Tyr Phe Pro Thr Trp
1               5                   10                  15

Phe Asp Pro

<210> SEQ ID NO 341
<211> LENGTH: 15
<212> TYPE: PRT
<213> ORGANISM: Homo sapiens

<400> SEQUENCE: 341

Leu Asp Ser Ser Ser Gly Trp Glu Glu Val Gly Tyr Phe Asp Arg
1               5                   10                  15

<210> SEQ ID NO 342
<211> LENGTH: 17
<212> TYPE: PRT
<213> ORGANISM: Homo sapiens

<400> SEQUENCE: 342

Ser Leu Thr Gly Arg Leu His Leu Gly Glu Leu Ser Ser Gly Ile Gly
1               5                   10                  15

Pro

<210> SEQ ID NO 343
<211> LENGTH: 21
<212> TYPE: PRT
<213> ORGANISM: Homo sapiens

<400> SEQUENCE: 343

Cys Ser Ile Val Gly Asn Gly Asp Phe Leu Glu Glu Asp Ser His Tyr
1               5                   10                  15

Pro Ala Met Asp Val
            20

<210> SEQ ID NO 344
<211> LENGTH: 19
<212> TYPE: PRT
<213> ORGANISM: Homo sapiens

<400> SEQUENCE: 344

Asn Tyr Leu Ile Glu Ser Arg Tyr Asp Glu Lys Asp Tyr Tyr Ala
1               5                   10                  15

Met Asp Val

<210> SEQ ID NO 345
<211> LENGTH: 20
<212> TYPE: PRT
<213> ORGANISM: Homo sapiens

<400> SEQUENCE: 345

Asp Ser Gly Phe Asp Leu Asp Tyr Tyr Asp Thr Asn Glu Leu Tyr Phe
1               5                   10                  15

Gly Phe Asp Tyr
            20

<210> SEQ ID NO 346
<211> LENGTH: 20
<212> TYPE: PRT
<213> ORGANISM: Homo sapiens

<400> SEQUENCE: 346

Asp Ser Gly Phe Asp Leu Asp Tyr Tyr Asp Thr Asn Glu Leu Tyr Phe
1               5                   10                  15

Gly Phe Asp Tyr
            20

<210> SEQ ID NO 347
<211> LENGTH: 23
<212> TYPE: PRT
<213> ORGANISM: Homo sapiens

<400> SEQUENCE: 347

Gln Asn Ile Ala Ala Arg Thr Ala Glu Arg Leu Tyr Glu Asn Asp Tyr
1               5                   10                  15

Tyr Phe Tyr Gly Met Asp Val
            20

<210> SEQ ID NO 348
<211> LENGTH: 23
<212> TYPE: PRT
<213> ORGANISM: Homo sapiens

<400> SEQUENCE: 348

Gln Asn Ile Ala Ala Arg Ala Ala Glu Lys Leu Tyr Glu Asn Asp Tyr
1               5                   10                  15

Tyr Phe Tyr Gly Met Asp Val
            20

<210> SEQ ID NO 349
<211> LENGTH: 12
<212> TYPE: PRT
<213> ORGANISM: Homo sapiens

<400> SEQUENCE: 349

Cys Tyr Ser Gly Arg Ser Arg Tyr Phe Phe Asp Ser
1               5                   10

<210> SEQ ID NO 350
<211> LENGTH: 18
<212> TYPE: PRT
<213> ORGANISM: Homo sapiens

<400> SEQUENCE: 350

Asp Leu Ala Arg Tyr Gly Val Thr Ser Ile Val Pro Glu Phe Gly Phe
1               5                   10                  15

Asp Phe

<210> SEQ ID NO 351
<211> LENGTH: 20
<212> TYPE: PRT
<213> ORGANISM: Homo sapiens

<400> SEQUENCE: 351

Asp Arg Trp Val Arg Pro Gln Phe Pro Ser Met Asp Phe Gln Tyr Asn
1               5                   10                  15

Gly Leu Asp Val
            20

<210> SEQ ID NO 352
<211> LENGTH: 19
<212> TYPE: PRT
<213> ORGANISM: Homo sapiens

<400> SEQUENCE: 352

Gly Phe His Phe Trp Ser Gly Thr Gly Thr Arg Pro Arg Asn Trp Tyr
1               5                   10                  15

Phe Asp Leu

<210> SEQ ID NO 353
<211> LENGTH: 17
<212> TYPE: PRT
<213> ORGANISM: Homo sapiens

<400> SEQUENCE: 353

Val Ala Ile Ser Tyr Ala Gly Leu Ile Val Val Pro Gly Pro Phe Asp
1               5                   10                  15

Val

<210> SEQ ID NO 354
<211> LENGTH: 17
<212> TYPE: PRT
<213> ORGANISM: Homo sapiens

<400> SEQUENCE: 354

Val Ser Ile Thr Tyr Ala Gly Leu Ile Val Val Pro Gly Ala Phe Asp
1               5                   10                  15

Val

<210> SEQ ID NO 355
<211> LENGTH: 14
<212> TYPE: PRT
<213> ORGANISM: Homo sapiens

<400> SEQUENCE: 355

Val Leu Thr Asp Leu Asp Gln Gly Asn Pro Arg Met Asp Val
1               5                   10

<210> SEQ ID NO 356
<211> LENGTH: 14
<212> TYPE: PRT
<213> ORGANISM: Homo sapiens

<400> SEQUENCE: 356

Val Leu Thr Asp Leu Asp Gln Gly Asn Pro Arg Met Asp Val
1               5                   10

<210> SEQ ID NO 357
<211> LENGTH: 18
<212> TYPE: PRT
<213> ORGANISM: Homo sapiens

<400> SEQUENCE: 357

Gly Arg Gly Ser Thr Phe Pro Ser Ala Gln Phe Ser Tyr Phe Gly Leu
1               5                   10                  15

Asp Val

<210> SEQ ID NO 358
<211> LENGTH: 18
<212> TYPE: PRT
<213> ORGANISM: Homo sapiens

<400> SEQUENCE: 358

Gly Arg Gly Ser Phe Thr Gly Phe Asp Gln Tyr His Tyr Tyr Gly Met
1               5                   10                  15

Asp Val

```
<210> SEQ ID NO 359
<211> LENGTH: 18
<212> TYPE: PRT
<213> ORGANISM: Homo sapiens

<400> SEQUENCE: 359

Gly Arg Gly Tyr Ser His Gly Phe Gln Gln Tyr Asn Tyr Tyr Gly Met
1               5                   10                  15

Asp Val

<210> SEQ ID NO 360
<211> LENGTH: 18
<212> TYPE: PRT
<213> ORGANISM: Homo sapiens

<400> SEQUENCE: 360

Gly Arg Gly Ser Phe Gln Gly Phe Gln Gln Tyr Glu Tyr Tyr Gly Met
1               5                   10                  15

Asp Val

<210> SEQ ID NO 361
<211> LENGTH: 18
<212> TYPE: PRT
<213> ORGANISM: Homo sapiens

<400> SEQUENCE: 361

Gly Arg Gly Ser Phe Gln Gly Phe Gln Gln Tyr Glu Tyr Tyr Gly Met
1               5                   10                  15

Asp Val

<210> SEQ ID NO 362
<211> LENGTH: 15
<212> TYPE: PRT
<213> ORGANISM: Homo sapiens

<400> SEQUENCE: 362

Gly Gly Gly Tyr Ala Val Val Gly Pro Lys Tyr Gly Leu Asp Val
1               5                   10                  15

<210> SEQ ID NO 363
<211> LENGTH: 15
<212> TYPE: PRT
<213> ORGANISM: Homo sapiens

<400> SEQUENCE: 363

Gly Gly Gly Tyr Ala Val Val Gly Pro Lys Tyr Gly Leu Asp Val
1               5                   10                  15

<210> SEQ ID NO 364
<211> LENGTH: 17
<212> TYPE: PRT
<213> ORGANISM: Homo sapiens

<400> SEQUENCE: 364

Gln Val Arg Ala Pro Thr Leu Arg Phe Arg His Gly Gly Tyr Phe Glu
1               5                   10                  15

Thr

<210> SEQ ID NO 365
<211> LENGTH: 17
<212> TYPE: PRT
```

```
<400> SEQUENCE: 365

Gln Leu Arg Ala Pro Thr Thr Arg Phe Arg His Gly Gly Tyr Phe Glu
1               5                   10                  15
Asn

<210> SEQ ID NO 366
<211> LENGTH: 13
<212> TYPE: PRT
<213> ORGANISM: Homo sapiens

<400> SEQUENCE: 366

Ser Asp Pro Ala Ile Ala Ala Ala Gly Ser Leu Asp Leu
1               5                   10

<210> SEQ ID NO 367
<211> LENGTH: 13
<212> TYPE: PRT
<213> ORGANISM: Homo sapiens

<400> SEQUENCE: 367

Ser Asp Pro Ala Ile Ala Ala Ala Gly Ser Leu Asp Leu
1               5                   10

<210> SEQ ID NO 368
<211> LENGTH: 13
<212> TYPE: PRT
<213> ORGANISM: Homo sapiens

<400> SEQUENCE: 368

Ser Asp Pro Ala Ile Ala Ala Ala Gly Ser Leu Asp Leu
1               5                   10

<210> SEQ ID NO 369
<211> LENGTH: 13
<212> TYPE: PRT
<213> ORGANISM: Homo sapiens

<400> SEQUENCE: 369

Ser Asp Pro Ala Ile Ala Ala Ala Gly Ser Leu Asp Leu
1               5                   10

<210> SEQ ID NO 370
<211> LENGTH: 17
<212> TYPE: PRT
<213> ORGANISM: Homo sapiens

<400> SEQUENCE: 370

Arg Asp Lys Tyr Gln Tyr Ile Asp Ser Ser Gly Asp Tyr Pro Phe Asp
1               5                   10                  15
Arg

<210> SEQ ID NO 371
<211> LENGTH: 11
<212> TYPE: PRT
<213> ORGANISM: Homo sapiens

<400> SEQUENCE: 371

His Ile Gly Ala Gly Gly Pro Tyr Ser Glu Tyr
1               5                   10

<210> SEQ ID NO 372
<211> LENGTH: 12
<212> TYPE: PRT
<213> ORGANISM: Homo sapiens
```

```
<400> SEQUENCE: 372

Arg Thr Thr Leu Val Asn Phe Gly Val Phe Asp Leu
1               5                   10

<210> SEQ ID NO 373
<211> LENGTH: 14
<212> TYPE: PRT
<213> ORGANISM: Homo sapiens

<400> SEQUENCE: 373

Asp Lys Asp Ala Ser Ile Tyr Gly Tyr Arg Ile Leu Asn His
1               5                   10

<210> SEQ ID NO 374
<211> LENGTH: 17
<212> TYPE: PRT
<213> ORGANISM: Homo sapiens

<400> SEQUENCE: 374

Asp Gln Gly Gly Tyr Pro Val Ser Pro Val Gly Pro Lys Trp Phe Asp
1               5                   10                  15

Pro

<210> SEQ ID NO 375
<211> LENGTH: 8
<212> TYPE: PRT
<213> ORGANISM: Homo sapiens

<400> SEQUENCE: 375

Gln Gln Thr Tyr Ala Ser Val Thr
1               5

<210> SEQ ID NO 376
<211> LENGTH: 8
<212> TYPE: PRT
<213> ORGANISM: Homo sapiens

<400> SEQUENCE: 376

Gln Gln Ser His Thr Ser Val Thr
1               5

<210> SEQ ID NO 377
<211> LENGTH: 8
<212> TYPE: PRT
<213> ORGANISM: Homo sapiens

<400> SEQUENCE: 377

Gln Gln Thr Tyr Ser Ser Val Thr
1               5

<210> SEQ ID NO 378
<211> LENGTH: 8
<212> TYPE: PRT
<213> ORGANISM: Homo sapiens

<400> SEQUENCE: 378

Gln Gln Ser Tyr Ser Ser Val Thr
1               5

<210> SEQ ID NO 379
<211> LENGTH: 9
<212> TYPE: PRT
<213> ORGANISM: Homo sapiens
```

```
<400> SEQUENCE: 379

His Gln Tyr Gly Ser Ser Pro Gln Ser
1               5

<210> SEQ ID NO 380
<211> LENGTH: 9
<212> TYPE: PRT
<213> ORGANISM: Homo sapiens

<400> SEQUENCE: 380

His Gln Tyr Gly Ser Ser Pro Gln Ser
1               5

<210> SEQ ID NO 381
<211> LENGTH: 9
<212> TYPE: PRT
<213> ORGANISM: Homo sapiens

<400> SEQUENCE: 381

His Gln Tyr Gly Ser Ser Pro Gln Thr
1               5

<210> SEQ ID NO 382
<211> LENGTH: 9
<212> TYPE: PRT
<213> ORGANISM: Homo sapiens

<400> SEQUENCE: 382

Gln Gln Phe Gly Ser Ser Pro Gly Thr
1               5

<210> SEQ ID NO 383
<211> LENGTH: 9
<212> TYPE: PRT
<213> ORGANISM: Homo sapiens

<400> SEQUENCE: 383

Gln Gln Ser Tyr Asp Thr Pro Arg Thr
1               5

<210> SEQ ID NO 384
<211> LENGTH: 9
<212> TYPE: PRT
<213> ORGANISM: Homo sapiens

<400> SEQUENCE: 384

Gln Gln Ser Asn Ser Ser Pro Trp Thr
1               5

<210> SEQ ID NO 385
<211> LENGTH: 11
<212> TYPE: PRT
<213> ORGANISM: Homo sapiens

<400> SEQUENCE: 385

Gln Gln Arg Ser Ile Trp Pro Pro Ser Leu Thr
1               5                   10

<210> SEQ ID NO 386
<211> LENGTH: 8
<212> TYPE: PRT
<213> ORGANISM: Homo sapiens

<400> SEQUENCE: 386

Gln Gln Cys Thr Leu Pro Leu Thr
```

```
1               5
```

\<210\> SEQ ID NO 387
\<211\> LENGTH: 9
\<212\> TYPE: PRT
\<213\> ORGANISM: Homo sapiens

\<400\> SEQUENCE: 387

```
Gln Gln Tyr Asp Ile Leu Pro Leu Thr
1               5
```

\<210\> SEQ ID NO 388
\<211\> LENGTH: 11
\<212\> TYPE: PRT
\<213\> ORGANISM: Homo sapiens

\<400\> SEQUENCE: 388

```
Gly Thr Trp Asp Ser Ser Leu Arg Ala Ala Leu
1               5                   10
```

\<210\> SEQ ID NO 389
\<211\> LENGTH: 11
\<212\> TYPE: PRT
\<213\> ORGANISM: Homo sapiens

\<400\> SEQUENCE: 389

```
Ala Thr Trp Asp Ser Ser Leu Arg Thr Ala Leu
1               5                   10
```

\<210\> SEQ ID NO 390
\<211\> LENGTH: 8
\<212\> TYPE: PRT
\<213\> ORGANISM: Homo sapiens

\<400\> SEQUENCE: 390

```
Gln Gln Tyr Asp Asn Leu Pro Thr
1               5
```

\<210\> SEQ ID NO 391
\<211\> LENGTH: 8
\<212\> TYPE: PRT
\<213\> ORGANISM: Homo sapiens

\<400\> SEQUENCE: 391

```
Gln Gln Tyr Asp Asn Leu Pro Thr
1               5
```

\<210\> SEQ ID NO 392
\<211\> LENGTH: 9
\<212\> TYPE: PRT
\<213\> ORGANISM: Homo sapiens

\<400\> SEQUENCE: 392

```
Gln Gln Ser Gln Arg Thr Pro His Thr
1               5
```

\<210\> SEQ ID NO 393
\<211\> LENGTH: 6
\<212\> TYPE: PRT
\<213\> ORGANISM: Homo sapiens

\<400\> SEQUENCE: 393

```
Gln Gln Tyr Pro Ser Thr
1               5
```

```
<210> SEQ ID NO 394
<211> LENGTH: 5
<212> TYPE: PRT
<213> ORGANISM: Homo sapiens

<400> SEQUENCE: 394

Gln Gln Leu Gly Thr
1               5

<210> SEQ ID NO 395
<211> LENGTH: 9
<212> TYPE: PRT
<213> ORGANISM: Homo sapiens

<400> SEQUENCE: 395

Gln Gln Tyr Gly Ser Ser Pro Ser Thr
1               5

<210> SEQ ID NO 396
<211> LENGTH: 7
<212> TYPE: PRT
<213> ORGANISM: Homo sapiens

<400> SEQUENCE: 396

Gln Lys Tyr Asp Thr Ala Pro
1               5

<210> SEQ ID NO 397
<211> LENGTH: 7
<212> TYPE: PRT
<213> ORGANISM: Homo sapiens

<400> SEQUENCE: 397

Gln Lys Tyr Asp Thr Ala Pro
1               5

<210> SEQ ID NO 398
<211> LENGTH: 9
<212> TYPE: PRT
<213> ORGANISM: Homo sapiens

<400> SEQUENCE: 398

Gln Gln Tyr Glu Thr Tyr Pro Trp Thr
1               5

<210> SEQ ID NO 399
<211> LENGTH: 9
<212> TYPE: PRT
<213> ORGANISM: Homo sapiens

<400> SEQUENCE: 399

Gln Gln Tyr Glu Thr Tyr Pro Trp Thr
1               5

<210> SEQ ID NO 400
<211> LENGTH: 5
<212> TYPE: PRT
<213> ORGANISM: Homo sapiens

<400> SEQUENCE: 400

Gln Gln Leu Gly Thr
1               5

<210> SEQ ID NO 401
<211> LENGTH: 5
<212> TYPE: PRT
```

<213> ORGANISM: Homo sapiens

<400> SEQUENCE: 401

Gln Gln Leu Gly Thr
1               5

<210> SEQ ID NO 402
<211> LENGTH: 5
<212> TYPE: PRT
<213> ORGANISM: Homo sapiens

<400> SEQUENCE: 402

Gln Gln Leu Gly Thr
1               5

<210> SEQ ID NO 403
<211> LENGTH: 10
<212> TYPE: PRT
<213> ORGANISM: Homo sapiens

<400> SEQUENCE: 403

Gly Ala Tyr Thr Thr Thr Ser Thr Leu Val
1               5                   10

<210> SEQ ID NO 404
<211> LENGTH: 10
<212> TYPE: PRT
<213> ORGANISM: Homo sapiens

<400> SEQUENCE: 404

Gly Ala Tyr Thr Thr Thr Ser Thr Leu Val
1               5                   10

<210> SEQ ID NO 405
<211> LENGTH: 12
<212> TYPE: PRT
<213> ORGANISM: Homo sapiens

<400> SEQUENCE: 405

Gln Ser Tyr Asp Thr Ser Leu Ser Asp Thr Gly Val
1               5                   10

<210> SEQ ID NO 406
<211> LENGTH: 12
<212> TYPE: PRT
<213> ORGANISM: Homo sapiens

<400> SEQUENCE: 406

Gln Ser Tyr Asp Thr Ser Leu Thr Asp Thr Gly Val
1               5                   10

<210> SEQ ID NO 407
<211> LENGTH: 5
<212> TYPE: PRT
<213> ORGANISM: Homo sapiens

<400> SEQUENCE: 407

His Gln Leu Asp Ser
1               5

<210> SEQ ID NO 408
<211> LENGTH: 5
<212> TYPE: PRT
<213> ORGANISM: Homo sapiens

<400> SEQUENCE: 408

His Gln Leu Asp Ser
1               5

<210> SEQ ID NO 409
<211> LENGTH: 5
<212> TYPE: PRT
<213> ORGANISM: Homo sapiens

<400> SEQUENCE: 409

His Gln Leu Asp Ser
1               5

<210> SEQ ID NO 410
<211> LENGTH: 5
<212> TYPE: PRT
<213> ORGANISM: Homo sapiens

<400> SEQUENCE: 410

His Gln Leu Asp Thr
1               5

<210> SEQ ID NO 411
<211> LENGTH: 10
<212> TYPE: PRT
<213> ORGANISM: Homo sapiens

<400> SEQUENCE: 411

Gln Gln Tyr Asp Asn Leu Pro Arg Val Thr
1               5                   10

<210> SEQ ID NO 412
<211> LENGTH: 11
<212> TYPE: PRT
<213> ORGANISM: Homo sapiens

<400> SEQUENCE: 412

Gln Gln Arg Thr Thr Trp Pro Pro Glu Tyr Thr
1               5                   10

<210> SEQ ID NO 413
<211> LENGTH: 9
<212> TYPE: PRT
<213> ORGANISM: Homo sapiens

<400> SEQUENCE: 413

Gln His Tyr Gly Asn Ser Arg Trp Thr
1               5

<210> SEQ ID NO 414
<211> LENGTH: 10
<212> TYPE: PRT
<213> ORGANISM: Homo sapiens

<400> SEQUENCE: 414

Gln Tyr Tyr Asp His Arg Pro Ala Ile Ala
1               5                   10

<210> SEQ ID NO 415
<211> LENGTH: 8
<212> TYPE: PRT
<213> ORGANISM: Homo sapiens

<400> SEQUENCE: 415

Cys Ser Tyr Ala Gly Ser Tyr Thr
1               5

<210> SEQ ID NO 416
<211> LENGTH: 11
<212> TYPE: PRT
<213> ORGANISM: Homo sapiens

<400> SEQUENCE: 416

Asp Val Arg Leu Val Ala Val Pro Gly Ala Asp
1               5                   10

<210> SEQ ID NO 417
<211> LENGTH: 18
<212> TYPE: PRT
<213> ORGANISM: Homo sapiens

<400> SEQUENCE: 417

Glu His Arg Leu Pro Pro Pro Thr Gly Arg Arg Thr Arg Asn Trp Phe
1               5                   10                  15

Asp Pro

<210> SEQ ID NO 418
<211> LENGTH: 16
<212> TYPE: PRT
<213> ORGANISM: Homo sapiens

<400> SEQUENCE: 418

Asp Arg Val Gly Arg Arg Leu Gly Glu Leu Ser Ala Gly Phe Asp Tyr
1               5                   10                  15

<210> SEQ ID NO 419
<211> LENGTH: 22
<212> TYPE: PRT
<213> ORGANISM: Homo sapiens

<400> SEQUENCE: 419

Gly Ser Leu Tyr Asp Tyr Arg Asp Asn Ala Asp Leu Lys Pro Ser Tyr
1               5                   10                  15

Tyr Tyr Ala Met Asp Val
            20

<210> SEQ ID NO 420
<211> LENGTH: 10
<212> TYPE: PRT
<213> ORGANISM: Homo sapiens

<400> SEQUENCE: 420

Tyr Glu Gly Lys Arg Ser Gly Met Asp Val
1               5                   10

<210> SEQ ID NO 421
<211> LENGTH: 24
<212> TYPE: PRT
<213> ORGANISM: Homo sapiens

<400> SEQUENCE: 421

Ser Val Ile Thr Asp Leu His Thr Phe Gly Asp Tyr Glu Ser Gly Asp
1               5                   10                  15

Pro Ser Tyr Tyr Tyr Met Asp Val
            20

<210> SEQ ID NO 422
<211> LENGTH: 21
<212> TYPE: PRT
<213> ORGANISM: Homo sapiens

<400> SEQUENCE: 422

Asp Trp Ile Gly Tyr Asp Tyr Asp Gly Ser Gly Ser His Leu Arg Asp
1               5                   10                  15

Glu Ser Phe Asp Ile
            20

<210> SEQ ID NO 423
<211> LENGTH: 15
<212> TYPE: PRT
<213> ORGANISM: Homo sapiens

<400> SEQUENCE: 423

Arg Tyr Lys Tyr Leu Pro Gly Asp Gln His Met Pro Trp Asp Tyr
1               5                   10                  15

<210> SEQ ID NO 424
<211> LENGTH: 15
<212> TYPE: PRT
<213> ORGANISM: Homo sapiens

<400> SEQUENCE: 424

Arg Tyr Lys Tyr Leu Pro Gly Asp Gln His Met Pro Trp Asp Asn
1               5                   10                  15

<210> SEQ ID NO 425
<211> LENGTH: 19
<212> TYPE: PRT
<213> ORGANISM: Homo sapiens

<400> SEQUENCE: 425

His Arg Ala Asn Tyr Asp Phe Trp Gly Gly Ser Asn Leu Arg Gly Tyr
1               5                   10                  15

Phe Asp Pro

<210> SEQ ID NO 426
<211> LENGTH: 19
<212> TYPE: PRT
<213> ORGANISM: Homo sapiens

<400> SEQUENCE: 426

His Arg Ala Asp Tyr Asp Phe Trp Asn Gly Ser Asn Leu Arg Gly Tyr
1               5                   10                  15

Phe Asp Pro

<210> SEQ ID NO 427
<211> LENGTH: 19
<212> TYPE: PRT
<213> ORGANISM: Homo sapiens

<400> SEQUENCE: 427

His Arg Ala Asn Tyr Asp Phe Trp Gly Gly Ser Asn Leu Arg Gly Tyr
1               5                   10                  15

Phe Asp Pro

<210> SEQ ID NO 428
<211> LENGTH: 18
<212> TYPE: PRT
<213> ORGANISM: Homo sapiens

<400> SEQUENCE: 428

Asp Arg Tyr Glu Ala Ala Trp Phe Gly Ala Asp Lys Val Tyr Gly Met
1               5                   10                  15

Asp Val

<210> SEQ ID NO 429
<211> LENGTH: 20
<212> TYPE: PRT
<213> ORGANISM: Homo sapiens

<400> SEQUENCE: 429

Asp Gln Arg Asp Cys Ser Thr Asn Arg Cys Phe Gly Val Phe Gly Tyr
1               5                   10                  15

Tyr Met Asp Val
            20

<210> SEQ ID NO 430
<211> LENGTH: 12
<212> TYPE: PRT
<213> ORGANISM: Homo sapiens

<400> SEQUENCE: 430

Arg Gly Ile Ala Ala Ala Gly Phe Tyr Phe Gln Asn
1               5                   10

<210> SEQ ID NO 431
<211> LENGTH: 12
<212> TYPE: PRT
<213> ORGANISM: Homo sapiens

<400> SEQUENCE: 431

Arg Gly Ile Ala Ala Ala Ala Phe Tyr Phe Gln Thr
1               5                   10

<210> SEQ ID NO 432
<211> LENGTH: 12
<212> TYPE: PRT
<213> ORGANISM: Homo sapiens

<400> SEQUENCE: 432

Arg Gly Ile Ala Ala Ala Gly Phe Tyr Phe Gln His
1               5                   10

<210> SEQ ID NO 433
<211> LENGTH: 7
<212> TYPE: PRT
<213> ORGANISM: Homo sapiens

<400> SEQUENCE: 433

Glu Ile Gly Val Ala Glu His
1               5

<210> SEQ ID NO 434
<211> LENGTH: 10
<212> TYPE: PRT
<213> ORGANISM: Homo sapiens

<400> SEQUENCE: 434

Ser Ser Tyr Thr Ser Ser Leu Thr Leu Val
1               5                   10

<210> SEQ ID NO 435
<211> LENGTH: 10
<212> TYPE: PRT
<213> ORGANISM: Homo sapiens

<400> SEQUENCE: 435

```
Gln Ser Tyr Asp Ser Ser Val Ser Val Val
1               5                   10
```

<210> SEQ ID NO 436
<211> LENGTH: 11
<212> TYPE: PRT
<213> ORGANISM: Homo sapiens

<400> SEQUENCE: 436

```
Gln Gln Arg Ser Ile Trp Pro Pro Ser Leu Thr
1               5                   10
```

<210> SEQ ID NO 437
<211> LENGTH: 9
<212> TYPE: PRT
<213> ORGANISM: Homo sapiens

<400> SEQUENCE: 437

```
Ser Ser Tyr Ser Ala Thr Gly Val Ala
1               5
```

<210> SEQ ID NO 438
<211> LENGTH: 9
<212> TYPE: PRT
<213> ORGANISM: Homo sapiens

<400> SEQUENCE: 438

```
Gln Gln Tyr Asp Asn Leu Pro Leu Ala
1               5
```

<210> SEQ ID NO 439
<211> LENGTH: 9
<212> TYPE: PRT
<213> ORGANISM: Homo sapiens

<400> SEQUENCE: 439

```
Gln Arg Tyr Asn Arg Asp Pro Tyr Ile
1               5
```

<210> SEQ ID NO 440
<211> LENGTH: 9
<212> TYPE: PRT
<213> ORGANISM: Homo sapiens

<400> SEQUENCE: 440

```
Met Gln Ala Thr His Trp Pro Pro Gly
1               5
```

<210> SEQ ID NO 441
<211> LENGTH: 11
<212> TYPE: PRT
<213> ORGANISM: Homo sapiens

<400> SEQUENCE: 441

```
Gln Gln Tyr Asp Asn Leu Pro Pro Arg Val Thr
1               5                   10
```

<210> SEQ ID NO 442
<211> LENGTH: 9
<212> TYPE: PRT
<213> ORGANISM: Homo sapiens

<400> SEQUENCE: 442

```
Gln Gln Tyr Gly Thr Ser Pro Thr Thr
1               5
```

```
<210> SEQ ID NO 443
<211> LENGTH: 9
<212> TYPE: PRT
<213> ORGANISM: Homo sapiens

<400> SEQUENCE: 443

Gln Gln Tyr Gly Ser Ser Pro Thr Thr
1               5

<210> SEQ ID NO 444
<211> LENGTH: 9
<212> TYPE: PRT
<213> ORGANISM: Homo sapiens

<400> SEQUENCE: 444

Gln Gln Tyr Gly Thr Ser Pro Gly Thr
1               5

<210> SEQ ID NO 445
<211> LENGTH: 9
<212> TYPE: PRT
<213> ORGANISM: Homo sapiens

<400> SEQUENCE: 445

Leu Gln His His Ser Tyr Pro Trp Thr
1               5

<210> SEQ ID NO 446
<211> LENGTH: 9
<212> TYPE: PRT
<213> ORGANISM: Homo sapiens

<400> SEQUENCE: 446

Gln His Arg Ser Ser Trp Pro Leu Thr
1               5

<210> SEQ ID NO 447
<211> LENGTH: 9
<212> TYPE: PRT
<213> ORGANISM: Homo sapiens

<400> SEQUENCE: 447

His His Tyr Lys Ser Asp Cys Gln Thr
1               5

<210> SEQ ID NO 448
<211> LENGTH: 9
<212> TYPE: PRT
<213> ORGANISM: Homo sapiens

<400> SEQUENCE: 448

His His Tyr Ser Ser Ser Ser His Thr
1               5

<210> SEQ ID NO 449
<211> LENGTH: 9
<212> TYPE: PRT
<213> ORGANISM: Homo sapiens

<400> SEQUENCE: 449

His His Tyr Met Ser Asp Leu Gln Thr
1               5

<210> SEQ ID NO 450
<211> LENGTH: 9
```

```
<212> TYPE: PRT
<213> ORGANISM: Homo sapiens

<400> SEQUENCE: 450

Gln Gln Tyr Phe Thr Ser Val Ile Thr
1               5

<210> SEQ ID NO 451
<211> LENGTH: 13
<212> TYPE: PRT
<213> ORGANISM: Homo sapiens

<400> SEQUENCE: 451

Asp Glu Ile Val Gly Ala Leu Leu Gly Ala Phe Asp Ile
1               5                   10

<210> SEQ ID NO 452
<211> LENGTH: 10
<212> TYPE: PRT
<213> ORGANISM: Homo sapiens

<400> SEQUENCE: 452

Ser Ala Tyr Tyr Arg Asn Trp Phe Asp Ser
1               5                   10

<210> SEQ ID NO 453
<211> LENGTH: 17
<212> TYPE: PRT
<213> ORGANISM: Homo sapiens

<400> SEQUENCE: 453

Gly Val Trp Glu Ala Pro Asp Gly Ser Ser Tyr Tyr Tyr Met Ala
1               5                   10                  15

Asp

<210> SEQ ID NO 454
<211> LENGTH: 13
<212> TYPE: PRT
<213> ORGANISM: Homo sapiens

<400> SEQUENCE: 454

Asp Ser Arg Pro Gln Ala Leu Val Ala Ala Leu Asp Val
1               5                   10

<210> SEQ ID NO 455
<211> LENGTH: 10
<212> TYPE: PRT
<213> ORGANISM: Homo sapiens

<400> SEQUENCE: 455

Val Arg Arg Gly Ser Ser Tyr Pro Asp Tyr
1               5                   10

<210> SEQ ID NO 456
<211> LENGTH: 18
<212> TYPE: PRT
<213> ORGANISM: Homo sapiens

<400> SEQUENCE: 456

Leu Phe Gly Ala Lys Arg Leu Gly Val Ala Pro Ser Gly Tyr Tyr Met
1               5                   10                  15

Asp Val

<210> SEQ ID NO 457
```

```
<211> LENGTH: 11
<212> TYPE: PRT
<213> ORGANISM: Homo sapiens

<400> SEQUENCE: 457

Arg Gly Ser Leu Leu Ile Lys Tyr Phe Asp Tyr
1               5                   10

<210> SEQ ID NO 458
<211> LENGTH: 17
<212> TYPE: PRT
<213> ORGANISM: Homo sapiens

<400> SEQUENCE: 458

Thr Tyr Tyr Asn Phe Trp Ser Asp Gln Ser Gln Gly Leu Asp Phe Asp
1               5                   10                  15

Tyr

<210> SEQ ID NO 459
<211> LENGTH: 13
<212> TYPE: PRT
<213> ORGANISM: Homo sapiens

<400> SEQUENCE: 459

His Leu Ile Ala Pro Thr Ala Gly Asn Tyr Phe Tyr Pro
1               5                   10

<210> SEQ ID NO 460
<211> LENGTH: 15
<212> TYPE: PRT
<213> ORGANISM: Homo sapiens

<400> SEQUENCE: 460

Lys Val Tyr Ser Asp Gly Trp Ser Pro Pro Thr Gly Phe Val Tyr
1               5                   10                  15

<210> SEQ ID NO 461
<211> LENGTH: 18
<212> TYPE: PRT
<213> ORGANISM: Homo sapiens

<400> SEQUENCE: 461

Gly Gly Ser Met Ile Arg Gly Val Pro Ser Pro Phe Tyr Tyr Gly Met
1               5                   10                  15

Asp Val

<210> SEQ ID NO 462
<211> LENGTH: 9
<212> TYPE: PRT
<213> ORGANISM: Homo sapiens

<400> SEQUENCE: 462

Phe Gly Arg Thr Pro Trp Phe Asp Pro
1               5

<210> SEQ ID NO 463
<211> LENGTH: 10
<212> TYPE: PRT
<213> ORGANISM: Homo sapiens

<400> SEQUENCE: 463

Gly Asp Ser Gly Pro Thr Gly Phe Asp Tyr
1               5                   10
```

```
<210> SEQ ID NO 464
<211> LENGTH: 23
<212> TYPE: PRT
<213> ORGANISM: Homo sapiens

<400> SEQUENCE: 464

Asp Lys Pro Ala Tyr Asp Glu Tyr Ala Glu Glu Thr Ile Ala Pro His
1               5                   10                  15

Asn Tyr His Ala Met Asp Leu
            20

<210> SEQ ID NO 465
<211> LENGTH: 13
<212> TYPE: PRT
<213> ORGANISM: Homo sapiens

<400> SEQUENCE: 465

Asp Val Ile Val Gly Ala Leu Leu Gly Ala Phe Asp Ile
1               5                   10

<210> SEQ ID NO 466
<211> LENGTH: 14
<212> TYPE: PRT
<213> ORGANISM: Homo sapiens

<400> SEQUENCE: 466

Ser Phe Tyr Asp Asn Gly Gly Tyr Tyr Leu Gly Leu Asp Tyr
1               5                   10

<210> SEQ ID NO 467
<211> LENGTH: 11
<212> TYPE: PRT
<213> ORGANISM: Homo sapiens

<400> SEQUENCE: 467

Ser Ile Tyr Ser Thr Gly Pro Ala Pro Val Tyr
1               5                   10

<210> SEQ ID NO 468
<211> LENGTH: 4
<212> TYPE: PRT
<213> ORGANISM: Homo sapiens

<400> SEQUENCE: 468

Asp Leu Ile Asp
1

<210> SEQ ID NO 469
<211> LENGTH: 15
<212> TYPE: PRT
<213> ORGANISM: Homo sapiens

<400> SEQUENCE: 469

Ile Lys Gly Pro Pro Arg Gly Asn Phe Gly Val Ala Phe Tyr Phe
1               5                   10                  15

<210> SEQ ID NO 470
<211> LENGTH: 15
<212> TYPE: PRT
<213> ORGANISM: Homo sapiens

<400> SEQUENCE: 470

Gly Thr Gln Ser Tyr Ser Ala Val Ala Pro Gly Trp Phe Asp Pro
1               5                   10                  15
```

```
<210> SEQ ID NO 471
<211> LENGTH: 15
<212> TYPE: PRT
<213> ORGANISM: Homo sapiens

<400> SEQUENCE: 471

Gly Gly Tyr Asp Tyr Gly Asp His Tyr Tyr Tyr Met Asp Val
1               5                   10                  15

<210> SEQ ID NO 472
<211> LENGTH: 20
<212> TYPE: PRT
<213> ORGANISM: Homo sapiens

<400> SEQUENCE: 472

Asp Val Val Glu Arg Pro Gly Phe Gly Asp Phe Arg Tyr Asp Tyr Tyr
1               5                   10                  15

Gly Met Asp Val
            20

<210> SEQ ID NO 473
<211> LENGTH: 13
<212> TYPE: PRT
<213> ORGANISM: Homo sapiens

<400> SEQUENCE: 473

Asp Arg Leu Ser Ser Phe Trp Ser Gly Gly Ile Asp Gln
1               5                   10

<210> SEQ ID NO 474
<211> LENGTH: 12
<212> TYPE: PRT
<213> ORGANISM: Homo sapiens

<400> SEQUENCE: 474

Ala Pro Tyr Ile Ser Ser Ser His Leu Asp Tyr Trp
1               5                   10

<210> SEQ ID NO 475
<211> LENGTH: 8
<212> TYPE: PRT
<213> ORGANISM: Homo sapiens

<400> SEQUENCE: 475

Gln Arg Trp Glu Thr Ile Asp Tyr
1               5

<210> SEQ ID NO 476
<211> LENGTH: 16
<212> TYPE: PRT
<213> ORGANISM: Homo sapiens

<400> SEQUENCE: 476

Ala Arg Glu Gly Arg Trp Phe Ser Asp Asn Tyr Tyr Ala Met Asp Val
1               5                   10                  15

<210> SEQ ID NO 477
<211> LENGTH: 12
<212> TYPE: PRT
<213> ORGANISM: Homo sapiens

<400> SEQUENCE: 477

Gly Val Gly Thr Arg Tyr Tyr Val Tyr Phe Asp Ser
1               5                   10
```

```
<210> SEQ ID NO 478
<211> LENGTH: 13
<212> TYPE: PRT
<213> ORGANISM: Homo sapiens

<400> SEQUENCE: 478

Asp Arg Gly Ser Ser Gly Trp Tyr Gly Trp Leu Asp Pro
1               5                   10

<210> SEQ ID NO 479
<211> LENGTH: 11
<212> TYPE: PRT
<213> ORGANISM: Homo sapiens

<400> SEQUENCE: 479

Glu Met Ala Ala Thr Ser Asp Ala Phe Asp Ile
1               5                   10

<210> SEQ ID NO 480
<211> LENGTH: 14
<212> TYPE: PRT
<213> ORGANISM: Homo sapiens

<400> SEQUENCE: 480

Ser Ile Ala Ala Asp Asp Tyr Tyr Tyr Tyr Tyr Met Asp Val
1               5                   10

<210> SEQ ID NO 481
<211> LENGTH: 6
<212> TYPE: PRT
<213> ORGANISM: Homo sapiens

<400> SEQUENCE: 481

Leu Glu Gly Thr Asp Tyr
1               5

<210> SEQ ID NO 482
<211> LENGTH: 15
<212> TYPE: PRT
<213> ORGANISM: Homo sapiens

<400> SEQUENCE: 482

Ala Gln Phe His Asn Ser Gly Tyr Tyr Tyr Ser Gly Leu Asp Tyr
1               5                   10                  15

<210> SEQ ID NO 483
<211> LENGTH: 15
<212> TYPE: PRT
<213> ORGANISM: Homo sapiens

<400> SEQUENCE: 483

Ala Pro Pro Pro Gly Ser Thr Glu Trp Ala Tyr Tyr Phe Asp Tyr
1               5                   10                  15

<210> SEQ ID NO 484
<211> LENGTH: 10
<212> TYPE: PRT
<213> ORGANISM: Homo sapiens

<400> SEQUENCE: 484

Arg Glu Gly Ser Gln Gly Ala Phe Asp Ile
1               5                   10

<210> SEQ ID NO 485
<211> LENGTH: 15
<212> TYPE: PRT
```

<213> ORGANISM: Homo sapiens

<400> SEQUENCE: 485

Ala Ala Ile Pro Ile Gly Asp Ser Lys Tyr Ser Tyr Phe Asp Ser
1               5                   10                  15

<210> SEQ ID NO 486
<211> LENGTH: 12
<212> TYPE: PRT
<213> ORGANISM: Homo sapiens

<400> SEQUENCE: 486

Gly Val Arg Ser Ile Val Gly Ala His Phe Asp Tyr
1               5                   10

<210> SEQ ID NO 487
<211> LENGTH: 14
<212> TYPE: PRT
<213> ORGANISM: Homo sapiens

<400> SEQUENCE: 487

Gly His Ser Ser Ser Trp Thr Lys Phe Asn Trp Phe Gly Pro
1               5                   10

<210> SEQ ID NO 488
<211> LENGTH: 13
<212> TYPE: PRT
<213> ORGANISM: Homo sapiens

<400> SEQUENCE: 488

Arg Asp Arg Tyr Asn Trp Lys Tyr Tyr Tyr Leu Asp Val
1               5                   10

<210> SEQ ID NO 489
<211> LENGTH: 13
<212> TYPE: PRT
<213> ORGANISM: Homo sapiens

<400> SEQUENCE: 489

Gly Leu Thr Val Ala Thr Leu Tyr Asp Ala Phe Asp Val
1               5                   10

<210> SEQ ID NO 490
<211> LENGTH: 13
<212> TYPE: PRT
<213> ORGANISM: Homo sapiens

<400> SEQUENCE: 490

His Ser Arg Pro Gly Ala Pro Pro His Tyr Phe Asp Tyr
1               5                   10

<210> SEQ ID NO 491
<211> LENGTH: 16
<212> TYPE: PRT
<213> ORGANISM: Homo sapiens

<400> SEQUENCE: 491

Leu Tyr Tyr Asn Phe Gly Ser Gly Tyr Asp Thr Gly Ile Gly Asp His
1               5                   10                  15

<210> SEQ ID NO 492
<211> LENGTH: 12
<212> TYPE: PRT
<213> ORGANISM: Homo sapiens

<400> SEQUENCE: 492

```
Val Lys Gln Phe Leu Glu Trp Leu Tyr Leu Asp Tyr
1               5                  10
```

<210> SEQ ID NO 493
<211> LENGTH: 15
<212> TYPE: PRT
<213> ORGANISM: Homo sapiens

<400> SEQUENCE: 493

```
Pro Ser Tyr Gly Gly Tyr Asp Asp Gln Gly Trp Tyr Phe Glu Tyr
1               5                  10                  15
```

<210> SEQ ID NO 494
<211> LENGTH: 11
<212> TYPE: PRT
<213> ORGANISM: Homo sapiens

<400> SEQUENCE: 494

```
Lys Gly Arg Gly Tyr Gly Tyr Trp Phe Asp Ser
1               5                  10
```

<210> SEQ ID NO 495
<211> LENGTH: 19
<212> TYPE: PRT
<213> ORGANISM: Homo sapiens

<400> SEQUENCE: 495

```
Ala Phe Gln Ala Ser Met Val Arg Gly Val Ile Val Asp Pro Tyr Gly
1               5                  10                  15

Met Asp Val
```

<210> SEQ ID NO 496
<211> LENGTH: 9
<212> TYPE: PRT
<213> ORGANISM: Homo sapiens

<400> SEQUENCE: 496

```
Gln Gln Tyr Asn Thr Tyr Pro Leu Thr
1               5
```

<210> SEQ ID NO 497
<211> LENGTH: 10
<212> TYPE: PRT
<213> ORGANISM: Homo sapiens

<400> SEQUENCE: 497

```
Gln Gln Phe Asn Ser Tyr Pro Pro Leu Thr
1               5                  10
```

<210> SEQ ID NO 498
<211> LENGTH: 9
<212> TYPE: PRT
<213> ORGANISM: Homo sapiens

<400> SEQUENCE: 498

```
Gln Gln Gly Phe Ser Ala Pro Phe Thr
1               5
```

<210> SEQ ID NO 499
<211> LENGTH: 9
<212> TYPE: PRT
<213> ORGANISM: Homo sapiens

<400> SEQUENCE: 499

```
Met Gln Gly Thr Tyr Trp Leu Trp Thr
1               5
```

<210> SEQ ID NO 500
<211> LENGTH: 9
<212> TYPE: PRT
<213> ORGANISM: Homo sapiens

<400> SEQUENCE: 500

```
Gln Gln Tyr His Asn Trp Pro Pro Ser
1               5
```

<210> SEQ ID NO 501
<211> LENGTH: 8
<212> TYPE: PRT
<213> ORGANISM: Homo sapiens

<400> SEQUENCE: 501

```
Gln Gln Ser Tyr Thr Thr Pro Leu
1               5
```

<210> SEQ ID NO 502
<211> LENGTH: 11
<212> TYPE: PRT
<213> ORGANISM: Homo sapiens

<400> SEQUENCE: 502

```
Gln Gln Arg Ser Asn Trp Pro Pro Gly Leu Thr
1               5                   10
```

<210> SEQ ID NO 503
<211> LENGTH: 9
<212> TYPE: PRT
<213> ORGANISM: Homo sapiens

<400> SEQUENCE: 503

```
Gln Gln Tyr Asn Ser Tyr Phe Arg Thr
1               5
```

<210> SEQ ID NO 504
<211> LENGTH: 11
<212> TYPE: PRT
<213> ORGANISM: Homo sapiens

<400> SEQUENCE: 504

```
Cys Ser Tyr Ala Gly Arg Asp Thr Ser Trp Val
1               5                   10
```

<210> SEQ ID NO 505
<211> LENGTH: 10
<212> TYPE: PRT
<213> ORGANISM: Homo sapiens

<400> SEQUENCE: 505

```
Gln Gln Tyr Gly Ser Ser Arg Arg Trp Thr
1               5                   10
```

<210> SEQ ID NO 506
<211> LENGTH: 9
<212> TYPE: PRT
<213> ORGANISM: Homo sapiens

<400> SEQUENCE: 506

```
His Gln Cys Gly Ser Ser Pro Arg Thr
1               5
```

<210> SEQ ID NO 507
<211> LENGTH: 9
<212> TYPE: PRT
<213> ORGANISM: Homo sapiens

<400> SEQUENCE: 507

Met Gln Gly Thr His Trp Pro Trp Thr
1               5

<210> SEQ ID NO 508
<211> LENGTH: 9
<212> TYPE: PRT
<213> ORGANISM: Homo sapiens

<400> SEQUENCE: 508

Gln Gln Tyr Asn Trp Pro Pro Phe Thr
1               5

<210> SEQ ID NO 509
<211> LENGTH: 9
<212> TYPE: PRT
<213> ORGANISM: Homo sapiens

<400> SEQUENCE: 509

Gln Gln Tyr Tyr Ser Thr Pro Val Thr
1               5

<210> SEQ ID NO 510
<211> LENGTH: 9
<212> TYPE: PRT
<213> ORGANISM: Homo sapiens

<400> SEQUENCE: 510

Gln Gln Tyr Lys Thr Tyr Pro Val Thr
1               5

<210> SEQ ID NO 511
<211> LENGTH: 8
<212> TYPE: PRT
<213> ORGANISM: Homo sapiens

<400> SEQUENCE: 511

His Gln Tyr Asn Lys Trp Asp Thr
1               5

<210> SEQ ID NO 512
<211> LENGTH: 12
<212> TYPE: PRT
<213> ORGANISM: Homo sapiens

<400> SEQUENCE: 512

Tyr Ser Thr Asp Asn Ser Gly Lys Gln His Trp Val
1               5                   10

<210> SEQ ID NO 513
<211> LENGTH: 9
<212> TYPE: PRT
<213> ORGANISM: Homo sapiens

<400> SEQUENCE: 513

Gln Gln Ser Tyr Ser Thr Pro Tyr Thr
1               5

<210> SEQ ID NO 514
<211> LENGTH: 9

```
<212> TYPE: PRT
<213> ORGANISM: Homo sapiens

<400> SEQUENCE: 514

Gln Gln His Asp Thr Phe Pro Phe Thr
1               5

<210> SEQ ID NO 515
<211> LENGTH: 9
<212> TYPE: PRT
<213> ORGANISM: Homo sapiens

<400> SEQUENCE: 515

Gln Gln Tyr Tyr Ser Ser Pro Leu Thr
1               5

<210> SEQ ID NO 516
<211> LENGTH: 8
<212> TYPE: PRT
<213> ORGANISM: Homo sapiens

<400> SEQUENCE: 516

Gln Gln Tyr Gly Ser Ser Ile Thr
1               5

<210> SEQ ID NO 517
<211> LENGTH: 9
<212> TYPE: PRT
<213> ORGANISM: Homo sapiens

<400> SEQUENCE: 517

Met Gln Ser Leu His Leu Pro Tyr Thr
1               5

<210> SEQ ID NO 518
<211> LENGTH: 10
<212> TYPE: PRT
<213> ORGANISM: Homo sapiens

<400> SEQUENCE: 518

Gln Ser Tyr Asn Gly Asp Pro Pro Val Thr
1               5                   10

<210> SEQ ID NO 519
<211> LENGTH: 11
<212> TYPE: PRT
<213> ORGANISM: Homo sapiens

<400> SEQUENCE: 519

Leu Ser Ala Asp Ser Ser Ser Thr Tyr Gln Val
1               5                   10

<210> SEQ ID NO 520
<211> LENGTH: 11
<212> TYPE: PRT
<213> ORGANISM: Homo sapiens

<400> SEQUENCE: 520

Gly Ser Trp Asp Gly Ser Leu Asn Ala Gly Val
1               5                   10

<210> SEQ ID NO 521
<211> LENGTH: 10
<212> TYPE: PRT
<213> ORGANISM: Homo sapiens
```

```
<400> SEQUENCE: 521

Gln Gln Tyr Gly Phe Ser Leu Pro Val Thr
1               5                   10

<210> SEQ ID NO 522
<211> LENGTH: 11
<212> TYPE: PRT
<213> ORGANISM: Homo sapiens

<400> SEQUENCE: 522

Gln Ser Tyr Asp Ser Ser Leu Ser Gly Trp Val
1               5                   10

<210> SEQ ID NO 523
<211> LENGTH: 9
<212> TYPE: PRT
<213> ORGANISM: Homo sapiens

<400> SEQUENCE: 523

Gln Gln Tyr Asp Val Trp Pro Leu Thr
1               5

<210> SEQ ID NO 524
<211> LENGTH: 10
<212> TYPE: PRT
<213> ORGANISM: Homo sapiens

<400> SEQUENCE: 524

Gln Gln Tyr Lys Lys Trp Pro Pro Trp Thr
1               5                   10

<210> SEQ ID NO 525
<211> LENGTH: 9
<212> TYPE: PRT
<213> ORGANISM: Homo sapiens

<400> SEQUENCE: 525

Gln Gln Tyr Gly Ser Ser Pro Ile Thr
1               5

<210> SEQ ID NO 526
<211> LENGTH: 9
<212> TYPE: PRT
<213> ORGANISM: Homo sapiens

<400> SEQUENCE: 526

Gln Gln Tyr Asp Arg Leu Pro Ile Thr
1               5

<210> SEQ ID NO 527
<211> LENGTH: 10
<212> TYPE: PRT
<213> ORGANISM: Homo sapiens

<400> SEQUENCE: 527

Gln His His Gly Ser Ser Pro Thr Trp Thr
1               5                   10

<210> SEQ ID NO 528
<211> LENGTH: 9
<212> TYPE: PRT
<213> ORGANISM: Homo sapiens

<400> SEQUENCE: 528

Gln His Tyr Asn Asn Trp Pro Tyr Thr
```

```
1               5

<210> SEQ ID NO 529
<211> LENGTH: 9
<212> TYPE: PRT
<213> ORGANISM: Homo sapiens

<400> SEQUENCE: 529

Gln Ala Trp Asp Ser Ser Thr Ala Val
1               5

<210> SEQ ID NO 530
<211> LENGTH: 8
<212> TYPE: PRT
<213> ORGANISM: Homo sapiens

<400> SEQUENCE: 530

Gln Gln Tyr Tyr Thr Val Pro Ser
1               5

<210> SEQ ID NO 531
<211> LENGTH: 9
<212> TYPE: PRT
<213> ORGANISM: Homo sapiens

<400> SEQUENCE: 531

Met Gln Ala Leu Gln Thr Ser Leu Thr
1               5

<210> SEQ ID NO 532
<211> LENGTH: 8
<212> TYPE: PRT
<213> ORGANISM: Homo sapiens

<400> SEQUENCE: 532

Gln Gln Tyr Ser Gly Pro Leu Thr
1               5

<210> SEQ ID NO 533
<211> LENGTH: 10
<212> TYPE: PRT
<213> ORGANISM: Homo sapiens

<400> SEQUENCE: 533

Gln Gln Leu Asn Ser Asp Pro Pro Trp Thr
1               5                   10

<210> SEQ ID NO 534
<211> LENGTH: 9
<212> TYPE: PRT
<213> ORGANISM: Homo sapiens

<400> SEQUENCE: 534

Met Gln Ser Ile Gln Leu Pro Leu Thr
1               5

<210> SEQ ID NO 535
<211> LENGTH: 10
<212> TYPE: PRT
<213> ORGANISM: Homo sapiens

<400> SEQUENCE: 535

Gln Gln Tyr Gly Ser Ser Ala Pro Tyr Thr
1               5                   10
```

```
<210> SEQ ID NO 536
<211> LENGTH: 9
<212> TYPE: PRT
<213> ORGANISM: Homo sapiens

<400> SEQUENCE: 536

Gln Asn Tyr Asn Lys Pro Pro Arg Thr
1               5

<210> SEQ ID NO 537
<211> LENGTH: 9
<212> TYPE: PRT
<213> ORGANISM: Homo sapiens

<400> SEQUENCE: 537

Gln Gln Ser Tyr Ser Ile Ala Gly Thr
1               5

<210> SEQ ID NO 538
<211> LENGTH: 11
<212> TYPE: PRT
<213> ORGANISM: Homo sapiens

<400> SEQUENCE: 538

Gln Val Trp Asp Ser Gly Arg Asp Ser Trp Val
1               5                   10

<210> SEQ ID NO 539
<211> LENGTH: 10
<212> TYPE: PRT
<213> ORGANISM: Homo sapiens

<400> SEQUENCE: 539

Gln Gln Tyr Tyr Lys Trp Pro Pro Ile Thr
1               5                   10

<210> SEQ ID NO 540
<211> LENGTH: 9
<212> TYPE: PRT
<213> ORGANISM: Homo sapiens

<400> SEQUENCE: 540

Gln Gln Tyr Tyr Ser Thr Pro His Thr
1               5

<210> SEQ ID NO 541
<211> LENGTH: 16
<212> TYPE: PRT
<213> ORGANISM: Homo sapiens

<400> SEQUENCE: 541

Glu Gly Gly Tyr Ser Asp Phe Trp Ser Gly Tyr Ser Gly Phe Asp Tyr
1               5                   10                  15

<210> SEQ ID NO 542
<211> LENGTH: 13
<212> TYPE: PRT
<213> ORGANISM: Homo sapiens

<400> SEQUENCE: 542

Ala Asn Tyr Tyr Asp Ser Ser Gly Tyr Gly Leu Asp Ile
1               5                   10

<210> SEQ ID NO 543
<211> LENGTH: 17
<212> TYPE: PRT
```

-continued

<213> ORGANISM: Homo sapiens

<400> SEQUENCE: 543

His Tyr Tyr Gly Ser Gly Leu Thr Lys Asp Tyr Tyr Glu Tyr Ile Asp
1               5                   10                  15

Val

<210> SEQ ID NO 544
<211> LENGTH: 14
<212> TYPE: PRT
<213> ORGANISM: Homo sapiens

<400> SEQUENCE: 544

Asp Arg Phe Asn Trp Asn Asp Gly Gly Tyr Phe Phe Asp Ser
1               5                   10

<210> SEQ ID NO 545
<211> LENGTH: 16
<212> TYPE: PRT
<213> ORGANISM: Homo sapiens

<400> SEQUENCE: 545

Arg Met Ala Thr Leu Thr Gly Gly Tyr Tyr Tyr Tyr Tyr Met Asp Val
1               5                   10                  15

<210> SEQ ID NO 546
<211> LENGTH: 23
<212> TYPE: PRT
<213> ORGANISM: Homo sapiens

<400> SEQUENCE: 546

Arg Ile Ser Ser Ser Ser Trp Tyr Met Val Asp Asn Ser His Thr Leu
1               5                   10                  15

His Phe Tyr Tyr Met Asp Val
            20

<210> SEQ ID NO 547
<211> LENGTH: 13
<212> TYPE: PRT
<213> ORGANISM: Homo sapiens

<400> SEQUENCE: 547

Ala Ala Arg Arg Ala Phe Tyr Tyr Tyr Met Asp Val
1               5                   10

<210> SEQ ID NO 548
<211> LENGTH: 19
<212> TYPE: PRT
<213> ORGANISM: Homo sapiens

<400> SEQUENCE: 548

Gly Ala Thr Tyr Tyr Tyr Asp Ser Ser Gly His Gln Ser Arg Arg Ala
1               5                   10                  15

Phe Asp Ile

<210> SEQ ID NO 549
<211> LENGTH: 12
<212> TYPE: PRT
<213> ORGANISM: Homo sapiens

<400> SEQUENCE: 549

Ala Ser Gly Ser Tyr Ile Leu Gly Thr Met Asp Val
1               5                   10

```
<210> SEQ ID NO 550
<211> LENGTH: 21
<212> TYPE: PRT
<213> ORGANISM: Homo sapiens

<400> SEQUENCE: 550

Met Asn Pro Pro Trp Phe Arg Gly Gly Ser Asn Asn Pro Tyr Ser Tyr
1               5                   10                  15

Tyr Tyr Met Asp Val
            20

<210> SEQ ID NO 551
<211> LENGTH: 15
<212> TYPE: PRT
<213> ORGANISM: Homo sapiens

<400> SEQUENCE: 551

Gln Thr Thr Asp Glu Gly Arg Gln Trp Leu Val Gly Phe Gln His
1               5                   10                  15

<210> SEQ ID NO 552
<211> LENGTH: 14
<212> TYPE: PRT
<213> ORGANISM: Homo sapiens

<400> SEQUENCE: 552

Ile Tyr Asp Gly Arg Gly Tyr Tyr Ser Tyr Phe Phe Asp Leu
1               5                   10

<210> SEQ ID NO 553
<211> LENGTH: 12
<212> TYPE: PRT
<213> ORGANISM: Homo sapiens

<400> SEQUENCE: 553

Leu Gly Cys Ser Gly Gly Ser Cys Tyr Glu Asp Ser
1               5                   10

<210> SEQ ID NO 554
<211> LENGTH: 19
<212> TYPE: PRT
<213> ORGANISM: Homo sapiens

<400> SEQUENCE: 554

Leu Thr Lys Asn Pro Ser Gln Asp Phe Trp Gly Ser Tyr Leu Tyr Tyr
1               5                   10                  15

Phe Glu Asp

<210> SEQ ID NO 555
<211> LENGTH: 9
<212> TYPE: PRT
<213> ORGANISM: Homo sapiens

<400> SEQUENCE: 555

Ala Gly Arg Glu Gly Trp Phe Asp Pro
1               5

<210> SEQ ID NO 556
<211> LENGTH: 16
<212> TYPE: PRT
<213> ORGANISM: Homo sapiens

<400> SEQUENCE: 556

Gln Val Ser Ser Tyr Ser Ser Ser Gly Tyr Arg Arg Glu Phe Asp Tyr
```

<210> SEQ ID NO 557
<211> LENGTH: 8
<212> TYPE: PRT
<213> ORGANISM: Homo sapiens

<400> SEQUENCE: 557

Ser Gly Val His Tyr Met Asp Val
1               5

<210> SEQ ID NO 558
<211> LENGTH: 10
<212> TYPE: PRT
<213> ORGANISM: Homo sapiens

<400> SEQUENCE: 558

Phe Thr Gln Arg Gln Gly Gly Phe Asp Tyr
1               5                   10

<210> SEQ ID NO 559
<211> LENGTH: 17
<212> TYPE: PRT
<213> ORGANISM: Homo sapiens

<400> SEQUENCE: 559

His Gly Arg Thr Val Phe Gly Val Val Arg Asn Tyr Tyr Tyr Met Asp
1               5                   10                  15

Val

<210> SEQ ID NO 560
<211> LENGTH: 13
<212> TYPE: PRT
<213> ORGANISM: Homo sapiens

<400> SEQUENCE: 560

Asn Gly His Ser Ala Leu Gly Gly Glu Tyr Phe Gln His
1               5                   10

<210> SEQ ID NO 561
<211> LENGTH: 22
<212> TYPE: PRT
<213> ORGANISM: Homo sapiens

<400> SEQUENCE: 561

Asp His Gly Ile Lys Pro Asp Asn Tyr Tyr Asp Ile Ser Gly Tyr Asn
1               5                   10                  15

Leu Asp Tyr Phe Asp Tyr
            20

<210> SEQ ID NO 562
<211> LENGTH: 13
<212> TYPE: PRT
<213> ORGANISM: Homo sapiens

<400> SEQUENCE: 562

Asn Gly His Ser Ser Leu Gly Gly Gly Tyr Phe Pro His
1               5                   10

<210> SEQ ID NO 563
<211> LENGTH: 16
<212> TYPE: PRT
<213> ORGANISM: Homo sapiens

<400> SEQUENCE: 563

Ala Gly His Cys Ser Ser Thr Ser Ser Val Tyr Cys Pro Phe Asp Met
1               5                   10                  15

<210> SEQ ID NO 564
<211> LENGTH: 16
<212> TYPE: PRT
<213> ORGANISM: Homo sapiens

<400> SEQUENCE: 564

Thr Asn Trp Ala Asn Asp Phe Val Thr Gly Tyr Tyr Arg Phe Asp Phe
1               5                   10                  15

<210> SEQ ID NO 565
<211> LENGTH: 12
<212> TYPE: PRT
<213> ORGANISM: Homo sapiens

<400> SEQUENCE: 565

Gly Leu Tyr Asp Ser Ser Gly Tyr Tyr Phe Gly Tyr
1               5                   10

<210> SEQ ID NO 566
<211> LENGTH: 10
<212> TYPE: PRT
<213> ORGANISM: Homo sapiens

<400> SEQUENCE: 566

Thr Leu Asp Gly Asn Phe His Trp Asp Phe
1               5                   10

<210> SEQ ID NO 567
<211> LENGTH: 13
<212> TYPE: PRT
<213> ORGANISM: Homo sapiens

<400> SEQUENCE: 567

Asp Arg Ala Pro Tyr Gly Ala Phe Glu Pro Phe Asp Phe
1               5                   10

<210> SEQ ID NO 568
<211> LENGTH: 15
<212> TYPE: PRT
<213> ORGANISM: Homo sapiens

<400> SEQUENCE: 568

Arg Tyr Cys Ser Ser Thr Thr Cys Tyr Arg Gly His Phe Asp Tyr
1               5                   10                  15

<210> SEQ ID NO 569
<211> LENGTH: 18
<212> TYPE: PRT
<213> ORGANISM: Homo sapiens

<400> SEQUENCE: 569

Leu Thr Gly Pro Ser Gly Tyr Cys Asp Ser Ser Gly Cys Tyr Trp Phe
1               5                   10                  15

Asp Pro

<210> SEQ ID NO 570
<211> LENGTH: 10
<212> TYPE: PRT
<213> ORGANISM: Homo sapiens

<400> SEQUENCE: 570

Asp Arg Asp Tyr Asp Glu Asp Phe Asp Phe
1               5                  10

<210> SEQ ID NO 571
<211> LENGTH: 21
<212> TYPE: PRT
<213> ORGANISM: Homo sapiens

<400> SEQUENCE: 571

Asp Leu Val Ser Val Ser Pro Pro Tyr Gly Asn Tyr Gly Pro Asp Asn
1               5                   10                  15

Asn Trp Phe Asp Phe
            20

<210> SEQ ID NO 572
<211> LENGTH: 13
<212> TYPE: PRT
<213> ORGANISM: Homo sapiens

<400> SEQUENCE: 572

Asp Phe Gly Arg Ala Tyr Ala Ile Gly Tyr Phe Glu Tyr
1               5                   10

<210> SEQ ID NO 573
<211> LENGTH: 10
<212> TYPE: PRT
<213> ORGANISM: Homo sapiens

<400> SEQUENCE: 573

Leu Ile Pro Val Ser Gly Ala Phe Asp Val
1               5                   10

<210> SEQ ID NO 574
<211> LENGTH: 6
<212> TYPE: PRT
<213> ORGANISM: Homo sapiens

<400> SEQUENCE: 574

Gly Gly Ser Pro Glu His
1               5

<210> SEQ ID NO 575
<211> LENGTH: 19
<212> TYPE: PRT
<213> ORGANISM: Homo sapiens

<400> SEQUENCE: 575

Asp Gly Arg Tyr Ser Gly Asp Asp Gln Tyr Tyr His Tyr Tyr Tyr
1               5                   10                  15

Met Asp Val

<210> SEQ ID NO 576
<211> LENGTH: 15
<212> TYPE: PRT
<213> ORGANISM: Homo sapiens

<400> SEQUENCE: 576

Glu Ser Trp Leu Tyr Ser Asn Gly Asp Tyr Tyr Tyr Met Asp Val
1               5                   10                  15

<210> SEQ ID NO 577
<211> LENGTH: 13
<212> TYPE: PRT
<213> ORGANISM: Homo sapiens

```
<400> SEQUENCE: 577

Glu Ala Gly Ser Val Thr Ala Thr Gly Pro Phe Asp Ser
1               5                   10

<210> SEQ ID NO 578
<211> LENGTH: 12
<212> TYPE: PRT
<213> ORGANISM: Homo sapiens

<400> SEQUENCE: 578

Leu Tyr Phe Asp Trp Ala Pro His Ala Phe Asp Ile
1               5                   10

<210> SEQ ID NO 579
<211> LENGTH: 10
<212> TYPE: PRT
<213> ORGANISM: Homo sapiens

<400> SEQUENCE: 579

Gln Glu Trp Glu Leu Gln Pro Phe Asp Tyr
1               5                   10

<210> SEQ ID NO 580
<211> LENGTH: 9
<212> TYPE: PRT
<213> ORGANISM: Homo sapiens

<400> SEQUENCE: 580

Glu Glu Pro Arg Asp Ala Phe Asp Leu
1               5

<210> SEQ ID NO 581
<211> LENGTH: 9
<212> TYPE: PRT
<213> ORGANISM: Homo sapiens

<400> SEQUENCE: 581

Ser Gln Gly Asn Thr Ala Ile Asp Tyr
1               5

<210> SEQ ID NO 582
<211> LENGTH: 15
<212> TYPE: PRT
<213> ORGANISM: Homo sapiens

<400> SEQUENCE: 582

Asp Leu Leu Pro Asp Tyr Pro Val Ser Ser Ala Pro Glu Asp Phe
1               5                   10                  15

<210> SEQ ID NO 583
<211> LENGTH: 18
<212> TYPE: PRT
<213> ORGANISM: Homo sapiens

<400> SEQUENCE: 583

Leu Pro Lys Ser Arg Met Val Gly Gly Asp His Leu Pro Phe Tyr Pro
1               5                   10                  15

Asp Phe

<210> SEQ ID NO 584
<211> LENGTH: 17
<212> TYPE: PRT
<213> ORGANISM: Homo sapiens

<400> SEQUENCE: 584
```

```
Asp Leu Asn Phe Gly Val Val Thr Pro Tyr Tyr Tyr Tyr Leu Asp
1               5                   10                  15
Val
```

<210> SEQ ID NO 585
<211> LENGTH: 14
<212> TYPE: PRT
<213> ORGANISM: Homo sapiens

<400> SEQUENCE: 585

```
Asp Asn Thr Ile Ser Gly Val Val Pro Arg Trp Phe Asp Tyr
1               5                   10
```

<210> SEQ ID NO 586
<211> LENGTH: 15
<212> TYPE: PRT
<213> ORGANISM: Homo sapiens

<400> SEQUENCE: 586

```
Pro Gly Tyr Cys Asn Asn Ile Cys Thr His Trp Phe Asp Thr
1               5                   10                  15
```

<210> SEQ ID NO 587
<211> LENGTH: 13
<212> TYPE: PRT
<213> ORGANISM: Homo sapiens

<400> SEQUENCE: 587

```
Leu Ser Ser Asp Arg Ile Val Val Gly Pro Asp Tyr
1               5                   10
```

<210> SEQ ID NO 588
<211> LENGTH: 10
<212> TYPE: PRT
<213> ORGANISM: Homo sapiens

<400> SEQUENCE: 588

```
Ser Ser Tyr Thr Ile Ser Ser Pro Arg Val
1               5                   10
```

<210> SEQ ID NO 589
<211> LENGTH: 9
<212> TYPE: PRT
<213> ORGANISM: Homo sapiens

<400> SEQUENCE: 589

```
Gln Ser Tyr Asp Ser Ser Leu Ser Gly
1               5
```

<210> SEQ ID NO 590
<211> LENGTH: 11
<212> TYPE: PRT
<213> ORGANISM: Homo sapiens

<400> SEQUENCE: 590

```
Gln Ser Tyr Asp Ser Ser Leu Gly Val Glu Val
1               5                   10
```

<210> SEQ ID NO 591
<211> LENGTH: 9
<212> TYPE: PRT
<213> ORGANISM: Homo sapiens

<400> SEQUENCE: 591

Gln Gln Tyr Asn Ser Tyr Pro Leu Thr
1               5

<210> SEQ ID NO 592
<211> LENGTH: 9
<212> TYPE: PRT
<213> ORGANISM: Homo sapiens

<400> SEQUENCE: 592

Met Gln Ser Leu Gln Thr Pro Ile Thr
1               5

<210> SEQ ID NO 593
<211> LENGTH: 13
<212> TYPE: PRT
<213> ORGANISM: Homo sapiens

<400> SEQUENCE: 593

Ala Ala Trp Asp Asp Ser Leu Ser Gly Leu Asn Trp Val
1               5                   10

<210> SEQ ID NO 594
<211> LENGTH: 9
<212> TYPE: PRT
<213> ORGANISM: Homo sapiens

<400> SEQUENCE: 594

Gln Gln Phe Asn Thr Tyr Ser Gln Thr
1               5

<210> SEQ ID NO 595
<211> LENGTH: 11
<212> TYPE: PRT
<213> ORGANISM: Homo sapiens

<400> SEQUENCE: 595

Met Gln Gly Thr Tyr Trp Pro Pro Ser Ile Thr
1               5                   10

<210> SEQ ID NO 596
<211> LENGTH: 9
<212> TYPE: PRT
<213> ORGANISM: Homo sapiens

<400> SEQUENCE: 596

Gln Gln Arg Thr Ser Trp Pro Gln Thr
1               5

<210> SEQ ID NO 597
<211> LENGTH: 8
<212> TYPE: PRT
<213> ORGANISM: Homo sapiens

<400> SEQUENCE: 597

Gln Gln Tyr Glu Asn Trp Leu Thr
1               5

<210> SEQ ID NO 598
<211> LENGTH: 9
<212> TYPE: PRT
<213> ORGANISM: Homo sapiens

<400> SEQUENCE: 598

Gln Leu Tyr Asn Ser Val Pro Gln Thr
1               5

```
<210> SEQ ID NO 599
<211> LENGTH: 9
<212> TYPE: PRT
<213> ORGANISM: Homo sapiens

<400> SEQUENCE: 599

Gln Gln Tyr Ser Thr Thr Pro Arg Thr
1               5

<210> SEQ ID NO 600
<211> LENGTH: 9
<212> TYPE: PRT
<213> ORGANISM: Homo sapiens

<400> SEQUENCE: 600

Gln Gln Gly Tyr Ser Thr Pro Trp Thr
1               5

<210> SEQ ID NO 601
<211> LENGTH: 9
<212> TYPE: PRT
<213> ORGANISM: Homo sapiens

<400> SEQUENCE: 601

His Gln Ser Tyr Ser Thr Pro Pro Thr
1               5

<210> SEQ ID NO 602
<211> LENGTH: 11
<212> TYPE: PRT
<213> ORGANISM: Homo sapiens

<400> SEQUENCE: 602

Gln Gln Tyr Tyr Ser Ile Pro Pro Trp Thr Phe
1               5                   10

<210> SEQ ID NO 603
<211> LENGTH: 9
<212> TYPE: PRT
<213> ORGANISM: Homo sapiens

<400> SEQUENCE: 603

Gln Gln Ser Phe Ser Thr Leu Trp Thr
1               5

<210> SEQ ID NO 604
<211> LENGTH: 11
<212> TYPE: PRT
<213> ORGANISM: Homo sapiens

<400> SEQUENCE: 604

Gln Ser Tyr Asp Asn Ser Leu Ser Gly Trp Val
1               5                   10

<210> SEQ ID NO 605
<211> LENGTH: 9
<212> TYPE: PRT
<213> ORGANISM: Homo sapiens

<400> SEQUENCE: 605

His Gln Cys Asp Asn Leu Ile Ala Arg
1               5

<210> SEQ ID NO 606
<211> LENGTH: 9
```

<212> TYPE: PRT
<213> ORGANISM: Homo sapiens

<400> SEQUENCE: 606

Gln Gln Tyr Gly Ser Ser Pro Pro Thr
1               5

<210> SEQ ID NO 607
<211> LENGTH: 9
<212> TYPE: PRT
<213> ORGANISM: Homo sapiens

<400> SEQUENCE: 607

Gln Gln Tyr Asp Asn Leu Leu Ala His
1               5

<210> SEQ ID NO 608
<211> LENGTH: 9
<212> TYPE: PRT
<213> ORGANISM: Homo sapiens

<400> SEQUENCE: 608

Gln Glu Tyr Tyr Ile Leu Pro Cys Ser
1               5

<210> SEQ ID NO 609
<211> LENGTH: 11
<212> TYPE: PRT
<213> ORGANISM: Homo sapiens

<400> SEQUENCE: 609

Gly Thr Trp Asp Gly Ser Leu Thr Thr Gly Val
1               5                   10

<210> SEQ ID NO 610
<211> LENGTH: 10
<212> TYPE: PRT
<213> ORGANISM: Homo sapiens

<400> SEQUENCE: 610

Tyr Ser Tyr Ala Gly Asn Ser Leu Gly Val
1               5                   10

<210> SEQ ID NO 611
<211> LENGTH: 11
<212> TYPE: PRT
<213> ORGANISM: Homo sapiens

<400> SEQUENCE: 611

Cys Ser Phe Thr Tyr Val Asn Pro Thr Tyr Leu
1               5                   10

<210> SEQ ID NO 612
<211> LENGTH: 9
<212> TYPE: PRT
<213> ORGANISM: Homo sapiens

<400> SEQUENCE: 612

Gln Gln Tyr Asn Arg Tyr Ser Tyr Thr
1               5

<210> SEQ ID NO 613
<211> LENGTH: 11
<212> TYPE: PRT
<213> ORGANISM: Homo sapiens

```
<400> SEQUENCE: 613

Ser Ser Tyr Ala Asp Thr Asn Asp Phe Gly Val
1               5                   10

<210> SEQ ID NO 614
<211> LENGTH: 10
<212> TYPE: PRT
<213> ORGANISM: Homo sapiens

<400> SEQUENCE: 614

Cys Ser Tyr Ala Gly Ser Tyr Ser Tyr Val
1               5                   10

<210> SEQ ID NO 615
<211> LENGTH: 9
<212> TYPE: PRT
<213> ORGANISM: Homo sapiens

<400> SEQUENCE: 615

Gln Gln Tyr Asn Asn Leu Pro Val Thr
1               5

<210> SEQ ID NO 616
<211> LENGTH: 9
<212> TYPE: PRT
<213> ORGANISM: Homo sapiens

<400> SEQUENCE: 616

Gln Gln Tyr Asp Ser Phe Ser Trp Thr
1               5

<210> SEQ ID NO 617
<211> LENGTH: 9
<212> TYPE: PRT
<213> ORGANISM: Homo sapiens

<400> SEQUENCE: 617

Gln Gln Arg Ser Thr Trp Pro Pro Thr
1               5

<210> SEQ ID NO 618
<211> LENGTH: 8
<212> TYPE: PRT
<213> ORGANISM: Homo sapiens

<400> SEQUENCE: 618

Gln Tyr Tyr Gly Met Ser Val Thr
1               5

<210> SEQ ID NO 619
<211> LENGTH: 9
<212> TYPE: PRT
<213> ORGANISM: Homo sapiens

<400> SEQUENCE: 619

Gln Gln Tyr His Asn Trp Pro Arg Thr
1               5

<210> SEQ ID NO 620
<211> LENGTH: 8
<212> TYPE: PRT
<213> ORGANISM: Homo sapiens

<400> SEQUENCE: 620

Gln Gln Tyr Ser His Tyr Arg Thr
```

```
1               5
```

<210> SEQ ID NO 621
<211> LENGTH: 10
<212> TYPE: PRT
<213> ORGANISM: Homo sapiens

<400> SEQUENCE: 621

```
Gln Gln Tyr Gly Ser Ser Leu Leu Tyr Thr
1               5                   10
```

<210> SEQ ID NO 622
<211> LENGTH: 13
<212> TYPE: PRT
<213> ORGANISM: Homo sapiens

<400> SEQUENCE: 622

```
Ser Thr Trp Asp Tyr Ser Leu Ser Ala His Glu Asp Val
1               5                   10
```

<210> SEQ ID NO 623
<211> LENGTH: 10
<212> TYPE: PRT
<213> ORGANISM: Homo sapiens

<400> SEQUENCE: 623

```
Met Gln Gly Thr Tyr Trp Pro Pro Leu Thr
1               5                   10
```

<210> SEQ ID NO 624
<211> LENGTH: 9
<212> TYPE: PRT
<213> ORGANISM: Homo sapiens

<400> SEQUENCE: 624

```
Gln Gln Arg His Asn Trp Pro Ile Ser
1               5
```

<210> SEQ ID NO 625
<211> LENGTH: 12
<212> TYPE: PRT
<213> ORGANISM: Homo sapiens

<400> SEQUENCE: 625

```
Ala Ala Trp Asp Asp Ser Leu Asn Gly His Gly Val
1               5                   10
```

<210> SEQ ID NO 626
<211> LENGTH: 4
<212> TYPE: PRT
<213> ORGANISM: Homo sapiens

<400> SEQUENCE: 626

```
Gln Ser Lys Thr
1
```

<210> SEQ ID NO 627
<211> LENGTH: 10
<212> TYPE: PRT
<213> ORGANISM: Homo sapiens

<400> SEQUENCE: 627

```
Gln Gln Tyr Asn Asn Trp Pro Pro Phe Thr
1               5                   10
```

-continued

```
<210> SEQ ID NO 628
<211> LENGTH: 10
<212> TYPE: PRT
<213> ORGANISM: Homo sapiens

<400> SEQUENCE: 628

Gln Gln Arg Ser Asn Trp Pro Arg Leu Thr
1               5                   10

<210> SEQ ID NO 629
<211> LENGTH: 19
<212> TYPE: PRT
<213> ORGANISM: Homo sapiens

<400> SEQUENCE: 629

Thr Asn Gly Thr Glu Ile Phe Arg Pro Gly Gly Gly Asp Met Arg Asp
1               5                   10                  15

Asn Trp Arg

<210> SEQ ID NO 630
<211> LENGTH: 15
<212> TYPE: PRT
<213> ORGANISM: Homo sapiens

<400> SEQUENCE: 630

Asn Asn Asn Thr Arg Lys Ser Ile Asn Ile Gly Pro Gly Arg Ala
1               5                   10                  15

<210> SEQ ID NO 631
<211> LENGTH: 20
<212> TYPE: PRT
<213> ORGANISM: Homo sapiens

<400> SEQUENCE: 631

Asp Thr Asn Gly Thr Glu Ile Phe Arg Pro Gly Gly Gly Asp Met Arg
1               5                   10                  15

Asp Asn Trp Arg
            20

<210> SEQ ID NO 632
<211> LENGTH: 17
<212> TYPE: PRT
<213> ORGANISM: Homo sapiens

<400> SEQUENCE: 632

Val Leu Asn Asn Asn Thr Arg Lys Ser Ile Asn Ile Gly Pro Gly Arg
1               5                   10                  15

Ala
```